（12） United States Patent
Von Deyn et al.

(10) Patent No.: US 12,134,616 B2
(45) Date of Patent: Nov. 5, 2024

(54) TRICYCLIC PESTICIDAL COMPOUNDS

(71) Applicant: BASF SE, Ludwigshafen (DE)

(72) Inventors: Wolfgang Von Deyn, Ludwigshafen (DE); Rizwan Shabbir Shaikh, Navi Mumbai (IN); Devendra Vyas, Research Triangle Park, NC (US); Arun Narine, Ludwigshafen (DE); Olesya Kuzmina, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 770 days.

(21) Appl. No.: 17/282,018

(22) PCT Filed: Oct. 11, 2019

(86) PCT No.: PCT/EP2019/077562
§ 371 (c)(1),
(2) Date: Apr. 1, 2021

(87) PCT Pub. No.: WO2020/083662
PCT Pub. Date: Apr. 30, 2020

(65) Prior Publication Data
US 2021/0347777 A1  Nov. 11, 2021

(30) Foreign Application Priority Data
Oct. 23, 2018 (EP) .................... 18202072

(51) Int. Cl.
C07D 471/14 (2006.01)
A01N 43/90 (2006.01)
C07D 471/04 (2006.01)

(52) U.S. Cl.
CPC .......... *C07D 471/14* (2013.01); *A01N 43/90* (2013.01); *C07D 471/04* (2013.01)

(58) Field of Classification Search
None
See application file for complete search history.

(56) References Cited

U.S. PATENT DOCUMENTS 4,753,951 A * 6/1988 Takada .................. C07D 495/14
546/82
5,167,695 A  12/1992 Brill et al.

2014/0018373 A1  1/2014 Takyo et al.
2014/0194290 A1  7/2014 Takahashi et al.
2015/0216168 A1 * 8/2015 Frackenpohl .......... A01N 43/52
504/276

FOREIGN PATENT DOCUMENTS

| JP | H03-95180 A | 4/1991 |
| JP | 2018-090578 A | 6/2018 |
| WO | WO-2013/059559 A2 | 4/2013 |
| WO | WO-2014/132971 A1 | 9/2014 |
| WO | WO-2016113261 A1 * | 7/2016 |
| WO | WO-2017/167832 A1 | 10/2017 |

OTHER PUBLICATIONS

Toja et al. (J. Med. Chem., 1984, 27, 610-616) (Year: 1984).*
Patani et al. (Chem. Rev., 1996, 96, 3147-3176) (Year: 1996).*
International Application No. PCT/EP2019/077562, International Search Report and Written Opinion, mailed Nov. 21, 2019.
European Search Report for EP Patent Application No. 18202072.7, Issued on Mar. 21, 2019, 3 pages.

* cited by examiner

*Primary Examiner* — Erin E Hirt
(74) *Attorney, Agent, or Firm* — MARSHALL, GERSTEIN & BORUN LLP

(57) ABSTRACT

The invention relates to compounds of formula (I), wherein the variables are as defined in the specification. It also relates to the use of compounds of formula (I) as an agrochemical pesticide; to pesticidal mixtures comprising compounds of formula (I); and to agrochemical or veterinary compositions comprising compounds of formula (I). Other objects are seed comprising compounds of formula (I); and methods for controlling invertebrate pests, infestation, or infection by invertebrate pests by application of compounds of formula (I).

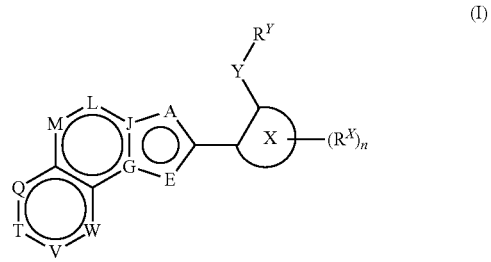

16 Claims, No Drawings

TRICYCLIC PESTICIDAL COMPOUNDS

CROSS-REFERENCE TO RELATED APPLICATIONS

This is the U.S. national phase of International Application No. PCT/EP2019/077562, filed Oct. 11, 2019, which claims the benefit of European Patent Application No. 18202072.7, filed on Oct. 23, 2018.

The invention relates to compounds of formula (I) or an agrochemically or veterinarily acceptable salt, stereoisomer, tautomer, or N-oxide thereof

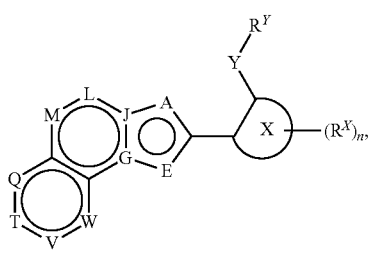

wherein the variables are as defined below. The invention also relates to the use of compounds of formula (I) as an agrochemical pesticide; to pesticidal mixtures comprising a compound of formula (I) and another agrochemically active ingredient; to agrochemical or veterinary compositions comprising a compound of formula (I) or the pesticidal mixture and a liquid or solid carrier; and to seed comprising a compound of formula (I) or the pesticidal mixture. The invention also relates to methods for controlling invertebrate pests, infestation, or infection by invertebrate pests by application of the compounds of formula (I) or the pesticidal mixtures comprising them.

Invertebrate pests and in particular insects, arachnids and nematodes destroy growing and harvested crops and attack wooden dwelling and commercial structures, thereby causing large economic loss to the food supply and to property. Accordingly, there is an ongoing need for new agents for combating invertebrate pests.

WO2017/167832A1 discloses bicyclic compounds and their use as agrochemical pesticides, whereas tricyclic compounds are not described.

Due to the ability of target pests to develop resistance to pesticidally active agents, there is an ongoing need to identify further compounds, which are suitable for combating invertebrate pests such as insects, arachnids and nematodes. Furthermore, there is a need for new compounds having a high pesticidal activity and showing a broad activity spectrum against a large number of different invertebrate pests, especially against difficult to control insects, arachnids and nematodes. There is furthermore a need to find compounds that display a higher efficacy as compared with known pesticides, which reduces the application rates and costs for the applicant, and decreases the environmental effects on soil and ground water.

It is therefore an object of the present invention to identify and provide compounds, which exhibit a high pesticidal activity and have a broad activity spectrum against invertebrate pests.

It has been found that these objects can be achieved by substituted tricyclic compounds of formula I as depicted and defined below, including their stereoisomers, their salts, in particular their agriculturally or veterinarily acceptable salts, their tautomers and their N-oxides.

Therefore, the invention provides in a first aspect compounds of formula (I), or an agrochemically or veterinarily acceptable salt, stereoisomer, tautomer, or N-oxide thereof

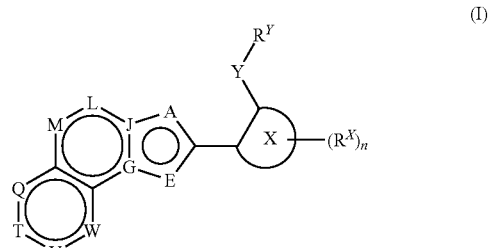

wherein the variables in formula (I) have the following meaning

A is CH, N, or NH;
E is N, O, S, $NR^E$, or $CR^E$;
G, J are independently C or N;
L is N or $CR^L$;
M is N or $CR^M$;
Q is N or $CR^Q$;
T is N or $CR^T$;
V is N or $CR^V$;
W is N or $CR^W$;
X is phenyl, or a 5- or 6-membered hetaryl;
Y is S, S(O), or $S(O)_2$;
$R^E$, $R^L$, $R^M$, $R^Q$, $R^T$, $R^V$, and $R^W$ are independently H, halogen, $N_3$, CN, $NO_2$, SCN, $SF_5$; $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, which groups are halogenated or non-halogenated,
C(=O)$OR^1$, $NR^2R^3$, $C_1$-$C_6$-alkylen-$NR^2R^3$, O—$C_1$-$C_6$-alkylen-$NR^2R^3$, $C_1$-$C_6$-alkylen-CN, NH—$C_1$-$C_6$-alkylen-$NR^2R^3$, C(=O)$NR^2R^3$, C(=O)$R^4$, $SO_2NR^2R^3$, $S(=O)_mR^5$, $OR^6$, $SR^6$, or $CH_2R^6$; phenyl, which is unsubstituted or substituted with one or more, same or different substituents $R^{11}$;
$R^1H$;
  $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, or $C_3$-$C_6$-cycloalkoxy-$C_1$-$C_4$-alkyl, which groups are halogenated or non-halogenated;
  $C_1$-$C_6$-alkylen-$NR^2R^3$, $C_1$-$C_6$-alkylen-CN, or $CH_2R^6$; or
  phenyl, which is unsubstituted, or substituted with one or more, same or different substituents $R^{11}$;
$R^{11}$ is halogen, $N_3$, OH, CN, $NO_2$, SCN, $SF_5$; $C_1$-$C_6$-alkyl, $C_1$-$C_6$-alkoxy, $C_2$-$C_6$-alkenyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, which groups are halogenated or non-halogenated;
$R^2$ is H;
  $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which groups are unsubstituted, or substituted with one or more, same or different substituents selected from halogen, CN, and OH;

C(=O)$R^{21}$, C(=O)O$R^{21}$, C(=O)N$R^{21}$, $C_1$-$C_6$-alkylen-CN, or $CH_2R^6$; or phenyl, which is unsubstituted or substituted with one or more, same or different substituents $R^{11}$;

$R^{21}$ is H;

$C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl;

$C_3$-$C_6$-cycloalkyl-$C_1$-$C_4$-alkyl, $C_3$-$C_6$-cycloalkoxy-$C_1$-$C_4$ alkyl, phenyl, or a saturated, partially-, or fully unsaturated 5- or 6-membered heterocycle, wherein the cyclic moieties are unsubstituted or substituted with one or more, same or different substituents $R^1$;

$R^3$ is H;

$C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which groups are halogenated or non-halogenated;

$C_1$-$C_6$-alkylen-CN, or $CH_2R^6$;

phenyl, which is unsubstituted or substituted with one or more, same or different substituents $R^{11}$; or $NR^2R^3$ may also form an N-bound, saturated 3- to 8-membered heterocycle, which in addition to the nitrogen atom may have 1 or 2 further heteroatoms or heteroatom moieties selected from O, S(=O)$_m$, NH, and N—$C_1$-$C_6$-alkyl, and wherein the N-bound heterocycle is unsubstituted or substituted with one or more, same or different substituents selected from halogen, $C_1$-$C_4$-alkyl, $C_1$-$C_4$-haloalkyl, $C_1$-$C_4$-alkoxy and $C_1$-$C_4$-haloalkoxy;

$R^4$ is H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, or $C_3$-$C_6$-cycloalkoxy-$C_1$-$C_4$-alkyl, which are unsubstituted, or substituted with one or more, same or different substituents selected from halogen, CN, and OH; $CH_2R^6$, or phenyl, which is unsubstituted, or substituted with one or more, same or different substituents $R^{11}$;

$R^5$ is $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, or $C_3$-$C_6$-cycloalkoxy-$C_1$-$C_4$-alkyl, which groups are halogenated or non-halogenated;

$C_1$-$C_6$-alkylen-$NR^2R^3$, $C_1$-$C_6$-alkylen-CN, $CH_2R^6$; or phenyl, which is unsubstituted, or substituted with one or more, same or different substituents $R^{11}$;

$R^6$ is phenyl, which is unsubstituted or substituted with one or more, same or different substituents $R^{11}$;

$R^X$ is halogen, $N_3$, OH, CN, $NO_2$, SCN, $SF_5$;

$C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, which groups are halogenated or non-halogenated;

C(=O)O$R^1$, $NR^2R^3$, $C_1$-$C_6$-alkylen-$NR^2R^3$, O—$C_1$-$C_6$-alkylen-$NR^2R^3$, $C_1$-$C_6$-alkylen-CN, NH—$C_1$-$C_6$-alkylen-$NR^2R^3$, C(=O)$NR^2R^3$, C(=O)$R^4$, $SO_2NR^2R^3$, S(=O)$_mR^1$, $OR^6$, $SR^6$, $CH_2R^6$; or OC(=O)$R^4$, OC(=O)O$R^1$, OC(=O)$NR^2R^3$, OC(=O)$SR^1$, OC(=S)$NR^2R^3$, OC(=S)$SR^1$, $ONR^2R^3$, ON=$CR^1R^4$, N=$CR^1R^4$, $NNR^2$, NC(=O)$R^4$, SC(=O)$SR^1$, SC(=O)$NR^2R^3$, C(=S)$R^6$, C(=S)O$R^4$, C(=$NR^2$)$R^4$, C(=$NOR^2$)$R^4$, C(CN)$R^7R^8$;

phenyl, which is unsubstituted or substituted with one or more, same or different substituents $R^{11}$;

a 5- or 6-membered saturated, partially unsaturated, or fully unsaturated heterocyclic ring, wherein said heterocyclic ring comprises one or more, same or different heteroatoms O, N, or S, and is unsubstituted, or substituted with one or more, same or different substituents $R^{31}$, and wherein said N- and S-atoms are independently oxidized, or non-oxidized; or $C_3$-$C_6$-cycloalkyl, which is substituted with one or more, same or different substituents $R^9$;

$R^7$, $R^8$ are independently H, halogen, CN, $C_1$-$C_6$-alkyl, $C_1$-$C_6$-haloalkyl, $C_3$-$C_6$-cycloalkyl, $C_1$-$C_4$-alkoxy, $C_1$-$C_4$-alkoxy-$C_1$-$C_4$-alkyl, $C_1$-$C_4$-alkylsulfanyl, $C_1$-$C_4$-alkylsulfanyl-$C_1$-$C_4$-alkyl, $C_1$-$C_4$-alkylsulfinyl-$C_1$-$C_4$-alkyl, $C_1$-$C_4$-alkylsulfonyl-$C_1$-$C_4$-alkyl or $C_1$-$C_4$-alkoxycarbonyl;

$R^9$ CN, $NH_2$, C(=O)H, OH, $C_3$-$C_6$-cycloalkyl, C(=O)OH, C(=O)$NH_2$, $C_1$-$C_4$-haloalkoxy, $C_1$-$C_4$-alkoxy, $C_1$-$C_4$-haloalkylsulfanyl, $C_1$-$C_4$-haloalkylsulfinyl, $C_1$-$C_4$-haloalkylsulfonyl, $C_1$-$C_4$-alkoxycarbonyl, $C_1$-$C_4$-haloalkoxycarbonyl, $C_1$-$C_4$-alkylcarbonyl, $C_1$-$C_4$-haloalkylcarbonyl, dli-($C_1$-$C_4$)alkylaminocarbonyl, $C_1$-$C_4$-alkylaminocarbonyl, $C_1$-$C_4$-alkylcarbonylamino, di($C_1$-$C_4$)alkylcarbonylamino, C1-$C_4$-alkoxycarbonylamino, or a group —C($R^{91}$)=$NOR^{92}$;

phenyl, which is unsubstituted or substituted with one or more, same or different substituents selected from halogen, CN, $C_1$-$C_4$-alkyl, $C_1$-$C_4$-haloalkyl, $C_1$-$C_4$-haloalkoxy, $C_1$-$C_4$-alkoxy, $C_1$-$C_4$-haloalkylsulfanyl, $C_1$-$C_4$-haloalkylsulfinyl, $C_1$-$C_4$haloalkylsulfonyl and C(=O)$C_1$-$C_4$-haloalkyl;

$C_1$-$C_4$-alkyl which is unsubstituted or substituted with one or more, same or different substituents $R^{93}$.

$R^{31}$ is halogen, $N_3$, OH, CN, $NO_2$, SCN, $SF_5$;

$C_1$-$C_6$-alkyl, $C_1$-$C_6$-haloalkyl, $C_1$-$C_6$-alkoxy, $C_2$-$C_6$-alkenyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_1$-$C_6$-alkoxycarbonyl, $C_3$-$C_6$-cycloalkyl;

$C_3$-$C_6$-cycloalkoxy, $C_3$-$C_6$-cycloalkyl-$C_1$-$C_4$-alkyl, $C_3$-$C_6$-cycloalkoxy-$C_1$-$C_4$ alkyl, phenyl, or a saturated, partially-, or fully unsaturated 5- or 6-membered heterocycle, wherein the cyclic moieties are unsubstituted or substituted with one or more, same or different substituents $R^{11}$; or two geminal substituents $R^{31}$ form together with the atom to which they are bound a group =O or =S.

$R^{91}$ and $R^{92}$ are independently H, $C_1$-$C_4$-alkyl, or $C_1$-$C_4$-haloalkyl;

$R^{93}$ is halogen, CN, $NH_2$, C(=O)H, OH, $C_3$-$C_6$-cycloalkyl, hydroxycarbonyl, aminocarbonyl, $C_1$-$C_4$-haloalkoxy, C1-$C_4$-alkoxy, $C_1$-$C_4$-haloalkylsulfanyl, $C_1$-$C_4$-haloalkylsulfinyl, $C_1$-$C_4$-haloalkylsulfonyl, $C_1$-$C_4$-alkoxycarbonyl, $C_1$-$C_4$-haloalkoxycarbonyl, $C_1$-$C_4$-alkylcarbonyl, $C_1$-$C_4$-haloalkylcarbonyl, di-($C_1$-$C_4$)alkylaminocarbonyl, $C_1$-$C_4$alkylaminocarbonyl, $C_1$-$C_4$-alkylcarbonylamino, di-($C_1$-$C_4$)alkylcarbonylamino, $C_1$-$C_4$-alkoxycarbonylamino, a group —C($R^{91}$)=NOR$^{92}$;

$R^Y$ is $C_1$-$C_6$-alkyl, $C_3$-$C_6$-cycloalkyl, $C_3$-$C_6$-cycloalkyl-$C_1$-$C_4$-alkyl, which groups are halogenated or non-halogenated;

$CH_2R^6$, or phenyl, which is unsubstituted or substituted with $R^{11}$;

the index n is 0, 1, 2, 3, or 4 if X is phenyl or a 6-membered hetaryl; or 0, 1, 2, or 3 if X is a 5 membered hetaryl; and the index m is 0, 1, or 2.

The tricyclic compounds of the formula (I), and their agriculturally acceptable salts are highly active against animal pest, i.e. harmful arthropods and nematodes, especially against insects and acaridae which are difficult to control by other means.

Moreover, the present invention relates to and includes the following embodiments:

compositions comprising at least one compound of formula (I) as defined above;

agricultural and veterinary compositions comprising an amount of at least one compound of formula (I) or an enantiomer, diastereomer or salt thereof as defined above;

methods for combating invertebrate pests, infestation, or infection by invertebrate pests, which method comprises contacting said pest or its food supply, habitat or breeding grounds with a pesticidally effective amount of at least one compound of formula (I) as defined above or a composition thereof;

methods for controlling invertebrate pests, infestation, or infection by invertebrate pests, which method comprises contacting said pest or its food supply, habitat or breeding grounds with a pesticidally effective amount of at least one compound of formula (I) as defined above or a composition comprising at least one compound of formula (I);

methods for preventing or protecting against invertebrate pests comprising contacting the invertebrate pests, or their food supply, habitat or breeding grounds with compounds of the general formula (I) as defined above or a composition comprising at least one compound of formula (I) as defined above or a composition comprising at least one compound of formula (I);

methods for protecting crops, plants, plant propagation material and/or growing plants from attack or infestation by invertebrate pests comprising contacting or treating the crops, plants, plant propagation material and growing plants, or soil, material, surface, space, area or water in which the crops, plants, plant propagation material is stored or the plant is growing, with a pesticidally effective amount of at least one compound of formula (I) as defined above or a composition comprising at least one compound of formula (I);

non-therapeutic methods for treating animals infested or infected by parasites or preventing animals of getting infected or infested by parasites or protecting animals against infestation or infection by parasites which comprises orally, topically or parenterally administering or applying to the animals a parasiticidally effective amount of a compound of formula (I) as defined above or a composition comprising at least one compound of formula (I);

methods for treating, controlling, preventing or protecting animals against infestation or infection by parasites by administering or applying orally, topically or parenterally to the animals a substituted compound of the general formula (I) as defined above or a composition comprising at least one compound of formula (I);

seed comprising a compound of formula (I) as defined above, in an amount of from 0.1 g to 10 kg per 100 kg of seed;

the use of the compounds of formula (I) as defined above for protecting growing plants or plant propagation material from attack or infestation by invertebrate pests;

the use of compounds of formula (I) or the enantiomers, diastereomers or veterinary acceptable salts thereof for combating parasites in and on animals;

a process for the preparation of a veterinary composition for treating, controlling, preventing or protecting animals against infestation or infection by parasites which comprises adding a parasiticidally effective amount of an compound of formula (I) or the enantiomers, diastereomers and/or veterinary acceptable salt thereof to a carrier composition suitable for veterinary use;

the use of a compound of formula (I) or the enantiomers, diastereomers and/or veterinary acceptable salt thereof for the preparation of a medicament for treating, controlling, preventing or protecting animals against infestation or infection by parasites.

All the compounds of formula (I) and, if applicable, their stereoisomers, their tautomers, their salts or their N-oxides as well as compositions thereof are particularly useful for controlling invertebrate pests, in particular for controlling arthropods and nematodes and especially insects. Therefore, the invention relates to the use of a compound of formula (I) as an agrochemical pesticide, preferably for combating or controlling invertebrate pests, in particular invertebrate pests of the group of insects, arachnids or nematodes.

The term "compound(s) according to the invention" or "compound(s) of formula (I)" as used in the present invention refers to and comprises the compound(s) as defined herein and/or stereoisomer(s), salt(s), tautomer(s) or N-oxide(s) thereof. The term "compound(s) of the present invention" is to be understood as equivalent to the term "compound(s) according to the invention", therefore also comprising stereoisomer(s), salt(s), tautomer(s) or N-oxide(s) of compounds of formula (I).

The terms "tricyclic scaffold" or "tricyclic moiety" relate to the following moiety of formula (I)

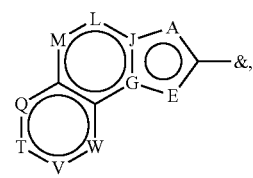

wherein "&" means the remainder of formula (I) and wherein the other variables have a meaning as defined form formula (I).

The term "composition(s) according to the invention" or "composition(s) of the present invention" encompasses composition(s) comprising at least one compound of formula (I) according to the invention as defined above, therefore also including a stereoisomer, an agriculturally or veterinary acceptable salt, tautomer or an N-oxide of the compounds of formula (I).

The compounds of the present invention may be amorphous or may exist in one or more different crystalline states (polymorphs) or modifications which may have a different macroscopic properties such as stability or show different biological properties such as activities. The present invention includes both amorphous and crystalline compounds of the formula (I), mixtures of different crystalline states or modifications of the respective compound I, as well as amorphous or crystalline salts thereof.

The compounds of the formula (I) may have one or, depending on the substitution pattern, more centers of chirality, in which case they are present as mixtures of enantiomers or diastereomers. The invention provides both the single pure enantiomers or pure diastereomers of the compounds of formula (I), and their mixtures and the use according to the invention of the pure enantiomers or pure diastereomers of the compound of formula (I) or its mixtures. Suitable compounds of the formula (I) also include all possible geometrical stereoisomers (cis/trans isomers) and mixtures thereof. Cis/trans isomers may be present with respect to an alkene, carbon-nitrogen double-bond or amide group. The term "stereoisomer(s)" encompasses both optical isomers, such as enantiomers or diastereomers, the latter existing due to more than one center of chirality in the molecule, as well as geometrical isomers (cis/trans isomers). The present invention relates to every possible stereoisomer of the compounds of formula (I), i.e. to single enantiomers or diastereomers, as well as to mixtures thereof.

Depending on the substitution pattern, the compounds of the formula (I) may be present in the form of their tautomers. Hence the invention also relates to the tautomers of the formula (I) and the stereoisomers, salts, tautomers and N-oxides of said tautomers.

Salts of the compounds of the formula (I) are preferably agriculturally and/or veterinary acceptable salts. They can be formed in a customary method, e.g. by reacting the compound with an acid of the anion in question if the compound of formula (I) has a basic functionality or by reacting an acidic compound of formula (I) with a suitable base.

Suitable agriculturally or veterinary useful salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethyl-ammonium, bis(2-hydroxyethyl)ammonium, benzyltrimethylammonium and benzyltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting the compounds of the formulae I with an acid of the corresponding anion, preferably of hydrochloric acid, hydrobromic acid, sulfuric acid, phosphoric acid or nitric acid.

The term "N-oxide" includes any compound of the present invention which has at least one tertiary nitrogen atom that is oxidized to an N-oxide moiety.

The organic moieties groups mentioned in the above definitions of the variables are—like the term halogen—collective terms for individual listings of the individual group members. The prefix $C_n$-$C_m$ indicates in each case the possible number of carbon atoms in the group. "Halogen" will be taken to mean F, Cl, Br, and I, preferably F.

The term "substituted with", e.g. as used in "partially, or fully substituted with" means that one or more, e.g. 1, 2, 3, 4 or 5 or all of the hydrogen atoms of a given radical have been replaced by one or more, same or different substituents, such as a halogen, in particular F. Accordingly, for substituted cyclic moieties, e.g. 1-cyanocyclopropyl, one or more of the hydrogen atoms of the cyclic moiety may be replaced by one or more, same or different substituents.

The term "$C_n$-$C_m$-alkyl" as used herein (and also in $C_n$-$C_m$-alkylamino, di-$C_n$-$C_m$-alkylamino, $C_n$-$C_m$-alkylaminocarbonyl, di-($C_n$-$C_m$-alkylamino)carbonyl, $C_n$-$C_m$-alkylthio, $C_n$-$C_m$-alkylsulfinyl and $C_n$-$C_m$-alkylsulfonyl) refers to a branched or unbranched saturated hydrocarbon group having n to m, e.g. 1 to 10 carbon atoms, preferably 1 to 6 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

The term "$C_n$-$C_m$-haloalkyl" as used herein (and also in $C_n$-$C_m$-haloalkylsulfinyl and $C_n$-$C_m$-haloalkylsulfonyl) refers to a straight-chain or branched alkyl group having n to m carbon atoms, e.g. 1 to 10 in particular 1 to 6 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like. The term $C_1$-$C_{10}$-haloalkyl in particular comprises $C_1$-$C_2$-fluoroalkyl, which is synonym with methyl or ethyl, wherein 1, 2, 3, 4 or 5 hydrogen atoms are substituted with fluorine atoms, such as fluoromethyl, difluoromethyl, trifluoromethyl, 1-fluoroethyl, 2-fluoroethyl, 2,2-difluoroethyl, 2,2,2-trifluoroethyl and pentafluoromethyl.

Similarly, "$C_n$-$C_m$-alkoxy" and "$C_n$-$C_m$-alkylthio" (or $C_n$-$C_m$-alkylsulfenyl, respectively) refer to straight-chain or branched alkyl groups having n to m carbon atoms, e.g. 1 to 10, in particular 1 to 6 or 1 to 4 carbon atoms (as mentioned above) bonded through oxygen (or sulfur linkages, respectively) at any bond in the alkyl group. Examples include $C_1$-$C_4$-alkoxy such as methoxy, ethoxy, propoxy, isopropoxy, butoxy, sec-butoxy, isobutoxy and tert-butoxy, further $C_1$-$C_4$-alkylthio such as methylthio, ethylthio, propylthio, isopropylthio, and n-butylthio.

Accordingly, the terms "$C_n$-$C_m$-haloalkoxy" and "$C_n$-$C_m$-haloalkylthio" (or $C_n$-$C_m$-haloalkyl-sulfenyl, respectively) refer to straight-chain or branched alkyl groups having n to m carbon atoms, e.g. 1 to 10, in particular 1 to 6 or 1 to 4 carbon atoms (as mentioned above) bonded through oxygen or sulfur linkages, respectively, at any bond in the alkyl group, where some or all of the hydrogen atoms in these groups may be replaced by halogen atoms as mentioned above, for example $C_1$-$C_2$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, further $C_1$-$C_2$-haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio and the like. Similarly, the terms $C_1$-$C_2$-fluoroalkoxy and $C_1$-$C_2$-fluoroalkylthio refer to $C_1$-$C_2$-fluoroalkyl which is bound to the remainder of the molecule via an oxygen atom or a sulfur atom, respectively.

The term "$C_2$-$C_m$-alkenyl" as used herein intends a branched or unbranched unsaturated hydrocarbon group having 2 to m, e.g. 2 to 10 or 2 to 6 carbon atoms and a double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "$C_2$-$C_m$-alkynyl" as used herein refers to a branched or unbranched unsaturated hydrocarbon group having 2 to m, e.g. 2 to 10 or 2 to 6 carbon atoms and containing at least one triple bond, such as ethynyl, propynyl, 1-butynyl, 2-butynyl, and the like.

The term "$C_n$-$C_m$-alkoxy-$C_n$-$C_m$-alkyl" as used herein refers to alkyl having n to m carbon atoms, e.g. like specific examples mentioned above, wherein one hydrogen atom of the alkyl radical is replaced by an $C_n$-$C_m$-alkoxy group; wherein the value of n and m of the alkoxy group are independently chosen from that of the alkyl group.

The suffix "-carbonyl" in a group or "C(=O)" denotes in each case that the group is bound to the remainder of the molecule via a carbonyl C=O group. This is the case e.g. in alkylcarbonyl, haloalkylcarbonyl, aminocarbonyl, alkylaminocarbonyl, dialkylaminocarbonyl, alkoxycarbonyl, haloalkoxycarbonyl.

The term "aryl" as used herein refers to a mono-, bi- or tricyclic aromatic hydrocarbon radical such as phenyl or naphthyl, in particular phenyl (also referred as to $C_6H_5$ as substituent).

The term "$C_3$-$C_m$-cycloalkyl" as used herein refers to a monocyclic ring of 3- to m-membered saturated cycloaliphatic radicals, e.g. cyclopropyl, cyclobutyl, cyclopentyl, cyclohexyl, cycloheptyl, cyclooctyl and cyclodecyl.

The term "alkylcycloalkyl" denotes as well as the term "alkyl which may be substituted with cycloalkyl" an alkyl group which is substituted with a cycloalkyl ring, wherein alkyl and cycloakyl are as herein defined.

The term "cycloalkylalkyl" denotes as well as the term "cycloalkyl which may be substituted with alkyl" a cycloalkyl ring which is substituted with an alkyl group, wherein alkyl and cycloakyl are as herein defined.

The term "alkylcycloalkylalkyl" denotes as well as the term "alkylcycloalkyl which may be substituted with alkyl" an alkylcycloalkyl group which is substituted with an alkyl, wherein alkyl and alkylcycloalkyl are as herein defined.

The term "$C_3$-$C_m$-cycloalkenyl" as used herein refers to a monocyclic ring of 3- to m-membered partially unsaturated cycloaliphatic radicals.

The term "cycloalkylcycloalkyl" denotes as well as the term "cycloalkyl which may be substituted with cycloalkyl" a cycloalkyl substitution on another cycloalkyl ring, wherein each cycloalkyl ring independently has from 3 to 7 carbon atom ring members and the cycloalkyls are linked through one single bond or have one common carbon atom. Examples of cycloalkylcycloalkyl include cyclopropylcyclopropyl (e.g. 1,1'-bicyclopropyl-2-yl), cyclohexylcyclohexyl wherein the two rings are linked through one single common carbon atom (e.g. 1,1'-bicyclohexyl-2-yl), cyclohexylcyclopentyl wherein the two rings are linked through one single bond (e.g. 4-cyclopentylcyclohexyl) and their different stereoisomers such as (1R,2S)-1,1'-bicyclopropyl-2-yl and (1R,2R)-1,1'-bicyclopropyl-2-yl. The term "carbocycle" or "carbocyclyl" includes, unless otherwise indicated, in general a 3- to 12-membered, preferably a 3- to 8-membered or a 5- to 8-membered, more preferably a 5- or 6-membered mono-cyclic, ring comprising 3 to 12, preferably 3 to 8 or 5 to 8, more preferably 5 or 6 carbon atoms.

The carbocyclic radicals may be saturated, partially unsaturated, or fully unsaturated. Preferably, the term "carbocycle" covers cycloalkyl and cycloalkenyl groups as defined above, for example cyclopropane, cyclobutane, cyclopentane and cyclohexane rings. When it is referred to "fully unsaturated" carbocycles, this term also includes "aromatic" carbocycles. In certain preferred embodiments, a fully unsaturated carbocycle is an aromatic carbocycle as defined below, preferably a 6-membered aromatic carbocycle.

The term "hetaryl" or "aromatic heterocycle" or "aromatic heterocyclic ring" includes monocyclic 5- or 6-membered heteroaromatic radicals comprising as ring members 1, 2, 3 or 4 heteroatoms selected from N, O and S. Examples of 5- or 6-membered heteroaromatic radicals include pyridyl, i.e. 2-, 3-, or 4-pyridyl, pyrimidinyl, i.e. 2-, 4- or 5-pyrimidinyl, pyrazinyl, pyridazinyl, i.e. 3- or 4-pyridazinyl, thienyl, i.e. 2- or 3-thienyl, furyl, i.e. 2- or 3-furyl, pyrrolyl, i.e. 2- or 3-pyrrolyl, oxazolyl, i.e. 2-, 3- or 5-oxazolyl, isoxazolyl, i.e. 3-, 4- or 5-isoxazolyl, thiazolyl, i.e. 2-, 3- or 5-thiazolyl, isothiazolyl, i.e. 3-, 4- or 5-isothiazolyl, pyrazolyl, i.e. 1-, 3-, 4- or 5-pyrazolyl, i.e. 1-, 2-, 4- or 5-imidazolyl, oxadiazolyl, e.g. 2- or 5-[1,3,4]oxadiazolyl, 4- or 5-(1,2,3-oxadiazol)yl, 3- or 5-(1,2,4-oxadiazol)yl, 2- or 5-(1,3,4-thiadiazol)yl, thiadiazolyl, e.g. 2- or 5-(1,3,4-thiadiazol)yl, 4- or 5-(1,2,3-thiadiazol)yl, 3- or 5-(1,2,4-thiadiazol)yl, triazolyl, e.g. 1H-, 2H- or 3H-1,2,3-triazol-4-yl, 2H-triazol-3-yl, 1H-, 2H-, or 4H-1,2,4-triazolyl and tetrazolyl, i.e. 1H- or 2H-tetrazolyl. The term "hetaryl" also includes bicyclic 8 to 10-membered heteroaromatic radicals comprising as ring members 1, 2 or 3 heteroatoms selected from N, O and S, wherein a 5- or 6-membered heteroaromatic ring is fused to a phenyl ring or to a 5- or 6-membered heteroaromatic radical. Examples of a 5- or 6-membered heteroaromatic ring fused to a phenyl ring or to a 5- or 6-membered heteroaromatic radical include benzofuranyl, benzothienyl, indolyl, indazolyl, benzimidazolyl, benzoxathiazolyl, benzoxadiazolyl, benzothiadiazolyl, benzoxazinyl, chinolinyl, isochinolinyl, purinyl, 1,8-naphthyridyl, pteridyl, pyrido[3,2-d]pyrimidyl or pyridoimidazolyl and the like. These fused hetaryl radicals may be bonded to the remainder of the molecule via any ring atom of 5- or 6-membered heteroaromatic ring or via a carbon atom of the fused phenyl moiety.

The terms "heterocycle", "heterocyclyl" or "heterocyclic ring" includes, unless otherwise indicated, in general 3- to 12-membered, preferably 3- to 8-membered, 3- to 7-membered, or 5- to 8-membered, more preferably 5- or 6-membered, in particular 6-membered monocyclic heterocyclic radicals. The heterocyclic radicals may be saturated, partially unsaturated, or fully unsaturated. As used in this context, the term "fully unsaturated" also includes "aromatic". In a preferred embodiment, a fully unsaturated heterocycle is thus an aromatic heterocycle, preferably a 5- or 6-membered aromatic heterocycle comprising one or more, e.g. 1, 2, 3, or 4, preferably 1, 2, or 3 heteroatoms selected from N, O and S as ring members. Examples of aromatic heterocycles are provided above in connection with the definition of "hetaryl". Unless otherwise indicated, "hetaryls" are thus covered by the term "heterocycles". The heterocyclic nonaromatic radicals usually comprise 1, 2, 3, 4 or 5, preferably 1, 2 or 3 heteroatoms selected from N, O and S as ring members, where S-atoms as ring members may be present as S, SO or $SO_2$. Examples of 5- or 6-membered heterocyclic radicals comprise saturated or unsaturated, non-aromatic heterocyclic rings, such as oxiranyl, oxetanyl, thietanyl, thietanyl-S-oxide (S-oxothietanyl), thietanyl-S-dioxide (S-dioxothiethanyl), pyrrolidinyl, pyrrolinyl, pyrazolinyl, tetrahydrofuranyl, dihydrofuranyl, 1,3-dioxolanyl, thiolanyl, S-oxothiolanyl, S-dioxothiolanyl, dihydrothienyl, S-oxodihydrothienyl, S-dioxodihydrothienyl, oxazolidinyl, oxazolinyl, thiazolinyl, oxathiolanyl, piperidinyl, piperazinyl, pyranyl, dihydropyranyl, tetrahydropyranyl, 1,3- and 1,4-dioxanyl, thiopyranyl, S-oxothiopyranyl, S-dioxothiopyranyl, dihydrothiopyranyl, S-oxodihydrothiopyranyl, S-dioxodihydrothiopyranyl, tetrahydrothiopyranyl, S-oxotetrahydrothiopyranyl, S-dioxotetrahydrothiopyranyl, morpholinyl, thiomorpholinyl, S-oxothiomorpholinyl, S-dioxothiomorpholinyl, thiazinyl and the like. Examples for heterocyclic ring also comprising 1 or 2 carbonyl groups as ring members comprise pyrrolidin-2-onyl, pyrrolidin-2,5-dionyl, imidazolidin-2-onyl, oxazolidin-2-onyl, thiazolidin-2-onyl and the like.

Table A contains abbreviations of heterocycles Het-1 to Het-19

TABLE A

Definitions Het-1 to Het-19 by chemical structure.

| Het No. | Het structure |
|---|---|
| Het-1 | [1H-1,2,4-triazol-1-yl] |
| Het-2 | [3-(trifluoromethyl)-1H-1,2,4-triazol-1-yl] |
| Het-3 | [ethyl 1H-1,2,4-triazole-3-carboxylate, N1-yl] |
| Het-4 | [1H-pyrazol-1-yl] |
| Het-5 | [3-(trifluoromethyl)-1H-pyrazol-1-yl] |
| Het-6 | [ethyl 1H-pyrazole-3-carboxylate, N1-yl] |
| Het-7 | [1H-imidazol-1-yl] |

TABLE A-continued

Definitions Het-1 to Het-19 by chemical structure.

| Het No. | Het structure |
|---|---|
| Het-8 | 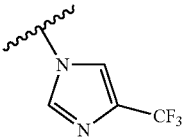 [SMILES: *n1cnc(C(F)(F)F)c1] |
| Het-9 | 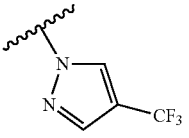 [SMILES: *n1cc(C(F)(F)F)cn1] |
| Het-10 | 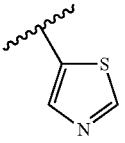 [SMILES: *c1cncs1] |
| Het-11 | 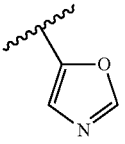 [SMILES: *c1cnco1] |
| Het-12 | 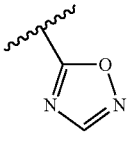 [SMILES: *c1ncno1] |
| Het-13 | 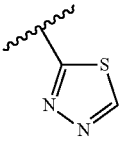 [SMILES: *c1nncs1] |
| Het-14 | 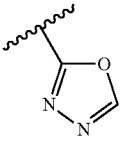 [SMILES: *c1nnco1] |
| Het-15 | 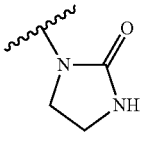 [SMILES: *N1CCNC1=O] |
| Het-16 | 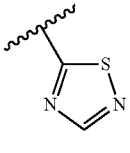 [SMILES: *c1ncns1] |
| Het-17 | 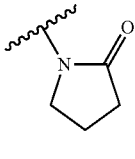 [SMILES: *N1CCCC1=O] |
| Het-18 | 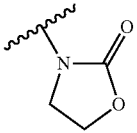 [SMILES: *N1CCOC1=O] |
| Het-19 | 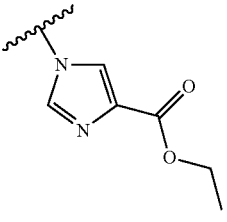 [SMILES: *n1cnc(C(=O)OCC)c1] |

The terms "alkylene", "alkenylene", and "alkynylene" refer to alkyl, alkenyl, and alkynyl as defined above, respectively, which are bonded to the remainder of the molecule, via two atoms, preferably via two carbon atoms, of the respective group, so that they represent a linker between two moieties of the molecule. In particular, the term "alkylene" may refer to alkyl chains such as $CH_2CH_2$, —$CH(CH_3)$—, $CH_2CH_2CH_2$, $CH(CH_3)CH_2$, $CH_2CH(CH_3)$, $CH_2CH_2CH_2CH_2$, $CH_2CH_2CH_2CH_2CH_2$, $CH_2CH_2CH_2CH_2CH_2CH_2$, and $CH_2CH_2CH_2CH_2CH_2CH_2CH_2$. Similarly, "alkenylene" and "alkynylene" may refer to alkenyl and alkynyl chains, respectively.

The term "5- to 6-membered carbocyclic ring" as used herein refers to cyclopentane and cyclohexane rings.

Examples of 5- or 6-membered saturated heterocyclic rings include: 2-tetrahydrofuranyl, 3-tetrahydrofuranyl, 2-tetrahydrothienyl, 3-tetrahydrothienyl, 2-pyrrolidinyl, 3-pyrrolidinyl, 3-pyrazolidinyl, 4-pyrazolidinyl, 5-pyrazolidinyl, 2-imidazolidinyl, 4-imidazolidinyl, 2-oxazolidinyl, 4-oxazolidinyl, 5-oxazolidinyl, 3-isoxazolidinyl, 4-isoxazolidinyl, 5-isoxazolidinyl, 2-thiazolidinyl, 4-thiazolidinyl, 5-thiazolidinyl, 3-isothiazolidinyl, 4-isothiazolidinyl, 5-isothiazolidinyl, 1,2,4-oxadiazolidin-3-yl, 1,2,4-oxadiazolidin 5 yl, 1,2,4-thiadiazolidin-3-yl, 1,2,4-thiadiazolidin-5-yl, 1,2,4-triazolidin-3-yl,-1,3,4-oxadiazolidin-2-yl, 1,3,4-thiadiazolidin-2-yl, 1,3,4-triazolidin-2-yl, 2-tetrahydropyranyl, 4-tetrahydropyranyl, 1,3-dioxan-5-yl, 1,4-dioxan-2-yl, 2-piperidinyl, 3-piperidinyl, 4-piperidinyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl, 2-morpholinyl, 3-morpholinyl, 2-thiomorpholinyl, 3-thiomorpholinyl, 1-oxothiomorpholin-2-yl, 1-oxothiomorpholin-3-yl, 1,1-dioxothiomorpholin-2-yl, 1,1-dioxothiomorpholin-3-yl.

Examples of 5- or 6-membered partially unsaturated heterocyclyl or heterocyclic rings include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3 dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl.

Examples of 5- or 6-membered fully unsaturated heterocyclic (hetaryl) or heteroaromatic rings are: 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

A "$C_2$-$C_m$-alkylene" is divalent branched or preferably unbranched saturated aliphatic chain having 2 to m, e.g. 2 to 7 carbon atoms, for example $CH_2CH_2$, —$CH(CH_3)$—, $CH_2CH_2CH_2$, $CH(CH_3)CH_2$, $CH_2CH(CH_3)$, $CH_2CH_2CH_2CH_2$, $CH_2CH_2CH_2CH_2CH_2$, $CH_2CH_2CH_2CH_2CH_2CH_2$, and $CH_2CH_2CH_2CH_2CH_2CH_2CH_2$.

The term "alkylamino" as used herein refers to a straight-chain or branched saturated alkyl group having 1 to 10 carbon atoms, preferably 1 to 4 carbon atoms, more preferably 1 to 3 carbon atoms, which is bonded via a nitrogen atom, e.g. an —NH— group.

The term "dialkylamino" as used herein refers to a straight-chain or branched saturated alkyl group having 1 to 10 carbon atoms, preferably 1 to 4 carbon atoms, more preferably 1 to 3 carbon atoms, which is bonded via a nitrogen atom, which is substituted by another straight-chain or branched saturated alkyl group having 1 to 10 carbon atoms, preferably 1 to 4 carbon atoms, more preferably 1 to 3 carbon atoms, e.g. a methylamino or ethylamino group.

The term "alkylthio "(alkylsulfanyl: alkyl-S—)" as used herein refers to a straight-chain or branched saturated alkyl group having 1 to 10 carbon atoms, preferably 1 to 4 carbon atoms (=$C_1$-$C_4$-alkylthio), more preferably 1 to 3 carbon atoms, which is attached via a sulfur atom. Examples include methylthio, ethylthio, propylthio, isopropylthio, and n-butylthio.

The term "haloalkylthio" as used herein refers to an alkylthio group as mentioned above wherein the hydrogen atoms are partially or fully substituted by fluorine, chlorine, bromine and/or iodine. Examples include chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio and the like.

The term "alkylsulfinyl" (alkylsulfoxyl: $C_1$-$C_6$-alkyl-S(=O)—), as used herein refers to a straight-chain or branched saturated alkyl group (as mentioned above) having 1 to 10 carbon atoms, preferably 1 to 4 carbon atoms (=$C_1$-$C_4$-alkylsulfinyl), more preferably 1 to 3 carbon atoms bonded through the sulfur atom of the sulfinyl group at any position in the alkyl group.

The term "alkylsulfonyl" (alkyl-S(=O)$_2$—) as used herein refers to a straight-chain or branched saturated alkyl group having 1 to 10 carbon atoms, preferably 1 to 4 carbon atoms (=$C_1$-$C_4$-alkylsulfonyl), preferably 1 to 3 carbon atoms, which is bonded via the sulfur atom of the sulfonyl group at any position in the alkyl group.

The term "alkylcarbonyl" ($C_1$-$C_6$—C(=O)—) refers to a straight-chain or branched alkyl group as defined above, which is bonded via the carbon atom of a carbonyl group (C=O) to the remainder of the molecule.

The term "alkoxycarbonyl" refers to an alkoxygroup group as defined above, which is bonded via the carbon atom of a carbonyl group (C=O) to the remainder of the molecule.

The term "alkylaminocarbonyl" ($C_1$-$C_6$—NH—C(=O)—) refers to a straight-chain or branched alkylamino group as defined above, which is bonded via the carbon atom of a carbonyl group (C=O) to the remainder of the molecule. Similarly, the term "dialkylaminocarbonyl" refers to a straight-chain or branched saturated alkyl group as defined above, which is bonded to a nitrogen atom, which is substituted with another straight-chain or branched saturated alkyl group as defined above, which nitrogen atom in turn is bonded via a carbonyl group (C=O) to the remainder of the molecule.

Preparation Methods

The compounds of formula (I) can be prepared by standard methods of organic chemistry. If certain derivatives cannot be prepared by the processes outlined below, they can be obtained by derivatization of other compounds of formula (I) that are accessible by these methods.

The substituted or unsubstituted tricyclic scaffold can for example be prepared by the methods disclosed in WO2013/059559 A2, Examples 1-31 and p. 109-113.

For compounds of formula (I) in which A and G are N, such as in compounds of formula (IC), WO2013/059559 A2 describes the condensation reaction of diketones of formula (II) with 1,6-bisamino pyridines of formula (III) to result in 1,8-napthyridines of formula (IV)

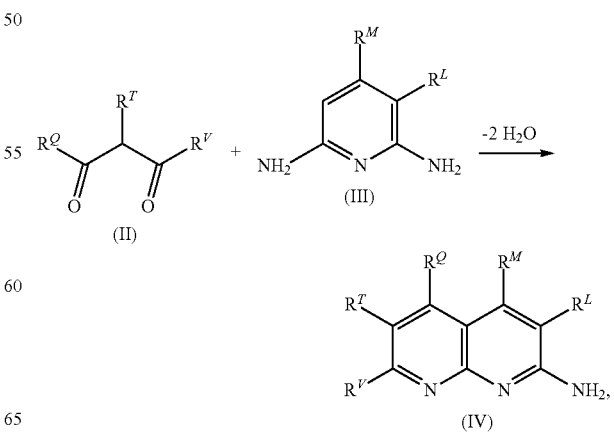

wherein the variables of formulae (II), (III) and (IV) have a meaning as defined for formula (I). Such reactions are usually carried out in the presence of an acid catalyst, e.g. CH₃COOH, at elevated temperatures, e.g. 100-200° C. in an aprotic solvent. Suitable reaction conditions are described in WO2013/059559 A2, paragraphs [00185], or [00189].

Compounds of formula (IV) may then be reacted with 2-bromo-ethanone compounds of formula (V) to result in compounds of formula (VI), which fall under the definition of compounds of formula (I)

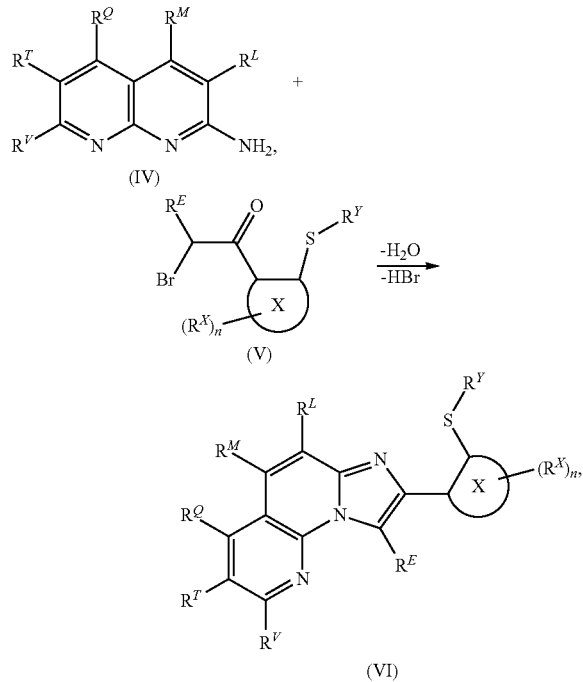

wherein the variables of formulae (IV), (V), and (VI) have a meaning as defined for formula (I). Suitable conditions and solvents for the reaction are described in WO2013/059559 A2, e.g. [00186], or [00190]. Compounds of formula (V) are commercially available or may be prepared as described in Campiani et al, Journal of Medicinal Chemistry, 1998, vol. 41, no. 20, p. 3763-3772.

Similarly to the synthesis as described for compounds of formula (VI), compounds of formula (I), wherein A and G are N, J is C, E is CR$^E$, L is CR$^L$, M is CR$^M$, Q is CR$^Q$, T is CR$^T$, V is CR$^V$, and W is CR$^W$, corresponding to compounds of formula (IT),

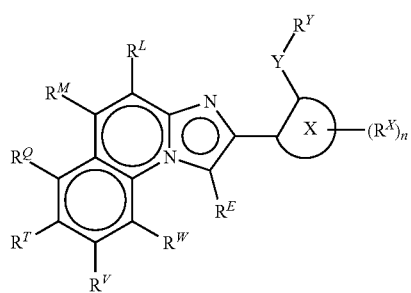

can be prepared from compounds of formula (IVa), which are commercially available,

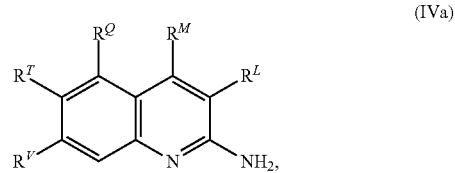

wherein all variables of formulae (IT) and (IVa) are as defined for compounds of formula (I).

Compounds of formula (I), wherein A and G are N, can alternatively be prepared in analogy to WO2013/059559 A2, Example 24. Typically, a compound of formula VIII is reacted with methyl acrylate in a Heck-type cross-coupling reaction to a compound of formula (IX)

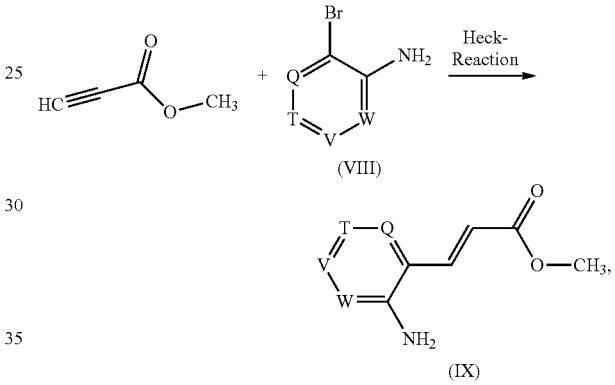

wherein the variables of formulae (VIII) and (IX) have a meaning as defined for formula (I). The reaction is typically carried out in the presence of a Pd(0)-catalyst, which is produced in situ from a Pd(II)-salt in the presence of a suitable ligand, e.g. triphenylphosphane. The reaction may also require the addition of a base, such as an organic base, e.g. triethylamine. Compounds of formula (IX) may then over a series of reaction steps be converted to compounds of formula (XI), as described in WO2013/059559 A2, Example 24,

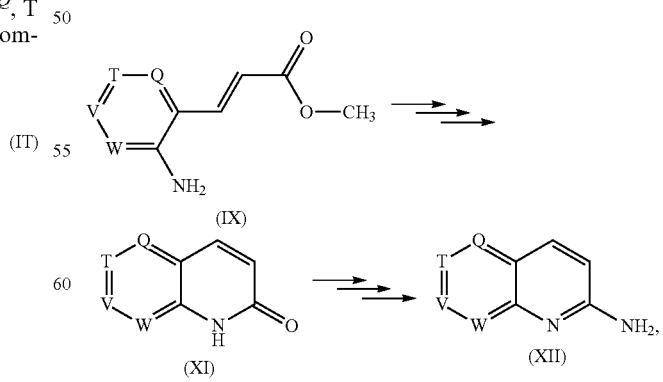

wherein the variables in formulae (IX), (XI), and (XII) have a meaning as defined for formula (I).

Compounds of formula (XII) may be reacted with compounds of formula (V) to yield compounds of formula (XIII), falling under the definition of compounds of formula (I)

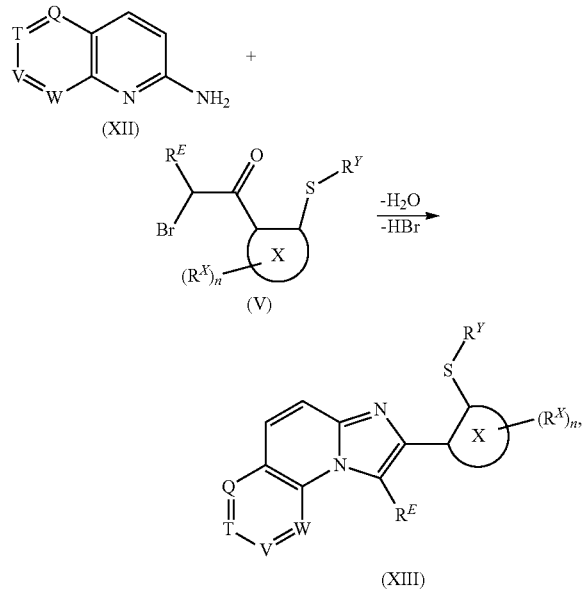

wherein the variables of formulae (V), (XII) and (XIII) have a meaning as defined for formula (I). Reactions of this type have been described in WO2013/059559 A2, Example 24, Step F. The reaction is typically carried out at temperatures of from 50-100° C. in an aprotic polar solvent, e.g. DMF.

Compounds of formula (I), wherein A and E are N, and J and G are C, such as in compounds of formulae (IA), (IB), and (ID), may be prepared as follows and as exemplified in the Synthesis Examples. The synthesis typically starts with compounds of formula (XIV)

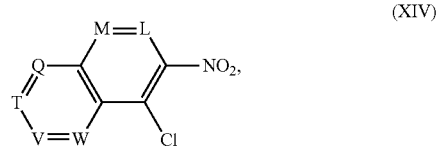

wherein all variables have a meaning as defined for formula (I). Compounds of formula (XIV) are commercially available or may be prepared as described in Bachmann et al, Journal of the American Chemical Society, 1947, vol. 69, p. 365-371. Alternatively, compounds of formula (XIV) may be prepared from compounds of formula (XV) by nitration and chloro-dehydroxylation as described in Gouley et al., Journal of the American Chemical Society, 1947, vol. 69, p. 303-306,

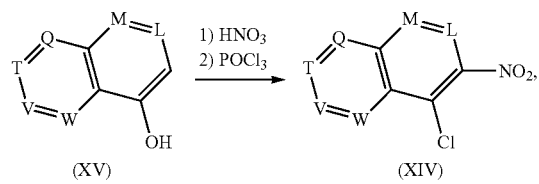

wherein the variables have a meaning as defined for formula (I). Nitration reactions of this type are typically carried out in fuming $HNO_3$, preferably in the presence of concentrated $H_2SO_4$ at a temperature of from −5° C. to 30° C.

In a first step, compounds of formula (XV) are then reacted with an amine compound $R^E$—$NH_2$ to yield compounds of formula (XVI)

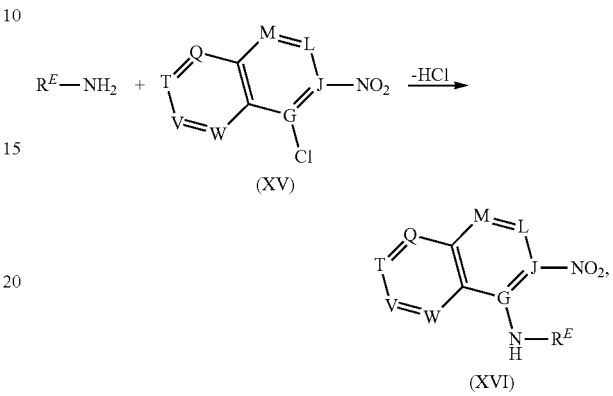

wherein the variables of formulae (XV) and (XVI) are as defined for formula (I). The reaction is typically carried out under elevated temperatures of 40-60° C. in a non-protic solvent, such as an ether, or an aromatic or aliphatic hydrocarbon solvent, e.g. tetrahydrofuran.

In a second step, compounds of formula (XVI) are typically reduced by addition of a reducing agent, such as nascent hydrogen, to form compounds of formula (XVII)

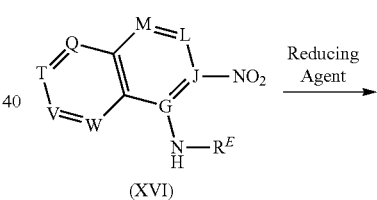

wherein the variables of formulae (XVI) and (XVII) are as defined for formula (I). The nascent hydrogen may for example be produced in situ by the addition of Zn and $CH_3COOH$, which also serves as a solvent to the reaction.

In a third step, compounds of formula (XVII) are then reacted with a carbonic acid of formula (XVIII) in the presence of a Coupling Agent to yield compounds of formula (XIX)

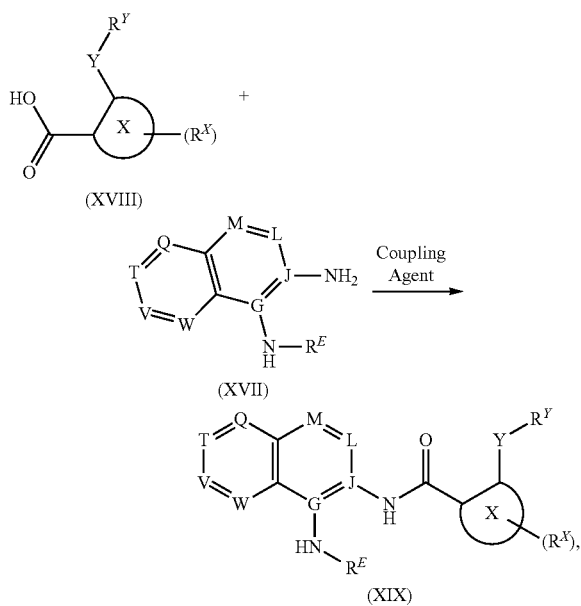

(XVIII)

(XVII)

(XIX)

wherein the variables of formulae (XVII), (XVIII) and (XIX) are as defined for formula (I). Typical Coupling Agents are hexafluorophosphate azabenzotriazole tetramethyl uronium (HATU), 3-[Bis(dimethylamino)methyliumyl]-3H-benzotriazol-1-oxide hexafluorophosphate (HBTU), or O-(1H-6-Chlorobenzotriazole-1-yl)-1,1,3,3-tetramethyluronium hexafluorophosphate (HCTU). The reaction may be carried out in a polar aprotic solvent, such as DMF, in the presence of a base. Compounds of formula (XVIII) are commercially available or may be prepared as described in CN201711238342; Blank et al., Journal of Medicinal Chemistry, 1974, vol. 17, issue 10, p. 1065-1071; WO2004011430A1, WO2011049223A1, or Ye et al., Journal of Agricultural and Food Chemistry, vol. 62, issue 18, p. 4063-4071.

In a fourth step, compounds of formula (XIX) are treated with an Acid Catalyst, such as $CH_3COOH$, or toluene sulfonic acid, to produce compounds of formula (XX), which fall under the definition of compounds of formula (I), in a condensation reaction

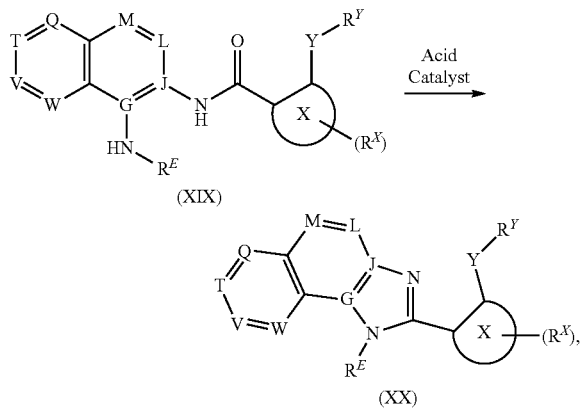

(XIX)

(XX)

wherein the variables of formulae (XIX), and (XX) have a meaning as defined for formula (I).

Compounds of formula (I), wherein A is CH and E is NH may be prepared starting form compounds of formula (XXI)

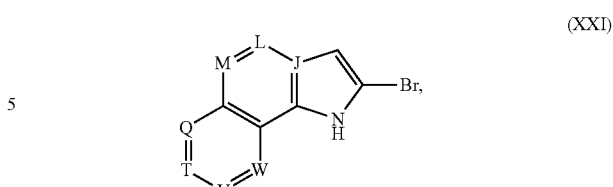

wherein the variables of formula (XXI) have a meaning as defined for formula (I). Compounds of formula XXI are commercially available, or as described in Wang et al., RSC Advances, 2014, vol. 4, issue 51, p. 26918-26923. Compounds of formula (XXI) are also available by methods analogous to those disclosed in WO2013/059559A2, Example 14.

Compounds of formula (XXI) may be reacted with compounds of formula (XXII) in a cross-coupling reaction to yield compounds of formula (XIII) falling under the definition of compounds of formula (I)

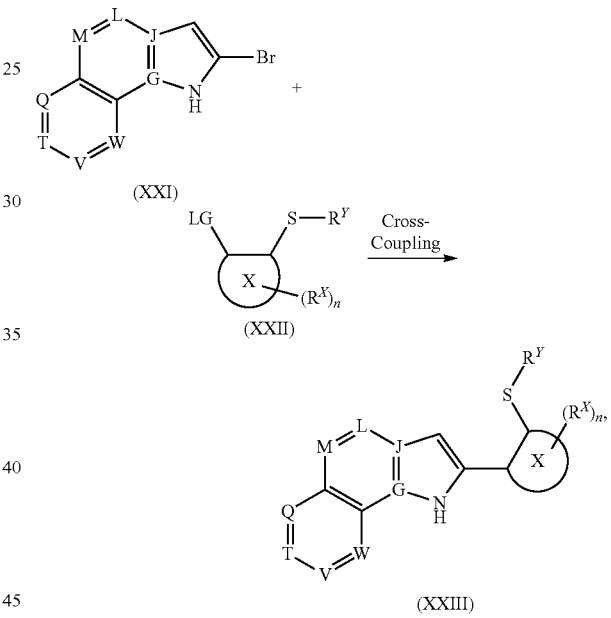

(XXI)

(XXII)

(XXIII)

wherein LG is a Leaving Group the other variables of formulae (XXI) and (XXIII) have a meaning as defined for formula (I). Typical cross-coupling reactions are Suzuki, Stille and Negishi-type cross-couplings. These reaction are typically carried out in the presence of a Pd(0)-catalyst, which is produced in situ from a Pd(II)-salt in the presence of a suitable ligand, e.g. triphenylphosphane. Suitable Leaving Groups depend on the type of cross-coupling reaction. Leaving Groups suitable in Suzuki-type cross-coupling reactions include boronates, as described in Wesela-Bauman et al., Organic & Biomolecular Chemistry, 2015, vol. 13, issue 11, p. 3268-3279. Suitable Leaving Groups in Stille-type cross-coupling reactions include trialkyl-tin moieties, which are accessible as described in Stille, Angewandte Chemie, 1986, vol. 98, p. 504-519. Suitable Leaving Groups in Negishi-type cross-coupling reactions include zink halogenides, which are accessible as described in Krasovskiy et al, Angewandte Chemie, 2006, volume 45, p. 6040-6044.

Compounds of formula (I), wherein A is NH and E is $CR^E$ may be prepared starting form compounds of formula (XXIV)

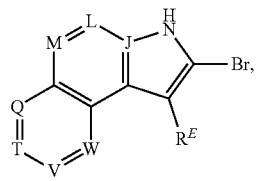
(XXIV)

wherein the variables of formula (XXIV) have a meaning as defined for formula (I).

Compounds of formula (XXIV) may be reacted with compounds of formula (XXII) in a cross-coupling reaction as described above to yield compounds of formula (XXV) falling under the definition of compounds of formula (I)

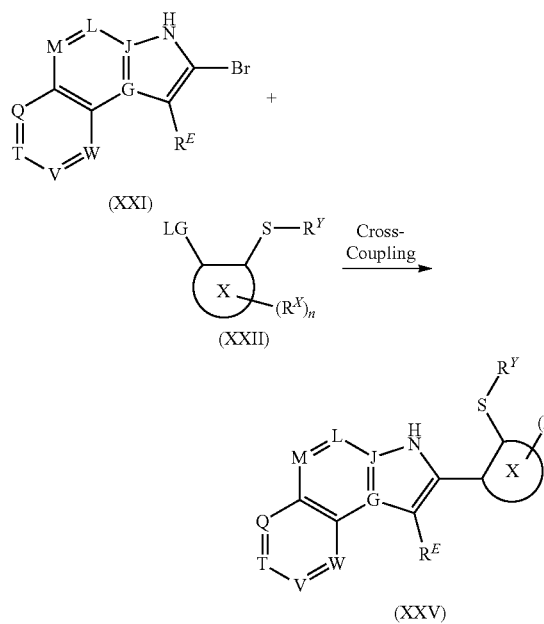
(XXI)
(XXII)
(XXV)

wherein LG is a Leaving Group the other variables of formulae (XXII), (XXIV), (XXV) have a meaning as defined for formula (I). Typical cross-coupling reactions are Suzuki, Stille and Negishi-type cross-couplings. These reaction are typically carried out in the presence of a Pd(0)-catalyst, which is produced in situ from a Pd(II)-salt in the presence of a suitable ligand, e.g. triphenylphosphane. Suitable Leaving Groups depend on the type of cross-coupling reaction. Leaving Groups suitable in Suzuki-type cross-coupling reactions include boronates, as described in Wesela-Bauman et al., Organic & Biomolecular Chemistry, 2015, vol. 13, issue 11, p. 3268-3279. Suitable Leaving Groups in Stille-type cross-coupling reactions include trialkyl-tin moieties, which are accessible as described in Stille, Angewandte Chemie, 1986, vol. 98, p. 504-519. Suitable Leaving Groups in Negishi-type cross-coupling reactions include zink halogenides, which are accessible as described in Krasovskiy et al, Angewandte Chemie, 2006, volume 45, p. 6040-6044.

Compounds of formula (I), wherein either A or E is N, may also be available via the Bischler-Möhlau-Indole synthesis. Typical educts are compounds of formula (XXVI) or compounds of formula (XXVII),

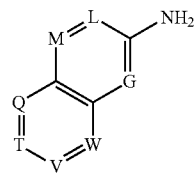
(XXVI)

(XXVII)

wherein the variables of formulae (XXVI) and (XXVII) have a meaning as defined for formula (I). Compounds of formulae (XXVI) or (XXVII) are commercially available. They are typically reacted with a compound of formula (V) to form compounds of formula (XXVIII) or (XXIX), falling under the definition of compounds of formula (I)

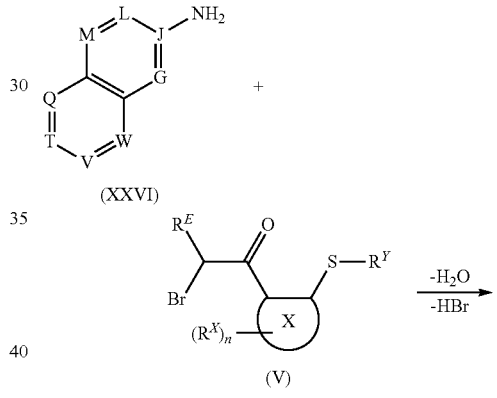
(XXVI)
(V)

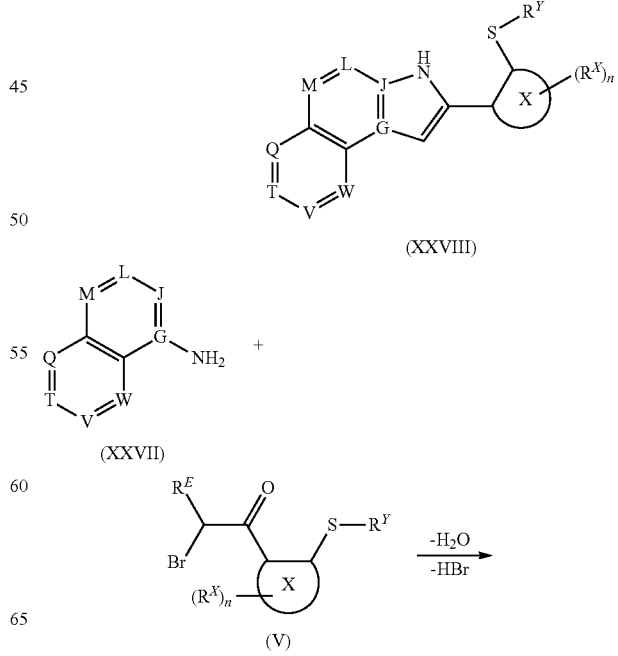
(XXVIII)
(XXVII)
(V)

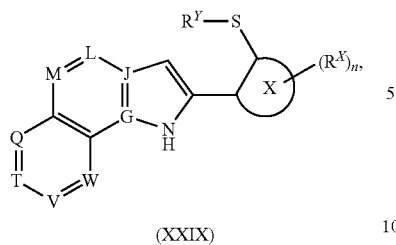

(XXIX)

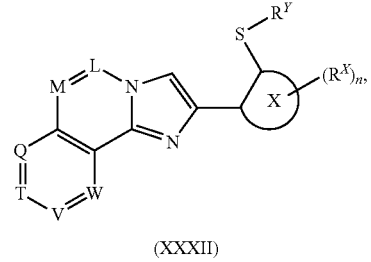

(XXXII)

wherein the variables of formulae (XXVI) and (XXVII) have a meaning as defined for formula (I). The reaction is typically carried out in the presence of a base, e.g. $Na_2CO_3$, under irradiation of microwaves. Reactions of this type have been described by Sridharan et al., Synlett, 2006, p. 91-95. Alternatively, the reaction may be carried out in the presence of a catalyst and a base, such as LiBr and $Na_2CO_3$, as described by Pchalek et al., Tetrahedron, 2005, vol. 61, issue 3, p. 77-82.

Compounds of formula (I), wherein E and J are N, A is CH, and G is C may be prepared from compounds of formula (XXX)

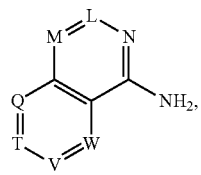

(XXX)

wherein the variables of formulae (XXVI) and (XXVII) have a meaning as defined for formula (I). Compounds of formula (XXX) are commercially available or may be prepared as described in WO2003/016275 A1; WO2017/111076 A1; WO2017/014323 A1; WO2014/053208 A1; Van den Haak et al., Journal of Organic Chemistry, 1982, vol. 47, issue 9, p. 1673-7; or US2015/0322090. Compounds of formula (XXX) may be reacted with compounds of formula (V) to yield compounds of formula (XXXI), which fall under the definition of compounds of formula (I)

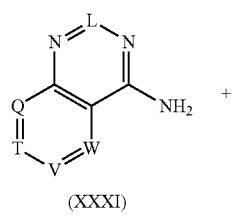

(XXXI)

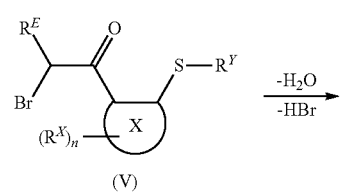

(V)

wherein the variables of formulae (V), (XXXI) and (XXXII) have a meaning as defined for formula (I). Suitable conditions and solvents for the reaction are described in WO2013/059559 A2, e.g. [00186], or [00190]. Compounds of formula (V) are commercially available or may be prepared as described in Campiani et al, Journal of Medicinal Chemistry, 1998, vol. 41, no. 20, p. 3763-3772.

Compounds of formula (I), wherein E is O, may be prepared from compounds of formula (XXXIII) by a Sonogashira-type coupling reaction with methyl prop-2-ynoate to yield compounds of formula (XXXIV)

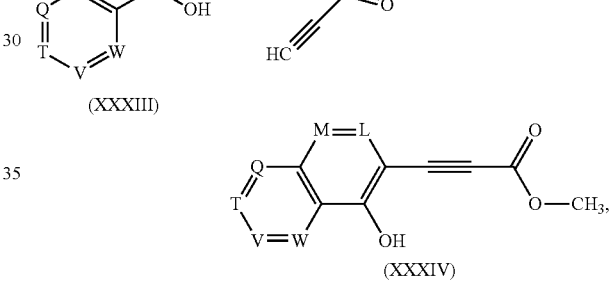

(XXXIII)

(XXXIV)

wherein the variables of formulae (XXXIII) and (XXXIV) have a meaning as defined for formula (I). The reaction is typically carried out in an inert solvent the presence of a Cu(I)-salt, such as CuI, a base, such as NaOH, Pd(0), which is produced in situ from $Pd(II)Cl_2$, and a ligand, such as triphenylphosphine. Compounds of formula (XXXIII) are commercially available.

Compounds of formula (XXXIV) may then be converted to the furan compounds of formula (XXXV) by cycloisomerization

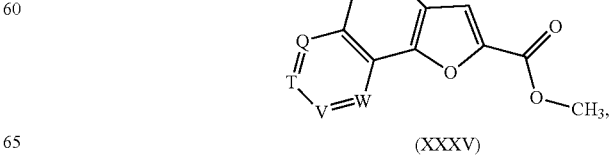

(XXXIV)

(XXXV)

wherein the variables of formulae (XXXIV) and (XXXV) have a meaning as defined for formula (I). The reaction is carried out in the presence of a Pt-catalyst, e.g. $PtCl_2$ in a non-polar solvent, such as toluene, at elevated temperatures of 50 to 100° C. Reactions of this type have been described by Fürstner et al., Journal of the American Chemical Society, 2005, vol. 127, issue 43, p. 15024-15025.

Compounds of formula (XXXV) may then be reacted with NaOH to generate the carboxylic acid compounds of formula (XXXVI)

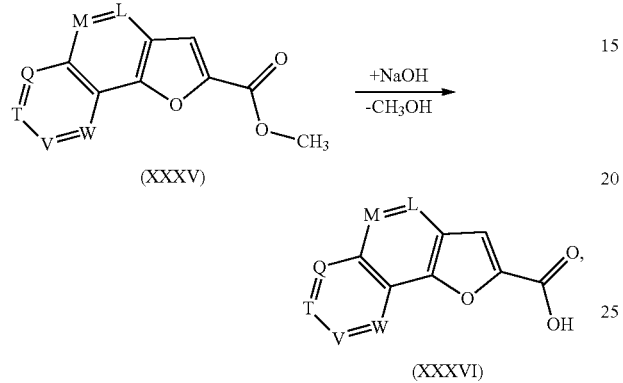

wherein the variables of formulae (XXXV) and (XXXVI) have a meaning as defined for formula (I). The reaction is typically carried out in an aqueous solution of NaOH at a temperature of 50 to 100° C.

Compounds of formula (XXXVI) may be used in a halo-decarboxylation reaction with $N(^nBu)_4Br_3$ to form compounds of formula (XXXVII)

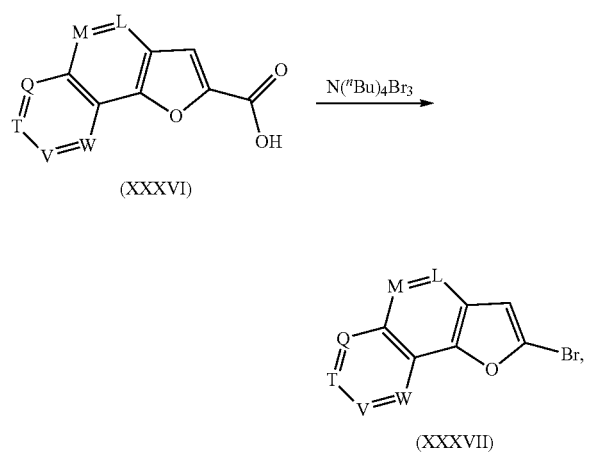

wherein the variables of formulae (XXXVI) and (XXXVII) have a meaning as defined for formula (I). The reaction is typically carried out in a non-protic polar solvent, e.g. acetonitrile, under addition of $K_3PO_4$, as described in Quibell et al., Chemical Science, 2018, vol. 9, p. 3860.

Compounds of formula (XXXVII) may then be reacted with compounds of formula (XXII) in a Suzuki-type coupling reaction to form compounds of formula (XXXVIII), which fall under the definition of compounds of formula (I)

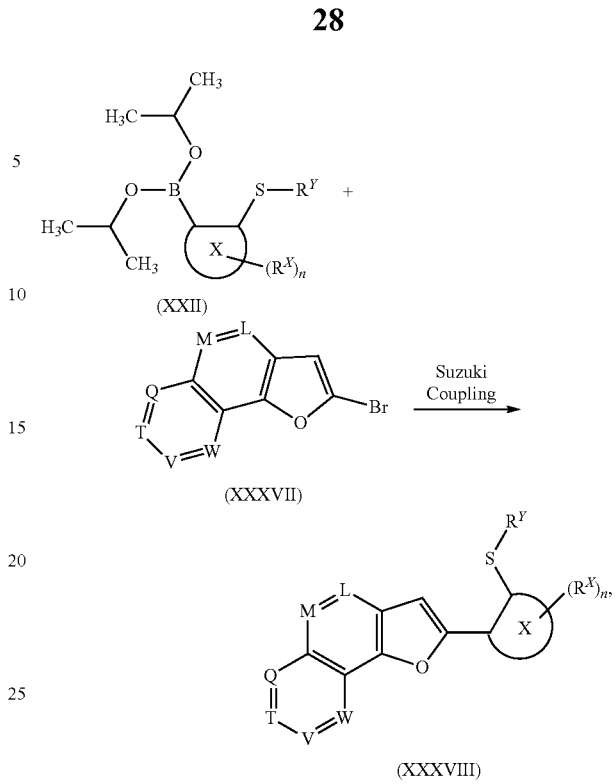

wherein the variables of formulae (XXII), (XXXVII) and (XXXVIII) have a meaning as defined for formula (I). The reaction is typically carried out in the presence of a Pd(0)-catalyst, which is produced in situ from a Pd(II)-salt in the presence of a suitable ligand, e.g. triphenylphosphane. Usually, a base is added to the reaction mixture, such as NaOH.

Compounds of formula (I), wherein E is O and A is N, can be prepared from compounds of formula (XXXIX)

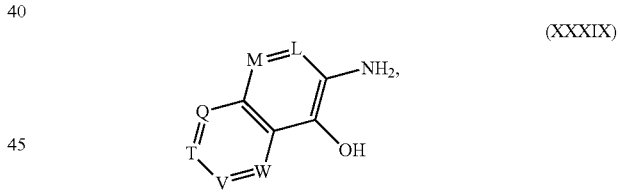

wherein the variables of formula (XXXIX) have a meaning as defined for formula (I). Compounds of formula (XXXIX) are commercially available or may be prepared as described in WO2008/082715 A2, or U.S. Pat. No. 7,364,881 B1.

In a first step, compounds of formula (XXXIX) are reacted with a carbonic acid of formula (XVIII) in the presence of a Coupling Agent to yield compounds of formula (XL), which fall under the definition of compounds of formula (I)

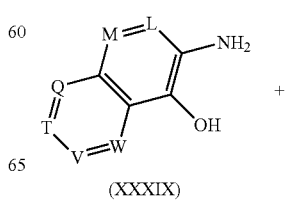

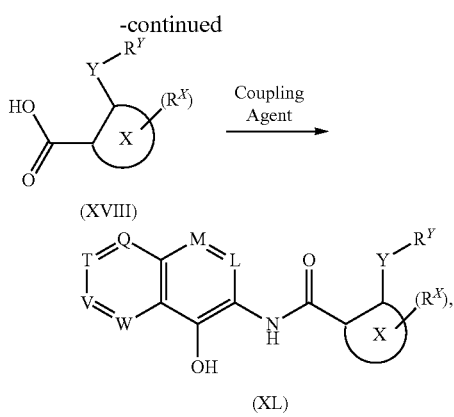

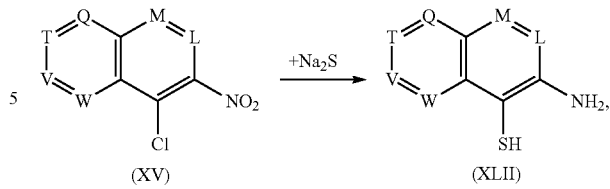

wherein the variables in formulae (XV) and (XLII) have a meaning as defined for formula (I). Reactions of this type have been described by Bachmann et al., Journal of the American Chemical Society, 1947, vol. 69, p. 365-371.

In a second step, compounds of formula (XLII) are then reacted with compounds of formula (XLIII) to yield compounds of formula (XLIV) falling under the definition of compounds of formula (I)

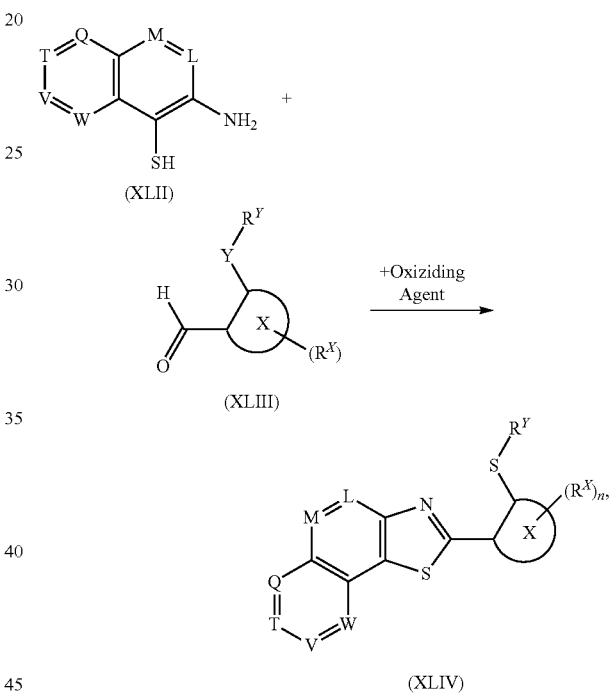

wherein the variables of formulae (XVIII), (XXXIX), and (XL) are as defined for formula (I). Typical Coupling Agents are hexafluorophosphate azabenzotriazole tetramethyl uronium (HATU), 3-[Bis(dimethylamino)methyliumyl]-3H-benzotriazol-1-oxide hexafluorophosphate (HBTU), or O-(1H-6-Chlorobenzotriazole-1-yl)-1,1,3,3-tetramethyluronium hexafluorophosphate (HCTU). The reaction may be carried out in a polar aprotic solvent, such as DMF.

In a second step, compounds of formula (XL) are then cyclized to the oxazol compound of formula (XLI), which fall under the definition of compounds of formula (I), under the addition of $POCl_3$

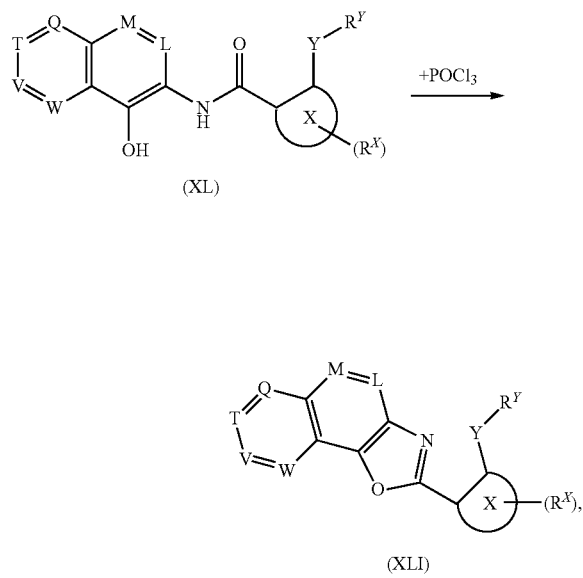

wherein the variables have a meaning as defined for formula (I).

The reaction usually takes place at conditions as described by Li et al., Journal of Organic Chemistry, 2009, vol. 74, issue 9, pp. 3286-3292.

Compounds of formula (I), wherein E is S, can be prepared analogously to the compounds of formula (I), wherein E is O. Compounds of formula (I), wherein E is S and A is N, can be prepared starting from compounds of formula (XV). In a first step, compounds of formula (XV) are reacted with $Na_2S$ to yield compounds of formula (XLII)

wherein the variables in formulae (XLII), (XLIII) and (XLIV) have a meaning as defined for formula (I). The reaction takes place in the presence of an Oxidizing Agent, e.g. $O_2$. Reactions of this type have been described in U.S. Pat. No. 4,904,669. Compounds of formula (XLIII) are commercially available or can be prepared from compounds of formula (XVIII).

Compounds of formula (I), wherein A, E and G are N, can be prepared starting from compounds of formula (XLV). In a first step, compounds of formula (XLV), which are commercially available, are reacted with ortho-tosylhydroxylamine ($TsNH_2$) to yield compounds of formula (XLVI)

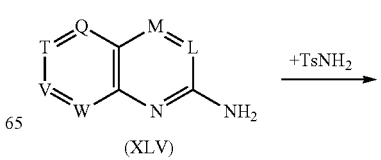

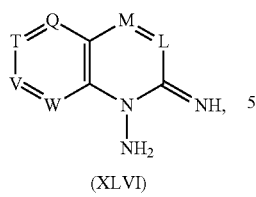

(XLVI)

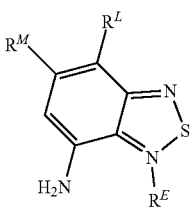

(XLVIII)

wherein the variables in formulae (XLV) and (XLVI) have a meaning as defined for formula (I). Reactions of this type have been described in Messmer et al., Journal of Organic Chemistry, 1981, vol. 46, p. 843.

Compounds of formula (XLVI) may then be reacted with compounds of formula (XLIII) to yield compounds of formula (XLVII) falling under the definition of compounds of formula (I)

wherein the variables of formula (XLVIII) are as defined for formula (I).

Syntheses of this type have been described in WO2013/059559, p. 143, Example 28. The inventive compounds can be prepared by analogy, wherein the quinoline-7,8-diamine derivative of formula (XLIX) as obtained in step B of Example 28 in WO2013/059558 is further reacted with a compound of formula (XVIII) in the presence of a Coupling Agent, as described above, to yield compounds of formula (L)

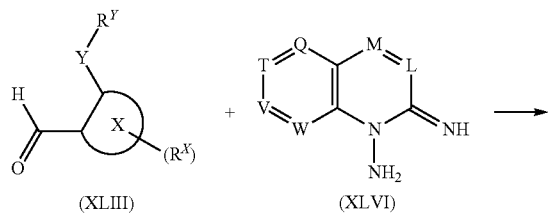

(XLIII)     (XLVI)

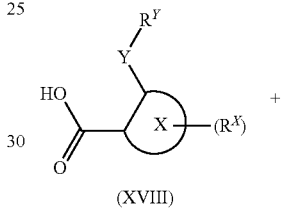

(XVIII)

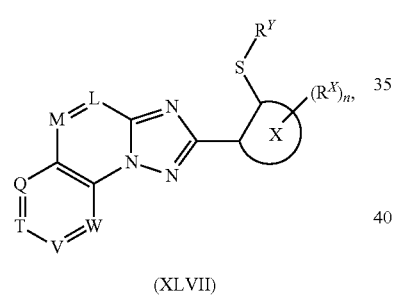

(XLVII)

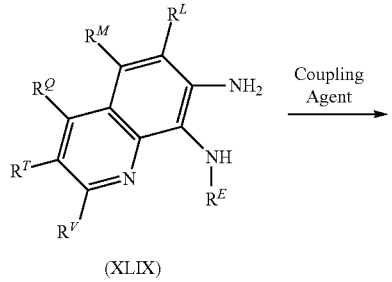

(XLIX)

wherein the variables in formulae (XLIII), (XLVI) and (XLVII) have a meaning as defined formula (I). Reactions of this type have been described in Hoang et al, ARKIVOC, 2001 (ii), 42-50. The reaction is typically carried out in the presence of a base, e.g. KOH, in a protic solvent at a temperature of from 15 to 100° C., preferably at approximately 25° C.

Compounds of formulae (VI), (XIII), (XX), (XXIII), (XXVIII), (XXIX), (XXXII), or (XL) may be oxidized by reaction with an oxidizing agent, e.g. $Na_2WO_4$, $H_2O_2$, $MnO_2$, in a suitable solvent to yield compounds falling under the definition of formula (I), wherein Y is SO or $SO_2$. Such oxidation reactions have been described in Voutyritsa et al., Synthesis, vol. 49, issue 4, p. 917-924; Tressler et al, Green Chemistry, vol. 18, issue 18, p. 4875-4878; or Nikkhoo et al., Applied Organometallic Chemistry, 2018, vol. 32, issue 6.

Compounds of formula (I), wherein A, E and W are N, and L is $CR^L$, M is $CR^M$, Q is $CR^Q$, T is $CR^T$, and V is $CR^V$ can be prepared starting from compounds of formula (XLVIII), which is commercially available,

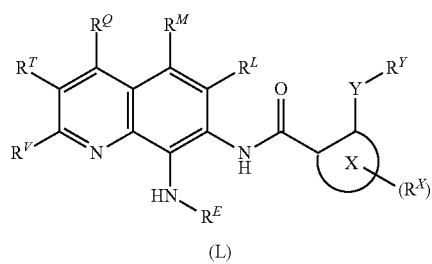

(L)

wherein the variables of formulae (XVIII), (XLIX) and (L) are as defined for formula (I).

Just as described for compounds of formula (XIX), compounds of formula (L) may then be treated with an Acid Catalyst to produce compounds of formula (LI), which fall under the definition of compounds of formula (I)

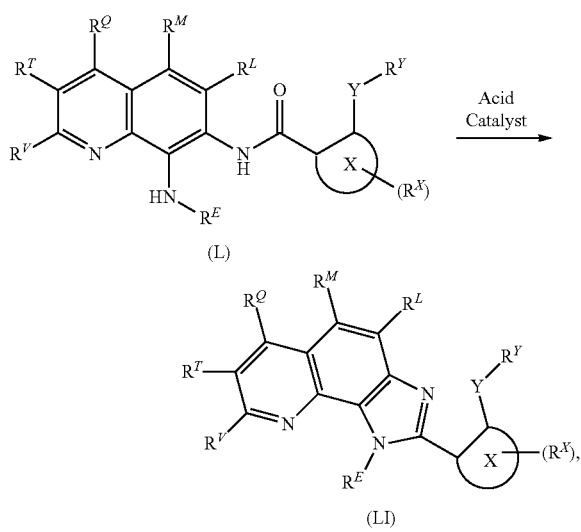

(L)

(LI)

wherein the variables of formulae (L) and (LI) are as defined for formula (I).

Compounds of formula (I), wherein $R^X$ is $C(CN)R^7R^3$ may be prepared in analogy to what has been described for bicyclic compounds in WO2019/053182A1, p. 55 to p. 59. Compounds of formula (I), wherein $R^X$ is $C_3$-$C_6$-cycloalkyl, which is unsubstituted or substituted with one or more, same or different substituents $R^9$ may be prepared in analogy to what has been described for bicyclic compounds in WO2018/108726, p. 48 to p. 49, Example H1.

Preferences

Embodiments and preferred compounds of the present invention for use in pesticidal methods and for insecticidal application purposes are outlined in the following paragraphs. The remarks made below concerning preferred embodiments of the variables of compounds of formula (I) are valid both on their own in combination with each other. The variables of the compounds of formula (I) have the following meanings, these meanings, both on their own and in combination with one another, being particular embodiments of the compounds of the formula (I).

The variable A is CH, N, or NH. In one embodiment, A is N. In another embodiment, A is NH. The variable E is N, NH, O, S, or $CR^E$. In one embodiment, E is $NR^E$ or $OR^E$. In another embodiment, A is N or NH, and E is $NR^E$ or $OR^E$.

Typically, only one of E or G is N. In one embodiment, both E and G are N.

The variables G and J are independently C or N. Typically, both G and J are C. In one embodiment, G is N and J is C, preferably wherein E is N.

The variable L is N or $CR^L$. In one embodiment, the variable L is N. In another embodiment, the variable L is $CR^L$, preferably wherein $R^L$ is H, $C_1$-$C_3$-alkyl, $C_1$-$C_3$-haloalkyl, or $C_1$-$C_3$-haloalkoxy, more preferably wherein $R^L$ is H, $C_1$-$C_3$-fluoroalkyl, or $C_1$-$C_3$-fluoroalkoxy, most preferably wherein $R^L$ is H, $CF_3$ or $OCF_3$, especially preferably wherein $R^L$ is H.

The variable M is N or $CR^M$. In one embodiment, the variable M is N. In another embodiment, the variable M is $CR^M$, preferably wherein $R^M$ is H, $C_1$-$C_3$-alkyl, $C_1$-$C_3$-haloalkyl, or $C_1$-$C_3$-haloalkoxy, more preferably wherein $R^M$ is H, $C_1$-$C_3$-fluoroalkyl, or $C_1$-$C_3$-fluoroalkoxy, most preferably wherein $R^M$ is H, $CHF_2$, $CF_3$, $OCHF_2$, or $OCF_3$, especially preferably wherein $R^M$ is H or $CF_3$.

The variable Q is N or $CR^Q$. In one embodiment, the variable Q is N. In another embodiment, the variable Q is $CR^Q$, preferably wherein $R^Q$ is H, $C_1$-$C_3$-alkyl, $C_1$-$C_3$-haloalkyl, or $C_1$-$C_3$-haloalkoxy, more preferably wherein $R^Q$ is H, $C_1$-$C_3$-fluoroalkyl, or $C_1$-$C_3$-fluoroalkoxy, most preferably wherein $R^Q$ is H, $CF_3$, $OCHF_2$, or $OCF_3$, especially preferably wherein $R^Q$ is H, $CF_3$, or $OCF_3$. In another embodiment, the variable Q is $CR^Q$, preferably wherein $R^Q$ is H, $C_1$-$C_3$-alkyl, $C_1$-$C_3$-alkoxy, $C_1$-$C_3$-haloalkyl, or $C_1$-$C_3$-haloalkoxy, more preferably wherein $R^Q$ is H, $C_1$-$C_3$-alkyl, $C_1$-$C_3$-fluoroalkyl, $C_1$-$C_3$-alkoxy, or $C_1$-$C_3$-fluoroalkoxy, most preferably wherein $R^Q$ is H, $CF_3$, $OCF_3$, $OCH_2CH_3$, $OCHF_2$, or $OCH_2CF_3$.

The variable T is N or $CR^T$. In one embodiment, the variable T is N. In another embodiment, the variable T is $CR^T$, preferably wherein $R^T$ is H, $C_1$-$C_3$-alkyl, $C_1$-$C_3$-haloalkyl, or $C_1$-$C_3$-haloalkoxy, more preferably wherein $R^T$ is H, $C_1$-$C_3$-fluoroalkyl, or $C_1$-$C_3$-fluoroalkoxy, most preferably wherein $R^T$ is H, or $CF_3$. In another embodiment, the variable T is $CR^T$, preferably wherein $R^T$ is H, $C_1$-$C_3$-alkyl, $C_1$-$C_3$-haloalkyl, $C_1$-$C_3$-alkoxy, or $C_1$-$C_3$-haloalkoxy, more preferably wherein $R^T$ is H, $C_1$-$C_3$-fluoroalkyl, or $C_1$-$C_3$-fluoroalkoxy, most preferably wherein $R^T$ is H, $CF_3$, or $OCF_3$.

The variable V is N or $CR^V$. In one embodiment, the variable V is N. In another embodiment, the variable V is $CR^V$, preferably wherein $R^V$ is H, $C_1$-$C_3$-alkyl, $C_1$-$C_3$-haloalkyl, or $C_1$-$C_3$-haloalkoxy, more preferably wherein $R^V$ is H, $C_1$-$C_3$-fluoroalkyl, or $C_1$-$C_3$-fluoroalkoxy, most preferably wherein $R^V$ is H, $CF_3$ or $OCF_3$, especially preferably wherein $R^V$ is H or $CF_3$, in particular wherein $R^V$ is H.

The variable W is N or $CR^W$. In one embodiment, the variable W is N. In another embodiment, the variable W is $CR^W$, preferably wherein $R^W$ is H, $C_1$-$C_3$-alkyl, $C_1$-$C_3$-haloalkyl, or $C_1$-$C_3$-haloalkoxy, more preferably wherein $R^W$ is H, $C_1$-$C_3$-fluoroalkyl, or $C_1$-$C_3$-fluoroalkoxy, most preferably wherein $R^W$ is H, $CF_3$ or $OCF_3$, especially preferably wherein $R^W$ is H. In another embodiment, the variable W is $CR^W$, preferably wherein $R^W$ is H, $C_1$-$C_3$-alkyl, $C_1$-$C_3$-haloalkyl, $C_1$-$C_3$-haloalkoxy, or $C_1$-$C_3$-alkoxy.

Preferred combinations of variables A, E, G, J, L, M, Q, T, V, and W are presented below as formulae (IA) to (IJJ), wherein the variables have a meaning as defined for formula (I).

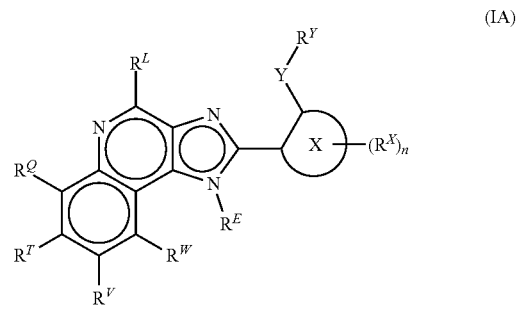

(IA)

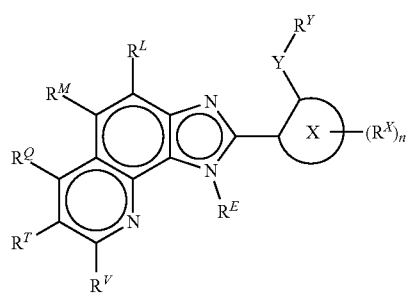 (IB)
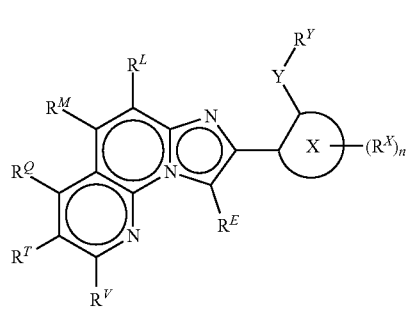 (IC)
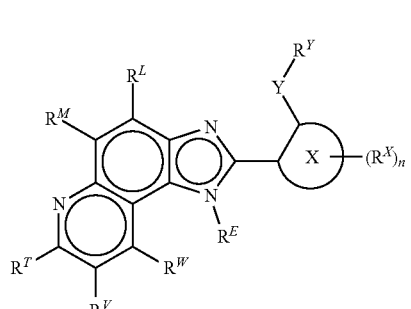 (ID)
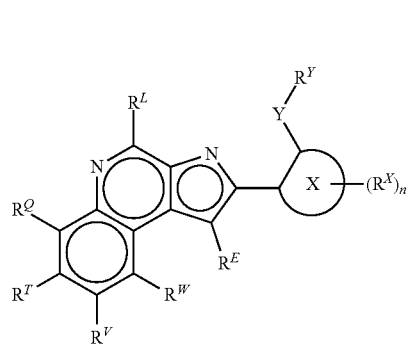 (IE)
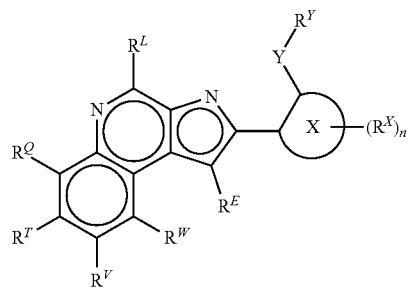 (IF)
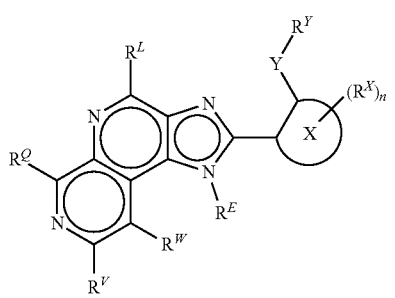 (IG)
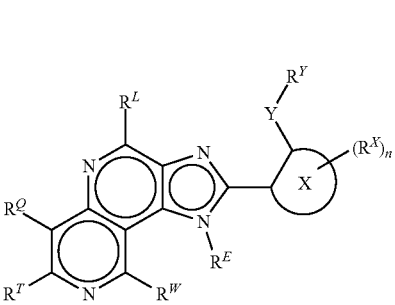 (IH)
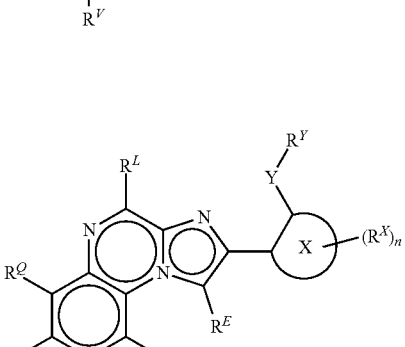 (IJ)
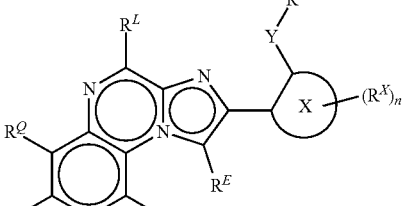 (IK)
(IL)

-continued
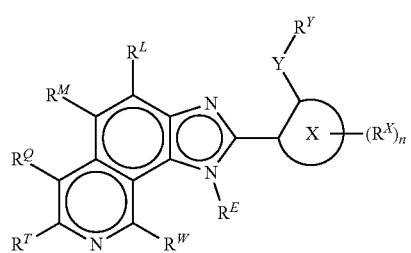
(IM)
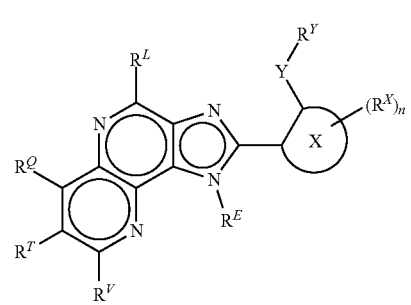
(IN)
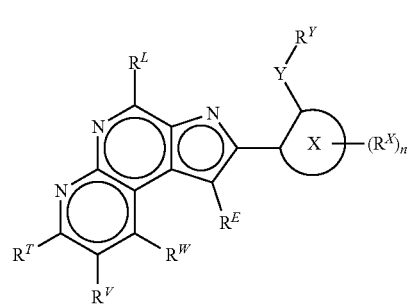
(IO)
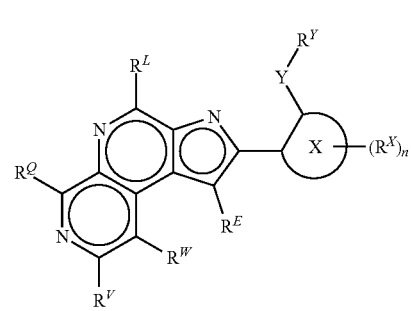
(IP)
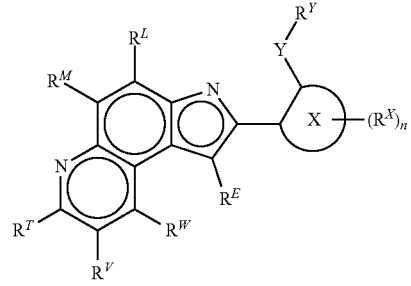
(IQ)
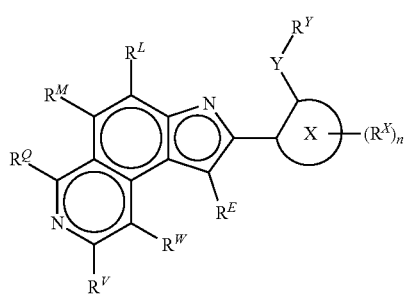
(IR)
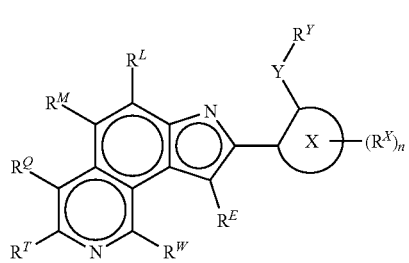
(IS)
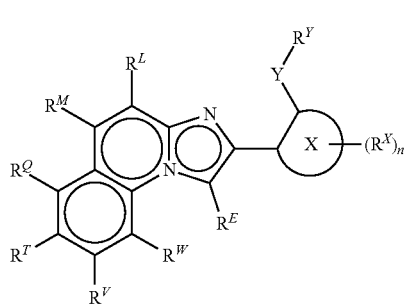
(IT)
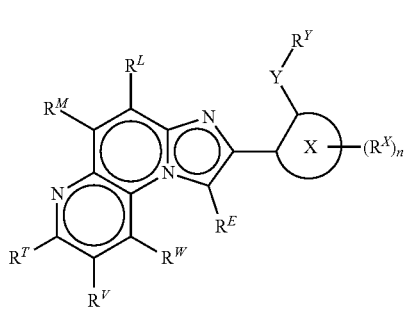
(IU)
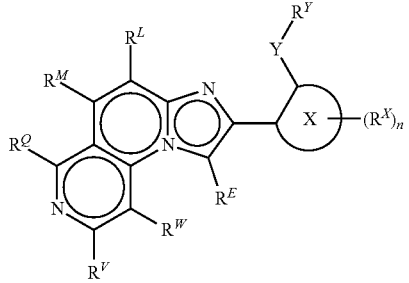
(IV)

-continued
(I-W)
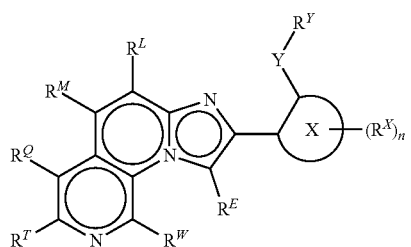
(I-X)
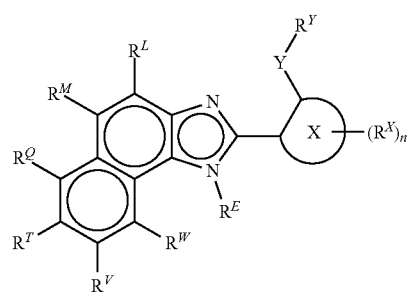
(I-Y)
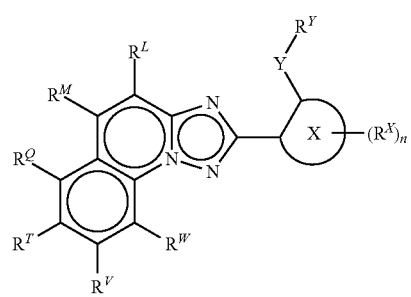
(I-Z)
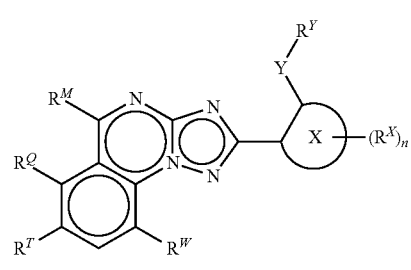
(I-AA)
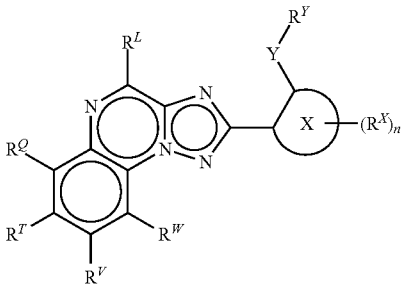
-continued
(I-BB)
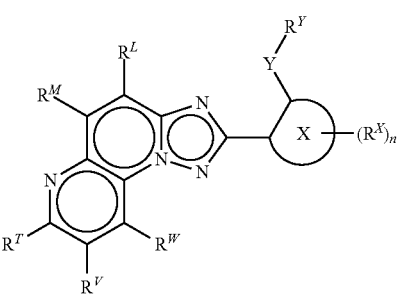
(I-CC)
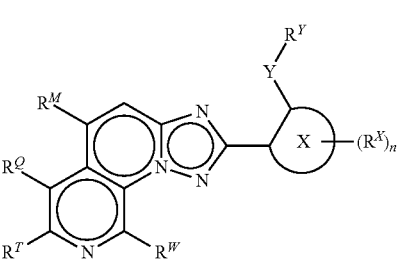
(I-DD)
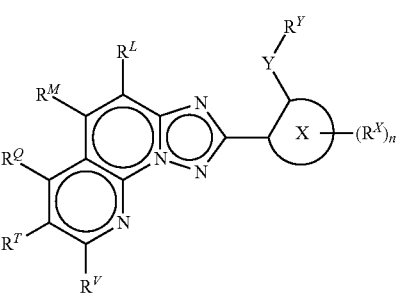
(I-EE)
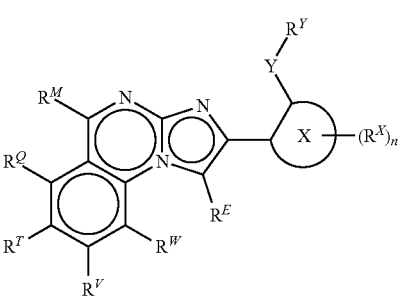
(I-FF)
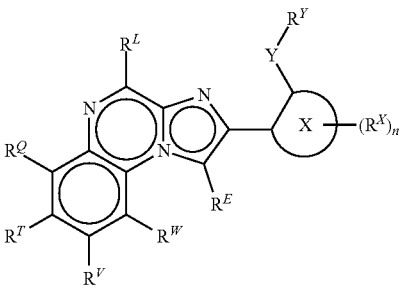

-continued

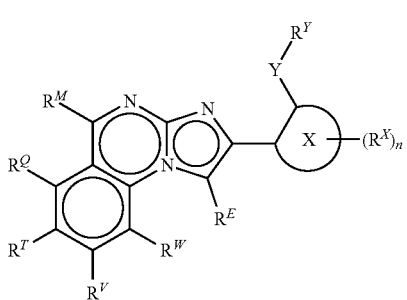
(I-GG)

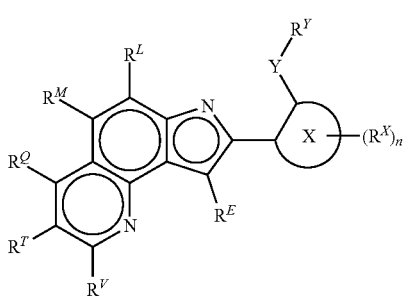
(I-HH)

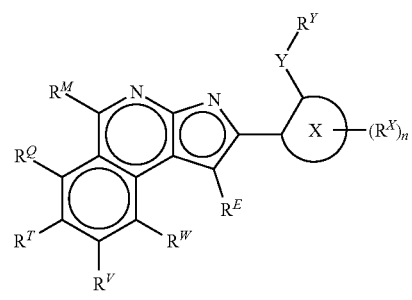
(I-JJ)

In one embodiment, compounds of formula (I) are compounds of formula (IA). In another embodiment, compounds of formula (I) are compounds of formula (IB). In another embodiment, compounds of formula (I) are compounds of formula (IC). In another embodiment, compounds of formula (I) are compounds of formula (ID). In another embodiment, compounds of formula (I) are compounds of formula (IT). In another embodiment, compounds of formula (I) are compounds of formula (IY). In another embodiment, compounds of formula (I) are compounds of formulae (IA), (IB), (IC), or (ID). In another embodiment, compounds of formula (I) are compounds of formulae (IA), (IB), (IC), or (IT). Typically, at least one of the variables M, Q, T or V is not N.

The variable Y is S, SO, or $SO_2$. In one embodiment, the variable Y is S. In one embodiment, the variable Y is SO. In one embodiment, the variable Y is $SO_2$. In another embodiment, the variable Y is S or $SO_2$.

The index n is 0, 1, 2, 3, or 4, if X is phenyl, or a 6-membered hetaryl, or 0, 1, 2, or 3 if X is a 5-membered hetaryl. Typically, n is 1. In one embodiment, n is 0. In another embodiment, n is 2. In another embodiment, n is 3.

$R^Y$ is $C_1$-$C_6$-alkyl, $C_3$-$C_6$-cycloalkyl, $C_3$-$C_6$-cycloalkyl-$C_1$-$C_4$-alkyl, which groups are halogenated or non-halogenated; $CH_2R^6$, or phenyl, which is unsubstituted or substituted with $R^{11}$. Typically, $R^Y$ is $C_1$-$C_4$-alkyl, which is halogenated or non-halogenated, preferably $C_1$-$C_3$-alkyl, or $C_1$-$C_3$-haloalkyl, preferably $CH_3CH_2$.

$R^E$, $R^L$, $R^M$, $R^Q$, $R^T$, $R^V$, and $R^W$ are independently H, halogen, $N_3$, CN, $NO_2$, SCN, $SF_5$; $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, which groups are halogenated or non-halogenated; $C(=O)OR^1$, $NR^2R^3$, $C_1$-$C_6$-alkylen-$NR^2R^3$, O—$C_1$-$C_6$-alkylen-$NR^2R^3$, $C_1$-$C_6$-alkylen-CN, NH—$C_1$-$C_6$-alkylen-$NR^2R^3$, $C(=O)NR^2R^3$, $C(=O)R^4$, $SO_2NR^2R^3$, $S(=O)_mR^5$, $OR^6$, $C(=O)R^6$, $SR^6$, or $CH_2R^6$; or phenyl, which is unsubstituted or substituted with one or more, same or different substituents $R^{11}$.

$R^E$ is typically H, halogen; $C_1$-$C_3$-alkyl, $C_1$-$C_3$-alkoxy, $C_2$-$C_3$-alkenyl, $C_2$-$C_3$-alkynyl, $C_3$-$C_5$-cycloalkyl, which groups are halogenated or non-halogenated. In one embodiment, $R^E$ is H, $C_1$-$C_1$-$C_3$-alkyl, or $C_1$-$C_3$-haloalkyl. In another embodiment, $R^E$ is H or $CH_3$. In another embodiment, $R^E$ is $CH_3$.

$R^L$ is typically H, halogen; $C_1$-$C_3$-alkyl, $C_1$-$C_3$-alkoxy, $C_2$-$C_3$-alkenyl, $C_2$-$C_3$-alkynyl, $C_3$-$C_5$-cycloalkyl, which groups are halogenated or non-halogenated. In one embodiment, $R^L$ is H, $C_1$-$C_1$-$C_3$-alkyl, $C_1$-$C_3$-haloalkyl, $C_1$-$C_3$-alkoxy, or $C_1$-$C_3$-haloalkoxy. In another embodiment, $R^L$ is H or $CF_3$. In another embodiment, $R^L$ is H.

$R^M$ is typically H, halogen; $C_1$-$C_3$-alkyl, $C_1$-$C_3$-alkoxy, $C_2$-$C_3$-alkenyl, $C_2$-$C_3$-alkynyl, $C_3$-$C_5$-cycloalkyl, which groups are halogenated or non-halogenated. In one embodiment, $R^M$ is H, $C_1$-$C_1$-$C_3$-alkyl, $C_1$-$C_3$-haloalkyl, $C_1$-$C_3$-alkoxy, or $C_1$-$C_3$-haloalkoxy. In another embodiment, $R^M$ is H or $CF_3$.

$R^Q$ is typically H, halogen; $C_1$-$C_3$-alkyl, $C_1$-$C_3$-alkoxy, $C_2$-$C_3$-alkenyl, $C_2$-$C_3$-alkynyl, $C_3$-$C_5$-cycloalkyl, which groups are halogenated or non-halogenated. In one embodiment, $R^Q$ is H, $C_1$-$C_1$-$C_3$-alkyl, $C_1$-$C_3$-haloalkyl, $C_1$-$C_3$-alkoxy, or $C_1$-$C_3$-haloalkoxy. In another embodiment, $R^Q$ is H, $CHF_2$, $CF_3$, $OCHF_2$, or $OCF_3$. In another embodiment, $R^Q$ is H, $CF_3$ or $OCF_3$. In another embodiment, $R^Q$ is H, $C_1$-$C_3$-alkyl, $C_1$-$C_3$-alkoxy, $C_1$-$C_3$-haloalkyl, or $C_1$-$C_3$-haloalkoxy, more preferably $R^Q$ is H, $C_1$-$C_3$-alkyl, $C_1$-$C_3$-fluoroalkyl, $C_1$-$C_3$-alkoxy, or $C_1$-$C_3$-fluoroalkoxy, most preferably $R^Q$ is H, $CF_3$, $OCF_3$, $OCH_2CH_3$, $OCHF_2$, or $OCH_2CF_3$.

$R^T$ is typically H, halogen; $C_1$-$C_3$-alkyl, $C_1$-$C_3$-alkoxy, $C_2$-$C_3$-alkenyl, $C_2$-$C_3$-alkynyl, $C_3$-$C_5$-cycloalkyl, which groups are halogenated or non-halogenated. In one embodiment, $R^T$ is H, $C_1$-$C_1$-$C_3$-alkyl, $C_1$-$C_3$-haloalkyl, $C_1$-$C_3$-alkoxy, or $C_1$-$C_3$-haloalkoxy. In another embodiment, $R^T$ is H, $CHF_2$, $CF_3$, $OCHF_2$, or $OCF_3$. In another embodiment, $R^Q$ is $R^T$ is H, $C_1$-$C_3$-haloalkyl, or $C_1$-$C_3$-haloalkoxy. In another embodiment, $R^T$ is H, or $CF_3$. In another embodiment, $R^T$ is H, $C_1$-$C_3$-alkyl, $C_1$-$C_3$-haloalkyl, $C_1$-$C_3$-alkoxy, or $C_1$-$C_3$-haloalkoxy, more preferably $R^T$ is H, $C_1$-$C_3$-fluoroalkyl, or $C_1$-$C_3$-fluoroalkoxy, most preferably $R^T$ is H, $CF_3$, or $OCF_3$.

$R^V$ is typically H, halogen; $C_1$-$C_3$-alkyl, $C_1$-$C_3$-alkoxy, $C_2$-$C_3$-alkenyl, $C_2$-$C_3$-alkynyl, $C_3$-$C_5$-cycloalkyl, which groups are halogenated or non-halogenated. In one embodiment, $R^V$ is H, $C_1$-$C_1$-$C_3$-alkyl, $C_1$-$C_3$-haloalkyl, $C_1$-$C_3$-alkoxy, or $C_1$-$C_3$-haloalkoxy. In another embodiment, $R^V$ is H, $CHF_2$, $CF_3$, $OCHF_2$, or $OCF_3$. In another embodiment, $R^V$ is H, $CF_3$ or $OCF_3$. In another embodiment, $R^V$ is H or $CF_3$. In another embodiment, $R^V$ is H.

$R^W$ is typically H, halogen; $C_1$-$C_3$-alkyl, $C_1$-$C_3$-alkoxy, $C_2$-$C_3$-alkenyl, $C_2$-$C_3$-alkynyl, $C_3$-$C_5$-cycloalkyl, which groups are halogenated or non-halogenated. In one embodiment, $R^V$ is H, $C_1$-$C_1$-$C_3$-alkyl, $C_1$-$C_3$-haloalkyl, $C_1$-$C_3$-alkoxy, or $C_1$-$C_3$-haloalkoxy. In another embodiment, $R^W$ is H, $CHF_2$, $CF_3$, $OCHF_2$, or $OCF_3$. In another embodiment, $R^W$ is H, $CF_3$ or $OCF_3$. In another embodiment, $R^W$ is H or $CF_3$. In another embodiment, $R^W$ is H.

In one embodiment, $R^M$, $R^Q$, $R^T$, and $R^V$ are independently H; or $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, $C_3$-$C_6$-cycloalkoxy, or $C_1$-$C_6$-alkyl-$S(O)_m$, which groups are halogenated or non-halogenated.

In another embodiment, $R^M$, $R^Q$, $R^T$, and $R^V$ are independently H; or $C_1$-$C_3$-alkyl, $C_1$-$C_3$-alkoxy, $C_2$-$C_3$-alkenyl, $C_2$-$C_3$-alkynyl, $C_3$-$C_6$-cycloalkyl, or $C_3$-$C_6$-cycloalkoxy, which groups are halogenated or non-halogenated. In another embodiment, $R^M$, $R^Q$, $R^T$, and $R^V$ are independently H; or $C_1$-$C_3$-alkyl, or $C_1$-$C_3$-alkoxy, which groups are halogenated or non-halogenated.

In another embodiment, $R^M$, $R^Q$, $R^T$, and $R^V$ are independently H; or $C_1$-$C_3$-haloalkyl, or $C_1$-$C_3$-haloalkoxy. In another embodiment, $R^M$, $R^Q$, $R^T$, and $R^V$ are independently H; or $C_1$-$C_3$-fluoroalkyl, or $C_1$-$C_3$-fluoroalkoxy, wherein at least one substituent $R^M$, $R^Q$, $R^T$, and $R^V$ is not H.

In one embodiment, $R^L$, $R^M$, $R^Q$, $R^T$, $R^V$, and $R^W$ are independently H, halogen; or $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, $C_3$-$C_6$-cycloalkoxy, or $C_1$-$C_6$-alkyl-$S(O)_m$, which groups are halogenated or non-halogenated.

In another embodiment, $R^L$, $R^M$, $R^Q$, $R^T$, $R^V$, and $R^W$ are independently H, halogen; or $C_1$-$C_3$-alkyl, $C_1$-$C_3$-alkoxy, $C_2$-$C_3$-alkenyl, $C_2$-$C_3$-alkynyl, $C_3$-$C_6$-cycloalkyl, or $C_3$-$C_6$-cycloalkoxy, which groups are halogenated or non-halogenated. In another embodiment, $R^L$, $R^M$, $R^Q$, $R^T$, $R^V$, and $R^W$ are independently H, halogen; or $C_1$-$C_3$-alkyl, or $C_1$-$C_3$-alkoxy, which groups are halogenated or non-halogenated. In another embodiment, $R^L$, $R^M$, $R^Q$, $R^T$, $R^V$, and $R^W$ are independently H, halogen; or $C_1$-$C_3$-alkyl, or $C_1$-$C_3$-alkoxy, which groups are halogenated or non-halogenated, wherein at least one variable selected from $R^L$, $R^M$, $R^Q$, $R^T$, $R^V$, and $R^W$ is not H. In another embodiment, $R^L$ and $R^W$ are H, and $R^M$, $R^Q$, $R^T$, and $R^V$ are independently H, halogen; or $C_1$-$C_3$-alkyl, or $C_1$-$C_3$-alkoxy, which groups are halogenated or non-halogenated.

In one embodiment, $R^M$, $R^Q$, $R^T$, and $R^V$ are independently H, halogen; or $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, $C_3$-$C_6$-cycloalkoxy, or $C_1$-$C_6$-alkyl-$S(O)_m$, which groups are halogenated or non-halogenated.

In another embodiment, $R^M$, $R^Q$, $R^T$, and $R^V$ are independently H, halogen; or $C_1$-$C_3$-alkyl, $C_1$-$C_3$-alkoxy, $C_2$-$C_3$-alkenyl, $C_2$-$C_3$-alkynyl, $C_3$-$C_6$-cycloalkyl, or $C_3$-$C_6$-cycloalkoxy, which groups are halogenated or non-halogenated. In another embodiment, $R^M$, $R^Q$, $R^T$, and $R^V$ are independently H, halogen; or $C_1$-$C_3$-alkyl, or $C_1$-$C_3$-alkoxy, which groups are halogenated or non-halogenated. In another embodiment, $R^M$, $R^Q$, $R^T$, and $R^V$ are independently H, halogen; or $C_1$-$C_3$-alkyl, or $C_1$-$C_3$-alkoxy, which groups are halogenated or non-halogenated, wherein at least one variable selected from $R^M$, $R^Q$, $R^T$, and $R^V$ is not H.

In one embodiment, $R^E$ and $R^L$ are independently H, halogen; $C_1$-$C_4$-alkyl, $C_1$-$C_4$-alkoxy, $C_2$-$C_4$-alkenyl, or $C_2$-$C_4$-alkynyl, which groups are halogenated or non-halogenated. In another embodiment, $R^E$ and $R^L$ are independently H, $C_1$-$C_3$-alkyl, or $C_1$-$C_3$-haloalkyl. In another embodiment, $R^E$ and $R^L$ are independently H, or $C_1$-$C_3$-alkyl. In another embodiment, $R^L$ is H and $R^E$ is H or $C_1$-$C_3$-alkyl.

The cycle X is phenyl, or a 5- or 6-membered hetaryl, preferably 2-pyridyl. For the avoidance of doubt, the cycle X is substituted with n substituents $R^X$. Also, for the avoidance of doubt, X is connected to Y and to the tricyclic system by direct chemical bonds to two adjacent ring members of X.

In one embodiment, X is phenyl. In another embodiment, X is a 5-membered hetaryl. In another embodiment, X is a 6-membered hetaryl. In another embodiment, X is a 5-membered hetaryl comprising one N-atom. In another embodiment, X is a 6-membered hetaryl comprising at least one N-atom. In another embodiment, X is a 6-membered hetaryl comprising two N-atoms.

Preferred 5- or 6-membered hetaryls X are depicted below as formulae A1 to A48, wherein "&" stands for the connection to the tricyclic scaffold of compounds of formula (I). For the avoidance of doubt, the formulae A1 to A48 are preferred embodiments on their own and in combination for the following moiety of formula (I)

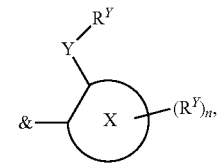

wherein "&" stands for the connection to the tricyclic scaffold in formula (I). In other words, the substituents $R^Y$—Y and $(R^X)_n$ in formulae A1 to A48 are mere illustrations but are not part of the hetaryl X.

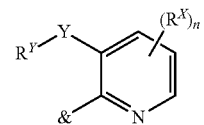
A1

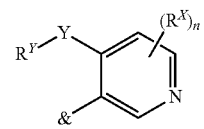
A2

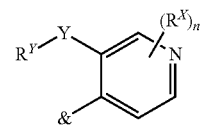
A3

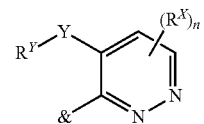
A4

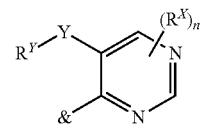
A5

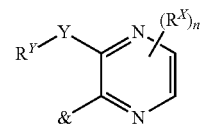
A6

| | |
|---|---|
| 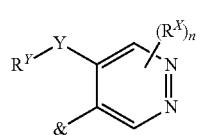 | A7 |
| 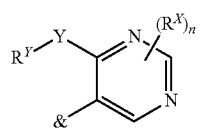 | A8 |
| 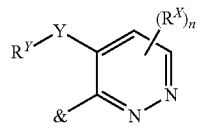 | A9 |
| 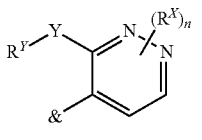 | A10 |
| 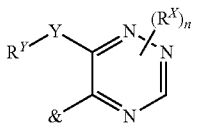 | A11 |
| 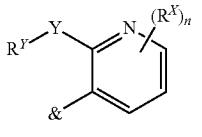 | A12 |
| 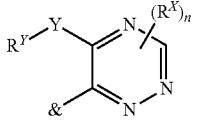 | A13 |
| 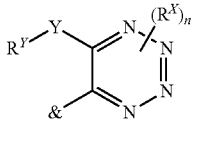 | A14 |
| 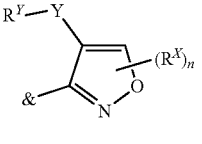 | A15 |
| 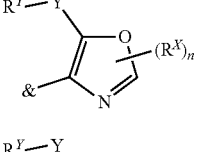 | A16 |
| 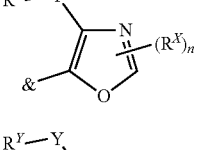 | A17 |
| 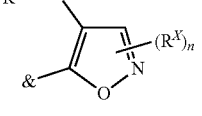 | A18 |
| 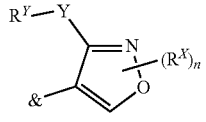 | A19 |
| 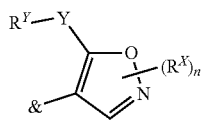 | A20 |
| 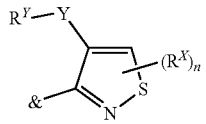 | A21 |
| 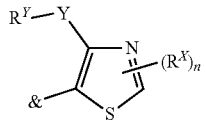 | A22 |
| 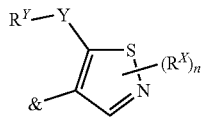 | A23 |
| 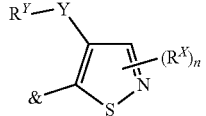 | A24 |
| 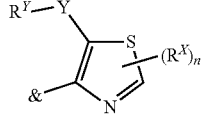 | A25 |
| 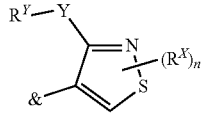 | A26 |
| 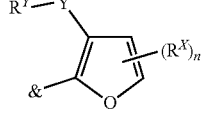 | A27 |
| 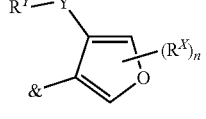 | A28 |
| 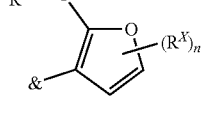 | A29 |
| 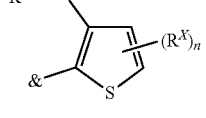 | A30 |

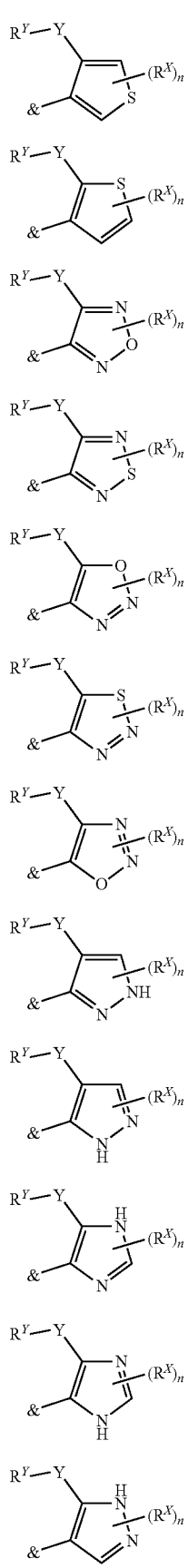

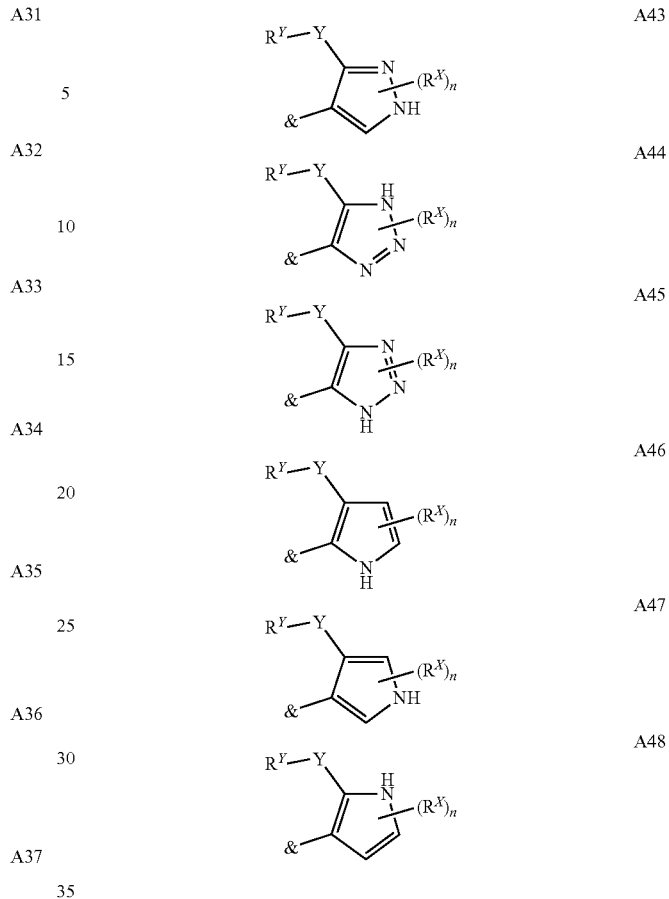

In one embodiment, X is selected from formulae A1 to A14. In one embodiment, X is selected from formulae A1 to A3. In another embodiment, X is A1. In another embodiment, X is A2. In another embodiment, X is A3. In another embodiment, X is A5. In another embodiment, X is A1 or A5. In another embodiment, X is selected from A1, A5, A6, A9, A11, A13, and A14. In another embodiment, X is selected from A1, A5, A6, A9, A11, A13, A14, A15, A16, A21, A25, A33, A34, A35, A36, A38, A39, A40, A41, A44, A45, and A46.

$R^1$ is H; $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, or $C_3$-$C_6$-cycloalkoxy-$C_1$-$C_4$-alkyl, which groups are halogenated or non-halogenated; $C_1$-$C_6$-alkylen-$NR^2R^3$, $C_1$-$C_6$-alkylen-CN, or $CH_2R^6$; or phenyl, which is unsubstituted, or substituted with one or more, same or different substituents $R^{11}$.

In one embodiment, $R^1$ is phenyl, which is unsubstituted or substituted with one or more, same or different substituents $R^{11}$. In another embodiment, $R^1$ is H; $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-Calkyl-$C_1$-$C_4$-alkyl, or $C_3$-$C_6$-cycloalkoxy-$C_1$-$C_4$-alkyl, which groups are halogenated or non-halogenated. In another embodiment, $R^1$ is H; $C_1$-$C_3$-alkyl, $C_2$-$C_3$-alkenyl, $C_2$-$C_3$-alkynyl, which groups are halogenated or non-halogenated. In another embodiment, $R^1$ is $C_1$-$C_3$-alkyl or $C_1$-$C_3$-haloalkyl.

$R^{11}$ is halogen, $N_3$, OH, CN, $NO_2$, SCN, $SF_5$; $C_1$-$C_6$-alkyl, $C_1$-$C_6$-alkoxy, $C_2$-$C_6$-alkenyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$- alkyl, $C_3$-$C_6$-cycloalkoxy-$C_1$-$C_4$-alkyl, which groups are halogenated or non-halogenated.

In one embodiment, $R^{11}$ is halogen, OH, CN, $SF_5$; $C_1$-$C_3$-alkyl, $C_1$-$C_3$-alkoxy, which groups are halogenated or non-halogenated. In one embodiment, $R^{11}$ is halogen; $C_1$-$C_3$-alkyl, or $C_1$-$C_3$-haloalkyl.

$R^2$ is H; $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which groups are halogenated or non-halogenated; C(=O)$R^{21}$, C(=O)O$R^{21}$, C(=O)N$R^{21}$, $C_1$-$C_6$-alkylen-CN, or $CH_2R^6$; or phenyl, which is unsubstituted or substituted with one or more, same or different substituents $R^{11}$.

In one embodiment, $R^2$ is H; $C_1$-$C_3$-alkyl, $C_2$-$C_3$-alkenyl, $C_2$-$C_3$-alkynyl, which groups are halogenated or non-halogenated. In another embodiment, $R_2$ is H. In another embodiment, $R^2$ is H; $C_1$-$C_3$-alkyl, or $C_1$-$C_3$-haloalkyl.

$R^{21}$ is H; $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl; $C_3$-$C_6$-cycloalkyl-$C_1$-$C_4$-alkyl, $C_3$-$C_6$-cycloalkoxy-$C_1$-$C_4$ alkyl, phenyl, or a saturated, partially-, or fully unsaturated 5- or 6-membered heterocycle, wherein the cyclic moieties are unsubstituted or substituted with one or more, same or different substituents $R^{11}$. In one embodiment, $R^{21}$ is H; $C_1$-$C_3$-alkyl, $C_1$-$C_3$-haloalkyl, or phenyl. In another embodiment, $R^{21}$ is $C_1$-$C_3$-alkyl.

$R^3$ is H; $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which groups are halogenated or non-halogenated; $C_1$-$C_6$-alkylen-CN, or $CH_2R^6$; phenyl, which is unsubstituted or substituted with one or more, same or different substituents $R^{11}$; or $NR^2R^3$ may also form an N-bound, saturated 3- to 8-membered heterocycle, which in addition to the nitrogen atom may have 1 or 2 further heteroatoms or heteroatom moieties selected from O, S(=O)$_m$, NH, and N—$C_1$-$C_6$-alkyl, and wherein the N-bound heterocycle is unsubstituted or substituted with one or more, same or different substituents selected from halogen, $C_1$-$C_4$-alkyl, $C_1$-$C_4$-haloalkyl, $C_1$-$C_4$-alkoxy and $C_1$-$C_4$-haloalkoxy. In one embodiment, $R^3$ is H, $C_1$-$C_3$-alkyl, $C_1$-$C_3$-haloalkyl, or phenyl. In another embodiment, $R^3$ is phenyl. In another embodiment, $R^3$ is H. In another embodiment, $R^2$ is H and $R^3$ is $C_1$-$C_3$-alkyl or phenyl.

$R^4$ is selected from H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which are unsubstituted or substituted with halogen; $CH_2R^6$, or phenyl, which is unsubstituted, or substituted with one or more, same or different substituents $R^{11}$. In one embodiment, $R^4$ is H, $C_1$-$C_3$-alkyl, $C_1$-$C_3$-haloalkyl, or phenyl. In another embodiment, $R^4$ is H. In another embodiment, $R^4$ is $C_1$-$C_3$-alkyl, or $C_1$-$C_3$-haloalkyl.

$R^5$ $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, or $C_3$-$C_6$-cycloalkoxy-$C_1$-$C_4$-alkyl, which groups are halogenated or non-halogenated; $C_1$-$C_6$-alkylen-$NR^2R^3$, $C_1$-$C_6$-alkylen-CN, $CH_2R^6$; or phenyl, which is unsubstituted, or substituted with one or more, same or different substituents $R^{11}$. In one embodiment, $R^5$ is $C_1$-$C_6$-alkyl, $C_2$-$C_6$-alkenyl, $C_2$-$C_6$-alkynyl, or phenyl, which groups are unhalogenated or halogenated. In another embodiment, $R^5$ is $C_1$-$C_3$-alkyl or $C_1$-$C_3$-haloalkyl.

$R^6$ is phenyl, which is unsubstituted or substituted with one or more, same or different substituents $R^{11}$. In one embodiment, $R^6$ is phenyl. In another embodiment, $R^6$ is phenyl that is unsubstituted or substituted with halogen, $C_1$-$C_3$-alkyl, $C_1$-$C_3$-haloalkyl, $C_1$-$C_3$-alkoxy, or $C_1$-$C_3$-haloalkoxy.

$R^7$, $R^8$ are independently H, halogen, CN, $C_1$-$C_6$-alkyl, $C_1$-$C_6$-haloalkyl, $C_3$-$C_6$-cycloalkyl, $C_1$-$C_4$-alkoxy, $C_1$-$C_4$-alkoxy-$C_1$-$C_4$-alkyl, $C_1$-$C_4$-alkylsulfanyl, $C_1$-$C_4$-alkylsulfanyl-$C_1$-$C_4$-alkyl, $C_1$-$C_4$-alkylsulfinyl-$C_1$-$C_4$-alkyl, $C_1$-$C_4$-alkylsulfonyl-$C_1$-$C_4$-alkyl or $C_1$-$C_4$-alkoxycarbonyl.

In one embodiment, $R^7$ and $R^8$ are independently H, halogen, CN, $C_1$-$C_6$-alkyl, $C_1$-$C_6$-haloalkyl, or $C_1$-$C_4$-alkoxycarbonyl. In one embodiment, $R^7$ and $R^8$ are independently halogen, CN, $C_1$-$C_6$-alkyl, or $C_1$-$C_4$-alkoxycarbonyl. In one embodiment, $R^7$ and $R^8$ are independently $C_1$-$C_6$-alkyl, preferably $C_1$-$C_3$-alkyl.

$R^9$ is CN, $NH_2$, C(=O)H, OH, $C_3$-$C_6$-cycloalkyl, C(=O)OH, C(=O)$NH_2$, $C_1$-$C_4$-haloalkoxy, $C_1$-$C_4$-alkoxy, $C_1$-$C_4$-haloalkylsulfanyl, $C_1$-$C_4$-haloalkylsulfinyl, $C_1$-$C_4$-haloalkylsulfonyl, $C_1$-$C_4$-alkoxycarbonyl, $C_1$-$C_4$-haloalkoxycarbonyl, $C_1$-$C_4$-alkylcarbonyl, $C_1$-$C_4$-haloalkylcarbonyl, di-($C_1$-$C_4$)alkylaminocarbonyl, $C_1$-$C_4$-alkylaminocarbonyl, $C_1$-$C_4$-alkylcarbonylamino, di-($C_1$-$C_4$)alkylcarbonylamino, $C_1$-$C_4$-alkoxycarbonylamino, or a group —C($R^{91}$)=$NOR^{92}$; phenyl, which is unsubstituted or substituted with one or more, same or different substituents selected from halogen, CN, $C_1$-$C_4$-alkyl, $C_1$-$C_4$-haloalkyl, $C_1$-$C_4$-haloalkoxy, $C_1$-$C_4$-alkoxy, $C_1$-$C_4$-haloalkylsulfanyl, $C_1$-$C_4$-haloalkylsulfinyl, $C_1$-$C_4$haloalkylsulfonyl and C(=O)$C_1$-$C_4$-haloalkyl; $C_1$-$C_4$-alkyl which is unsubstituted or substituted with one or more, same or different substituents $R^{93}$.

In one embodiment, $R^9$ is CN, $NH_2$, C(=O)H, C(=O)OH, C(=O)$NH_2$, $C_1$-$C_4$-alkoxycarbonyl, di($C_1$-$C_4$)alkylaminocarbonyl, $C_1$-$C_4$-alkylaminocarbonyl, $C_1$-$C_4$-alkylcarbonylamino, di-($C_1$-$C_4$)alkylcarbonylamino, ($C_1$-$C_4$) alkoxycarbonylamino, or a group —C($R^{91}$)=$NOR^{92}$. In one embodiment, $R^9$ is CN, $NH_2$, C(=O)H, C(=O)OH, C(=O)$NH_2$, $C_1$-$C_4$-alkoxycarbonyl, methylaminocarbonyl, dimethylaminocarbonyl, methoxycarbonylamino, hydroxymethylene or methylhydroxymethylene. In another embodiment, $R^9$ is CN.

$R^X$ is halogen, $N_3$, OH, CN, $NO_2$, SCN, $SF_5$; $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, which groups are halogenated or non-halogenated; C(=O)$OR^1$, $NR^2R^3$, $C_1$-$C_6$-alkylen-$NR^2R^3$, O—$C_1$-$C_6$-alkylen-$NR^2R^3$, $C_1$-$C_6$-alkylen-CN, NH—$C_1$-$C_6$-alkylen-$NR^2R^3$, C(=O)$NR^2R^3$, C(=O)$R^4$, $SO_2NR^2R^3$, S(=O)$_mR^1$, $OR^6$, $SR^6$, $CH_2R^6$; or OC(=O)$R^4$, OC(=O)$OR^1$, OC(=O)$NR^2R^3$, OC(=O)$SR^1$, OC(=S)$NR^2R^3$, OC(=S)$SR^1$, ON$R^2R^3$, ON=C$R^1R^4$, N=C$R^1R^4$, $NNR^2$, NC(=O)$R^4$, SC(=O)$SR^1$, SC(=O)$NR^2R^3$, C(=S)$R^6$, C(=S)$OR^4$, C(=$NR^2$)$R^4$, C(=$NOR^2$)$R^4$, C(CN)$R^7R^8$; phenyl, which is unsubstituted or substituted with one or more, same or different substituents $R^{11}$; a 5- or 6-membered saturated, partially unsaturated, or fully unsaturated heterocyclic ring, wherein said heterocyclic ring comprises one or more, same or different heteroatoms O, N, or S, and is unsubstituted, or substituted with one or more, same or different substituents $R^{31}$, and wherein said N- and S-atoms are independently oxidized, or non-oxidized; or $C_3$-$C_6$-cycloalkyl, which is substituted with one or more, same or different substituents $R^9$;

Typically, $R^X$ is halogen, $N_3$, OH, CN, $NO_2$, SCN, $SF_5$; $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$- alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, which groups are halogenated or non-halogenated; C(=O)OR$^1$, NR$^2$R$^3$, $C_1$-$C_6$-alkylen-NR$^2$R$^3$, O—$C_1$-$C_6$-alkylen-NR$^2$R$^3$, $C_1$-$C_6$-alkylen-CN, NH—$C_1$-$C_6$-alkylen-NR$^2$R$^3$, C(=O)NR$^2$R$^3$, C(=O)R$^4$, SO$_2$NR$^2$R$^3$, S(=O)$_m$R$^1$, OR$^6$, SR$^6$, CH$_2$R$^6$; or OC(=O)R$^4$, OC(=O)OR$^1$, OC(=O)NR$^2$R$^3$, OC(=O)SR$^1$, OC(=S)NR$^2$R$^3$, OC(=S)SR$^1$, ONR$^2$R$^3$, ON=CR$^1$R$^4$, N=CR$^1$R$^4$, NNR$^2$, NC(=O)R$^4$, SC(=O)SR$^1$, SC(=O)NR$^2$R$^3$, C(=S)R$^6$, C(=S)OR$^4$, C(=NR$^2$)R$^4$, C(=NOR$^2$)R$^4$; phenyl, which is unsubstituted or substituted with one or more, same or different substituents R$^{11}$; or a 5- or 6-membered saturated, partially unsaturated, or fully unsaturated heterocyclic ring, wherein said heterocyclic ring comprises one or more, same or different heteroatoms O, N, or S, and is unsubstituted, or substituted with one or more, same or different substituents R$^{31}$, and wherein said N- and S-atoms are independently oxidized, or non-oxidized.

In one embodiment, R$^X$ is halogen, OH, CN; $C_1$-$C_3$-alkyl, $C_1$-$C_3$-alkoxy, $C_2$-$C_3$-alkenyl, $C_2$-$C_3$-alkynyl, $C_3$-$C_5$-cycloalkyl, $C_3$-$C_5$-cycloalkoxy, which groups are halogenated or non-halogenated; S(=O)$_m$R$^1$, OR$^6$, CH$_2$R$^6$; or phenyl, which is unsubstituted or substituted with one or more, same or different substituents R$^{11}$; or a 5- or 6-membered saturated, partially unsaturated, or fully unsaturated heterocyclic ring, wherein said heterocyclic ring comprises one or more, same or different heteroatoms O, N, or S, and is unsubstituted, or substituted with one or more, same or different substituents R$^{31}$, and wherein said N- and S-atoms are independently oxidized, or non-oxidized.

In one embodiment, R$^X$ is or a 5- or 6-membered saturated, partially unsaturated, or fully unsaturated heterocyclic ring, wherein said heterocyclic ring comprises one or more, same or different heteroatoms O, N, or S, and is unsubstituted, or substituted with one or more, same or different substituents R$^{31}$, and wherein said N- and S-atoms are independently oxidized, or non-oxidized.

In one embodiment, R$^X$ is halogen; $C_1$-$C_3$-alkyl, $C_1$-$C_3$-alkoxy, $C_2$-$C_3$-alkenyl, $C_2$-$C_3$-alkynyl, $C_3$-$C_5$-cycloalkyl, $C_3$-$C_5$-cycloalkoxy, which groups are halogenated or non-halogenated; S(=O)$_m$R$^1$, OR$^6$, CH$_2$R$^6$; or phenyl, which is unsubstituted or substituted with one or more, same or different substituents R$^1$; or a 5- or 6-membered saturated, partially unsaturated, or fully unsaturated heterocyclic ring selected from Het-1 to Het-19 in Table A.

In one embodiment, R$^X$ is halogen; $C_1$-$C_3$-alkyl, $C_2$-$C_3$-alkenyl, $C_2$-$C_3$-alkynyl, which groups are halogenated or non-halogenated; SO$_2$NR$^2$R$^3$, S(=O)$_m$R$^1$; or phenyl, which is unhalogenated or halogenated. In one embodiment, R$^X$ is halogen; $C_1$-$C_3$-alkyl, which groups are halogenated or non-halogenated; S(=O)$_m$R$^1$; or phenyl, which is halogenated or non-halogenated. In one embodiment, R$^X$ is halogen; $C_1$-$C_3$-haloalkyl, $C_1$-$C_3$-alkyl-S(=O)$_m$; or phenyl, which is halogenated or non-halogenated. In another embodiment, R$^X$ is $C_1$-$C_3$-alkyl, which is halogenated or non-halogenated. In another embodiment, R$^X$ is $C_1$-$C_3$-haloalkyl. In another embodiment, R$^X$ is C(=NOR$^2$)R$^4$, preferably wherein R$^2$ is $C_1$-$C_3$ haloalkyl.

In one embodiment, R$^X$ is C(CN)R$^7$R$^8$, preferably wherein R$^7$, R$^8$ are independently H, or $C_1$-$C_3$-alkyl, more preferably independently $C_1$-$C_3$-alkyl.

In another embodiment, R$^X$ is $C_3$-$C_6$-cycloalkyl, which is unsubstituted or substituted with one or more, same or different substituents R$^9$, preferably cyclopropyl, which is substituted at position 1 with R$^9$ (i.e. 1-R$^9$-cyclopropyl, such as in 1-cyano-cyclopropyl), more preferably wherein R$^9$ is CN, NH$_2$, C(=O)H, C(=O)OH, C(=O)NH$_2$, $C_1$-$C_4$-alkoxycarbonyl, di-($C_1$-$C_4$)-alkylaminocarbonyl, $C_1$-$C_4$-alkylaminocarbonyl, $C_1$-$C_4$-alkylcarbonylamino, di-($C_1$-$C_4$)-alkylcarbonylamino, ($C_1$-$C_4$)alkoxycarbonylamino, or a group —C(R$^{91}$)=NOR$^{92}$, most preferably wherein R$^9$ is CN, NH$_2$, C(=O)H, C(=O)OH, C(=O)NH$_2$, $C_1$-$C_4$-alkoxycarbonyl, methylaminocarbonyl, dimethylaminocarbonyl, methoxycarbonylamino, hydroxymethylene or methylhydroxymethylene, utmost preferably wherein R$^9$ is CN.

In one embodiment, R$^X$ is halogen, OH, CN; $C_1$-$C_3$-alkyl, $C_1$-$C_3$-alkoxy, $C_2$-$C_3$-alkenyl, $C_2$-$C_3$-alkynyl, $C_3$-$C_5$-cycloalkyl, $C_3$-$C_5$-cycloalkoxy, which groups are halogenated or non-halogenated; S(=O)$_m$R$^1$, OR$^6$, CH$_2$R$^6$; phenyl, which is unsubstituted or substituted with one or more, same or different substituents R$^{11}$; a 5- or 6-membered saturated, partially unsaturated, or fully unsaturated heterocyclic ring, wherein said heterocyclic ring comprises one or more, same or different heteroatoms O, N, or S, and is unsubstituted, or substituted with one or more, same or different substituents R$^{31}$, and wherein said N- and S-atoms are independently oxidized, or non-oxidized; C(CN)R$^7$R$^8$; or $C_3$-$C_6$-cycloalkyl, which is substituted with one or more, same or different substituents R$^9$.

In one embodiment, R$^X$ is or a 5- or 6-membered saturated, partially unsaturated, or fully unsaturated heterocyclic ring, wherein said heterocyclic ring comprises one or more, same or different heteroatoms O, N, or S, and is unsubstituted, or substituted with one or more, same or different substituents R$^{31}$, and wherein said N- and S-atoms are independently oxidized, or non-oxidized.

In one embodiment, R$^X$ is halogen; $C_1$-$C_3$-alkyl, $C_1$-$C_3$-alkoxy, $C_2$-$C_3$-alkenyl, $C_2$-$C_3$-alkynyl, $C_3$-$C_5$-cycloalkyl, $C_3$-$C_5$-cycloalkoxy, which groups are halogenated or non-halogenated; S(=O)$_m$R$^1$, OR$^6$, CH$_2$R$^6$; or phenyl, which is unsubstituted or substituted with one or more, same or different substituents R$^1$; a 5- or 6-membered saturated, partially unsaturated, or fully unsaturated heterocyclic ring selected from Het-1 to Het-19 in Table A; C(CN)R$^7$R$^8$; or $C_3$-$C_6$-cycloalkyl, which is unsubstituted or substituted with one or more, same or different substituents R$^9$.

In one embodiment, R$^X$ is halogen; $C_1$-$C_3$-alkyl, $C_2$-$C_3$-alkenyl, $C_2$-$C_3$-alkynyl, which groups are halogenated or non-halogenated; SO$_2$NR$^2$R$^3$, S(=O)$_m$R$^1$; phenyl, which is unhalogenated or halogenated, C(CN)R$^7$R$^8$; or $C_3$-$C_6$-cycloalkyl, which is unsubstituted or substituted with one or more, same or different substituents R$^9$. In one embodiment, R$^X$ is halogen; $C_1$-$C_3$-alkyl, which groups are halogenated or non-halogenated; S(=O)$_m$R$^1$; phenyl, which is halogenated or non-halogenated, or C(CN)R$^7$R$^8$, wherein R$^7$ and R$^8$ are independently selected from $C_1$-$C_3$-alkyl; or $C_3$-$C_6$-cycloalkyl, which is substituted with CN. In one embodiment, R$^X$ is halogen; $C_1$-$C_3$-haloalkyl, $C_1$-$C_3$-alkyl-S(=O)$_m$; phenyl, which is halogenated or non-halogenated; or C(CN)R$^7$R$^8$, wherein R$^7$ and R$^8$ are independently selected from $C_1$-$C_3$-alkyl; or $C_3$-$C_6$-cycloalkyl, which is substituted with CN. In one embodiment, R$^X$ is halogen; $C_1$-$C_3$-haloalkyl, $C_1$-$C_3$-alkyl-S(=O)$_m$; phenyl, which is halogenated or non-halogenated; or C(CN)R$^7$R$^8$, wherein R$^7$ and R$^8$ are independently selected from $C_1$-$C_3$-alkyl. In another embodiment, R$^X$ is $C_1$-$C_3$-alkyl, which is halogenated or non-halogenated. In another embodiment, R$^X$ is $C_1$-$C_3$-haloalkyl. In another embodiment, R$^X$ is C(=NOR$^2$)R$^4$, preferably wherein R$^2$ is $C_1$-$C_3$ haloalkyl.

R$^{31}$ is halogen, N$_3$, OH, CN, NO$_2$, SCN, SF$_5$; $C_1$-$C_6$-alkyl, $C_1$-$C_6$-haloalkyl, $C_1$-$C_6$-alkoxy, $C_2$-$C_6$-alkenyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_1$-$C_6$-alkoxycarbonyl, $C_3$-$C_6$-cycloalkyl;

$C_3$-$C_6$-cycloalkoxy, $C_3$-$C_6$-cycloalkyl-$C_1$-$C_4$-alkyl, $C_3$-$C_6$-cycloalkoxy-$C_1$-$C_4$ alkyl, phenyl, or a saturated, partially-, or fully unsaturated 5- or 6-membered heterocycle, wherein the cyclic moieties are unsubstituted or substituted with one or more, same or different substituents $R^1$; or two geminal substituents $R^{31}$ form together with the atom to which they are bound a group =O or =S.

In one embodiment, $R^{31}$ is halogen, $C_1$-$C_3$-alkyl, $C_1$-$C_3$-haloalkyl, $C_1$-$C_3$-alkoxycarbonyl, or two geminal substituents form together with the atom to which they are bound a group =O. In one embodiment, $R^{31}$ is halogen, $C_1$-$C_3$-alkyl, $C_1$-$C_3$-haloalkyl, or two geminal substituents form together with the atom to which they are bound a group =O.

In one embodiment, $R^{31}$ is halogen, $C_1$-$C_3$-alkyl, $C_1$-$C_3$-haloalkyl, $C_1$-$C_3$-alkoxycarbonyl, or two geminal substituents form together with the atom to which they are bound a group =O. In one embodiment, $R^{31}$ is $C_1$-$C_3$-haloalkyl, or two geminal substituents form together with the atom to which they are bound a group =O.

$R^{91}$ and $R^{92}$ are independently H, $C_1$-$C_4$-alkyl, or $C_1$-$C_4$-haloalkyl, preferably H, $C_1$-$C_3$-alkyl, or $C_1$-$C_3$-haloalkyl.

$R^{93}$ is halogen, CN, $NH_2$, C(=O)H, OH, $C_3$-$C_6$-cycloalkyl, hydroxycarbonyl, aminocarbonyl, $C_1$-$C_4$-haloalkoxy, $C_1$-$C_4$-alkoxy, $C_1$-$C_4$-haloalkylsulfanyl, $C_1$-$C_4$-haloalkylsulfinyl, $C_1$-$C_4$-haloalkylsulfonyl, $C_1$-$C_4$-alkoxycarbonyl, $C_1$-$C_4$-haloalkoxycarbonyl, $C_1$-$C_4$-alkylcarbonyl, $C_1$-$C_4$-haloalkylcarbonyl, di-($C_1$-$C_4$)alkylaminocarbonyl, $C_1$-$C_4$alkylaminocarbonyl, $C_1$-$C_4$-alkylcarbonylamino, di($C_1$-$C_4$)alkylcarbonylamino, $C_1$-$C_4$-alkoxycarbonylamino, or a group —C($R^{91}$)=$NOR^{92}$.

Typically, $R^{93}$ is halogen, CN, $NH_2$, C(=O)H, OH, $C_3$-$C_6$-cycloalkyl, hydroxycarbonyl, aminocarbonyl, $C_1$-$C_4$-haloalkoxy, $C_1$-$C_4$-alkoxy, $C_1$-$C_4$-alkoxycarbonyl, $C_1$-$C_4$-haloalkoxycarbonyl, $C_1$-$C_4$-alkylcarbonyl, or $C_1$-$C_4$-haloalkylcarbonyl.

The index m is 0, 1, or 2. Typically, m is 0 or 2. In one embodiment, m is 2. In another embodiment, m is 0.

Table B below contains combinations of meanings for variables $R^X$, Y, and $R^E$ in lines S-1 to S-168. The respective numbering S-1 to S-180 of the lines of Table B is used herein below as an abbreviation for the specific combination of meanings of the variables $R^X$, Y, and $R^E$ in this line.

Table C below contains combinations of meanings for variables $R^L$, $R^M$, $R^Q$, $R^T$, and $R^V$ in lines T-1 to T-815. The respective numbering T-1 to T-815 of the lines of Table C is used herein below as an abbreviation for the specific combination of meanings of the variables $R^L$, $R^M$, $R^Q$, $R^T$, and $R^V$ in the line of Table C. A dash in Table C refers to a situation in which the respective variable is not defined since it does not occur in a subset of compounds of formula (I). Moreover, the meanings mentioned for the individual variables in Table B and Table C are per se, independently of the combination in which they are mentioned, a particularly preferred embodiment of the substituents in question.

TABLE B

| Line | $R^X$ | $R^E$ | Y |
|---|---|---|---|
| S-1 | H | $CH_3$ | S |
| S-2 | $CF_3$ | $CH_3$ | S |
| S-3 | $OCF_3$ | $CH_3$ | S |
| S-4 | $SO_2CH_2CH_3$ | $CH_3$ | S |
| S-5 | F | $CH_3$ | S |
| S-6 | Br | $CH_3$ | S |
| S-7 | 3-fluorophenyl | $CH_3$ | S |
| S-8 | 4-fluorophenyl | $CH_3$ | S |
| S-9 | 4-chlorophenyl | $CH_3$ | S |

TABLE B-continued

| Line | $R^X$ | $R^E$ | Y |
|---|---|---|---|
| S-10 | cyclopropyl | $CH_3$ | S |
| S-11 | $OF_3OF_3$ | $CH_3$ | S |
| S-12 | 4-trifluoromethylphenyl | $CH_3$ | S |
| S-13 | 3-trifluoromethylphenyl | $CH_3$ | S |
| S-14 | Het-5 | $CH_3$ | S |
| S-15 | Het-6 | $CH_3$ | S |
| S-16 | Het-7 | $CH_3$ | S |
| S-17 | Het-8 | $CH_3$ | S |
| S-18 | Het-9 | $CH_3$ | S |
| S-19 | Het-10 | $CH_3$ | S |
| S-20 | Het-11 | $CH_3$ | S |
| S-21 | Het-12 | $CH_3$ | S |
| S-22 | Het-13 | $CH_3$ | S |
| S-23 | Het-14 | $CH_3$ | S |
| S-24 | Het-15 | $CH_3$ | S |
| S-25 | Het-16 | $CH_3$ | S |
| S-26 | Het-17 | $CH_3$ | S |
| S-27 | Het-18 | $CH_3$ | S |
| S-28 | Het-19 | $CH_3$ | S |
| S-29 | $C(CN)(OH_3)_2$ | $CH_3$ | S |
| S-30 | 1-cyanocyclopropyl | $CH_3$ | S |
| S-31 | H | $CH_3$ | SO |
| S-32 | $CF_3$ | $CH_3$ | SO |
| S-33 | SO | $CH_3$ | SO |
| S-34 | $SO_2OH_2OH_3$ | $CH_3$ | SO |
| S-35 | F | $CH_3$ | SO |
| S-36 | Br | $CH_3$ | SO |
| S-37 | 3-fluorophenyl | $CH_3$ | SO |
| S-38 | 4-fluorophenyl | $CH_3$ | SO |
| S-39 | 4-chlorophenyl | $CH_3$ | SO |
| S-40 | cyclopropyl | $CH_3$ | SO |
| S-41 | $CF_3CF_3$ | $CH_3$ | SO |
| S-42 | 4-trifluoromethylphenyl | $CH_3$ | SO |
| S-43 | 3-trifluoromethylphenyl | $CH_3$ | SO |
| S-44 | Het-5 | $CH_3$ | SO |
| S-45 | Het-6 | $CH_3$ | SO |
| S-46 | Het-7 | $CH_3$ | SO |
| S-47 | Het-8 | $CH_3$ | SO |
| S-48 | Het-9 | $CH_3$ | SO |
| S-49 | Het-10 | $CH_3$ | SO |
| S-50 | Het-11 | $CH_3$ | SO |
| S-51 | Het-12 | $CH_3$ | SO |
| S-52 | Het-13 | $CH_3$ | SO |
| S-53 | Het-14 | $CH_3$ | SO |
| S-54 | Het-15 | $CH_3$ | SO |
| S-55 | Het-16 | $CH_3$ | SO |
| S-56 | Het-17 | $CH_3$ | SO |
| S-57 | Het-18 | $CH_3$ | SO |
| S-58 | Het-19 | $CH_3$ | SO |
| S-59 | $C(CN)(OH_3)_2$ | $CH_3$ | SO |
| S-60 | 1-cyanocyclopropyl | $CH_3$ | SO |
| S-61 | H | $CH_3$ | $SO_2$ |
| S-62 | $CF_3$ | $CH_3$ | $SO_2$ |
| S-63 | $OCF_3$ | $CH_3$ | $SO_2$ |
| S-64 | $SO_2OH_2OH_3$ | $CH_3$ | $SO_2$ |
| S-65 | F | $CH_3$ | $SO_2$ |
| S-66 | Br | $CH_3$ | $SO_2$ |
| S-67 | 3-fluorophenyl | $CH_3$ | $SO_2$ |
| S-68 | 4-fluorophenyl | $CH_3$ | $SO_2$ |
| S-69 | 4-chlorophenyl | $CH_3$ | $SO_2$ |
| S-70 | cyclopropyl | $CH_3$ | $SO_2$ |
| S-71 | $OF_3OF_3$ | $CH_3$ | $SO_2$ |
| S-72 | 4-trifluoromethylphenyl | $CH_3$ | $SO_2$ |
| S-73 | 3-trifluoromethylphenyl | $CH_3$ | $SO_2$ |
| S-74 | Het-5 | $CH_3$ | $SO_2$ |
| S-75 | Het-6 | $CH_3$ | $SO_2$ |
| S-76 | Het-7 | $CH_3$ | $SO_2$ |
| S-77 | Het-8 | $CH_3$ | $SO_2$ |
| S-78 | Het-9 | $CH_3$ | $SO_2$ |
| S-79 | Het-10 | $CH_3$ | $SO_2$ |
| S-80 | Het-11 | $CH_3$ | $SO_2$ |
| S-81 | Het-12 | $CH_3$ | $SO_2$ |
| S-82 | Het-13 | $CH_3$ | $SO_2$ |
| S-83 | Het-14 | $CH_3$ | $SO_2$ |
| S-84 | Het-15 | $CH_3$ | $SO_2$ |
| S-85 | Het-16 | $CH_3$ | $SO_2$ |
| S-86 | Het-17 | $CH_3$ | $SO_2$ |
| S-87 | Het-18 | $CH_3$ | $SO_2$ |

TABLE B-continued

| Line | $R^X$ | $R^E$ | Y |
|---|---|---|---|
| S-88 | Het-19 | $CH_3$ | $SO_2$ |
| S-89 | $C(CN)(CH_3)_2$ | $CH_3$ | $SO_2$ |
| S-90 | 1-cyanocyclopropyl | $CH_3$ | $SO_2$ |
| S-91 | S | H | S |
| S-92 | $CF_3$ | H | S |
| S-93 | $OCF_3$ | H | S |
| S-94 | $SO_2OH_2OH_3$ | H | S |
| S-95 | F | H | S |
| S-96 | Br | H | S |
| S-97 | 3-fluorophenyl | H | S |
| S-98 | 4-fluorophenyl | H | S |
| S-99 | 4-chlorophenyl | H | S |
| S-100 | cyclopropyl | H | S |
| S-101 | $OF_3OF_3$ | H | S |
| S-102 | 4-trifluoromethylphenyl | H | S |
| S-103 | 3-trifluoromethylphenyl | H | S |
| S-104 | Het-5 | H | S |
| S-105 | Het-6 | H | S |
| S-106 | Het-7 | H | S |
| S-107 | Het-8 | H | S |
| S-108 | Het-9 | H | S |
| S-109 | Het-10 | H | S |
| S-110 | Het-11 | H | S |
| 5-111 | Het-12 | H | S |
| S-112 | Het-13 | H | S |
| S-113 | Het-14 | H | S |
| S-114 | Het-15 | H | S |
| S-115 | Het-16 | H | S |
| S-116 | Het-17 | H | S |
| S-117 | Het-18 | H | S |
| S-118 | Het-19 | H | S |
| S-119 | $C(CN)(OH_3)_2$ | H | S |
| S-120 | 1-cyanocyclopropyl | H | S |
| S-121 | H | H | SO |
| S-122 | $CF_3$ | H | SO |
| S-123 | $OCF_3$ | H | SO |
| S-124 | $SO_2CH_2CH_3$ | H | SO |
| S-125 | F | H | SO |
| S-126 | Br | H | SO |
| S-127 | 3-fluorophenyl | H | SO |
| S-128 | 4-fluorophenyl | H | SO |
| S-129 | 4-chlorophenyl | H | SO |
| S-130 | cyclopropyl | H | SO |
| S-131 | $CF_3CF_3$ | H | SO |
| S-132 | 4-trifluoromethylphenyl | H | SO |
| S-133 | 3-trifluoromethylphenyl | H | SO |
| S-134 | Het-5 | H | SO |
| S-135 | Het-6 | H | SO |
| S-136 | Het-7 | H | SO |
| S-137 | Het-8 | H | SO |
| S-138 | Het-9 | H | SO |
| S-139 | Het-10 | H | SO |
| S-140 | Het-11 | H | SO |
| S-141 | Het-12 | H | SO |
| S-142 | Het-13 | H | SO |
| S-143 | Het-14 | H | SO |
| S-144 | Het-15 | H | SO |
| S-145 | Het-16 | H | SO |
| S-146 | Het-17 | H | SO |
| S-147 | Het-18 | H | SO |
| S-148 | Het-19 | H | SO |
| S-149 | $C(CN)(OH_3)_2$ | H | SO |
| S-150 | 1-cyanocyclopropyl | H | SO |
| S-151 | H | H | $SO_2$ |
| S-152 | $CF_3$ | H | $SO_2$ |
| S-153 | $OCF_3$ | H | $SO_2$ |
| S-154 | $SO_2OH_2OH_3$ | H | $SO_2$ |
| S-155 | F | H | $SO_2$ |
| S-156 | Br | H | $SO_2$ |
| S-157 | 3-fluorophenyl | H | $SO_2$ |
| S-158 | 4-fluorophenyl | H | $SO_2$ |
| S-159 | 4-chlorophenyl | H | $SO_2$ |
| S-160 | cyclopropyl | H | $SO_2$ |
| S-161 | $OF_3OF_3$ | H | $SO_2$ |
| S-162 | 4-trifluoromethylphenyl | H | $SO_2$ |
| S-163 | 3-trifluoromethylphenyl | H | $SO_2$ |
| S-164 | Het-5 | H | $SO_2$ |
| S-165 | Het-6 | H | $SO_2$ |
| S-166 | Het-7 | H | $SO_2$ |
| S-167 | Het-8 | H | $SO_2$ |
| S-168 | Het-9 | H | $SO_2$ |
| S-169 | Het-10 | H | $SO_2$ |
| S-170 | Het-11 | H | $SO_2$ |
| S-171 | Het-12 | H | $SO_2$ |
| S-172 | Het-13 | H | $SO_2$ |
| S-173 | Het-14 | H | $SO_2$ |
| S-174 | Het-15 | H | $SO_2$ |
| S-175 | Het-16 | H | $SO_2$ |
| S-176 | Het-17 | H | $SO_2$ |
| S-177 | Het-18 | H | $SO_2$ |
| S-178 | Het-19 | H | $SO_2$ |
| S-179 | $C(CN)(CH_3)_2$ | H | S |
| S-180 | 1-cyanocyclopropyl | H | S | assignment of lines S-1 to S-180 to combinations of $R^E$, $R^X$ and Y.

TABLE C

| Line | $R^L$ | $R^M$ | $R^Q$ | $R^T$ | $R^V$ |
|---|---|---|---|---|---|
| T-1 | H | — | H | H | H |
| T-2 | $CF_3$ | — | H | H | H |
| T-3 | $CHF_2$ | — | H | H | H |
| T-4 | $OCF_3$ | — | H | H | H |
| T-5 | $OCHF_2$ | — | H | H | H |
| T-6 | $OCH_2CF_3$ | — | H | H | H |
| T-7 | $OCH_2C_2F_5$ | — | H | H | H |
| T-8 | $CH_3$ | — | H | H | H |
| T-9 | $CH_2CH_3$ | — | H | H | H |
| T-10 | $OCH_3$ | — | H | H | H |
| T-11 | $OCH_2CH_3$ | — | H | H | H |
| T-12 | F | — | H | H | H |
| T-13 | Cl | — | H | H | H |
| T-14 | Br | — | H | H | H |
| T-15 | I | — | H | H | H |
| T-16 | $CF_3$ | — | $CF_3$ | H | H |
| T-17 | $CHF_2$ | — | $CHF_2$ | H | H |
| T-18 | $OCF_3$ | — | $OCF_3$ | H | H |
| T-19 | $OCHF_2$ | — | $OCHF_2$ | H | H |
| T-20 | $OCH_2CF_3$ | — | $OCH_2CF_3$ | H | H |
| T-21 | $OCH_2C_2F_5$ | — | $OCH_2C_2F_5$ | H | H |
| T-22 | $CH_3$ | — | $CH_3$ | H | H |
| T-23 | $CH_2CH_3$ | — | $CH_2CH_3$ | H | H |
| T-24 | $OCH_3$ | — | $OCH_3$ | H | H |
| T-25 | $OCH_2CH_3$ | — | $OCH_2CH_3$ | H | H |
| T-26 | F | — | F | H | H |
| T-27 | Cl | — | Cl | H | H |
| T-28 | Br | — | Br | H | H |
| T-29 | I | — | I | H | H |
| T-30 | $CF_3$ | — | H | $CF_3$ | H |
| T-31 | $CHF_2$ | — | H | $CHF_2$ | H |
| T-32 | $OCF_3$ | — | H | $OCF_3$ | H |
| T-33 | $OCHF_2$ | — | H | $OCHF_2$ | H |
| T-34 | $OCH_2CF_3$ | — | H | $OCH_2CF_3$ | H |
| T-35 | $OCH_2C_2F_5$ | — | H | $OCH_2C_2F_5$ | H |
| T-36 | $CH_3$ | — | H | $CH_3$ | H |
| T-37 | $CH_2CH_3$ | — | H | $CH_2CH_3$ | H |
| T-38 | $OCH_3$ | — | H | $OCH_3$ | H |
| T-39 | $OCH_2CH_3$ | — | H | $OCH_2CH_3$ | H |
| T-40 | F | — | H | F | H |
| T-41 | Cl | — | H | Cl | H |
| T-42 | Br | — | H | Br | H |
| T-43 | I | — | H | I | H |
| T-44 | $CF_3$ | — | H | H | $CF_3$ |
| T-45 | $CHF_2$ | — | H | H | $CHF_2$ |
| T-46 | $OCF_3$ | — | H | H | $OCF_3$ |
| T-47 | $OCHF_2$ | — | H | H | $OCHF_2$ |
| T-48 | $OCH_2OF_3$ | — | H | H | $OCH_2OF_3$ |
| T-49 | $OCH_2O_2F_5$ | — | H | H | $OCH_2O_2F_5$ |
| T-50 | $CH_3$ | — | H | H | $CH_3$ |
| T-51 | $CH_2CH_3$ | — | H | H | $CH_2CH_3$ |
| T-52 | $OCH_3$ | — | H | H | $OCH_3$ |
| T-53 | $OCH_2CH_3$ | — | H | H | $OCH_2CH_3$ |
| T-54 | F | — | H | H | F |

TABLE C-continued

| Line | $R^L$ | $R^M$ | $R^Q$ | $R^T$ | $R^V$ |
|---|---|---|---|---|---|
| T-55 | Cl | — | H | H | Cl |
| T-56 | Br | — | H | H | Br |
| T-57 | I | — | H | H | I |
| T-58 | H | — | $CF_3$ | H | H |
| T-59 | H | — | $CHF_2$ | H | H |
| T-60 | H | — | $OCF_3$ | H | H |
| T-61 | H | — | $OCHF_2$ | H | H |
| T-62 | H | — | $OCH_2CF_3$ | H | H |
| T-63 | H | — | $OCH_2C_2F_5$ | H | H |
| T-64 | H | — | $CH_3$ | H | H |
| T-65 | H | — | $OH_2OH_3$ | H | H |
| T-66 | H | — | $OCH_3$ | H | H |
| T-67 | H | — | $OCH_2OH_3$ | H | H |
| T-68 | H | — | F | H | H |
| T-69 | H | — | Cl | H | H |
| T-70 | H | — | Br | H | H |
| T-71 | H | — | I | H | H |
| T-72 | H | — | $CF_3$ | $CF_3$ | H |
| T-73 | H | — | $CHF_2$ | $CHF_2$ | H |
| T-74 | H | — | $OCF_3$ | $OCF_3$ | H |
| T-75 | H | — | $OCHF_2$ | $OCHF_2$ | H |
| T-76 | H | — | $OCH_2CF_3$ | $OCH_2CF_3$ | H |
| T-77 | H | — | $OCH_2C_2F_5$ | $OCH_2C_2F_5$ | H |
| T-78 | H | — | $CH_3$ | $CH_3$ | H |
| T-79 | H | — | $CH_2CH_3$ | $CH_2CH_3$ | H |
| T-80 | H | — | $OCH_3$ | $OCH_3$ | H |
| T-81 | H | — | $OCH_2CH_3$ | $OCH_2CH_3$ | H |
| T-82 | H | — | F | F | H |
| T-83 | H | — | Cl | Cl | H |
| T-84 | H | — | Br | Br | H |
| T-85 | H | — | I | I | H |
| T-86 | H | — | $CF_3$ | H | $CF_3$ |
| T-87 | H | — | $CHF_2$ | H | $CHF_2$ |
| T-88 | H | — | $OCF_3$ | H | $OCF_3$ |
| T-89 | H | — | $OCHF_2$ | H | $OCHF_2$ |
| T-90 | H | — | $OCH_2OF_3$ | H | $OCH_2OF_3$ |
| T-91 | H | — | $OCH_2O_2F_5$ | H | $OCH_2O_2F_5$ |
| T-92 | H | — | $CH_3$ | H | $CH_3$ |
| T-93 | H | — | $CH_2CH_3$ | H | $CH_2CH_3$ |
| T-94 | H | — | $OCH_3$ | H | $OCH_3$ |
| T-95 | H | — | $OCH_2CH_3$ | H | $OCH_2CH_3$ |
| T-96 | H | — | F | H | F |
| T-97 | H | — | Cl | H | Cl |
| T-98 | H | — | Br | H | Br |
| T-99 | H | — | I | H | I |
| T-100 | H | — | $CF_3$ | H | $CHF_2$ |
| T-101 | H | — | $CF_3$ | H | $OCF_3$ |
| T-102 | H | — | $CF_3$ | H | $OCHF_2$ |
| T-103 | H | — | $CF_3$ | H | $OCH_2CF_3$ |
| T-104 | H | — | $CF_3$ | H | $OCH_2C_2F_5$ |
| T-105 | H | — | $CF_3$ | H | $CH_3$ |
| T-106 | H | — | $CF_3$ | H | $CH_2CH_3$ |
| T-107 | H | — | $CF_3$ | H | $OCH_3$ |
| T-108 | H | — | $CF_3$ | H | $OCH_2OH_3$ |
| T-109 | H | — | $CF_3$ | H | F |
| T-110 | H | — | $CF_3$ | H | Cl |
| T-111 | H | — | $CF_3$ | H | Br |
| T-112 | H | — | $CF_3$ | H | I |
| T-113 | H | — | $CHF_2$ | H | $CF_3$ |
| T-114 | H | — | $CHF_2$ | H | $OCF_3$ |
| T-115 | H | — | $CHF_2$ | H | $OCHF_2$ |
| T-116 | H | — | $CHF_2$ | H | $OCH_2CF_3$ |
| T-117 | H | — | $CHF_2$ | H | $OCH_2C_2F_5$ |
| T-118 | H | — | $CHF_2$ | H | $CH_3$ |
| T-119 | H | — | $CHF_2$ | H | $CH_2CH_3$ |
| T-120 | H | — | $CHF_2$ | H | $OCH_3$ |
| T-121 | H | — | $CHF_2$ | H | $OCH_2CH_3$ |
| T-122 | H | — | $CHF_2$ | H | F |
| T-123 | H | — | $CHF_2$ | H | Cl |
| T-124 | H | — | $CHF_2$ | H | Br |
| T-125 | H | — | $CHF_2$ | H | I |
| T-126 | H | — | $OCF_3$ | H | $CF_3$ |
| T-127 | H | — | $OCF_3$ | H | $CHF_2$ |
| T-128 | H | — | $OCF_3$ | H | $OCHF_2$ |
| T-129 | H | — | $OCF_3$ | H | $OCH_2CF_3$ |
| T-130 | H | — | $OCF_3$ | H | $OCH_2C_2F_5$ |
| T-131 | H | — | $OCF_3$ | H | $CH_3$ |
| T-132 | H | — | $OCF_3$ | H | $OH_2OH_3$ |
| T-133 | H | — | $OCF_3$ | H | $OCH_3$ |
| T-134 | H | — | $OCF_3$ | H | $OCH_2CH_3$ |
| T-135 | H | — | $OCF_3$ | H | F |
| T-136 | H | — | $OCF_3$ | H | Cl |
| T-137 | H | — | $OCF_3$ | H | Br |
| T-138 | H | — | $OCF_3$ | H | I |
| T-139 | H | — | $OCHF_2$ | H | $CF_3$ |
| T-140 | H | — | $OCHF_2$ | H | $CHF_2$ |
| T-141 | H | — | $OCHF_2$ | H | $OCF_3$ |
| T-142 | H | — | $OCHF_2$ | H | $OCH_2OF_3$ |
| T-143 | H | — | $OCHF_2$ | H | $OCH_2O_2F_5$ |
| T-144 | H | — | $OCHF_2$ | H | $CH_3$ |
| T-145 | H | — | $OCHF_2$ | H | $OH_2OH_3$ |
| T-146 | H | — | $OCHF_2$ | H | $OCH_3$ |
| T-147 | H | — | $OCHF_2$ | H | $OCH_2OH_3$ |
| T-148 | H | — | $OCHF_2$ | H | F |
| T-149 | H | — | $OCHF_2$ | H | Cl |
| T-150 | H | — | $OCHF_2$ | H | Br |
| T-151 | H | — | $OCHF_2$ | H | I |
| T-152 | H | — | $OCH_2OF_3$ | H | $CF_3$ |
| T-153 | H | — | $OCH_2CF_3$ | H | $CHF_2$ |
| T-154 | H | — | $OCH_2CF_3$ | H | $OCF_3$ |
| T-155 | H | — | $OCH_2CF_3$ | H | $OCHF_2$ |
| T-156 | H | — | $OCH_2CF_3$ | H | $OCH_2C_2F_5$ |
| T-157 | H | — | $OCH_2CF_3$ | H | $CH_3$ |
| T-158 | H | — | $OCH_2CF_3$ | H | $CH_2CH_3$ |
| T-159 | H | — | $OCH_2CF_3$ | H | $OCH_3$ |
| T-160 | H | — | $OCH_2CF_3$ | H | $OCH_2CH_3$ |
| T-161 | H | — | $OCH_2CF_3$ | H | F |
| T-162 | H | — | $OCH_2CF_3$ | H | Cl |
| T-163 | H | — | $OCH_2CF_3$ | H | Br |
| T-164 | H | — | $OCH_2CF_3$ | H | I |
| T-165 | H | — | $OCH_2C_2F_5$ | H | $CF_3$ |
| T-166 | H | — | $OCH_2C_2F_5$ | H | $CHF_2$ |
| T-167 | H | — | $OCH_2C_2F_5$ | H | $OCF_3$ |
| T-168 | H | — | $OCH_2C_2F_5$ | H | $OCHF_2$ |
| T-169 | H | — | $OCH_2C_2F_5$ | H | $OCH_2CF_3$ |
| T-170 | H | — | $OCH_2C_2F_5$ | H | $CH_3$ |
| T-171 | H | — | $OCH_2C_2F_5$ | H | $OH_2OH_3$ |
| T-172 | H | — | $OCH_2C_2F_5$ | H | $OCH_3$ |
| T-173 | H | — | $OCH_2C_2F_5$ | H | $OCH_2CH_3$ |
| T-174 | H | — | $OCH_2C_2F_5$ | H | F |
| T-175 | H | — | $OCH_2C_2F_5$ | H | Cl |
| T-176 | H | — | $OCH_2C_2F_5$ | H | Br |
| T-177 | H | — | $OCH_2C_2F_5$ | H | I |
| T-178 | H | — | $CH_3$ | H | $CF_3$ |
| T-179 | H | — | $CH_3$ | H | $CHF_2$ |
| T-180 | H | — | $CH_3$ | H | $OCF_3$ |
| T-181 | H | — | $CH_3$ | H | $OCHF_2$ |
| T-182 | H | — | $CH_3$ | H | $OCH_2CF_3$ |
| T-183 | H | — | $CH_3$ | H | $OCH_2C_2F_5$ |
| T-184 | H | — | $CH_3$ | H | $CH_2CH_3$ |
| T-185 | H | — | $CH_3$ | H | $OCH_3$ |
| T-186 | H | — | $CH_3$ | H | $OCH_2CH_3$ |
| T-187 | H | — | $CH_3$ | H | F |
| T-188 | H | — | $CH_3$ | H | Cl |
| T-189 | H | — | $CH_3$ | H | Br |
| T-190 | H | — | $CH_3$ | H | I |
| T-191 | H | — | $OH_2OH_3$ | H | $CF_3$ |
| T-192 | H | — | $OH_2OH_3$ | H | $CHF_2$ |
| T-193 | H | — | $OH_2OH_3$ | H | $OCF_3$ |
| T-194 | H | — | $CH_2CH_3$ | H | $OCHF_2$ |
| T-195 | H | — | $CH_2CH_3$ | H | $OCH_2CF_3$ |
| T-196 | H | — | $CH_2CH_3$ | H | $OCH_2C_2F_5$ |
| T-197 | H | — | $CH_2CH_3$ | H | $CH_3$ |
| T-198 | H | — | $CH_2CH_3$ | H | $OCH_3$ |
| T-199 | H | — | $CH_2CH_3$ | H | $OCH_2CH_3$ |
| T-200 | H | — | $CH_2CH_3$ | H | F |
| T-201 | H | — | $CH_2CH_3$ | H | Cl |
| T-202 | H | — | $CH_2CH_3$ | H | Br |
| T-203 | H | — | $CH_2CH_3$ | H | I |
| T-204 | H | — | $OCH_3$ | H | $CF_3$ |
| T-205 | H | — | $OCH_3$ | H | $CHF_2$ |
| T-206 | H | — | $OCH_3$ | H | $OCF_3$ |
| T-207 | H | — | $OCH_3$ | H | $OCHF_2$ |
| T-208 | H | — | $OCH_3$ | H | $OCH_2CF_3$ |
| T-209 | H | — | $OCH_3$ | H | $OCH_2C_2F_5$ |
| T-210 | H | — | $OCH_3$ | H | $CH_3$ |

TABLE C-continued

| Line | R$^L$ | R$^M$ | R$^Q$ | R$^T$ | R$^V$ |
|---|---|---|---|---|---|
| T-211 | H | — | OCH$_3$ | H | CH$_2$CH$_3$ |
| T-212 | H | — | OCH$_3$ | H | OCH$_2$CH$_3$ |
| T-213 | H | — | OCH$_3$ | H | F |
| T-214 | H | — | OCH$_3$ | H | Cl |
| T-215 | H | — | OCH$_3$ | H | Br |
| T-216 | H | — | OCH$_3$ | H | I |
| T-217 | H | — | OCH$_2$CH$_3$ | H | CF$_3$ |
| T-218 | H | — | OCH$_2$OH$_3$ | H | CHF$_2$ |
| T-219 | H | — | OCH$_2$OH$_3$ | H | OCF$_3$ |
| T-220 | H | — | OCH$_2$OH$_3$ | H | OCHF$_2$ |
| T-221 | H | — | OCH$_2$OH$_3$ | H | OCH$_2$OF$_3$ |
| T-222 | H | — | OCH$_2$OH$_3$ | H | OCH$_2$O$_2$F$_5$ |
| T-223 | H | — | OCH$_2$OH$_3$ | H | CH$_3$ |
| T-224 | H | — | OCH$_2$OH$_3$ | H | OH$_2$OH$_3$ |
| T-225 | H | — | OCH$_2$OH$_3$ | H | OCH$_3$ |
| T-226 | H | — | OCH$_2$OH$_3$ | H | F |
| T-227 | H | — | OCH$_2$OH$_3$ | H | Cl |
| T-228 | H | — | OCH$_2$OH$_3$ | H | Br |
| T-229 | H | — | OCH$_2$OH$_3$ | H | I |
| T-230 | H | — | F | H | CF$_3$ |
| T-231 | H | — | F | H | CHF$_2$ |
| T-232 | H | — | F | H | OCF$_3$ |
| T-233 | H | — | F | H | OCHF$_2$ |
| T-234 | H | — | F | H | OCH$_2$OF$_3$ |
| T-235 | H | — | F | H | OCH$_2$C$_2$F$_5$ |
| T-236 | H | — | F | H | CH$_3$ |
| T-237 | H | — | F | H | CH$_2$CH$_3$ |
| T-238 | H | — | F | H | OCH$_3$ |
| T-239 | H | — | F | H | OCH$_2$CH$_3$ |
| T-240 | H | — | F | H | Cl |
| T-241 | H | — | F | H | Br |
| T-242 | H | — | F | H | I |
| T-243 | H | — | Cl | H | CF$_3$ |
| T-244 | H | — | Cl | H | CHF$_2$ |
| T-245 | H | — | Cl | H | OCF$_3$ |
| T-246 | H | — | Cl | H | OCHF$_2$ |
| T-247 | H | — | Cl | H | OCH$_2$OF$_3$ |
| T-248 | H | — | Cl | H | OCH$_2$O$_2$F$_5$ |
| T-249 | H | — | Cl | H | CH$_3$ |
| T-250 | H | — | Cl | H | OH$_2$OH$_3$ |
| T-251 | H | — | Cl | H | OCH$_3$ |
| T-252 | H | — | Cl | H | OCH$_2$OH$_3$ |
| T-253 | H | — | Cl | H | F |
| T-254 | H | — | Cl | H | Br |
| T-255 | H | — | Cl | H | I |
| T-256 | H | — | Br | H | CF$_3$ |
| T-257 | H | — | Br | H | CHF$_2$ |
| T-258 | H | — | Br | H | OCF$_3$ |
| T-259 | H | — | Br | H | OCHF$_2$ |
| T-260 | H | — | Br | H | OCH$_2$OF$_3$ |
| T-261 | H | — | Br | H | OCH$_2$O$_2$F$_5$ |
| T-262 | H | — | Br | H | CH$_3$ |
| T-263 | H | — | Br | H | OH$_2$OH$_3$ |
| T-264 | H | — | Br | H | OCH$_3$ |
| T-265 | H | — | Br | H | OCH$_2$OH$_3$ |
| T-266 | H | — | Br | H | F |
| T-267 | H | — | Br | H | Cl |
| T-268 | H | — | Br | H | I |
| T-269 | H | — | I | H | CF$_3$ |
| T-270 | H | — | I | H | CHF$_2$ |
| T-271 | H | — | I | H | OCF$_3$ |
| T-272 | H | — | I | H | OCHF$_2$ |
| T-273 | H | — | I | H | OCH$_2$OF$_3$ |
| T-274 | H | — | I | H | OCH$_2$O$_2$F$_5$ |
| T-275 | H | — | I | H | CH$_3$ |
| T-276 | H | — | I | H | CH$_2$CH$_3$ |
| T-277 | H | — | I | H | OCH$_3$ |
| T-278 | H | — | I | H | OCH$_2$CH$_3$ |
| T-279 | H | — | I | H | F |
| T-280 | H | — | I | H | Cl |
| T-281 | H | — | I | H | Br |
| T-282 | H | — | H | CF$_3$ | H |
| T-283 | H | — | H | CHF$_2$ | H |
| T-284 | H | — | H | OCF$_3$ | H |
| T-285 | H | — | H | OCHF$_2$ | H |
| T-286 | H | — | H | OCH$_2$CF$_3$ | H |
| T-287 | H | — | H | OCH$_2$C$_2$F$_5$ | H |
| T-288 | H | — | H | CH$_3$ | H |
| T-289 | H | — | H | CH$_2$CH$_3$ | H |
| T-290 | H | — | H | OCH$_3$ | H |
| T-291 | H | — | H | OCH$_2$CH$_3$ | H |
| T-292 | H | — | H | F | H |
| T-293 | H | — | H | Cl | H |
| T-294 | H | — | H | Br | H |
| T-295 | H | — | H | I | H |
| T-296 | H | — | H | CF$_3$ | CF$_3$ |
| T-297 | H | — | H | CHF$_2$ | CHF$_2$ |
| T-298 | H | — | H | OCF$_3$ | OCF$_3$ |
| T-299 | H | — | H | OCHF$_2$ | OCHF$_2$ |
| T-300 | H | — | H | OCH$_2$CF$_3$ | OCH$_2$CF$_3$ |
| T-301 | H | — | H | OCH$_2$C$_2$F$_5$ | OCH$_2$C$_2$F$_5$ |
| T-302 | H | — | H | CH$_3$ | CH$_3$ |
| T-303 | H | — | H | CH$_2$CH$_3$ | CH$_2$CH$_3$ |
| T-304 | H | — | H | OCH$_3$ | OCH$_3$ |
| T-305 | H | — | H | OCH$_2$CH$_3$ | OCH$_2$CH$_3$ |
| T-306 | H | — | H | F | F |
| T-307 | H | — | H | Cl | Cl |
| T-308 | H | — | H | Br | Br |
| T-309 | H | — | H | I | I |
| T-310 | H | H | — | H | H |
| T-311 | CF$_3$ | H | — | H | H |
| T-312 | CHF$_2$ | H | — | H | H |
| T-313 | OCF$_3$ | H | — | H | H |
| T-314 | OCHF$_2$ | H | — | H | H |
| T-315 | OCH$_2$OF$_3$ | H | — | H | H |
| T-316 | OCH$_2$O$_2$F$_5$ | H | — | H | H |
| T-317 | CH$_3$ | H | — | H | H |
| T-318 | CH$_2$CH$_3$ | H | — | H | H |
| T-319 | OCH$_3$ | H | — | H | H |
| T-320 | OCH$_2$CH$_3$ | H | — | H | H |
| T-321 | F | H | — | H | H |
| T-322 | Cl | H | — | H | H |
| T-323 | Br | H | — | H | H |
| T-324 | I | H | — | H | H |
| T-325 | CF$_3$ | CF$_3$ | — | H | H |
| T-326 | CHF$_2$ | CHF$_2$ | — | H | H |
| T-327 | OCF$_3$ | OCF$_3$ | — | H | H |
| T-328 | OCHF$_2$ | OCHF$_2$ | — | H | H |
| T-329 | OCH$_2$CF$_3$ | OCH$_2$CF$_3$ | — | H | H |
| T-330 | OCH$_2$C$_2$F$_5$ | OCH$_2$C$_2$F$_5$ | — | H | H |
| T-331 | CH$_3$ | CH$_3$ | — | H | H |
| T-332 | CH$_2$CH$_3$ | CH$_2$CH$_3$ | — | H | H |
| T-333 | OCH$_3$ | OCH$_3$ | — | H | H |
| T-334 | OCH$_2$CH$_3$ | OCH$_2$CH$_3$ | — | H | H |
| T-335 | F | F | — | H | H |
| T-336 | Cl | Cl | — | H | H |
| T-337 | Br | Br | — | H | H |
| T-338 | I | I | — | H | H |
| T-339 | CF$_3$ | H | — | CF$_3$ | H |
| T-340 | CHF$_2$ | H | — | CHF$_2$ | H |
| T-341 | OCF$_3$ | H | — | OCF$_3$ | H |
| T-342 | OCHF$_2$ | H | — | OCHF$_2$ | H |
| T-343 | OCH$_2$CF$_3$ | H | — | OCH$_2$CF$_3$ | H |
| T-344 | OCH$_2$C$_2$F$_5$ | H | — | OCH$_2$C$_2$F$_5$ | H |
| T-345 | CH$_3$ | H | — | CH$_3$ | H |
| T-346 | OH$_2$OH$_3$ | H | — | OH$_2$OH$_3$ | H |
| T-347 | OCH$_3$ | H | — | OCH$_3$ | H |
| T-348 | OCH$_2$OH$_3$ | H | — | OCH$_2$OH$_3$ | H |
| T-349 | F | H | — | F | H |
| T-350 | Cl | H | — | Cl | H |
| T-351 | Br | H | — | Br | H |
| T-352 | I | H | — | I | H |
| T-353 | CF$_3$ | H | — | H | CF$_3$ |
| T-354 | CHF$_2$ | H | — | H | CHF$_2$ |
| T-355 | OCF$_3$ | H | — | H | OCF$_3$ |
| T-356 | OCHF$_2$ | H | — | H | OCHF$_2$ |
| T-357 | OCH$_2$OF$_3$ | H | — | H | OCH$_2$OF$_3$ |
| T-358 | OCH$_2$C$_2$F$_5$ | H | — | H | OCH$_2$C$_2$F$_5$ |
| T-359 | CH$_3$ | H | — | H | CH$_3$ |
| T-360 | CH$_2$CH$_3$ | H | — | H | CH$_2$CH$_3$ |
| T-361 | OCH$_3$ | H | — | H | OCH$_3$ |
| T-362 | OCH$_2$CH$_3$ | H | — | H | OCH$_2$CH$_3$ |
| T-363 | F | H | — | H | F |
| T-364 | Cl | H | — | H | Cl |
| T-365 | Br | H | — | H | Br |
| T-366 | I | H | — | H | I |

TABLE C-continued

| Line | $R^L$ | $R^M$ | $R^Q$ | $R^T$ | $R^V$ |
|---|---|---|---|---|---|
| T-367 | H | CF$_3$ | — | H | H |
| T-368 | H | CHF$_2$ | — | H | H |
| T-369 | H | OCF$_3$ | — | H | H |
| T-370 | H | OCHF$_2$ | — | H | H |
| T-371 | H | OCH$_2$CF$_3$ | — | H | H |
| T-372 | H | OCH$_2$C$_2$F$_5$ | — | H | H |
| T-373 | H | CH$_3$ | — | H | H |
| T-374 | H | OH$_2$OH$_3$ | — | H | H |
| T-375 | H | OCH$_3$ | — | H | H |
| T-376 | H | OCH$_2$OH$_3$ | — | H | H |
| T-377 | H | F | — | H | H |
| T-378 | H | Cl | — | H | H |
| T-379 | H | Br | — | H | H |
| T-380 | H | I | — | H | H |
| T-381 | H | CF$_3$ | — | CF$_3$ | H |
| T-382 | H | CHF$_2$ | — | CHF$_2$ | H |
| T-383 | H | OCF$_3$ | — | OCF$_3$ | H |
| T-384 | H | OCHF$_2$ | — | OCHF$_2$ | H |
| T-385 | H | OCH$_2$CF$_3$ | — | OCH$_2$CF$_3$ | H |
| T-386 | H | OCH$_2$C$_2$F$_5$ | — | OCH$_2$C$_2$F$_5$ | H |
| T-387 | H | CH$_3$ | — | CH$_3$ | H |
| T-388 | H | CH$_2$CH$_3$ | — | CH$_2$CH$_3$ | H |
| T-389 | H | OCH$_3$ | — | OCH$_3$ | H |
| T-390 | H | OCH$_2$CH$_3$ | — | OCH$_2$CH$_3$ | H |
| T-391 | H | F | — | F | H |
| T-392 | H | Cl | — | Cl | H |
| T-393 | H | Br | — | Br | H |
| T-394 | H | I | — | I | H |
| T-395 | H | CF$_3$ | — | H | CF$_3$ |
| T-396 | H | CHF$_2$ | — | H | CHF$_2$ |
| T-397 | H | OCF$_3$ | — | H | OCF$_3$ |
| T-398 | H | OCHF$_2$ | — | H | OCHF$_2$ |
| T-399 | H | OCH$_2$CF$_3$ | — | H | OCH$_2$CF$_3$ |
| T-400 | H | OCH$_2$C$_2$F$_5$ | — | H | OCH$_2$C$_2$F$_5$ |
| T-401 | H | CH$_3$ | — | H | CH$_3$ |
| T-402 | H | CH$_2$CH$_3$ | — | H | CH$_2$CH$_3$ |
| T-403 | H | OCH$_3$ | — | H | OCH$_3$ |
| T-404 | H | OCH$_2$CH$_3$ | — | H | OCH$_2$CH$_3$ |
| T-405 | H | F | — | H | F |
| T-406 | H | Cl | — | H | Cl |
| T-407 | H | Br | — | H | Br |
| T-408 | H | I | — | H | I |
| T-409 | H | H | — | CF$_3$ | H |
| T-410 | H | H | — | CHF$_2$ | H |
| T-411 | H | H | — | OCF$_3$ | H |
| T-412 | H | H | — | OCHF$_2$ | H |
| T-413 | H | H | — | OCH$_2$CF$_3$ | H |
| T-414 | H | H | — | OCH$_2$C$_2$F$_5$ | H |
| T-415 | H | H | — | CH$_3$ | H |
| T-416 | H | H | — | OH$_2$OH$_3$ | H |
| T-417 | H | H | — | OCH$_3$ | H |
| T-418 | H | H | — | OCH$_2$OH$_3$ | H |
| T-419 | H | H | — | F | H |
| T-420 | H | H | — | Cl | H |
| T-421 | H | H | — | Br | H |
| T-422 | H | H | — | I | H |
| T-423 | H | H | — | CF$_3$ | CF$_3$ |
| T-424 | H | H | — | CHF$_2$ | CHF$_2$ |
| T-425 | H | H | — | OCF$_3$ | OCF$_3$ |
| T-426 | H | H | — | OCHF$_2$ | OCHF$_2$ |
| T-427 | H | H | — | OCH$_2$CF$_3$ | OCH$_2$CF$_3$ |
| T-428 | H | H | — | OCH$_2$C$_2$F$_5$ | OCH$_2$C$_2$F$_5$ |
| T-429 | H | H | — | CH$_3$ | CH$_3$ |
| T-430 | H | H | — | CH$_2$CH$_3$ | CH$_2$CH$_3$ |
| T-431 | H | H | — | OCH$_3$ | OCH$_3$ |
| T-432 | H | H | — | OCH$_2$CH$_3$ | OCH$_2$CH$_3$ |
| T-433 | H | H | — | F | F |
| T-434 | H | H | — | Cl | Cl |
| T-435 | H | H | — | Br | Br |
| T-436 | H | H | — | I | I |
| T-437 | H | H | H | H | H |
| T-438 | CF$_3$ | H | H | H | H |
| T-439 | CHF$_2$ | H | H | H | H |
| T-440 | OCF$_3$ | H | H | H | H |
| T-441 | OCHF$_2$ | H | H | H | H |
| T-442 | OCH$_2$CF$_3$ | H | H | H | H |
| T-443 | OCH$_2$C$_2$F$_5$ | H | H | H | H |
| T-444 | CH$_3$ | H | H | H | H |
| T-445 | CH$_2$CH$_3$ | H | H | H | H |
| T-446 | OCH$_3$ | H | H | H | H |
| T-447 | OCH$_2$CH$_3$ | H | H | H | H |
| T-448 | F | H | H | H | H |
| T-449 | Cl | H | H | H | H |
| T-450 | Br | H | H | H | H |
| T-451 | I | H | H | H | H |
| T-452 | CF$_3$ | CF$_3$ | H | H | H |
| T-453 | CHF$_2$ | CHF$_2$ | H | H | H |
| T-454 | OCF$_3$ | OCF$_3$ | H | H | H |
| T-455 | OCHF$_2$ | OCHF$_2$ | H | H | H |
| T-456 | OCH$_2$CF$_3$ | OCH$_2$CF$_3$ | H | H | H |
| T-457 | OCH$_2$C$_2$F$_5$ | OCH$_2$C$_2$F$_5$ | H | H | H |
| T-458 | CH$_3$ | CH$_3$ | H | H | H |
| T-459 | CH$_2$CH$_3$ | CH$_2$CH$_3$ | H | H | H |
| T-460 | OCH$_3$ | OCH$_3$ | H | H | H |
| T-461 | OCH$_2$CH$_3$ | OCH$_2$CH$_3$ | H | H | H |
| T-462 | F | F | H | H | H |
| T-463 | Cl | Cl | H | H | H |
| T-464 | Br | Br | H | H | H |
| T-465 | I | I | H | H | H |
| T-466 | CF$_3$ | H | CF$_3$ | H | H |
| T-467 | CHF$_2$ | H | CHF$_2$ | H | H |
| T-468 | OCF$_3$ | H | OCF$_3$ | H | H |
| T-469 | OCHF$_2$ | H | OCHF$_2$ | H | H |
| T-470 | OCH$_2$CF$_3$ | H | OCH$_2$CF$_3$ | H | H |
| T-471 | OCH$_2$C$_2$F$_5$ | H | OCH$_2$C$_2$F$_5$ | H | H |
| T-472 | CH$_3$ | H | CH$_3$ | H | H |
| T-473 | OH$_2$OH$_3$ | H | OH$_2$OH$_3$ | H | H |
| T-474 | OCH$_3$ | H | OCH$_3$ | H | H |
| T-475 | OCH$_2$OH$_3$ | H | OCH$_2$OH$_3$ | H | H |
| T-476 | F | H | F | H | H |
| T-477 | Cl | H | Cl | H | H |
| T-478 | Br | H | Br | H | H |
| T-479 | I | H | I | H | H |
| T-480 | CF$_3$ | H | H | CF$_3$ | H |
| T-481 | CHF$_2$ | H | H | CHF$_2$ | H |
| T-482 | OCF$_3$ | H | H | OCF$_3$ | H |
| T-483 | OCHF$_2$ | H | H | OCHF$_2$ | H |
| T-484 | OCH$_2$CF$_3$ | H | H | OCH$_2$CF$_3$ | H |
| T-485 | OCH$_2$C$_2$F$_5$ | H | H | OCH$_2$C$_2$F$_5$ | H |
| T-486 | CH$_3$ | H | H | CH$_3$ | H |
| T-487 | CH$_2$CH$_3$ | H | H | CH$_2$CH$_3$ | H |
| T-488 | OCH$_3$ | H | H | OCH$_3$ | H |
| T-489 | OCH$_2$CH$_3$ | H | H | OCH$_2$CH$_3$ | H |
| T-490 | F | H | H | F | H |
| T-491 | Cl | H | H | Cl | H |
| T-492 | Br | H | H | Br | H |
| T-493 | I | H | H | I | H |
| T-494 | CF$_3$ | H | H | H | CF$_3$ |
| T-495 | CHF$_2$ | H | H | H | CHF$_2$ |
| T-496 | OCF$_3$ | H | H | H | OCF$_3$ |
| T-497 | OCHF$_2$ | H | H | H | OCHF$_2$ |
| T-498 | OCH$_2$OF$_3$ | H | H | H | OCH$_2$OF$_3$ |
| T-499 | OCH$_2$O$_2$F$_5$ | H | H | H | OCH$_2$O$_2$F$_5$ |
| T-500 | CH$_3$ | H | H | H | CH$_3$ |
| T-501 | CH$_2$CH$_3$ | H | H | H | CH$_2$CH$_3$ |
| T-502 | OCH$_3$ | H | H | H | OCH$_3$ |
| T-503 | OCH$_2$CH$_3$ | H | H | H | OCH$_2$CH$_3$ |
| T-504 | F | H | H | H | F |
| T-505 | Cl | H | H | H | Cl |
| T-506 | Br | H | H | H | Br |
| T-507 | I | H | H | H | I |
| T-508 | H | CF$_3$ | H | H | H |
| T-509 | H | CHF$_2$ | H | H | H |
| T-510 | H | OCF$_3$ | H | H | H |
| T-511 | H | OCHF$_2$ | H | H | H |
| T-512 | H | OCH$_2$CF$_3$ | H | H | H |
| T-513 | H | OCH$_2$C$_2$F$_5$ | H | H | H |
| T-514 | H | CH$_3$ | H | H | H |
| T-515 | H | OH$_2$OH$_3$ | H | H | H |
| T-516 | H | OCH$_3$ | H | H | H |
| T-517 | H | OCH$_2$OH$_3$ | H | H | H |
| T-518 | H | F | H | H | H |
| T-519 | H | Cl | H | H | H |
| T-520 | H | Br | H | H | H |
| T-521 | H | I | H | H | H |
| T-522 | H | CF$_3$ | CF$_3$ | H | H |

TABLE C-continued

| Line | $R^L$ | $R^M$ | $R^Q$ | $R^T$ | $R^V$ |
|---|---|---|---|---|---|
| T-523 | H | CHF$_2$ | CHF$_2$ | H | H |
| T-524 | H | OCF$_3$ | OCF$_3$ | H | H |
| T-525 | H | OCHF$_2$ | OCHF$_2$ | H | H |
| T-526 | H | OCH$_2$CF$_3$ | OCH$_2$CF$_3$ | H | H |
| T-527 | H | OCH$_2$C$_2$F$_5$ | OCH$_2$C$_2$F$_5$ | H | H |
| T-528 | H | CH$_3$ | CH$_3$ | H | H |
| T-529 | H | CH$_2$CH$_3$ | CH$_2$CH$_3$ | H | H |
| T-530 | H | OCH$_3$ | OCH$_3$ | H | H |
| T-531 | H | OCH$_2$CH$_3$ | OCH$_2$CH$_3$ | H | H |
| T-532 | H | F | F | H | H |
| T-533 | H | Cl | Cl | H | H |
| T-534 | H | Br | Br | H | H |
| T-535 | H | I | I | H | H |
| T-536 | H | CF$_3$ | H | CF$_3$ | H |
| T-537 | H | CHF$_2$ | H | CHF$_2$ | H |
| T-538 | H | OCF$_3$ | H | OCF$_3$ | H |
| T-539 | H | OCHF$_2$ | H | OCHF$_2$ | H |
| T-540 | H | OCH$_2$OF$_3$ | H | OCH$_2$OF$_3$ | H |
| T-541 | H | OCH$_2$O$_2$F$_5$ | H | OCH$_2$O$_2$F$_5$ | H |
| T-542 | H | CH$_3$ | H | CH$_3$ | H |
| T-543 | H | OH$_2$OH$_3$ | H | OH$_2$OH$_3$ | H |
| T-544 | H | OCH$_3$ | H | OCH$_3$ | H |
| T-545 | H | OCH$_2$OH$_3$ | H | OCH$_2$OH$_3$ | H |
| T-546 | H | F | H | F | H |
| T-547 | H | Cl | H | Cl | H |
| T-548 | H | Br | H | Br | H |
| T-549 | H | I | H | I | H |
| T-550 | H | CF$_3$ | H | H | CF$_3$ |
| T-551 | H | CHF$_2$ | H | H | CHF$_2$ |
| T-552 | H | OCF$_3$ | H | H | OCF$_3$ |
| T-553 | H | OCHF$_2$ | H | H | OCHF$_2$ |
| T-554 | H | OCH$_2$OF$_3$ | H | H | OCH$_2$OF$_3$ |
| T-555 | H | OCH$_2$O$_2$F$_5$ | H | H | OCH$_2$O$_2$F$_5$ |
| T-556 | H | CH$_3$ | H | H | CH$_3$ |
| T-557 | H | OH$_2$OH$_3$ | H | H | OH$_2$OH$_3$ |
| T-558 | H | OCH$_3$ | H | H | OCH$_3$ |
| T-559 | H | OCH$_2$OH$_3$ | H | H | OCH$_2$OH$_3$ |
| T-560 | H | F | H | H | F |
| T-561 | H | Cl | H | H | Cl |
| T-562 | H | Br | H | H | Br |
| T-563 | H | I | H | H | I |
| T-564 | H | H | CF$_3$ | H | H |
| T-565 | H | H | CHF$_2$ | H | H |
| T-566 | H | H | OCF$_3$ | H | H |
| T-567 | H | H | OCHF$_2$ | H | H |
| T-568 | H | H | OCH$_2$CF$_3$ | H | H |
| T-569 | H | H | OCH$_2$C$_2$F$_5$ | H | H |
| T-570 | H | H | CH$_3$ | H | H |
| T-571 | H | H | CH$_2$CH$_3$ | H | H |
| T-572 | H | H | OCH$_3$ | H | H |
| T-573 | H | H | OCH$_2$CH$_3$ | H | H |
| T-574 | H | H | F | H | H |
| T-575 | H | H | Cl | H | H |
| T-576 | H | H | Br | H | H |
| T-577 | H | H | I | H | H |
| T-578 | H | H | CF$_3$ | CF$_3$ | H |
| T-579 | H | H | CHF$_2$ | CHF$_2$ | H |
| T-580 | H | H | OCF$_3$ | OCF$_3$ | H |
| T-581 | H | H | OCHF$_2$ | OCHF$_2$ | H |
| T-582 | H | H | OCH$_2$CF$_3$ | OCH$_2$CF$_3$ | H |
| T-583 | H | H | OCH$_2$C$_2$F$_5$ | OCH$_2$C$_2$F$_5$ | H |
| T-584 | H | H | CH$_3$ | CH$_3$ | H |
| T-585 | H | H | CH$_2$CH$_3$ | CH$_2$CH$_3$ | H |
| T-586 | H | H | OCH$_3$ | OCH$_3$ | H |
| T-587 | H | H | OCH$_2$CH$_3$ | OCH$_2$CH$_3$ | H |
| T-588 | H | H | F | F | H |
| T-589 | H | H | Cl | Cl | H |
| T-590 | H | H | Br | Br | H |
| T-591 | H | H | I | I | H |
| T-592 | H | H | CF$_3$ | H | CF$_3$ |
| T-593 | H | H | CHF$_2$ | H | CHF$_2$ |
| T-594 | H | H | OCF$_3$ | H | OCF$_3$ |
| T-595 | H | H | OCHF$_2$ | H | OCHF$_2$ |
| T-596 | H | H | OCH$_2$CF$_3$ | H | OCH$_2$CF$_3$ |
| T-597 | H | H | OCH$_2$C$_2$F$_5$ | H | OCH$_2$C$_2$F$_5$ |
| T-598 | H | H | CH$_3$ | H | CH$_3$ |
| T-599 | H | H | OH$_2$OH$_3$ | H | OH$_2$OH$_3$ |
| T-600 | H | H | OCH$_3$ | H | OCH$_3$ |
| T-601 | H | H | OCH$_2$OH$_3$ | H | OCH$_2$OH$_3$ |
| T-602 | H | H | F | H | F |
| T-603 | H | H | Cl | H | Cl |
| T-604 | H | H | Br | H | Br |
| T-605 | H | H | I | H | I |
| T-606 | H | H | CF$_3$ | H | CHF$_2$ |
| T-607 | H | H | CF$_3$ | H | OCF$_3$ |
| T-608 | H | H | CF$_3$ | H | OCHF$_2$ |
| T-609 | H | H | CF$_3$ | H | OCH$_2$CF$_3$ |
| T-610 | H | H | CF$_3$ | H | OCH$_2$C$_2$F$_5$ |
| T-611 | H | H | CF$_3$ | H | CH$_3$ |
| T-612 | H | H | CF$_3$ | H | CH$_2$CH$_3$ |
| T-613 | H | H | CF$_3$ | H | OCH$_3$ |
| T-614 | H | H | CF$_3$ | H | OCH$_2$CH$_3$ |
| T-615 | H | H | CF$_3$ | H | F |
| T-616 | H | H | CF$_3$ | H | Cl |
| T-617 | H | H | CF$_3$ | H | Br |
| T-618 | H | H | CF$_3$ | H | I |
| T-619 | H | H | CHF$_2$ | H | CF$_3$ |
| T-620 | H | H | CHF$_2$ | H | OCF$_3$ |
| T-621 | H | H | CHF$_2$ | H | OCHF$_2$ |
| T-622 | H | H | CHF$_2$ | H | OCH$_2$CF$_3$ |
| T-623 | H | H | CHF$_2$ | H | OCH$_2$C$_2$F$_5$ |
| T-624 | H | H | CHF$_2$ | H | CH$_3$ |
| T-625 | H | H | CHF$_2$ | H | OH$_2$OH$_3$ |
| T-626 | H | H | CHF$_2$ | H | OCH$_3$ |
| T-627 | H | H | CHF$_2$ | H | OCH$_2$OH$_3$ |
| T-628 | H | H | CHF$_2$ | H | F |
| T-629 | H | H | CHF$_2$ | H | Cl |
| T-630 | H | H | CHF$_2$ | H | Br |
| T-631 | H | H | CHF$_2$ | H | I |
| T-632 | H | H | OCF$_3$ | H | CF$_3$ |
| T-633 | H | H | OCF$_3$ | H | CHF$_2$ |
| T-634 | H | H | OCF$_3$ | H | OCHF$_2$ |
| T-635 | H | H | OCF$_3$ | H | OCH$_2$OF$_3$ |
| T-636 | H | H | OCF$_3$ | H | OCH$_2$O$_2$F$_5$ |
| T-637 | H | H | OCF$_3$ | H | CH$_3$ |
| T-638 | H | H | OCF$_3$ | H | OH$_2$OH$_3$ |
| T-639 | H | H | OCF$_3$ | H | OCH$_3$ |
| T-640 | H | H | OCF$_3$ | H | OCH$_2$OH$_3$ |
| T-641 | H | H | OCF$_3$ | H | F |
| T-642 | H | H | OCF$_3$ | H | Cl |
| T-643 | H | H | OCF$_3$ | H | Br |
| T-644 | H | H | OCF$_3$ | H | I |
| T-645 | H | H | OCHF$_2$ | H | CF$_3$ |
| T-646 | H | H | OCHF$_2$ | H | CHF$_2$ |
| T-647 | H | H | OCHF$_2$ | H | OCF$_3$ |
| T-648 | H | H | OCHF$_2$ | H | OCH$_2$CF$_3$ |
| T-649 | H | H | OCHF$_2$ | H | OCH$_2$C$_2$F$_5$ |
| T-650 | H | H | OCHF$_2$ | H | CH$_3$ |
| T-651 | H | H | OCHF$_2$ | H | CH$_2$CH$_3$ |
| T-652 | H | H | OCHF$_2$ | H | OCH$_3$ |
| T-653 | H | H | OCHF$_2$ | H | OCH$_2$CH$_3$ |
| T-654 | H | H | OCHF$_2$ | H | F |
| T-655 | H | H | OCHF$_2$ | H | Cl |
| T-656 | H | H | OCHF$_2$ | H | Br |
| T-657 | H | H | OCHF$_2$ | H | I |
| T-658 | H | H | OCH$_2$CF$_3$ | H | CF$_3$ |
| T-659 | H | H | OCH$_2$CF$_3$ | H | CHF$_2$ |
| T-660 | H | H | OCH$_2$CF$_3$ | H | OCF$_3$ |
| T-661 | H | H | OCH$_2$CF$_3$ | H | OCHF$_2$ |
| T-662 | H | H | OCH$_2$CF$_3$ | H | OCH$_2$C$_2$F$_5$ |
| T-663 | H | H | OCH$_2$CF$_3$ | H | CH$_3$ |
| T-664 | H | H | OCH$_2$CF$_3$ | H | OH$_2$OH$_3$ |
| T-665 | H | H | OCH$_2$CF$_3$ | H | OCH$_3$ |
| T-666 | H | H | OCH$_2$CF$_3$ | H | OCH$_2$CH$_3$ |
| T-667 | H | H | OCH$_2$CF$_3$ | H | F |
| T-668 | H | H | OCH$_2$CF$_3$ | H | Cl |
| T-669 | H | H | OCH$_2$CF$_3$ | H | Br |
| T-670 | H | H | OCH$_2$CF$_3$ | H | I |
| T-671 | H | H | OCH$_2$C$_2$F$_5$ | H | CF$_3$ |
| T-672 | H | H | OCH$_2$O$_2$F$_5$ | H | CHF$_2$ |
| T-673 | H | H | OCH$_2$O$_2$F$_5$ | H | OCF$_3$ |
| T-674 | H | H | OCH$_2$O$_2$F$_5$ | H | OCHF$_2$ |
| T-675 | H | H | OCH$_2$O$_2$F$_5$ | H | OCH$_2$OF$_3$ |
| T-676 | H | H | OCH$_2$O$_2$F$_5$ | H | CH$_3$ |
| T-677 | H | H | OCH$_2$O$_2$F$_5$ | H | OH$_2$OH$_3$ |
| T-678 | H | H | OCH$_2$O$_2$F$_5$ | H | OCH$_3$ |

TABLE C-continued

| Line | $R^L$ | $R^M$ | $R^Q$ | $R^T$ | $R^V$ |
|---|---|---|---|---|---|
| T-679 | H | H | $OCH_2O_2F_5$ | H | $OCH_2OH_3$ |
| T-680 | H | H | $OCH_2O_2F_5$ | H | F |
| T-681 | H | H | $OCH_2O_2F_5$ | H | Cl |
| T-682 | H | H | $OCH_2O_2F_5$ | H | Br |
| T-683 | H | H | $OCH_2O_2F_5$ | H | I |
| T-684 | H | H | $CH_3$ | H | $CF_3$ |
| T-685 | H | H | $CH_3$ | H | $CHF_2$ |
| T-686 | H | H | $CH_3$ | H | $OCF_3$ |
| T-687 | H | H | $CH_3$ | H | $OCHF_2$ |
| T-688 | H | H | $CH_3$ | H | $OCH_2CF_3$ |
| T-689 | H | H | $CH_3$ | H | $OCH_2C_2F_5$ |
| T-690 | H | H | $CH_3$ | H | $CH_2CH_3$ |
| T-691 | H | H | $CH_3$ | H | $OCH_3$ |
| T-692 | H | H | $CH_3$ | H | $OCH_2CH_3$ |
| T-693 | H | H | $CH_3$ | H | F |
| T-694 | H | H | $CH_3$ | H | Cl |
| T-695 | H | H | $CH_3$ | H | Br |
| T-696 | H | H | $CH_3$ | H | I |
| T-697 | H | H | $CH_2CH_3$ | H | $CF_3$ |
| T-698 | H | H | $CH_2CH_3$ | H | $CHF_2$ |
| T-699 | H | H | $CH_2CH_3$ | H | $OCF_3$ |
| T-700 | H | H | $CH_2CH_3$ | H | $OCHF_2$ |
| T-701 | H | H | $OH_2OH_3$ | H | $OCH_2OF_3$ |
| T-702 | H | H | $OH_2OH_3$ | H | $OCH_2O_2F_5$ |
| T-703 | H | H | $OH_2OH_3$ | H | $CH_3$ |
| T-704 | H | H | $OH_2OH_3$ | H | $OCH_3$ |
| T-705 | H | H | $OH_2OH_3$ | H | $OCH_2OH_3$ |
| T-706 | H | H | $OH_2OH_3$ | H | F |
| T-707 | H | H | $OH_2OH_3$ | H | Cl |
| T-708 | H | H | $OH_2OH_3$ | H | Br |
| T-709 | H | H | $OH_2OH_3$ | H | I |
| T-710 | H | H | $OCH_3$ | H | $CF_3$ |
| T-711 | H | H | $OCH_3$ | H | $CHF_2$ |
| T-712 | H | H | $OCH_3$ | H | $OCF_3$ |
| T-713 | H | H | $OCH_3$ | H | $OCHF_2$ |
| T-714 | H | H | $OCH_3$ | H | $OCH_2OF_3$ |
| T-715 | H | H | $OCH_3$ | H | $OCH_2O_2F_5$ |
| T-716 | H | H | $OCH_3$ | H | $CH_3$ |
| T-717 | H | H | $OCH_3$ | H | $OH_2OH_3$ |
| T-718 | H | H | $OCH_3$ | H | $OCH_2OH_3$ |
| T-719 | H | H | $OCH_3$ | H | F |
| T-720 | H | H | $OCH_3$ | H | Cl |
| T-721 | H | H | $OCH_3$ | H | Br |
| T-722 | H | H | $OCH_3$ | H | I |
| T-723 | H | H | $OCH_2OH_3$ | H | $CF_3$ |
| T-724 | H | H | $OCH_2OH_3$ | H | $CHF_2$ |
| T-725 | H | H | $OCH_2OH_3$ | H | $OCF_3$ |
| T-726 | H | H | $OCH_2OH_3$ | H | $OCHF_2$ |
| T-727 | H | H | $OCH_2CH_3$ | H | $OCH_2CF_3$ |
| T-728 | H | H | $OCH_2CH_3$ | H | $OCH_2C_2F_5$ |
| T-729 | H | H | $OCH_2CH_3$ | H | $CH_3$ |
| T-730 | H | H | $OCH_2CH_3$ | H | $CH_2CH_3$ |
| T-731 | H | H | $OCH_2CH_3$ | H | $OCH_3$ |
| T-732 | H | H | $OCH_2CH_3$ | H | F |
| T-733 | H | H | $OCH_2CH_3$ | H | Cl |
| T-734 | H | H | $OCH_2CH_3$ | H | Br |
| T-735 | H | H | $OCH_2CH_3$ | H | I |
| T-736 | H | H | F | H | $CF_3$ |
| T-737 | H | H | F | H | $CHF_2$ |
| T-738 | H | H | F | H | $OCF_3$ |
| T-739 | H | H | F | H | $OCHF_2$ |
| T-740 | H | H | F | H | $OCH_2CF_3$ |
| T-741 | H | H | F | H | $OCH_2C_2F_5$ |
| T-742 | H | H | F | H | $CH_3$ |
| T-743 | H | H | F | H | $CH_2CH_3$ |
| T-744 | H | H | F | H | $OCH_3$ |
| T-745 | H | H | F | H | $OCH_2CH_3$ |
| T-746 | H | H | F | H | Cl |
| T-747 | H | H | F | H | Br |
| T-748 | H | H | F | H | I |
| T-749 | H | H | Cl | H | $CF_3$ |
| T-750 | H | H | Cl | H | $CHF_2$ |
| T-751 | H | H | Cl | H | $OCF_3$ |
| T-752 | H | H | Cl | H | $OCHF_2$ |
| T-753 | H | H | Cl | H | $OCH_2OF_3$ |
| T-754 | H | H | Cl | H | $OCH_2O_2F_5$ |
| T-755 | H | H | Cl | H | $CH_3$ |
| T-756 | H | H | Cl | H | $OH_2OH_3$ |
| T-757 | H | H | Cl | H | $OCH_3$ |
| T-758 | H | H | Cl | H | $OCH_2OH_3$ |
| T-759 | H | H | Cl | H | F |
| T-760 | H | H | Cl | H | Br |
| T-761 | H | H | Cl | H | I |
| T-762 | H | H | Br | H | $CF_3$ |
| T-763 | H | H | Br | H | $CHF_2$ |
| T-764 | H | H | Br | H | $OCF_3$ |
| T-765 | H | H | Br | H | $OCHF_2$ |
| T-766 | H | H | Br | H | $OCH_2OF_3$ |
| T-767 | H | H | Br | H | $OCH_2O_2F_5$ |
| T-768 | H | H | Br | H | $CH_3$ |
| T-769 | H | H | Br | H | $CH_2CH_3$ |
| T-770 | H | H | Br | H | $OCH_3$ |
| T-771 | H | H | Br | H | $OCH_2CH_3$ |
| T-772 | H | H | Br | H | F |
| T-773 | H | H | Br | H | Cl |
| T-774 | H | H | Br | H | I |
| T-775 | H | H | I | H | $CF_3$ |
| T-776 | H | H | I | H | $CHF_2$ |
| T-777 | H | H | I | H | $OCF_3$ |
| T-778 | H | H | I | H | $OCHF_2$ |
| T-779 | H | H | I | H | $OCH_2CF_3$ |
| T-780 | H | H | I | H | $OCH_2C_2F_5$ |
| T-781 | H | H | I | H | $CH_3$ |
| T-782 | H | H | I | H | $CH_2CH_3$ |
| T-783 | H | H | I | H | $OCH_3$ |
| T-784 | H | H | I | H | $OCH_2CH_3$ |
| T-785 | H | H | I | H | F |
| T-786 | H | H | I | H | Cl |
| T-787 | H | H | I | H | Br |
| T-788 | H | H | H | $CF_3$ | H |
| T-789 | H | H | H | $CHF_2$ | H |
| T-790 | H | H | H | $OCF_3$ | H |
| T-791 | H | H | H | $OCHF_2$ | H |
| T-792 | H | H | H | $OCH_2OF_3$ | H |
| T-793 | H | H | H | $OCH_2O_2F_5$ | H |
| T-794 | H | H | H | $CH_3$ | H |
| T-795 | H | H | H | $OH_2OH_3$ | H |
| T-796 | H | H | H | $OCH_3$ | H |
| T-797 | H | H | H | $OCH_2OH_3$ | H |
| T-798 | H | H | H | F | H |
| T-799 | H | H | H | Cl | H |
| T-800 | H | H | H | Br | H |
| T-801 | H | H | H | I | H |
| T-802 | H | H | H | $CF_3$ | $CF_3$ |
| T-803 | H | H | H | $CHF_2$ | $CHF_2$ |
| T-804 | H | H | H | $OCF_3$ | $OCF_3$ |
| T-805 | H | H | H | $OCHF_2$ | $OCHF_2$ |
| T-806 | H | H | H | $OCH_2CF_3$ | $OCH_2CF_3$ |
| T-807 | H | H | H | $OCH_2C_2F_5$ | $OCH_2C_2F_5$ |
| T-808 | H | H | H | $CH_3$ | $CH_3$ |
| T-809 | H | H | H | $CH_2CH_3$ | $CH_2CH_3$ |
| T-810 | H | H | H | $OCH_3$ | $OCH_3$ |
| T-811 | H | H | H | $OCH_2CH_3$ | $OCH_2CH_3$ |
| T-812 | H | H | H | F | F |
| T-813 | H | H | H | Cl | Cl |
| T-814 | H | H | H | Br | Br |
| T-815 | H | H | H | I | I | assignment of lines T-1 to T-815 to combinations of $R^L$, $R^M$, $R^Q$, $R^T$ and $R^V$.

In one embodiment, the compounds of formula (I) are compounds of formula (IA), (IB), (IC), or (ID) wherein $R^E$, $R^L$, $R^M$, $R^Q$, $R^T$, $R^V$ are independently H; or
  $C_1$-$C_3$-alkyl, $C_1$-$C_3$-alkoxy, $C_2$-$C_3$-alkenyl, $C_2$-$C_3$-alkynyl, which groups are unhalogenated or halogenated;
$R^X$ is halogen;
  $C_1$-$C_3$-alkyl, $C_1$-$C_3$-alkoxy, $C_2$-$C_4$-alkenyl, $C_2$-$C_3$-alkynyl, $C_3$-$C_5$-cycloalkyl, which groups are unhalogenated or halogenated;
  $C_1$-$C_3$-alkyl-S(O)$_m$, which group is halogenated or non-halogenated;
  phenyl, which is unsubstituted or substituted with halogen, $C_1$-$C_3$-alkyl, or $C_1$-$C_3$-haloalkyl; a 5- or 6-membered saturated, partially unsaturated, or fully saturated heterocyclic ring, wherein said heterocyclic ring comprises one or more, same or different heteroatoms O, N, or S and is unsubstituted or substituted with one or more, same or different groups selected from $C_1$-$C_3$-alkyl, $C_1$-$C_3$-haloalkyl, $C_1$-$C_3$-alkoxycarbonyl, $C_1$-$C_3$-haloalkoxycarbonyl;

$R^Y$ is $C_1$-$C_3$-alkyl, which is unhalogenated or halogenated.

X is phenyl, or a 5- or 6-membered hetaryl;

Y is S, SO, or $SO_2$ m is 0, 1, or 2;

n is 0 or 1.

In one embodiment, the compounds of formula (I) are compounds of formula (IA), (IB), (IC), or (ID) wherein $R^E$ is H or $C_1$-$C_3$-alkyl;

$R^L$, $R^M$, $R^Q$, $R^T$, $R^V$ are independently H; or
$C_1$-$C_3$-haloalkyl, $C_1$-$C_3$-haloalkoxy;

$R^X$ is halogen;
$C_1$-$C_3$-alkyl, $C_1$-$C_3$-alkoxy, $C_2$-$C_4$-alkenyl, $C_2$-$C_3$-alkynyl, $C_3$-$C_5$-cycloalkyl, which groups are unhalogenated or halogenated;
$C_1$-$C_3$-alkyl-S(O)$_m$;
phenyl, which is unsubstituted or substituted with halogen, $C_1$-$C_3$-alkyl, or $C_1$-$C_3$-haloalkyl; a 5-membered saturated, partially unsaturated, or fully saturated heterocyclic ring, wherein said heterocyclic ring comprises one or more, same or different heteroatoms O, N, or S and is unsubstituted or substituted with one or more, same or different groups selected from $C_1$-$C_3$-alkyl, $C_1$-$C_3$-haloalkyl, $C_1$-$C_3$-alkoxycarbonyl, $C_1$-$C_3$-haloalkoxycarbonyl;

$R^Y$ is $C_1$-$C_3$-alkyl, which is unhalogenated or halogenated.

X is phenyl, or a 5- or 6-membered hetaryl;

Y is S, SO, or $SO_2$, m is 0, 1, or 2;

n is 0 or 1.

In one embodiment, the compounds of formula (I) are compounds of formula (IA), (IB), (IC), or (ID) wherein $R^E$ is H or $C_1$-$C_3$-alkyl;

$R^L$, $R^M$, $R^Q$, $R^T$, $R^V$ are independently H; or
$C_1$-$C_3$-haloalkyl, $C_1$-$C_3$-haloalkoxy;

$R^X$ is halogen;
$C_1$-$C_3$-alkyl, or $C_1$-$C_3$-haloalkyl;
$C_1$-$C_3$-alkyl-S(O)$_m$;
phenyl, which is unsubstituted or substituted with halogen;

$R^Y$ is $C_1$-$C_3$-alkyl;

X is a 6-membered hetaryl, preferably pyridyl, more preferably 2-pyridyl;

Y is S, SO, or $SO_2$.

In one embodiment, the compounds of formula (I) are compounds of formula (IA) wherein $R^E$ is H or $C_1$-$C_3$-alkyl, preferably $C_1$-$C_3$-alkyl;

$R^L$, $R^Q$, $R^T$, $R^V$ are independently H; or
$C_1$-$C_3$-haloalkyl, $C_1$-$C_3$-haloalkoxy;

$R^X$ is halogen, preferably F;
$C_1$-$C_3$-alkyl-S(O)$_m$;
$C_1$-$C_3$-alkyl, or $C_1$-$C_3$-haloalkyl, preferably $C_1$-$C_3$-haloalkyl;

$R^Y$ is $C_1$-$C_3$-alkyl, preferably ethyl;

X is a 6-membered hetaryl, preferably pyridyl, more preferably 2-pyridyl;

Y is S, SO, or $SO_2$, preferably S or $SO_2$.

In one embodiment, the compounds of formula (I) are compounds of formula (I) wherein $R^E$, $R^L$, $R^M$, $R^Q$, $R^T$, $R^V$ are independently H, halogen; or
$C_1$-$C_3$-alkyl, $C_1$-$C_3$-alkoxy, $C_2$-$C_3$-alkenyl, $C_2$-$C_3$-alkynyl, which groups are unhalogenated or halogenated;

$R^X$ is halogen;
$C_1$-$C_3$-alkyl, $C_1$-$C_3$-alkoxy, $C_2$-$C_4$-alkenyl, $C_2$-$C_3$-alkynyl, $C_3$-$C_5$-cycloalkyl, which groups are unhalogenated or halogenated;
$C_1$-$C_3$-alkyl-S(O)$_m$, which group is halogenated or nonhalogenated;
$C_3$-$C_6$-cycloalkyl, which is substituted with CN, $NH_2$, C(=O)H, OH, $C_3$-$C_6$-cycloalkyl, C(=O)OH, or C(=O)$NH_2$;
C(CN)$R^7R^8$, wherein $R^7$, $R^8$ are independently selected from H, halogen, CN, $C_1$-$C_6$-alkyl, $C_1$-$C_6$-haloalkyl, and $C_1$-$C_4$-alkoxy;
phenyl, which is unsubstituted or substituted with halogen, $C_1$-$C_3$-alkyl, or $C_1$-$C_3$-haloalkyl;
a 5- or 6-membered saturated, partially unsaturated, or fully saturated heterocyclic ring, wherein said heterocyclic ring comprises one or more, same or different heteroatoms O, N, or S and is unsubstituted or substituted with one or more, same or different groups selected from $C_1$-$C_3$-alkyl, $C_1$-$C_3$-haloalkyl, $C_1$-$C_3$-alkoxycarbonyl, $C_1$-$C_3$-haloalkoxycarbonyl;

$R^Y$ is $C_1$-$C_3$-alkyl, which is unhalogenated or halogenated.

X is phenyl, or a 5- or 6-membered hetaryl;

Y is S, SO, or $SO_2$ m is 0, 1, or 2;

n is 0 or 1.

In one embodiment, the compounds of formula (I) are compounds of formula (I) wherein $R^E$ is H or $C_1$-$C_3$-alkyl;

$R^L$, $R^M$, $R^Q$, $R^T$, $R^V$ are independently H, halogen; or
$C_1$-$C_3$-alkyl, $C_1$-$C_3$-alkoxy, $C_1$-$C_3$-haloalkyl, $C_1$-$C_3$-haloalkoxy;

$R^X$ is halogen;
$C_1$-$C_3$-alkyl, $C_1$-$C_3$-alkoxy, $C_2$-$C_4$-alkenyl, $C_2$-$C_3$-alkynyl, $C_3$-$C_5$-cycloalkyl, which groups are unhalogenated or halogenated;
$C_1$-$C_3$-alkyl-S(O)$_m$;
$C_3$-$C_6$-cycloalkyl, which is substituted with CN;
C(CN)$R^7R^8$, wherein $R^7$, $R^8$ are independently selected $C_1$-$C_6$-alkyl;
phenyl, which is unsubstituted or substituted with halogen, $C_1$-$C_3$-alkyl, or $C_1$-$C_3$-haloalkyl;
a 5-membered saturated, partially unsaturated, or fully saturated heterocyclic ring, wherein said heterocyclic ring comprises one or more, same or different heteroatoms O, N, or S and is unsubstituted or substituted with one or more, same or different groups selected from $C_1$-$C_3$-alkyl, $C_1$-$C_3$-haloalkyl, $C_1$-$C_3$-alkoxycarbonyl, $C_1$-$C_3$-haloalkoxycarbonyl;

$R^Y$ is $C_1$-$C_3$-alkyl, which is unhalogenated or halogenated.

X is phenyl, or a 5- or 6-membered hetaryl;

Y is S, SO, or $SO_2$, m is 0, 1, or 2;

n is 0 or 1.

In one embodiment, the compounds of formula (I) are compounds of formula (IA), (IB), (IC), (IT), or (IY) wherein $R^E$ is H or $C_1$-$C_3$-alkyl;

$R^L$, $R^M$, $R^Q$, $R^T$, $R^V$ are independently H, halogen; or
$C_1$-$C_3$-haloalkyl, $C_1$-$C_3$-haloalkoxy;

$R^X$ is halogen;
$C_1$-$C_3$-alkyl, or $C_1$-$C_3$-haloalkyl;
$C_1$-$C_3$-alkyl-S(O)$_m$;
phenyl, which is unsubstituted or substituted with halogen;

cyclopropyl, which is substituted with CN;
isopropyl, which is substituted with CN;
$R^Y$ is $C_1$-$C_3$-alkyl;
X is a 6-membered hetaryl, preferably pyridyl or pyrimidyl, more preferably 2-pyridyl or 2,4-pyrimidyl;
Y is S, SO, or $SO_2$.

In one embodiment, the compounds of formula (I) are compounds of formulae (IA), (IB), (IC), (IT), or (IY) wherein
$R^E$ is H or $C_1$-$C_3$-alkyl;
$R^L$, $R^Q$, $R^T$, $R^V$ are independently H; or
$C_1$-$C_3$-haloalkyl, $C_1$-$C_3$-haloalkoxy;
$R^X$ is halogen, preferably Br;
$C_1$-$C_3$-alkyl-$S(O)_m$;
1-CN-isopropyl, $C_1$-$C_3$-alkyl, or $C_1$-$C_3$-haloalkyl, preferably $C_1$-$C_3$-haloalkyl; phenyl, which is unsubstituted or substituted with halogen;
$R^Y$ is $C_1$-$C_3$-alkyl, preferably ethyl;
X is a 6-membered hetaryl, preferably pyridyl or pyrimidyl, more preferably 2-pyridyl or 2,4-pyrimidyl;
Y is S, SO, or $SO_2$, preferably S or $SO_2$.

Examples of preferred meanings for variables Y, $R^X$, $R^E$, $R^L$, $R^Q$, $R^M$, $R^V$, and $R^T$ are compiled in Tables 1 to 540 below by referring to the meanings of $R^X$, Y, and $R^E$ in a line S-1 to S-180 in Table B and the meanings or $R^L$, $R^M$, $R^Q$, $R^V$ and $R^T$ in lines T-1 to T-815 in Table C.

Table-1: line S-1 and a line selected from T-1 to T-309. Table 2: line S-2 and a line selected from T-1 to T-309. Table 3: line S-3 and a line selected from T-1 to T-309. Table 4: line S-4 and a line selected from T-1 to T-309. Table 5: line S-5 and a line selected from T-1 to T-309. Table 6: line S-6 and a line selected from T-1 to T-309. Table 7: line S-7 and a line selected from T-1 to T-309. Table 8: line S-8 and a line selected from T-1 to T-309. Table 9: line S-9 and a line selected from T-1 to T-309. Table 10: line S-10 and a line selected from T-1 to T-309. Table 11: line S-11 and a line selected from T-1 to T-309. Table 12: line S-12 and a line selected from T-1 to T-309. Table 13: line S-13 and a line selected from T-1 to T-309. Table 14: line S-14 and a line selected from T-1 to T-309. Table 15: line S-15 and a line selected from T-1 to T-309. Table 16: line S-16 and a line selected from T-1 to T-309. Table 17: line S-17 and a line selected from T-1 to T-309. Table 18: line S-18 and a line selected from T-1 to T-309. Table 19: line S-19 and a line selected from T-1 to T-309. Table 20: line S-20 and a line selected from T-1 to T-309. Table 21: line S-21 and a line selected from T-1 to T-309. Table 22: line S-22 and a line selected from T-1 to T-309. Table 23: line S-23 and a line selected from T-1 to T-309. Table 24: line S-24 and a line selected from T-1 to T-309. Table 25: line S-25 and a line selected from T-1 to T-309. Table 26: line S-26 and a line selected from T-1 to T-309. Table 27: line S-27 and a line selected from T-1 to T-309. Table 28: line S-28 and a line selected from T-1 to T-309. Table 29: line S-29 and a line selected from T-1 to T-309. Table 30: line S-30 and a line selected from T-1 to T-309. Table 31: line S-31 and a line selected from T-1 to T-309. Table 32: line S-32 and a line selected from T-1 to T-309. Table 33: line S-33 and a line selected from T-1 to T-309. Table 34: line S-34 and a line selected from T-1 to T-309. Table 35: line S-35 and a line selected from T-1 to T-309. Table 36: line S-36 and a line selected from T-1 to T-309. Table 37: line S-37 and a line selected from T-1 to T-309. Table 38: line S-38 and a line selected from T-1 to T-309. Table 39: line S-39 and a line selected from T-1 to T-309. Table 40: line S-40 and a line selected from T-1 to T-309. Table 41: line S-41 and a line selected from T-1 to T-309. Table 42: line S-42 and a line selected from T-1 to T-309. Table 43: line S-43 and a line selected from T-1 to T-309. Table 44: line S-44 and a line selected from T-1 to T-309. Table 45: line S-45 and a line selected from T-1 to T-309. Table 46: line S-46 and a line selected from T-1 to T-309. Table 47: line S-47 and a line selected from T-1 to T-309. Table 48: line S-48 and a line selected from T-1 to T-309. Table 49: line S-49 and a line selected from T-1 to T-309. Table 50: line S-50 and a line selected from T-1 to T-309. Table 51: line S-51 and a line selected from T-1 to T-309. Table 52: line S-52 and a line selected from T-1 to T-309. Table 53: line S-53 and a line selected from T-1 to T-309. Table 54: line S-54 and a line selected from T-1 to T-309. Table 55: line S-55 and a line selected from T-1 to T-309. Table 56: line S-56 and a line selected from T-1 to T-309. Table 57: line S-57 and a line selected from T-1 to T-309. Table 58: line S-58 and a line selected from T-1 to T-309. Table 59: line S-59 and a line selected from T-1 to T-309. Table 60: line S-60 and a line selected from T-1 to T-309. Table 61: line S-61 and a line selected from T-1 to T-309. Table 62: line S-62 and a line selected from T-1 to T-309. Table 63: line S-63 and a line selected from T-1 to T-309. Table 64: line S-64 and a line selected from T-1 to T-309. Table 65: line S-65 and a line selected from T-1 to T-309. Table 66: line S-66 and a line selected from T-1 to T-309. Table 67: line S-67 and a line selected from T-1 to T-309. Table 68: line S-68 and a line selected from T-1 to T-309. Table 69: line S-69 and a line selected from T-1 to T-309. Table 70: line S-70 and a line selected from T-1 to T-309. Table 71: line S-71 and a line selected from T-1 to T-309. Table 72: line S-72 and a line selected from T-1 to T-309. Table 73: line S-73 and a line selected from T-1 to T-309. Table 74: line S-74 and a line selected from T-1 to T-309. Table 75: line S-75 and a line selected from T-1 to T-309. Table 76: line S-76 and a line selected from T-1 to T-309. Table 77: line S-77 and a line selected from T-1 to T-309. Table 77: line S-78 and a line selected from T-1 to T-309. Table 79: line S-79 and a line selected from T-1 to T-309. Table 80: line S-80 and a line selected from T-1 to T-309. Table 81: line S-81 and a line selected from T-1 to T-309. Table 82: line S-82 and a line selected from T-1 to T-309. Table 83: line S-83 and a line selected from T-1 to T-309. Table 84: line S-84 and a line selected from T-1 to T-309. Table 85: line S-85 and a line selected from T-1 to T-309. Table 86: line S-86 and a line selected from T-1 to T-309. Table 87: line S-87 and a line selected from T-1 to T-309. Table 88: line S-88 and a line selected from T-1 to T-309. Table 89: line S-89 and a line selected from T-1 to T-309. Table 90: line S-90 and a line selected from T-1 to T-309. Table 91: line S-91 and a line selected from T-1 to T-309. Table 92: line S-92 and a line selected from T-1 to T-309. Table 93: line S-93 and a line selected from T-1 to T-309. Table 94: line S-94 and a line selected from T-1 to T-309. Table 95: line S-95 and a line selected from T-1 to T-309. Table 96: line S-96 and a line selected from T-1 to T-309. Table 97: line S-97 and a line selected from T-1 to T-309. Table 98: line S-98 and a line selected from T-1 to T-309. Table 99: line S-99 and a line selected from T-1 to T-309. Table 100: line S-100 and a line selected from T-1 to T-309. Table 101: line S-101 and a line selected from T-1 to T-309. Table 102: line S-102 and a line selected from T-1 to T-309. Table 103: line S-103 and a line selected from T-1 to T-309. Table 104: line S-104 and a line selected from T-1 to T-309. Table 105: line S-105 and a line selected from T-1 to T-309. Table 106: line S-106 and a line selected from T-1 to T-309. Table 107: line S-107 and a line selected from T-1 to T-309. Table 108: line S-108 and a line selected from T-1 to T-309. Table 109: line S-109 and a line selected from T-1 to T-309. Table 110: line S-110 and a line selected from T-1 to T-309. Table 111: line S-111 and a line selected from T-1 to T-309. Table 112: line S-112 and a line selected from T-1 to T-309. Table-113: line S-113 and a line selected from T-1 to T-309. Table 114: line S-114 and a line selected from T-1 to T-309. Table 115: line S-115 and a line selected from T-1 to T-309. Table 116: line S-116 and a line selected from T-1 to T-309. Table 117: line S-117 and a line selected from T-1 to T-309. Table 117: line S-118 and a line selected from T-1 to T-309. Table 119: line S-119 and a line selected from T-1 to T-309. Table 120: line S-120 and a line selected from T-1 to T-309. Table 121: line S-121 and a line selected from T-1 to T-309. Table 122: line S-122 and a line selected from T-1 to T-309. Table 123: line S-123 and a line selected from T-1 to T-309. Table 124: line S-124 and a line selected from T-1 to T-309. Table 125: line S-125 and a line selected from T-1 to T-309. Table 126: line S-126 and a line selected from T-1 to T-309. Table 127: line S-127 and a line selected from T-1 to T-309. Table 128: line S-128 and a line selected from T-1 to T-309. Table 129: line S-129 and a line selected from T-1 to T-309. Table 130: line S-130 and a line selected from T-1 to T-309. Table 131: line S-131 and a line selected from T-1 to T-309. Table 132: line S-132 and a line selected from T-1 to T-309. Table 134: line S-134 and a line selected from T-1 to T-309. Table 135: line S-135 and a line selected from T-1 to T-309. Table 136: line S-136 and a line selected from T-1 to T-309. Table 137: line S-137 and a line selected from T-1 to T-309. Table 138: line S-138 and a line selected from T-1 to T-309. Table 139: line S-139 and a line selected from T-1 to T-309. Table 140: line S-140 and a line selected from T-1 to T-309. Table 141: line S-141 and a line selected from T-1 to T-309. Table 142: line S-142 and a line selected from T-1 to T-309. Table 143: line S-143 and a line selected from T-1 to T-309. Table 144: line S-144 and a line selected from T-1 to T-309. Table 145: line S-145 and a line selected from T-1 to T-309. Table 146: line S-146 and a line selected from T-1 to T-309. Table 147: line S-147 and a line selected from T-1 to T-309. Table 148: line S-148 and a line selected from T-1 to T-309. Table 149: line S-149 and a line selected from T-1 to T-309. Table 150: line S-150 and a line selected from T-1 to T-309. Table 151: line S-151 and a line selected from T-1 to T-309. Table 152: line S-152 and a line selected from T-1 to T-309. Table 153: line S-153 and a line selected from T-1 to T-309. Table 154: line S-154 and a line selected from T-1 to T-309. Table 155: line S-155 and a line selected from T-1 to T-309. Table 156: line S-156 and a line selected from T-1 to T-309. Table 157: line S-157 and a line selected from T-1 to T-309. Table 158: line S-158 and a line selected from T-1 to T-309. Table 159: line S-159 and a line selected from T-1 to T-309. Table 160: line S-160 and a line selected from T-1 to T-309. Table 161: line S-161 and a line selected from T-1 to T-309. Table 162: line S-162 and a line selected from T-1 to T-309. Table 163: line S-163 and a line selected from T-1 to T-309. Table 164: line S-164 and a line selected from T-1 to T-309. Table 165: line S-165 and a line selected from T-1 to T-309. Table 166: line S-166 and a line selected from T-1 to T-309. Table 167: line S-167 and a line selected from T-1 to T-309. Table 168: line S-168 and a line selected from T-1 to T-309. Table 169: line S-167 and a line selected from T-1 to T-309. Table 170: line S-170 and a line selected from T-1 to T-309. Table 171: line S-171 and a line selected from T-1 to T-309. Table 172: line S-172 and a line selected from T-1 to T-309. Table 173: line S-173 and a line selected from T-1 to T-309. Table 174: line S-174 and a line selected from T-1 to T-309. Table 175: line S-175 and a line selected from T-1 to T-309. Table 176: line S-176 and a line selected from T-1 to T-309. Table 177: line S-177 and a line selected from T-1 to T-309. Table 178: line S-178 and a line selected from T-1 to T-309. Table 179: line S-179 and a line selected from T-1 to T-309. Table 180: line S-179 and a line selected from T-1 to T-309.

Table 181: line S-1 and a line selected from T-310 to T-436. Table 182: line S-2 and a line selected from T-310 to T-436. Table 183: line S-3 and a line selected from T-310 to T-436. Table 184: line S-4 and a line selected from T-310 to T-436. Table 185: line S-5 and a line selected from T-310 to T-436. Table 186: line S-6 and a line selected from T-310 to T-436. Table 187: line S-7 and a line selected from T-310 to T-436. Table 188: line S-8 and a line selected from T-310 to T-436. Table 189: line S-9 and a line selected from T-310 to T-436. Table 190: line S-10 and a line selected from T-310 to T-436. Table 191: line S-11 and a line selected from T-310 to T-436. Table 192: line S-12 and a line selected from T-310 to T-436. Table 193: line S-13 and a line selected from T-310 to T-436. Table 194: line S-14 and a line selected from T-310 to T-436. Table 195: line S-15 and a line selected from T-310 to T-436. Table 196: line S-16 and a line selected from T-310 to T-436. Table 197: line S-17 and a line selected from T-310 to T-436. Table 198: line S-18 and a line selected from T-310 to T-436. Table 199: line S-19 and a line selected from T-310 to T-436. Table 200: line S-20 and a line selected from T-310 to T-436. Table 201: line S-21 and a line selected from T-310 to T-436. Table 202: line S-22 and a line selected from T-310 to T-436. Table 203: line S-23 and a line selected from T-310 to T-436. Table 204: line S-24 and a line selected from T-310 to T-436. Table 205: line S-25 and a line selected from T-310 to T-436. Table 206: line S-26 and a line selected from T-310 to T-436. Table 207: line S-27 and a line selected from T-310 to T-436. Table 208: line S-28 and a line selected from T-310 to T-436. Table 209: line S-29 and a line selected from T-310 to T-436. Table 210: line S-30 and a line selected from T-310 to T-436. Table 211: line S-31 and a line selected from T-310 to T-436. Table 212: line S-32 and a line selected from T-310 to T-436. Table 213: line S-33 and a line selected from T-310 to T-436. Table 214: line S-34 and a line selected from T-310 to T-436. Table 215: line S-35 and a line selected from T-310 to T-436. Table 216: line S-36 and a line selected from T-310 to T-436. Table 217: line S-37 and a line selected from T-310 to T-436. Table 218: line S-38 and a line selected from T-310 to T-436. Table 219: line S-39 and a line selected from T-310 to T-436. Table 220: line S-40 and a line selected from T-310 to T-436. Table 221: line S-41 and a line selected from T-310 to T-436. Table 222: line S-42 and a line selected from T-310 to T-436. Table 223: line S-43 and a line selected from T-310 to T-436. Table 224: line S-44 and a line selected from T-310 to T-436. Table 225: line S-45 and a line selected from T-310 to T-436. Table 226: line S-46 and a line selected from T-310 to T-436. Table 227: line S-47 and a line selected from T-310 to T-436. Table 228: line S-48 and a line selected from T-310 to T-436. Table 229: line S-49 and a line selected from T-310 to T-436. Table 230: line S-50 and a line selected from T-310 to T-436. Table 231: line S-51 and a line selected from T-310 to T-436. Table 232: line S-52 and a line selected from T-310 to T-436. Table 233: line S-53 and a line selected from T-310 to T-436. Table 234: line S-54 and a line selected from T-310 to T-436. Table 235: line S-55 and a line selected from T-310 to T-436. Table 236: line S-56 and a line selected from T-310 to T-436. Table 237: line S-57 and a line selected from T-310 to T-436. Table 238: line S-58 and a line selected from T-310 to T-436. Table 239: line S-59 and a line selected from T-310 to T-436. Table 240: line S-60 and a line selected from T-310 to T-436. Table 241: line S-61 and a line selected from T-310 to T-436. Table 242: line S-62 and a line selected from T-310 to T-436. Table 243: line S-63 and a line selected from T-310 to T-436. Table 244: line S-64 and a line selected from T-310 to T-436. Table 245: line S-65 and a line selected from T-310 to T-436. Table 246: line S-66 and a line selected from T-310 to T-436. Table 247: line S-67 and a line selected from T-310 to T-436. Table 248: line S-68 and a line selected from T-310 to T-436. Table 249: line S-69 and a line selected from T-310 to T-436. Table 250: line S-70 and a line selected from T-310 to T-436. Table 251: line S-71 and a line selected from T-310 to T-436. Table 252: line S-72 and a line selected from T-310 to T-436. Table 253: line S-73 and a line selected from T-310 to T-436. Table 254: line S-74 and a line selected from T-310 to T-436. Table 255: line S-75 and a line selected from T-310 to T-436. Table 256: line S-76 and a line selected from T-310 to T-436. Table 257: line S-77 and a line selected from T-310 to T-436. Table 258: line S-78 and a line selected from T-310 to T-436. Table 259: line S-79 and a line selected from T-310 to T-436. Table 260: line S-80 and a line selected from T-310 to T-436. Table 261: line S-81 and a line selected from T-310 to T-436. Table 262: line S-82 and a line selected from T-310 to T-436. Table 263: line S-83 and a line selected from T-310 to T-436. Table 264: line S-84 and a line selected from T-310 to T-436. Table 265: line S-85 and a line selected from T-310 to T-436. Table 266: line S-86 and a line selected from T-310 to T-436. Table 267: line S-87 and a line selected from T-310 to T-436. Table 268: line S-88 and a line selected from T-310 to T-436. Table 269: line S-89 and a line selected from T-310 to T-436. Table 270: line S-90 and a line selected from T-310 to T-436. Table 271: line S-91 and a line selected from T-310 to T-436. Table 272: line S-92 and a line selected from T-310 to T-436. Table 273: line S-93 and a line selected from T-310 to T-436. Table 274: line S-94 and a line selected from T-310 to T-436. Table 275: line S-95 and a line selected from T-310 to T-436. Table 276: line S-96 and a line selected from T-310 to T-436. Table 277: line S-97 and a line selected from T-310 to T-436. Table 278: line S-98 and a line selected from T-310 to T-436. Table 279: line S-99 and a line selected from T-310 to T-436. Table 280: line S-100 and a line selected from T-310 to T-436. Table 281: line S-101 and a line selected from T-310 to T-436. Table 282: line S-102 and a line selected from T-310 to T-436. Table 283: line S-103 and a line selected from T-310 to T-436. Table 284: line S-104 and a line selected from T-310 to T-436. Table 285: line S-105 and a line selected from T-310 to T-436. Table 286: line S-106 and a line selected from T-310 to T-436. Table 287: line S-107 and a line selected from T-310 to T-436. Table 288: line S-108 and a line selected from T-310 to T-436. Table 289: line S-109 and a line selected from T-310 to T-436. Table 290: line S-110 and a line selected from T-310 to T-436. Table 291: line S-111 and a line selected from T-310 to T-436. Table 292: line S-112 and a line selected from T-310 to T-436. Table-293: line S-113 and a line selected from T-310 to T-436. Table 294: line S-114 and a line selected from T-310 to T-436. Table 295: line S-115 and a line selected from T-310 to T-436. Table 296: line S-116 and a line selected from T-310 to T-436. Table 297: line S-117 and a line selected from T-310 to T-436. Table 298: line S-118 and a line selected from T-310 to T-436. Table 299: line S-119 and a line selected from T-310 to T-436. Table 300: line S-120 and a line selected from T-310 to T-436. Table 301: line S-121 and a line selected from T-310 to T-436. Table 302: line S-122 and a line selected from T-310 to T-436. Table 303: line S-123 and a line selected from T-310 to T-436. Table 304: line S-124 and a line selected from T-310 to T-436. Table 305: line S-125 and a line selected from T-310 to T-436. Table 306: line S-126 and a line selected from T-310 to T-436. Table 307: line S-127 and a line selected from T-310 to T-436. Table 308: line S-128 and a line selected from T-310 to T-436. Table 309: line S-129 and a line selected from T-310 to T-436. Table 310: line S-130 and a line selected from T-310 to T-436. Table 311: line S-131 and a line selected from T-310 to T-436. Table 312: line S-132 and a line selected from T-310 to T-436. Table 313: line S-133 and a line selected from T-310 to T-436. Table 314: line S-134 and a line selected from T-310 to T-436. Table 315: line S-135 and a line selected from T-310 to T-436. Table 316: line S-136 and a line selected from T-310 to T-436. Table 317: line S-137 and a line selected from T-310 to T-436. Table 318: line S-138 and a line selected from T-310 to T-436. Table 319: line S-139 and a line selected from T-310 to T-436. Table 320: line S-140 and a line selected from T-310 to T-436. Table 321: line S-141 and a line selected from T-310 to T-436. Table 322: line S-142 and a line selected from T-310 to T-436. Table 323: line S-143 and a line selected from T-310 to T-436. Table 324: line S-144 and a line selected from T-310 to T-436. Table 325: line S-145 and a line selected from T-310 to T-436. Table 326: line S-146 and a line selected from T-310 to T-436. Table 327: line S-147 and a line selected from T-310 to T-436. Table 328: line S-148 and a line selected from T-310 to T-436. Table 329: line S-149 and a line selected from T-310 to T-436. Table 330: line S-150 and a line selected from T-310 to T-436. Table 331: line S-151 and a line selected from T-310 to T-436. Table 332: line S-152 and a line selected from T-310 to T-436. Table 333: line S-153 and a line selected from T-310 to T-436. Table 334: line S-154 and a line selected from T-310 to T-436. Table 335: line S-155 and a line selected from T-310 to T-436. Table 336: line S-156 and a line selected from T-310 to T-436. Table 337: line S-157 and a line selected from T-310 to T-436. Table 338: line S-158 and a line selected from T-310 to T-436. Table 339: line S-159 and a line selected from T-310 to T-436. Table 340: line S-160 and a line selected from T-310 to T-436. Table 341: line S-161 and a line selected from T-310 to T-436. Table 342: line S-162 and a line selected from T-310 to T-436. Table 343: line S-163 and a line selected from T-310 to T-436. Table 344: line S-164 and a line selected from T-310 to T-436. Table 345: line S-165 and a line selected from T-310 to T-436. Table 346: line S-166 and a line selected from T-310 to T-436. Table 347: line S-167 and a line selected from T-310 to T-436. Table 348: line S-168 and a line selected from T-310 to T-436. Table 349: line S-169 and a line selected from T-310 to T-436. Table 350: line S-170 and a line selected from T-310 to T-436. Table 351: line S-171 and a line selected from T-310 to T-436. Table 352: line S-172 and a line selected from T-310 to T-436. Table 353: line S-173 and a line selected from T-310 to T-436. Table 354: line S-174 and a line selected from T-310 to T-436. Table 355: line S-175 and a line selected from T-310 to T-436. Table 356: line S-176 and a line selected from T-310 to T-436. Table 357: line S-177 and a line selected from T-310 to T-436. Table 358: line S-178 and a line selected from T-310 to T-436. Table 359: line S-179 and a line selected from T-310 to T-436. Table 360: line S-180 and a line selected from T-310 to T-436.

Table 361: line S-1 and a line selected from T-473 to T-815. Table 362: line S-2 and a line selected from T-473 to T-815. Table 363: line S-3 and a line selected from T-473 to T-815. Table 364: line S-4 and a line selected from T-473 to T-815. Table 365: line S-5 and a line selected from T-473 to T-815. Table 366: line S-6 and a line selected from T-473 to T-815. Table 367: line S-7 and a line selected from T-473 to T-815. Table 368: line S-8 and a line selected from T-473 to T-815. Table 369: line S-9 and a line selected from T-473 to T-815.

Table 370: line S-10 and a line selected from T-473 to T-815.
Table 371: line S-11 and a line selected from T-473 to T-815.
Table 372: line S-12 and a line selected from T-473 to T-815.
Table 373: line S-13 and a line selected from T-473 to T-815.
Table 374: line S-14 and a line selected from T-473 to T-815.
Table 375: line S-15 and a line selected from T-473 to T-815.
Table 376: line S-16 and a line selected from T-473 to T-815.
Table 377: line S-17 and a line selected from T-473 to T-815.
Table 378: line S-18 and a line selected from T-473 to T-815.
Table 379: line S-19 and a line selected from T-473 to T-815.
Table 380: line S-20 and a line selected from T-473 to T-815.
Table 381: line S-21 and a line selected from T-473 to T-815.
Table 382: line S-22 and a line selected from T-473 to T-815.
Table 383: line S-23 and a line selected from T-473 to T-815.
Table 384: line S-24 and a line selected from T-473 to T-815.
Table 385: line S-25 and a line selected from T-473 to T-815.
Table 386: line S-26 and a line selected from T-473 to T-815.
Table 387: line S-27 and a line selected from T-473 to T-815.
Table 388: line S-28 and a line selected from T-473 to T-815.
Table 389: line S-29 and a line selected from T-473 to T-815.
Table 390: line S-30 and a line selected from T-473 to T-815.
Table 391: line S-31 and a line selected from T-473 to T-815.
Table 392: line S-32 and a line selected from T-473 to T-815.
Table 393: line S-33 and a line selected from T-473 to T-815.
Table 394: line S-34 and a line selected from T-473 to T-815.
Table 395: line S-35 and a line selected from T-473 to T-815.
Table 396: line S-36 and a line selected from T-473 to T-815.
Table 397: line S-37 and a line selected from T-473 to T-815.
Table 398: line S-38 and a line selected from T-473 to T-815.
Table 399: line S-39 and a line selected from T-473 to T-815.
Table 400: line S-40 and a line selected from T-473 to T-815.
Table 401: line S-41 and a line selected from T-473 to T-815.
Table 402: line S-42 and a line selected from T-473 to T-815.
Table 403: line S-43 and a line selected from T-473 to T-815.
Table 404: line S-44 and a line selected from T-473 to T-815.
Table 405: line S-45 and a line selected from T-473 to T-815.
Table 406: line S-46 and a line selected from T-473 to T-815.
Table 407: line S-47 and a line selected from T-473 to T-815.
Table 408: line S-48 and a line selected from T-473 to T-815.
Table 409: line S-49 and a line selected from T-473 to T-815.
Table 410: line S-50 and a line selected from T-473 to T-815.
Table 411: line S-51 and a line selected from T-473 to T-815.
Table 412: line S-52 and a line selected from T-473 to T-815.
Table 413: line S-53 and a line selected from T-473 to T-815.
Table 414: line S-54 and a line selected from T-473 to T-815.
Table 415: line S-55 and a line selected from T-473 to T-815.
Table 416: line S-56 and a line selected from T-473 to T-815.
Table 417: line S-57 and a line selected from T-473 to T-815.
Table 418: line S-58 and a line selected from T-473 to T-815.
Table 419: line S-59 and a line selected from T-473 to T-815.
Table 420: line S-60 and a line selected from T-473 to T-815.
Table 421: line S-61 and a line selected from T-473 to T-815.
Table 422: line S-62 and a line selected from T-473 to T-815.
Table 423: line S-63 and a line selected from T-473 to T-815.
Table 424: line S-64 and a line selected from T-473 to T-815.
Table 425: line S-65 and a line selected from T-473 to T-815.
Table 426: line S-66 and a line selected from T-473 to T-815.
Table 427: line S-67 and a line selected from T-473 to T-815.
Table 428: line S-68 and a line selected from T-473 to T-815.
Table 429: line S-69 and a line selected from T-473 to T-815.
Table 430: line S-70 and a line selected from T-473 to T-815.
Table 431: line S-71 and a line selected from T-473 to T-815.
Table 432: line S-72 and a line selected from T-473 to T-815.
Table 433: line S-73 and a line selected from T-473 to T-815.
Table 434: line S-74 and a line selected from T-473 to T-815.
Table 435: line S-75 and a line selected from T-473 to T-815.
Table 436: line S-76 and a line selected from T-473 to T-815.
Table 437: line S-77 and a line selected from T-473 to T-815.
Table 438: line S-78 and a line selected from T-473 to T-815.
Table 439: line S-79 and a line selected from T-473 to T-815.
Table 440: line S-80 and a line selected from T-473 to T-815.
Table 441: line S-81 and a line selected from T-473 to T-815.
Table 442: line S-82 and a line selected from T-473 to T-815.
Table 443: line S-83 and a line selected from T-473 to T-815.
Table 444: line S-84 and a line selected from T-473 to T-815.
Table 445: line S-85 and a line selected from T-473 to T-815.
Table 446: line S-86 and a line selected from T-473 to T-815.
Table 447: line S-87 and a line selected from T-473 to T-815.
Table 448: line S-88 and a line selected from T-473 to T-815.
Table 449: line S-89 and a line selected from T-473 to T-815.
Table 450: line S-90 and a line selected from T-473 to T-815.
Table 451: line S-91 and a line selected from T-473 to T-815.
Table 452: line S-92 and a line selected from T-473 to T-815.
Table 453: line S-93 and a line selected from T-473 to T-815.
Table 454: line S-94 and a line selected from T-473 to T-815.
Table 455: line S-95 and a line selected from T-473 to T-815.
Table 456: line S-96 and a line selected from T-473 to T-815.
Table 457: line S-97 and a line selected from T-473 to T-815.
Table 458: line S-98 and a line selected from T-473 to T-815.
Table 459: line S-99 and a line selected from T-473 to T-815.
Table 460: line S-100 and a line selected from T-473 to T-815. Table 461: line S-101 and a line selected from T-473 to T-815. Table 462: line S-102 and a line selected from T-473 to T-815. Table 463: line S-103 and a line selected from T-473 to T-815. Table 464: line S-104 and a line selected from T-473 to T-815. Table 465: line S-105 and a line selected from T-473 to T-815. Table 466: line S-106 and a line selected from T-473 to T-815. Table 467: line S-107 and a line selected from T-473 to T-815. Table 468: line S-108 and a line selected from T-473 to T-815. Table 469: line S-109 and a line selected from T-473 to T-815. Table 470: line S-110 and a line selected from T-473 to T-815. Table 471: line S-111 and a line selected from T-473 to T-815. Table 472: line S-112 and a line selected from T-473 to T-815. Table-473: line S-113 and a line selected from T-473 to T-815. Table 474: line S-114 and a line selected from T-473 to T-815. Table 475: line S-115 and a line selected from T-473 to T-815. Table 476: line S-116 and a line selected from T-473 to T-815. Table 477: line S-117 and a line selected from T-473 to T-815. Table 478: line S-118 and a line selected from T-473 to T-815. Table 479: line S-119 and a line selected from T-473 to T-815. Table 480: line S-120 and a line selected from T-473 to T-815. Table 481: line S-121 and a line selected from T-473 to T-815. Table 482: line S-122 and a line selected from T-473 to T-815. Table 483: line S-123 and a line selected from T-473 to T-815. Table 484: line S-124 and a line selected from T-473 to T-815. Table 485: line S-125 and a line selected from T-473 to T-815. Table 486: line S-126 and a line selected from T-473 to T-815. Table 487: line S-127 and a line selected from T-473 to T-815. Table 488: line S-128 and a line selected from T-473 to T-815. Table 489: line S-129 and a line selected from T-473 to T-815. Table 490: line S-130 and a line selected from T-473 to T-815. Table 491: line S-131 and a line selected from T-473 to T-815. Table 492: line S-132 and a line selected from T-473 to T-815. Table 493: line S-133 and a line selected from T-473 to T-815. Table 494: line S-134 and a line selected from T-473 to T-815. Table 495: line S-135 and a line selected from T-473 to T-815. Table 496: line S-136 and a line selected from T-473 to T-815. Table 497: line S-137 and a line selected from T-473 to T-815. Table 498: line S-138 and a line selected from T-473 to T-815. Table 499: line S-139 and a line selected from T-473 to T-815. Table 500: line S-140 and a line selected from T-473 to T-815. Table 501: line S-141 and a line selected from T-473 to T-815. Table 502: line S-142 and a line selected from T-473 to T-815. Table 503: line S-143 and a line selected from T-473 to T-815. Table 504: line S-144 and a line selected from T-473 to T-815. Table 505: line S-145 and a line selected from T-473 to T-815. Table 506: line S-146 and a line selected from T-473 to T-815. Table 507: line S-147 and a line selected from T-473 to T-815. Table 508: line S-148 and a line selected from T-473 to T-815. Table 509: line S-149 and a line selected from T-473 to T-815. Table 510: line S-150 and a line selected from T-473 to T-815. Table 511: line S-151 and a line selected from T-473 to T-815. Table 512: line S-152 and a line selected from T-473 to T-815. Table 513: line S-153 and a line selected from T-473 to T-815. Table 514: line S-154 and a line selected from T-473 to T-815. Table 515: line S-155 and a line selected from T-473 to T-815. Table 516: line S-156 and a line selected from T-473 to T-815. Table 517: line S-157 and a line selected from T-473 to T-815. Table 518: line S-158 and a line selected from T-473 to T-815. Table 519: line S-159 and a line selected from T-473 to T-815. Table 520: line S-160 and a line selected from T-473 to T-815. Table 521: line S-161 and a line selected from T-473 to T-815. Table 522: line S-162 and a line selected from T-473 to T-815. Table 523: line S-163 and a line selected from T-473 to T-815. Table 524: line S-164 and a line selected from T-473 to T-815. Table 525: line S-165 and a line selected from T-473 to T-815. Table 526: line S-166 and a line selected from T-473 to T-815. Table 527: line S-167 and a line selected from T-473 to T-815. Table 528: line S-168 and a line selected from T-473 to T-815. Table 529: line S-169 and a line selected from T-473 to T-815. Table 530: line S-170 and a line selected from T-473 to T-815. Table 531: line S-171 and a line selected from T-473 to T-815. Table 532: line S-172 and a line selected from T-473 to T-815. Table 533: line S-173 and a line selected from T-473 to T-815. Table 534: line S-174 and a line selected from T-473 to T-815. Table 535: line S-175 and a line selected from T-473 to T-815. Table 536: line S-176 and a line selected from T-473 to T-815. Table 537: line S-177 and a line selected from T-473 to T-815. Table 538: line S-178 and a line selected from T-473 to T-815. Table 539: line S-179 and a line selected from T-473 to T-815. Table 540: line S-180 and a line selected from T-473 to T-815.

Table D below contains embodiments number 1 to 3568 (as abbreviated with "#") for combinations of particularly preferred compounds of formulae IA.A1.1, IA.A1.2, IA.A1.3, IB.A1.1, IB.A1.2, IB.A1.3, IC.A1.1, IC.A1.1, IC.A1.1, ID.A1.1, ID.A1.2, ID.A1.3, IT.A1.1, IT.A1.2, IT.A1.3, IY.A1.1, IY.A1.2, IY.A1.3, IA.A5.1, and IA.A5.2 as depicted below, wherein $R^W$ is in each case H, and wherein the other variables have a meaning as defined in Table 1 to Table 540.

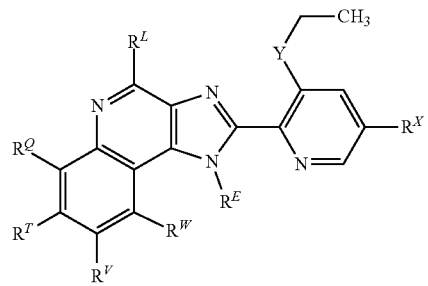
(IA.A1.1)

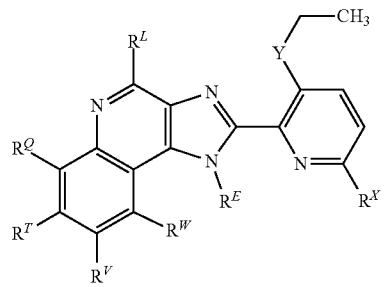
(IA.A1.2)

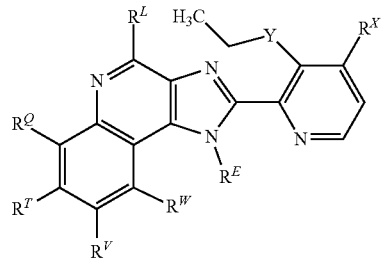
(IA.A1.3)

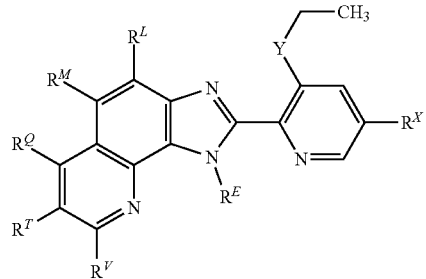
(IB.A1.1)

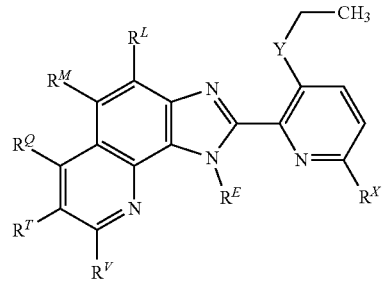
(IB.A1.2)

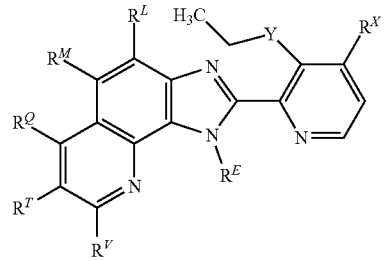
(IB.A1.3)

-continued
(IC.A1.1)
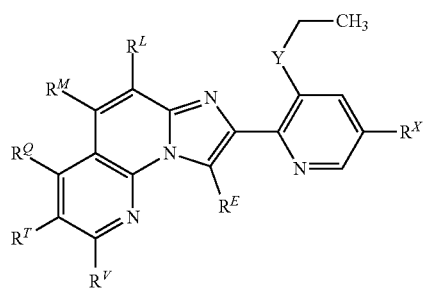
(IC.A1.2)
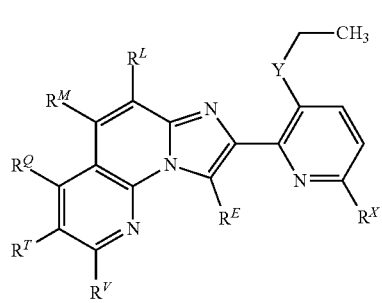
(IC.A1.3)
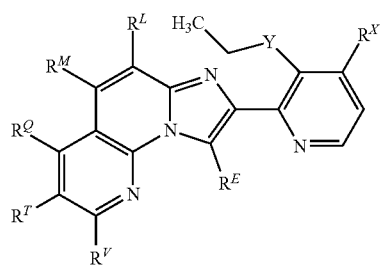
(ID.A1.1)
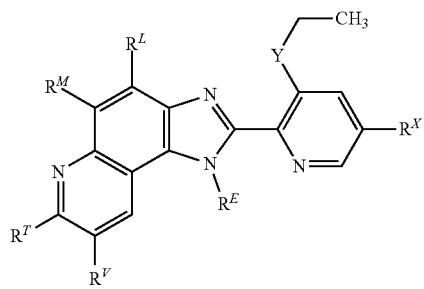
(ID.A1.2)
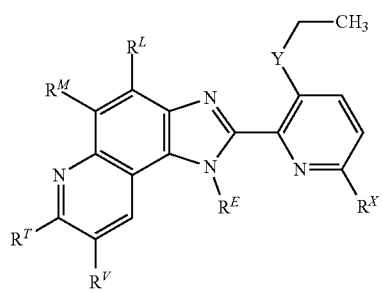
(ID.A1.3)
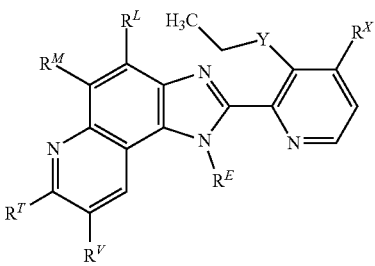
(IT.A1.1)
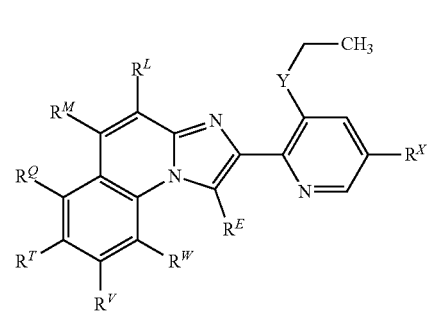
(IT.A1.2)
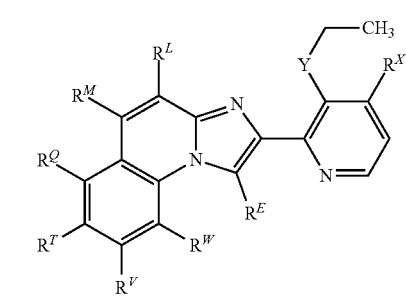
(IT.A1.3)
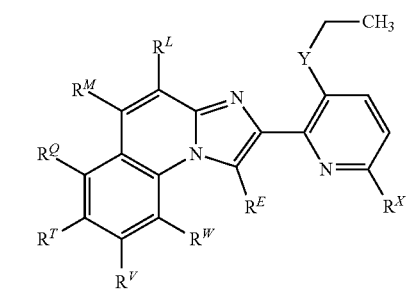
(IY.A1.1)
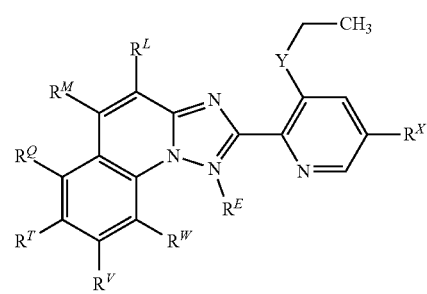

-continued (IY.A1.2)
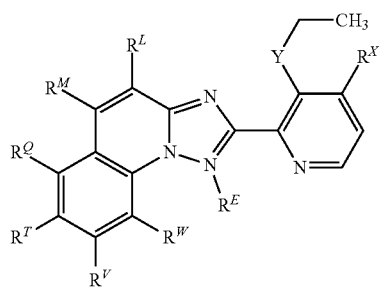

(IY.A1.3)
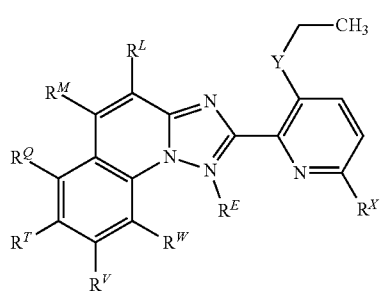

(IA.A5.1)
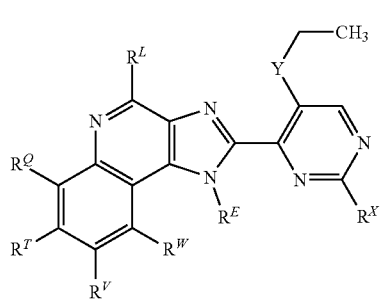

(IA.A5.2)
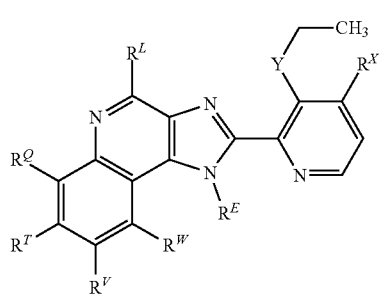

TABLE D

| # | Table | Formula |
|---|---|---|
| 1 | 1 | IA.A1.1 |
| 2 | 2 | IA.A1.1 |
| 3 | 3 | IA.A1.1 |
| 4 | 4 | IA.A1.1 |
| 5 | 5 | IA.A1.1 |
| 6 | 6 | IA.A1.1 |
| 7 | 7 | IA.A1.1 |
| 8 | 8 | IA.A1.1 |
| 9 | 9 | IA.A1.1 |
| 10 | 10 | IA.A1.1 |
| 11 | 11 | IA.A1.1 |
| 12 | 12 | IA.A1.1 |
| 13 | 13 | IA.A1.1 |
| 14 | 14 | IA.A1.1 |
| 15 | 15 | IA.A1.1 |
| 16 | 16 | IA.A1.1 |
| 17 | 17 | IA.A1.1 |

TABLE D-continued

| # | Table | Formula |
|---|---|---|
| 18 | 18 | IA.A1.1 |
| 19 | 19 | IA.A1.1 |
| 20 | 20 | IA.A1.1 |
| 21 | 21 | IA.A1.1 |
| 22 | 22 | IA.A1.1 |
| 23 | 23 | IA.A1.1 |
| 24 | 24 | IA.A1.1 |
| 25 | 25 | IA.A1.1 |
| 26 | 26 | IA.A1.1 |
| 27 | 27 | IA.A1.1 |
| 28 | 28 | IA.A1.1 |
| 29 | 29 | IA.A1.1 |
| 30 | 30 | IA.A1.1 |
| 31 | 31 | IA.A1.1 |
| 32 | 32 | IA.A1.1 |
| 33 | 33 | IA.A1.1 |
| 34 | 34 | IA.A1.1 |
| 35 | 35 | IA.A1.1 |
| 36 | 36 | IA.A1.1 |
| 37 | 37 | IA.A1.1 |
| 38 | 38 | IA.A1.1 |
| 39 | 39 | IA.A1.1 |
| 40 | 40 | IA.A1.1 |
| 41 | 41 | IA.A1.1 |
| 42 | 42 | IA.A1.1 |
| 43 | 43 | IA.A1.1 |
| 44 | 44 | IA.A1.1 |
| 45 | 45 | IA.A1.1 |
| 46 | 46 | IA.A1.1 |
| 47 | 47 | IA.A1.1 |
| 48 | 48 | IA.A1.1 |
| 49 | 49 | IA.A1.1 |
| 50 | 50 | IA.A1.1 |
| 51 | 51 | IA.A1.1 |
| 52 | 52 | IA.A1.1 |
| 53 | 53 | IA.A1.1 |
| 54 | 54 | IA.A1.1 |
| 55 | 55 | IA.A1.1 |
| 56 | 56 | IA.A1.1 |
| 57 | 57 | IA.A1.1 |
| 58 | 58 | IA.A1.1 |
| 59 | 59 | IA.A1.1 |
| 60 | 60 | IA.A1.1 |
| 61 | 61 | IA.A1.1 |
| 62 | 62 | IA.A1.1 |
| 63 | 63 | IA.A1.1 |
| 64 | 64 | IA.A1.1 |
| 65 | 65 | IA.A1.1 |
| 66 | 66 | IA.A1.1 |
| 67 | 67 | IA.A1.1 |
| 68 | 68 | IA.A1.1 |
| 69 | 69 | IA.A1.1 |
| 70 | 70 | IA.A1.1 |
| 71 | 71 | IA.A1.1 |
| 72 | 72 | IA.A1.1 |
| 73 | 73 | IA.A1.1 |
| 74 | 74 | IA.A1.1 |
| 75 | 75 | IA.A1.1 |
| 76 | 76 | IA.A1.1 |
| 77 | 77 | IA.A1.1 |
| 78 | 78 | IA.A1.1 |
| 79 | 79 | IA.A1.1 |
| 80 | 80 | IA.A1.1 |
| 81 | 81 | IA.A1.1 |
| 82 | 82 | IA.A1.1 |
| 83 | 83 | IA.A1.1 |
| 84 | 84 | IA.A1.1 |
| 85 | 85 | IA.A1.1 |
| 86 | 86 | IA.A1.1 |
| 87 | 87 | IA.A1.1 |
| 88 | 88 | IA.A1.1 |
| 89 | 89 | IA.A1.1 |
| 90 | 90 | IA.A1.1 |
| 91 | 91 | IA.A1.1 |
| 92 | 92 | IA.A1.1 |
| 93 | 93 | IA.A1.1 |
| 94 | 94 | IA.A1.1 |
| 95 | 95 | IA.A1.1 |

TABLE D-continued

| # | Table | Formula |
|---|---|---|
| 96 | 96 | IA.A1.1 |
| 97 | 97 | IA.A1.1 |
| 98 | 98 | IA.A1.1 |
| 99 | 99 | IA.A1.1 |
| 100 | 100 | IA.A1.1 |
| 101 | 101 | IA.A1.1 |
| 102 | 102 | IA.A1.1 |
| 103 | 103 | IA.A1.1 |
| 104 | 104 | IA.A1.1 |
| 105 | 105 | IA.A1.1 |
| 106 | 106 | IA.A1.1 |
| 107 | 107 | IA.A1.1 |
| 108 | 108 | IA.A1.1 |
| 109 | 109 | IA.A1.1 |
| 110 | 110 | IA.A1.1 |
| 111 | 111 | IA.A1.1 |
| 112 | 112 | IA.A1.1 |
| 113 | 113 | IA.A1.1 |
| 114 | 114 | IA.A1.1 |
| 115 | 115 | IA.A1.1 |
| 116 | 116 | IA.A1.1 |
| 117 | 117 | IA.A1.1 |
| 118 | 118 | IA.A1.1 |
| 119 | 119 | IA.A1.1 |
| 120 | 120 | IA.A1.1 |
| 121 | 121 | IA.A1.1 |
| 122 | 122 | IA.A1.1 |
| 123 | 123 | IA.A1.1 |
| 124 | 124 | IA.A1.1 |
| 125 | 125 | IA.A1.1 |
| 126 | 126 | IA.A1.1 |
| 127 | 127 | IA.A1.1 |
| 128 | 128 | IA.A1.1 |
| 129 | 129 | IA.A1.1 |
| 130 | 130 | IA.A1.1 |
| 131 | 131 | IA.A1.1 |
| 132 | 132 | IA.A1.1 |
| 133 | 133 | IA.A1.1 |
| 134 | 134 | IA.A1.1 |
| 135 | 135 | IA.A1.1 |
| 136 | 136 | IA.A1.1 |
| 137 | 137 | IA.A1.1 |
| 138 | 138 | IA.A1.1 |
| 139 | 139 | IA.A1.1 |
| 140 | 140 | IA.A1.1 |
| 141 | 141 | IA.A1.1 |
| 142 | 142 | IA.A1.1 |
| 143 | 143 | IA.A1.1 |
| 144 | 144 | IA.A1.1 |
| 145 | 145 | IA.A1.1 |
| 146 | 146 | IA.A1.1 |
| 147 | 147 | IA.A1.1 |
| 148 | 148 | IA.A1.1 |
| 149 | 149 | IA.A1.1 |
| 150 | 150 | IA.A1.1 |
| 151 | 151 | IA.A1.1 |
| 152 | 152 | IA.A1.1 |
| 153 | 153 | IA.A1.1 |
| 154 | 154 | IA.A1.1 |
| 155 | 155 | IA.A1.1 |
| 156 | 156 | IA.A1.1 |
| 157 | 157 | IA.A1.1 |
| 158 | 158 | IA.A1.1 |
| 159 | 159 | IA.A1.1 |
| 160 | 160 | IA.A1.1 |
| 161 | 161 | IA.A1.1 |
| 162 | 162 | IA.A1.1 |
| 163 | 163 | IA.A1.1 |
| 164 | 164 | IA.A1.1 |
| 165 | 165 | IA.A1.1 |
| 166 | 166 | IA.A1.1 |
| 167 | 167 | IA.A1.1 |
| 168 | 168 | IA.A1.1 |
| 169 | 169 | IA.A1.1 |
| 170 | 170 | IA.A1.1 |
| 171 | 171 | IA.A1.1 |
| 172 | 172 | IA.A1.1 |
| 173 | 173 | IA.A1.1 |
| 174 | 174 | IA.A1.1 |
| 175 | 175 | IA.A1.1 |
| 176 | 176 | IA.A1.1 |
| 177 | 177 | IA.A1.1 |
| 178 | 178 | IA.A1.1 |
| 179 | 179 | IA.A1.1 |
| 180 | 180 | IA.A1.1 |
| 181 | 1 | IA.A1.2 |
| 182 | 2 | IA.A1.2 |
| 183 | 3 | IA.A1.2 |
| 184 | 4 | IA.A1.2 |
| 185 | 5 | IA.A1.2 |
| 186 | 6 | IA.A1.2 |
| 187 | 7 | IA.A1.2 |
| 188 | 8 | IA.A1.2 |
| 189 | 9 | IA.A1.2 |
| 190 | 10 | IA.A1.2 |
| 191 | 11 | IA.A1.2 |
| 192 | 12 | IA.A1.2 |
| 193 | 13 | IA.A1.2 |
| 194 | 14 | IA.A1.2 |
| 195 | 15 | IA.A1.2 |
| 196 | 16 | IA.A1.2 |
| 197 | 17 | IA.A1.2 |
| 198 | 18 | IA.A1.2 |
| 199 | 19 | IA.A1.2 |
| 200 | 20 | IA.A1.2 |
| 201 | 21 | IA.A1.2 |
| 202 | 22 | IA.A1.2 |
| 203 | 23 | IA.A1.2 |
| 204 | 24 | IA.A1.2 |
| 205 | 25 | IA.A1.2 |
| 206 | 26 | IA.A1.2 |
| 207 | 27 | IA.A1.2 |
| 208 | 28 | IA.A1.2 |
| 209 | 29 | IA.A1.2 |
| 210 | 30 | IA.A1.2 |
| 211 | 31 | IA.A1.2 |
| 212 | 32 | IA.A1.2 |
| 213 | 33 | IA.A1.2 |
| 214 | 34 | IA.A1.2 |
| 215 | 35 | IA.A1.2 |
| 216 | 36 | IA.A1.2 |
| 217 | 37 | IA.A1.2 |
| 218 | 38 | IA.A1.2 |
| 219 | 39 | IA.A1.2 |
| 220 | 40 | IA.A1.2 |
| 221 | 41 | IA.A1.2 |
| 222 | 42 | IA.A1.2 |
| 223 | 43 | IA.A1.2 |
| 224 | 44 | IA.A1.2 |
| 225 | 45 | IA.A1.2 |
| 226 | 46 | IA.A1.2 |
| 227 | 47 | IA.A1.2 |
| 228 | 48 | IA.A1.2 |
| 229 | 49 | IA.A1.2 |
| 230 | 50 | IA.A1.2 |
| 231 | 51 | IA.A1.2 |
| 232 | 52 | IA.A1.2 |
| 233 | 53 | IA.A1.2 |
| 234 | 54 | IA.A1.2 |
| 235 | 55 | IA.A1.2 |
| 236 | 56 | IA.A1.2 |
| 237 | 57 | IA.A1.2 |
| 238 | 58 | IA.A1.2 |
| 239 | 59 | IA.A1.2 |
| 240 | 60 | IA.A1.2 |
| 241 | 61 | IA.A1.2 |
| 242 | 62 | IA.A1.2 |
| 243 | 63 | IA.A1.2 |
| 244 | 64 | IA.A1.2 |
| 245 | 65 | IA.A1.2 |
| 246 | 66 | IA.A1.2 |
| 247 | 67 | IA.A1.2 |
| 248 | 68 | IA.A1.2 |
| 249 | 69 | IA.A1.2 |
| 250 | 70 | IA.A1.2 |
| 251 | 71 | IA.A1.2 |

TABLE D-continued

| # | Table | Formula |
|---|---|---|
| 252 | 72 | IA.A1.2 |
| 253 | 73 | IA.A1.2 |
| 254 | 74 | IA.A1.2 |
| 255 | 75 | IA.A1.2 |
| 256 | 76 | IA.A1.2 |
| 257 | 77 | IA.A1.2 |
| 258 | 78 | IA.A1.2 |
| 259 | 79 | IA.A1.2 |
| 260 | 80 | IA.A1.2 |
| 261 | 81 | IA.A1.2 |
| 262 | 82 | IA.A1.2 |
| 263 | 83 | IA.A1.2 |
| 264 | 84 | IA.A1.2 |
| 265 | 85 | IA.A1.2 |
| 266 | 86 | IA.A1.2 |
| 267 | 87 | IA.A1.2 |
| 268 | 88 | IA.A1.2 |
| 269 | 89 | IA.A1.2 |
| 270 | 90 | IA.A1.2 |
| 271 | 91 | IA.A1.2 |
| 272 | 92 | IA.A1.2 |
| 273 | 93 | IA.A1.2 |
| 274 | 94 | IA.A1.2 |
| 275 | 95 | IA.A1.2 |
| 276 | 96 | IA.A1.2 |
| 277 | 97 | IA.A1.2 |
| 278 | 98 | IA.A1.2 |
| 279 | 99 | IA.A1.2 |
| 280 | 100 | IA.A1.2 |
| 281 | 101 | IA.A1.2 |
| 282 | 102 | IA.A1.2 |
| 283 | 103 | IA.A1.2 |
| 284 | 104 | IA.A1.2 |
| 285 | 105 | IA.A1.2 |
| 286 | 106 | IA.A1.2 |
| 287 | 107 | IA.A1.2 |
| 288 | 108 | IA.A1.2 |
| 289 | 109 | IA.A1.2 |
| 290 | 110 | IA.A1.2 |
| 291 | 111 | IA.A1.2 |
| 292 | 112 | IA.A1.2 |
| 293 | 113 | IA.A1.2 |
| 294 | 114 | IA.A1.2 |
| 295 | 115 | IA.A1.2 |
| 296 | 116 | IA.A1.2 |
| 297 | 117 | IA.A1.2 |
| 298 | 118 | IA.A1.2 |
| 299 | 119 | IA.A1.2 |
| 300 | 120 | IA.A1.2 |
| 301 | 121 | IA.A1.2 |
| 302 | 122 | IA.A1.2 |
| 303 | 123 | IA.A1.2 |
| 304 | 124 | IA.A1.2 |
| 305 | 125 | IA.A1.2 |
| 306 | 126 | IA.A1.2 |
| 307 | 127 | IA.A1.2 |
| 308 | 128 | IA.A1.2 |
| 309 | 129 | IA.A1.2 |
| 310 | 130 | IA.A1.2 |
| 311 | 131 | IA.A1.2 |
| 312 | 132 | IA.A1.2 |
| 313 | 133 | IA.A1.2 |
| 314 | 134 | IA.A1.2 |
| 315 | 135 | IA.A1.2 |
| 316 | 136 | IA.A1.2 |
| 317 | 137 | IA.A1.2 |
| 318 | 138 | IA.A1.2 |
| 319 | 139 | IA.A1.2 |
| 320 | 140 | IA.A1.2 |
| 321 | 141 | IA.A1.2 |
| 322 | 142 | IA.A1.2 |
| 323 | 143 | IA.A1.2 |
| 324 | 144 | IA.A1.2 |
| 325 | 145 | IA.A1.2 |
| 326 | 146 | IA.A1.2 |
| 327 | 147 | IA.A1.2 |
| 328 | 148 | IA.A1.2 |
| 329 | 149 | IA.A1.2 |
| 330 | 150 | IA.A1.2 |
| 331 | 151 | IA.A1.2 |
| 332 | 152 | IA.A1.2 |
| 333 | 153 | IA.A1.2 |
| 334 | 154 | IA.A1.2 |
| 335 | 155 | IA.A1.2 |
| 336 | 156 | IA.A1.2 |
| 337 | 157 | IA.A1.2 |
| 338 | 158 | IA.A1.2 |
| 339 | 159 | IA.A1.2 |
| 340 | 160 | IA.A1.2 |
| 341 | 161 | IA.A1.2 |
| 342 | 162 | IA.A1.2 |
| 343 | 163 | IA.A1.2 |
| 344 | 164 | IA.A1.2 |
| 345 | 165 | IA.A1.2 |
| 346 | 166 | IA.A1.2 |
| 347 | 167 | IA.A1.2 |
| 348 | 168 | IA.A1.2 |
| 349 | 169 | IA.A1.2 |
| 350 | 170 | IA.A1.2 |
| 351 | 171 | IA.A1.2 |
| 352 | 172 | IA.A1.2 |
| 353 | 173 | IA.A1.2 |
| 354 | 174 | IA.A1.2 |
| 355 | 175 | IA.A1.2 |
| 356 | 176 | IA.A1.2 |
| 357 | 177 | IA.A1.2 |
| 358 | 178 | IA.A1.2 |
| 359 | 179 | IA.A1.2 |
| 360 | 180 | IA.A1.2 |
| 361 | 1 | IA.A1.3 |
| 362 | 2 | IA.A1.3 |
| 363 | 3 | IA.A1.3 |
| 364 | 4 | IA.A1.3 |
| 365 | 5 | IA.A1.3 |
| 366 | 6 | IA.A1.3 |
| 367 | 7 | IA.A1.3 |
| 368 | 8 | IA.A1.3 |
| 369 | 9 | IA.A1.3 |
| 370 | 10 | IA.A1.3 |
| 371 | 11 | IA.A1.3 |
| 372 | 12 | IA.A1.3 |
| 373 | 13 | IA.A1.3 |
| 374 | 14 | IA.A1.3 |
| 375 | 15 | IA.A1.3 |
| 376 | 16 | IA.A1.3 |
| 377 | 17 | IA.A1.3 |
| 378 | 18 | IA.A1.3 |
| 379 | 19 | IA.A1.3 |
| 380 | 20 | IA.A1.3 |
| 381 | 21 | IA.A1.3 |
| 382 | 22 | IA.A1.3 |
| 383 | 23 | IA.A1.3 |
| 384 | 24 | IA.A1.3 |
| 385 | 25 | IA.A1.3 |
| 386 | 26 | IA.A1.3 |
| 387 | 27 | IA.A1.3 |
| 388 | 28 | IA.A1.3 |
| 389 | 29 | IA.A1.3 |
| 390 | 30 | IA.A1.3 |
| 391 | 31 | IA.A1.3 |
| 392 | 32 | IA.A1.3 |
| 393 | 33 | IA.A1.3 |
| 394 | 34 | IA.A1.3 |
| 395 | 35 | IA.A1.3 |
| 396 | 36 | IA.A1.3 |
| 397 | 37 | IA.A1.3 |
| 398 | 38 | IA.A1.3 |
| 399 | 39 | IA.A1.3 |
| 400 | 40 | IA.A1.3 |
| 401 | 41 | IA.A1.3 |
| 402 | 42 | IA.A1.3 |
| 403 | 43 | IA.A1.3 |
| 404 | 44 | IA.A1.3 |
| 405 | 45 | IA.A1.3 |
| 406 | 46 | IA.A1.3 |
| 407 | 47 | IA.A1.3 |

TABLE D-continued

| # | Table | Formula |
|---|---|---|
| 408 | 48 | IA.A1.3 |
| 409 | 49 | IA.A1.3 |
| 410 | 50 | IA.A1.3 |
| 411 | 51 | IA.A1.3 |
| 412 | 52 | IA.A1.3 |
| 413 | 53 | IA.A1.3 |
| 414 | 54 | IA.A1.3 |
| 415 | 55 | IA.A1.3 |
| 416 | 56 | IA.A1.3 |
| 417 | 57 | IA.A1.3 |
| 418 | 58 | IA.A1.3 |
| 419 | 59 | IA.A1.3 |
| 420 | 60 | IA.A1.3 |
| 421 | 61 | IA.A1.3 |
| 422 | 62 | IA.A1.3 |
| 423 | 63 | IA.A1.3 |
| 424 | 64 | IA.A1.3 |
| 425 | 65 | IA.A1.3 |
| 426 | 66 | IA.A1.3 |
| 427 | 67 | IA.A1.3 |
| 428 | 68 | IA.A1.3 |
| 429 | 69 | IA.A1.3 |
| 430 | 70 | IA.A1.3 |
| 431 | 71 | IA.A1.3 |
| 432 | 72 | IA.A1.3 |
| 433 | 73 | IA.A1.3 |
| 434 | 74 | IA.A1.3 |
| 435 | 75 | IA.A1.3 |
| 436 | 76 | IA.A1.3 |
| 437 | 77 | IA.A1.3 |
| 438 | 78 | IA.A1.3 |
| 439 | 79 | IA.A1.3 |
| 440 | 80 | IA.A1.3 |
| 441 | 81 | IA.A1.3 |
| 442 | 82 | IA.A1.3 |
| 443 | 83 | IA.A1.3 |
| 444 | 84 | IA.A1.3 |
| 445 | 85 | IA.A1.3 |
| 446 | 86 | IA.A1.3 |
| 447 | 87 | IA.A1.3 |
| 448 | 88 | IA.A1.3 |
| 449 | 89 | IA.A1.3 |
| 450 | 90 | IA.A1.3 |
| 451 | 91 | IA.A1.3 |
| 452 | 92 | IA.A1.3 |
| 453 | 93 | IA.A1.3 |
| 454 | 94 | IA.A1.3 |
| 455 | 95 | IA.A1.3 |
| 456 | 96 | IA.A1.3 |
| 457 | 97 | IA.A1.3 |
| 458 | 98 | IA.A1.3 |
| 459 | 99 | IA.A1.3 |
| 460 | 100 | IA.A1.3 |
| 461 | 101 | IA.A1.3 |
| 462 | 102 | IA.A1.3 |
| 463 | 103 | IA.A1.3 |
| 464 | 104 | IA.A1.3 |
| 465 | 105 | IA.A1.3 |
| 466 | 106 | IA.A1.3 |
| 467 | 107 | IA.A1.3 |
| 468 | 108 | IA.A1.3 |
| 469 | 109 | IA.A1.3 |
| 470 | 110 | IA.A1.3 |
| 471 | 111 | IA.A1.3 |
| 472 | 112 | IA.A1.3 |
| 473 | 113 | IA.A1.3 |
| 474 | 114 | IA.A1.3 |
| 475 | 115 | IA.A1.3 |
| 476 | 116 | IA.A1.3 |
| 477 | 117 | IA.A1.3 |
| 478 | 118 | IA.A1.3 |
| 479 | 119 | IA.A1.3 |
| 480 | 120 | IA.A1.3 |
| 481 | 121 | IA.A1.3 |
| 482 | 122 | IA.A1.3 |
| 483 | 123 | IA.A1.3 |
| 484 | 124 | IA.A1.3 |
| 485 | 125 | IA.A1.3 |
| 486 | 126 | IA.A1.3 |
| 487 | 127 | IA.A1.3 |
| 488 | 128 | IA.A1.3 |
| 489 | 129 | IA.A1.3 |
| 490 | 130 | IA.A1.3 |
| 491 | 131 | IA.A1.3 |
| 492 | 132 | IA.A1.3 |
| 493 | 133 | IA.A1.3 |
| 494 | 134 | IA.A1.3 |
| 495 | 135 | IA.A1.3 |
| 496 | 136 | IA.A1.3 |
| 497 | 137 | IA.A1.3 |
| 498 | 138 | IA.A1.3 |
| 499 | 139 | IA.A1.3 |
| 500 | 140 | IA.A1.3 |
| 501 | 141 | IA.A1.3 |
| 502 | 142 | IA.A1.3 |
| 503 | 143 | IA.A1.3 |
| 504 | 144 | IA.A1.3 |
| 505 | 145 | IA.A1.3 |
| 506 | 146 | IA.A1.3 |
| 507 | 147 | IA.A1.3 |
| 508 | 148 | IA.A1.3 |
| 509 | 149 | IA.A1.3 |
| 510 | 150 | IA.A1.3 |
| 511 | 151 | IA.A1.3 |
| 512 | 152 | IA.A1.3 |
| 513 | 153 | IA.A1.3 |
| 514 | 154 | IA.A1.3 |
| 515 | 155 | IA.A1.3 |
| 516 | 156 | IA.A1.3 |
| 517 | 157 | IA.A1.3 |
| 518 | 158 | IA.A1.3 |
| 519 | 159 | IA.A1.3 |
| 520 | 160 | IA.A1.3 |
| 521 | 161 | IA.A1.3 |
| 522 | 162 | IA.A1.3 |
| 523 | 163 | IA.A1.3 |
| 524 | 164 | IA.A1.3 |
| 525 | 165 | IA.A1.3 |
| 526 | 166 | IA.A1.3 |
| 527 | 167 | IA.A1.3 |
| 528 | 168 | IA.A1.3 |
| 529 | 169 | IA.A1.3 |
| 530 | 170 | IA.A1.3 |
| 531 | 171 | IA.A1.3 |
| 532 | 172 | IA.A1.3 |
| 533 | 173 | IA.A1.3 |
| 534 | 174 | IA.A1.3 |
| 535 | 175 | IA.A1.3 |
| 536 | 176 | IA.A1.3 |
| 537 | 177 | IA.A1.3 |
| 538 | 178 | IA.A1.3 |
| 539 | 179 | IA.A1.3 |
| 540 | 180 | IA.A1.3 |
| 541 | 361 | IB.A1.1 |
| 542 | 362 | IB.A1.1 |
| 543 | 363 | IB.A1.1 |
| 544 | 364 | IB.A1.1 |
| 545 | 365 | IB.A1.1 |
| 546 | 366 | IB.A1.1 |
| 547 | 367 | IB.A1.1 |
| 548 | 368 | IB.A1.1 |
| 549 | 369 | IB.A1.1 |
| 550 | 370 | IB.A1.1 |
| 551 | 371 | IB.A1.1 |
| 552 | 372 | IB.A1.1 |
| 553 | 373 | IB.A1.1 |
| 554 | 374 | IB.A1.1 |
| 555 | 375 | IB.A1.1 |
| 556 | 376 | IB.A1.1 |
| 557 | 377 | IB.A1.1 |
| 558 | 378 | IB.A1.1 |
| 559 | 379 | IB.A1.1 |
| 560 | 380 | IB.A1.1 |
| 561 | 381 | IB.A1.1 |
| 562 | 382 | IB.A1.1 |
| 563 | 383 | IB.A1.1 |

TABLE D-continued

| # | Table | Formula |
|---|---|---|
| 564 | 384 | IB.A1.1 |
| 565 | 385 | IB.A1.1 |
| 566 | 386 | IB.A1.1 |
| 567 | 387 | IB.A1.1 |
| 568 | 388 | IB.A1.1 |
| 569 | 389 | IB.A1.1 |
| 570 | 390 | IB.A1.1 |
| 571 | 391 | IB.A1.1 |
| 572 | 392 | IB.A1.1 |
| 573 | 393 | IB.A1.1 |
| 574 | 394 | IB.A1.1 |
| 575 | 395 | IB.A1.1 |
| 576 | 396 | IB.A1.1 |
| 577 | 397 | IB.A1.1 |
| 578 | 398 | IB.A1.1 |
| 579 | 399 | IB.A1.1 |
| 580 | 400 | IB.A1.1 |
| 581 | 401 | IB.A1.1 |
| 582 | 402 | IB.A1.1 |
| 583 | 403 | IB.A1.1 |
| 584 | 404 | IB.A1.1 |
| 585 | 405 | IB.A1.1 |
| 586 | 406 | IB.A1.1 |
| 587 | 407 | IB.A1.1 |
| 588 | 408 | IB.A1.1 |
| 589 | 409 | IB.A1.1 |
| 590 | 410 | IB.A1.1 |
| 591 | 411 | IB.A1.1 |
| 592 | 412 | IB.A1.1 |
| 593 | 413 | IB.A1.1 |
| 594 | 414 | IB.A1.1 |
| 595 | 415 | IB.A1.1 |
| 596 | 416 | IB.A1.1 |
| 597 | 417 | IB.A1.1 |
| 598 | 418 | IB.A1.1 |
| 599 | 419 | IB.A1.1 |
| 600 | 420 | IB.A1.1 |
| 601 | 421 | IB.A1.1 |
| 602 | 422 | IB.A1.1 |
| 603 | 423 | IB.A1.1 |
| 604 | 424 | IB.A1.1 |
| 605 | 425 | IB.A1.1 |
| 606 | 426 | IB.A1.1 |
| 607 | 427 | IB.A1.1 |
| 608 | 428 | IB.A1.1 |
| 609 | 429 | IB.A1.1 |
| 610 | 430 | IB.A1.1 |
| 611 | 431 | IB.A1.1 |
| 612 | 432 | IB.A1.1 |
| 613 | 433 | IB.A1.1 |
| 614 | 434 | IB.A1.1 |
| 615 | 435 | IB.A1.1 |
| 616 | 436 | IB.A1.1 |
| 617 | 437 | IB.A1.1 |
| 618 | 438 | IB.A1.1 |
| 619 | 439 | IB.A1.1 |
| 620 | 440 | IB.A1.1 |
| 621 | 441 | IB.A1.1 |
| 622 | 442 | IB.A1.1 |
| 623 | 443 | IB.A1.1 |
| 624 | 444 | IB.A1.1 |
| 625 | 445 | IB.A1.1 |
| 626 | 446 | IB.A1.1 |
| 627 | 447 | IB.A1.1 |
| 628 | 448 | IB.A1.1 |
| 629 | 449 | IB.A1.1 |
| 630 | 450 | IB.A1.1 |
| 631 | 451 | IB.A1.1 |
| 632 | 452 | IB.A1.1 |
| 633 | 453 | IB.A1.1 |
| 634 | 454 | IB.A1.1 |
| 635 | 455 | IB.A1.1 |
| 636 | 456 | IB.A1.1 |
| 637 | 457 | IB.A1.1 |
| 638 | 458 | IB.A1.1 |
| 639 | 459 | IB.A1.1 |
| 640 | 460 | IB.A1.1 |
| 641 | 461 | IB.A1.1 |
| 642 | 462 | IB.A1.1 |
| 643 | 463 | IB.A1.1 |
| 644 | 464 | IB.A1.1 |
| 645 | 465 | IB.A1.1 |
| 646 | 466 | IB.A1.1 |
| 647 | 467 | IB.A1.1 |
| 648 | 468 | IB.A1.1 |
| 649 | 469 | IB.A1.1 |
| 650 | 470 | IB.A1.1 |
| 651 | 471 | IB.A1.1 |
| 652 | 472 | IB.A1.1 |
| 653 | 473 | IB.A1.1 |
| 654 | 474 | IB.A1.1 |
| 655 | 475 | IB.A1.1 |
| 656 | 476 | IB.A1.1 |
| 657 | 477 | IB.A1.1 |
| 658 | 478 | IB.A1.1 |
| 659 | 479 | IB.A1.1 |
| 660 | 480 | IB.A1.1 |
| 661 | 481 | IB.A1.1 |
| 662 | 482 | IB.A1.1 |
| 663 | 483 | IB.A1.1 |
| 664 | 484 | IB.A1.1 |
| 665 | 485 | IB.A1.1 |
| 666 | 486 | IB.A1.1 |
| 667 | 487 | IB.A1.1 |
| 668 | 488 | IB.A1.1 |
| 669 | 489 | IB.A1.1 |
| 670 | 490 | IB.A1.1 |
| 671 | 491 | IB.A1.1 |
| 672 | 492 | IB.A1.1 |
| 673 | 493 | IB.A1.1 |
| 674 | 494 | IB.A1.1 |
| 675 | 495 | IB.A1.1 |
| 676 | 496 | IB.A1.1 |
| 677 | 497 | IB.A1.1 |
| 678 | 498 | IB.A1.1 |
| 679 | 499 | IB.A1.1 |
| 680 | 500 | IB.A1.1 |
| 681 | 501 | IB.A1.1 |
| 682 | 502 | IB.A1.1 |
| 683 | 503 | IB.A1.1 |
| 684 | 504 | IB.A1.1 |
| 685 | 505 | IB.A1.1 |
| 686 | 506 | IB.A1.1 |
| 687 | 507 | IB.A1.1 |
| 688 | 508 | IB.A1.1 |
| 689 | 509 | IB.A1.1 |
| 690 | 510 | IB.A1.1 |
| 691 | 511 | IB.A1.1 |
| 692 | 512 | IB.A1.1 |
| 693 | 513 | IB.A1.1 |
| 694 | 514 | IB.A1.1 |
| 695 | 515 | IB.A1.1 |
| 696 | 516 | IB.A1.1 |
| 697 | 517 | IB.A1.1 |
| 698 | 518 | IB.A1.1 |
| 699 | 519 | IB.A1.1 |
| 700 | 520 | IB.A1.1 |
| 701 | 521 | IB.A1.1 |
| 702 | 522 | IB.A1.1 |
| 703 | 523 | IB.A1.1 |
| 704 | 524 | IB.A1.1 |
| 705 | 525 | IB.A1.1 |
| 706 | 526 | IB.A1.1 |
| 707 | 527 | IB.A1.1 |
| 708 | 528 | IB.A1.1 |
| 709 | 529 | IB.A1.1 |
| 710 | 530 | IB.A1.1 |
| 711 | 531 | IB.A1.1 |
| 712 | 532 | IB.A1.1 |
| 713 | 533 | IB.A1.1 |
| 714 | 534 | IB.A1.1 |
| 715 | 535 | IB.A1.1 |
| 716 | 536 | IB.A1.1 |
| 717 | 537 | IB.A1.1 |
| 718 | 538 | IB.A1.1 |
| 719 | 539 | IB.A1.1 |

TABLE D-continued

| # | Table | Formula |
|---|---|---|
| 720 | 540 | IB.A1.1 |
| 721 | 361 | IB.A1.2 |
| 722 | 362 | IB.A1.2 |
| 723 | 363 | IB.A1.2 |
| 724 | 364 | IB.A1.2 |
| 725 | 365 | IB.A1.2 |
| 726 | 366 | IB.A1.2 |
| 727 | 367 | IB.A1.2 |
| 728 | 368 | IB.A1.2 |
| 729 | 369 | IB.A1.2 |
| 730 | 370 | IB.A1.2 |
| 731 | 371 | IB.A1.2 |
| 732 | 372 | IB.A1.2 |
| 733 | 373 | IB.A1.2 |
| 734 | 374 | IB.A1.2 |
| 735 | 375 | IB.A1.2 |
| 736 | 376 | IB.A1.2 |
| 737 | 377 | IB.A1.2 |
| 738 | 378 | IB.A1.2 |
| 739 | 379 | IB.A1.2 |
| 740 | 380 | IB.A1.2 |
| 741 | 381 | IB.A1.2 |
| 742 | 382 | IB.A1.2 |
| 743 | 383 | IB.A1.2 |
| 744 | 384 | IB.A1.2 |
| 745 | 385 | IB.A1.2 |
| 746 | 386 | IB.A1.2 |
| 747 | 387 | IB.A1.2 |
| 748 | 388 | IB.A1.2 |
| 749 | 389 | IB.A1.2 |
| 750 | 390 | IB.A1.2 |
| 751 | 391 | IB.A1.2 |
| 752 | 392 | IB.A1.2 |
| 753 | 393 | IB.A1.2 |
| 754 | 394 | IB.A1.2 |
| 755 | 395 | IB.A1.2 |
| 756 | 396 | IB.A1.2 |
| 757 | 397 | IB.A1.2 |
| 758 | 398 | IB.A1.2 |
| 759 | 399 | IB.A1.2 |
| 760 | 400 | IB.A1.2 |
| 761 | 401 | IB.A1.2 |
| 762 | 402 | IB.A1.2 |
| 763 | 403 | IB.A1.2 |
| 764 | 404 | IB.A1.2 |
| 765 | 405 | IB.A1.2 |
| 766 | 406 | IB.A1.2 |
| 767 | 407 | IB.A1.2 |
| 768 | 408 | IB.A1.2 |
| 769 | 409 | IB.A1.2 |
| 770 | 410 | IB.A1.2 |
| 771 | 411 | IB.A1.2 |
| 772 | 412 | IB.A1.2 |
| 773 | 413 | IB.A1.2 |
| 774 | 414 | IB.A1.2 |
| 775 | 415 | IB.A1.2 |
| 776 | 416 | IB.A1.2 |
| 777 | 417 | IB.A1.2 |
| 778 | 418 | IB.A1.2 |
| 779 | 419 | IB.A1.2 |
| 780 | 420 | IB.A1.2 |
| 781 | 421 | IB.A1.2 |
| 782 | 422 | IB.A1.2 |
| 783 | 423 | IB.A1.2 |
| 784 | 424 | IB.A1.2 |
| 785 | 425 | IB.A1.2 |
| 786 | 426 | IB.A1.2 |
| 787 | 427 | IB.A1.2 |
| 788 | 428 | IB.A1.2 |
| 789 | 429 | IB.A1.2 |
| 790 | 430 | IB.A1.2 |
| 791 | 431 | IB.A1.2 |
| 792 | 432 | IB.A1.2 |
| 793 | 433 | IB.A1.2 |
| 794 | 434 | IB.A1.2 |
| 795 | 435 | IB.A1.2 |
| 796 | 436 | IB.A1.2 |
| 797 | 437 | IB.A1.2 |
| 798 | 438 | IB.A1.2 |
| 799 | 439 | IB.A1.2 |
| 800 | 440 | IB.A1.2 |
| 801 | 441 | IB.A1.2 |
| 802 | 442 | IB.A1.2 |
| 803 | 443 | IB.A1.2 |
| 804 | 444 | IB.A1.2 |
| 805 | 445 | IB.A1.2 |
| 806 | 446 | IB.A1.2 |
| 807 | 447 | IB.A1.2 |
| 808 | 448 | IB.A1.2 |
| 809 | 449 | IB.A1.2 |
| 810 | 450 | IB.A1.2 |
| 811 | 451 | IB.A1.2 |
| 812 | 452 | IB.A1.2 |
| 813 | 453 | IB.A1.2 |
| 814 | 454 | IB.A1.2 |
| 815 | 455 | IB.A1.2 |
| 816 | 456 | IB.A1.2 |
| 817 | 457 | IB.A1.2 |
| 818 | 458 | IB.A1.2 |
| 819 | 459 | IB.A1.2 |
| 820 | 460 | IB.A1.2 |
| 821 | 461 | IB.A1.2 |
| 822 | 462 | IB.A1.2 |
| 823 | 463 | IB.A1.2 |
| 824 | 464 | IB.A1.2 |
| 825 | 465 | IB.A1.2 |
| 826 | 466 | IB.A1.2 |
| 827 | 467 | IB.A1.2 |
| 828 | 468 | IB.A1.2 |
| 829 | 469 | IB.A1.2 |
| 830 | 470 | IB.A1.2 |
| 831 | 471 | IB.A1.2 |
| 832 | 472 | IB.A1.2 |
| 833 | 473 | IB.A1.2 |
| 834 | 474 | IB.A1.2 |
| 835 | 475 | IB.A1.2 |
| 836 | 476 | IB.A1.2 |
| 837 | 477 | IB.A1.2 |
| 838 | 478 | IB.A1.2 |
| 839 | 479 | IB.A1.2 |
| 840 | 480 | IB.A1.2 |
| 841 | 481 | IB.A1.2 |
| 842 | 482 | IB.A1.2 |
| 843 | 483 | IB.A1.2 |
| 844 | 484 | IB.A1.2 |
| 845 | 485 | IB.A1.2 |
| 846 | 486 | IB.A1.2 |
| 847 | 487 | IB.A1.2 |
| 848 | 488 | IB.A1.2 |
| 849 | 489 | IB.A1.2 |
| 850 | 490 | IB.A1.2 |
| 851 | 491 | IB.A1.2 |
| 852 | 492 | IB.A1.2 |
| 853 | 493 | IB.A1.2 |
| 854 | 494 | IB.A1.2 |
| 855 | 495 | IB.A1.2 |
| 856 | 496 | IB.A1.2 |
| 857 | 497 | IB.A1.2 |
| 858 | 498 | IB.A1.2 |
| 859 | 499 | IB.A1.2 |
| 860 | 500 | IB.A1.2 |
| 861 | 501 | IB.A1.2 |
| 862 | 502 | IB.A1.2 |
| 863 | 503 | IB.A1.2 |
| 864 | 504 | IB.A1.2 |
| 865 | 505 | IB.A1.2 |
| 866 | 506 | IB.A1.2 |
| 867 | 507 | IB.A1.2 |
| 868 | 508 | IB.A1.2 |
| 869 | 509 | IB.A1.2 |
| 870 | 510 | IB.A1.2 |
| 871 | 511 | IB.A1.2 |
| 872 | 512 | IB.A1.2 |
| 873 | 513 | IB.A1.2 |
| 874 | 514 | IB.A1.2 |
| 875 | 515 | IB.A1.2 |

TABLE D-continued

| # | Table | Formula |
|---|---|---|
| 876 | 516 | IB.A1.2 |
| 877 | 517 | IB.A1.2 |
| 878 | 518 | IB.A1.2 |
| 879 | 519 | IB.A1.2 |
| 880 | 520 | IB.A1.2 |
| 881 | 521 | IB.A1.2 |
| 882 | 522 | IB.A1.2 |
| 883 | 523 | IB.A1.2 |
| 884 | 524 | IB.A1.2 |
| 885 | 525 | IB.A1.2 |
| 886 | 526 | IB.A1.2 |
| 887 | 527 | IB.A1.2 |
| 888 | 528 | IB.A1.2 |
| 889 | 529 | IB.A1.2 |
| 890 | 530 | IB.A1.2 |
| 891 | 531 | IB.A1.2 |
| 892 | 532 | IB.A1.2 |
| 893 | 533 | IB.A1.2 |
| 894 | 534 | IB.A1.2 |
| 895 | 535 | IB.A1.2 |
| 896 | 536 | IB.A1.2 |
| 897 | 537 | IB.A1.2 |
| 898 | 538 | IB.A1.2 |
| 899 | 539 | IB.A1.2 |
| 900 | 540 | IB.A1.2 |
| 901 | 361 | IB.A1.3 |
| 902 | 362 | IB.A1.3 |
| 903 | 363 | IB.A1.3 |
| 904 | 364 | IB.A1.3 |
| 905 | 365 | IB.A1.3 |
| 906 | 366 | IB.A1.3 |
| 907 | 367 | IB.A1.3 |
| 908 | 368 | IB.A1.3 |
| 909 | 369 | IB.A1.3 |
| 910 | 370 | IB.A1.3 |
| 911 | 371 | IB.A1.3 |
| 912 | 372 | IB.A1.3 |
| 913 | 373 | IB.A1.3 |
| 914 | 374 | IB.A1.3 |
| 915 | 375 | IB.A1.3 |
| 916 | 376 | IB.A1.3 |
| 917 | 377 | IB.A1.3 |
| 918 | 378 | IB.A1.3 |
| 919 | 379 | IB.A1.3 |
| 920 | 380 | IB.A1.3 |
| 921 | 381 | IB.A1.3 |
| 922 | 382 | IB.A1.3 |
| 923 | 383 | IB.A1.3 |
| 924 | 384 | IB.A1.3 |
| 925 | 385 | IB.A1.3 |
| 926 | 386 | IB.A1.3 |
| 927 | 387 | IB.A1.3 |
| 928 | 388 | IB.A1.3 |
| 929 | 389 | IB.A1.3 |
| 930 | 390 | IB.A1.3 |
| 931 | 391 | IB.A1.3 |
| 932 | 392 | IB.A1.3 |
| 933 | 393 | IB.A1.3 |
| 934 | 394 | IB.A1.3 |
| 935 | 395 | IB.A1.3 |
| 936 | 396 | IB.A1.3 |
| 937 | 397 | IB.A1.3 |
| 938 | 398 | IB.A1.3 |
| 939 | 399 | IB.A1.3 |
| 940 | 400 | IB.A1.3 |
| 941 | 401 | IB.A1.3 |
| 942 | 402 | IB.A1.3 |
| 943 | 403 | IB.A1.3 |
| 944 | 404 | IB.A1.3 |
| 945 | 405 | IB.A1.3 |
| 946 | 406 | IB.A1.3 |
| 947 | 407 | IB.A1.3 |
| 948 | 408 | IB.A1.3 |
| 949 | 409 | IB.A1.3 |
| 950 | 410 | IB.A1.3 |
| 951 | 411 | IB.A1.3 |
| 952 | 412 | IB.A1.3 |
| 953 | 413 | IB.A1.3 |
| 954 | 414 | IB.A1.3 |
| 955 | 415 | IB.A1.3 |
| 956 | 416 | IB.A1.3 |
| 957 | 417 | IB.A1.3 |
| 958 | 418 | IB.A1.3 |
| 959 | 419 | IB.A1.3 |
| 960 | 420 | IB.A1.3 |
| 961 | 421 | IB.A1.3 |
| 962 | 422 | IB.A1.3 |
| 963 | 423 | IB.A1.3 |
| 964 | 424 | IB.A1.3 |
| 965 | 425 | IB.A1.3 |
| 966 | 426 | IB.A1.3 |
| 967 | 427 | IB.A1.3 |
| 968 | 428 | IB.A1.3 |
| 969 | 429 | IB.A1.3 |
| 970 | 430 | IB.A1.3 |
| 971 | 431 | IB.A1.3 |
| 972 | 432 | IB.A1.3 |
| 973 | 433 | IB.A1.3 |
| 974 | 434 | IB.A1.3 |
| 975 | 435 | IB.A1.3 |
| 976 | 436 | IB.A1.3 |
| 977 | 437 | IB.A1.3 |
| 978 | 438 | IB.A1.3 |
| 979 | 439 | IB.A1.3 |
| 980 | 440 | IB.A1.3 |
| 981 | 441 | IB.A1.3 |
| 982 | 442 | IB.A1.3 |
| 983 | 443 | IB.A1.3 |
| 984 | 444 | IB.A1.3 |
| 985 | 445 | IB.A1.3 |
| 986 | 446 | IB.A1.3 |
| 987 | 447 | IB.A1.3 |
| 988 | 448 | IB.A1.3 |
| 989 | 449 | IB.A1.3 |
| 990 | 450 | IB.A1.3 |
| 991 | 451 | IB.A1.3 |
| 992 | 452 | IB.A1.3 |
| 993 | 453 | IB.A1.3 |
| 994 | 454 | IB.A1.3 |
| 995 | 455 | IB.A1.3 |
| 996 | 456 | IB.A1.3 |
| 997 | 457 | IB.A1.3 |
| 998 | 458 | IB.A1.3 |
| 999 | 459 | IB.A1.3 |
| 1000 | 460 | IB.A1.3 |
| 1001 | 461 | IB.A1.3 |
| 1002 | 462 | IB.A1.3 |
| 1003 | 463 | IB.A1.3 |
| 1004 | 464 | IB.A1.3 |
| 1005 | 465 | IB.A1.3 |
| 1006 | 466 | IB.A1.3 |
| 1007 | 467 | IB.A1.3 |
| 1008 | 468 | IB.A1.3 |
| 1009 | 469 | IB.A1.3 |
| 1010 | 470 | IB.A1.3 |
| 1011 | 471 | IB.A1.3 |
| 1012 | 472 | IB.A1.3 |
| 1013 | 473 | IB.A1.3 |
| 1014 | 474 | IB.A1.3 |
| 1015 | 475 | IB.A1.3 |
| 1016 | 476 | IB.A1.3 |
| 1017 | 477 | IB.A1.3 |
| 1018 | 478 | IB.A1.3 |
| 1019 | 479 | IB.A1.3 |
| 1020 | 480 | IB.A1.3 |
| 1021 | 481 | IB.A1.3 |
| 1022 | 482 | IB.A1.3 |
| 1023 | 483 | IB.A1.3 |
| 1024 | 484 | IB.A1.3 |
| 1025 | 485 | IB.A1.3 |
| 1026 | 486 | IB.A1.3 |
| 1027 | 487 | IB.A1.3 |
| 1028 | 488 | IB.A1.3 |
| 1029 | 489 | IB.A1.3 |
| 1030 | 490 | IB.A1.3 |
| 1031 | 491 | IB.A1.3 |

TABLE D-continued

| # | Table | Formula |
|---|---|---|
| 1032 | 492 | IB.A1.3 |
| 1033 | 493 | IB.A1.3 |
| 1034 | 494 | IB.A1.3 |
| 1035 | 495 | IB.A1.3 |
| 1036 | 496 | IB.A1.3 |
| 1037 | 497 | IB.A1.3 |
| 1038 | 498 | IB.A1.3 |
| 1039 | 499 | IB.A1.3 |
| 1040 | 500 | IB.A1.3 |
| 1041 | 501 | IB.A1.3 |
| 1042 | 502 | IB.A1.3 |
| 1043 | 503 | IB.A1.3 |
| 1044 | 504 | IB.A1.3 |
| 1045 | 505 | IB.A1.3 |
| 1046 | 506 | IB.A1.3 |
| 1047 | 507 | IB.A1.3 |
| 1048 | 508 | IB.A1.3 |
| 1049 | 509 | IB.A1.3 |
| 1050 | 510 | IB.A1.3 |
| 1051 | 511 | IB.A1.3 |
| 1052 | 512 | IB.A1.3 |
| 1053 | 513 | IB.A1.3 |
| 1054 | 514 | IB.A1.3 |
| 1055 | 515 | IB.A1.3 |
| 1056 | 516 | IB.A1.3 |
| 1057 | 517 | IB.A1.3 |
| 1058 | 518 | IB.A1.3 |
| 1059 | 519 | IB.A1.3 |
| 1060 | 520 | IB.A1.3 |
| 1061 | 521 | IB.A1.3 |
| 1062 | 522 | IB.A1.3 |
| 1063 | 523 | IB.A1.3 |
| 1064 | 524 | IB.A1.3 |
| 1065 | 525 | IB.A1.3 |
| 1066 | 526 | IB.A1.3 |
| 1067 | 527 | IB.A1.3 |
| 1068 | 528 | IB.A1.3 |
| 1069 | 529 | IB.A1.3 |
| 1070 | 530 | IB.A1.3 |
| 1071 | 531 | IB.A1.3 |
| 1072 | 532 | IB.A1.3 |
| 1073 | 533 | IB.A1.3 |
| 1074 | 534 | IB.A1.3 |
| 1075 | 535 | IB.A1.3 |
| 1076 | 536 | IB.A1.3 |
| 1077 | 537 | IB.A1.3 |
| 1078 | 538 | IB.A1.3 |
| 1079 | 539 | IB.A1.3 |
| 1080 | 540 | IB.A1.3 |
| 1081 | 361 | IC.A1.1 |
| 1082 | 362 | IC.A1.1 |
| 1083 | 363 | IC.A1.1 |
| 1084 | 364 | IC.A1.1 |
| 1085 | 365 | IC.A1.1 |
| 1086 | 366 | IC.A1.1 |
| 1087 | 367 | IC.A1.1 |
| 1088 | 368 | IC.A1.1 |
| 1089 | 369 | IC.A1.1 |
| 1090 | 370 | IC.A1.1 |
| 1091 | 371 | IC.A1.1 |
| 1092 | 372 | IC.A1.1 |
| 1093 | 373 | IC.A1.1 |
| 1094 | 374 | IC.A1.1 |
| 1095 | 375 | IC.A1.1 |
| 1096 | 376 | IC.A1.1 |
| 1097 | 377 | IC.A1.1 |
| 1098 | 378 | IC.A1.1 |
| 1099 | 379 | IC.A1.1 |
| 1100 | 380 | IC.A1.1 |
| 1101 | 381 | IC.A1.1 |
| 1102 | 382 | IC.A1.1 |
| 1103 | 383 | IC.A1.1 |
| 1104 | 384 | IC.A1.1 |
| 1105 | 385 | IC.A1.1 |
| 1106 | 386 | IC.A1.1 |
| 1107 | 387 | IC.A1.1 |
| 1108 | 388 | IC.A1.1 |
| 1109 | 389 | IC.A1.1 |
| 1110 | 390 | IC.A1.1 |
| 1111 | 391 | IC.A1.1 |
| 1112 | 392 | IC.A1.1 |
| 1113 | 393 | IC.A1.1 |
| 1114 | 394 | IC.A1.1 |
| 1115 | 395 | IC.A1.1 |
| 1116 | 396 | IC.A1.1 |
| 1117 | 397 | IC.A1.1 |
| 1118 | 398 | IC.A1.1 |
| 1119 | 399 | IC.A1.1 |
| 1120 | 400 | IC.A1.1 |
| 1121 | 401 | IC.A1.1 |
| 1122 | 402 | IC.A1.1 |
| 1123 | 403 | IC.A1.1 |
| 1124 | 404 | IC.A1.1 |
| 1125 | 405 | IC.A1.1 |
| 1126 | 406 | IC.A1.1 |
| 1127 | 407 | IC.A1.1 |
| 1128 | 408 | IC.A1.1 |
| 1129 | 409 | IC.A1.1 |
| 1130 | 410 | IC.A1.1 |
| 1131 | 411 | IC.A1.1 |
| 1132 | 412 | IC.A1.1 |
| 1133 | 413 | IC.A1.1 |
| 1134 | 414 | IC.A1.1 |
| 1135 | 415 | IC.A1.1 |
| 1136 | 416 | IC.A1.1 |
| 1137 | 417 | IC.A1.1 |
| 1138 | 418 | IC.A1.1 |
| 1139 | 419 | IC.A1.1 |
| 1140 | 420 | IC.A1.1 |
| 1141 | 421 | IC.A1.1 |
| 1142 | 422 | IC.A1.1 |
| 1143 | 423 | IC.A1.1 |
| 1144 | 424 | IC.A1.1 |
| 1145 | 425 | IC.A1.1 |
| 1146 | 426 | IC.A1.1 |
| 1147 | 427 | IC.A1.1 |
| 1148 | 428 | IC.A1.1 |
| 1149 | 429 | IC.A1.1 |
| 1150 | 430 | IC.A1.1 |
| 1151 | 431 | IC.A1.1 |
| 1152 | 432 | IC.A1.1 |
| 1153 | 433 | IC.A1.1 |
| 1154 | 434 | IC.A1.1 |
| 1155 | 435 | IC.A1.1 |
| 1156 | 436 | IC.A1.1 |
| 1157 | 437 | IC.A1.1 |
| 1158 | 438 | IC.A1.1 |
| 1159 | 439 | IC.A1.1 |
| 1160 | 440 | IC.A1.1 |
| 1161 | 441 | IC.A1.1 |
| 1162 | 442 | IC.A1.1 |
| 1163 | 443 | IC.A1.1 |
| 1164 | 444 | IC.A1.1 |
| 1165 | 445 | IC.A1.1 |
| 1166 | 446 | IC.A1.1 |
| 1167 | 447 | IC.A1.1 |
| 1168 | 448 | IC.A1.1 |
| 1169 | 449 | IC.A1.1 |
| 1170 | 450 | IC.A1.1 |
| 1171 | 451 | IC.A1.1 |
| 1172 | 452 | IC.A1.1 |
| 1173 | 453 | IC.A1.1 |
| 1174 | 454 | IC.A1.1 |
| 1175 | 455 | IC.A1.1 |
| 1176 | 456 | IC.A1.1 |
| 1177 | 457 | IC.A1.1 |
| 1178 | 458 | IC.A1.1 |
| 1179 | 459 | IC.A1.1 |
| 1180 | 460 | IC.A1.1 |
| 1181 | 461 | IC.A1.1 |
| 1182 | 462 | IC.A1.1 |
| 1183 | 463 | IC.A1.1 |
| 1184 | 464 | IC.A1.1 |
| 1185 | 465 | IC.A1.1 |
| 1186 | 466 | IC.A1.1 |
| 1187 | 467 | IC.A1.1 |

TABLE D-continued

| # | Table | Formula |
|---|---|---|
| 1188 | 468 | IC.A1.1 |
| 1189 | 469 | IC.A1.1 |
| 1190 | 470 | IC.A1.1 |
| 1191 | 471 | IC.A1.1 |
| 1192 | 472 | IC.A1.1 |
| 1193 | 473 | IC.A1.1 |
| 1194 | 474 | IC.A1.1 |
| 1195 | 475 | IC.A1.1 |
| 1196 | 476 | IC.A1.1 |
| 1197 | 477 | IC.A1.1 |
| 1198 | 478 | IC.A1.1 |
| 1199 | 479 | IC.A1.1 |
| 1200 | 480 | IC.A1.1 |
| 1201 | 481 | IC.A1.1 |
| 1202 | 482 | IC.A1.1 |
| 1203 | 483 | IC.A1.1 |
| 1204 | 484 | IC.A1.1 |
| 1205 | 485 | IC.A1.1 |
| 1206 | 486 | IC.A1.1 |
| 1207 | 487 | IC.A1.1 |
| 1208 | 488 | IC.A1.1 |
| 1209 | 489 | IC.A1.1 |
| 1210 | 490 | IC.A1.1 |
| 1211 | 491 | IC.A1.1 |
| 1212 | 492 | IC.A1.1 |
| 1213 | 493 | IC.A1.1 |
| 1214 | 494 | IC.A1.1 |
| 1215 | 495 | IC.A1.1 |
| 1216 | 496 | IC.A1.1 |
| 1217 | 497 | IC.A1.1 |
| 1218 | 498 | IC.A1.1 |
| 1219 | 499 | IC.A1.1 |
| 1220 | 500 | IC.A1.1 |
| 1221 | 501 | IC.A1.1 |
| 1222 | 502 | IC.A1.1 |
| 1223 | 503 | IC.A1.1 |
| 1224 | 504 | IC.A1.1 |
| 1225 | 505 | IC.A1.1 |
| 1226 | 506 | IC.A1.1 |
| 1227 | 507 | IC.A1.1 |
| 1228 | 508 | IC.A1.1 |
| 1229 | 509 | IC.A1.1 |
| 1230 | 510 | IC.A1.1 |
| 1231 | 511 | IC.A1.1 |
| 1232 | 512 | IC.A1.1 |
| 1233 | 513 | IC.A1.1 |
| 1234 | 514 | IC.A1.1 |
| 1235 | 515 | IC.A1.1 |
| 1236 | 516 | IC.A1.1 |
| 1237 | 517 | IC.A1.1 |
| 1238 | 518 | IC.A1.1 |
| 1239 | 519 | IC.A1.1 |
| 1240 | 520 | IC.A1.1 |
| 1241 | 521 | IC.A1.1 |
| 1242 | 522 | IC.A1.1 |
| 1243 | 523 | IC.A1.1 |
| 1244 | 524 | IC.A1.1 |
| 1245 | 525 | IC.A1.1 |
| 1246 | 526 | IC.A1.1 |
| 1247 | 527 | IC.A1.1 |
| 1248 | 528 | IC.A1.1 |
| 1249 | 529 | IC.A1.1 |
| 1250 | 530 | IC.A1.1 |
| 1251 | 531 | IC.A1.1 |
| 1252 | 532 | IC.A1.1 |
| 1253 | 533 | IC.A1.1 |
| 1254 | 534 | IC.A1.1 |
| 1255 | 535 | IC.A1.1 |
| 1256 | 536 | IC.A1.1 |
| 1257 | 537 | IC.A1.1 |
| 1258 | 538 | IC.A1.1 |
| 1259 | 539 | IC.A1.1 |
| 1260 | 540 | IC.A1.1 |
| 1261 | 361 | IC-A1.2 |
| 1262 | 362 | IC-A1.2 |
| 1263 | 363 | IC-A1.2 |
| 1264 | 364 | IC-A1.2 |
| 1265 | 365 | IC-A1.2 |
| 1266 | 366 | IC-A1.2 |
| 1267 | 367 | IC-A1.2 |
| 1268 | 368 | IC-A1.2 |
| 1269 | 369 | IC-A1.2 |
| 1270 | 370 | IC-A1.2 |
| 1271 | 371 | IC-A1.2 |
| 1272 | 372 | IC-A1.2 |
| 1273 | 373 | IC-A1.2 |
| 1274 | 374 | IC-A1.2 |
| 1275 | 375 | IC-A1.2 |
| 1276 | 376 | IC-A1.2 |
| 1277 | 377 | IC-A1.2 |
| 1278 | 378 | IC-A1.2 |
| 1279 | 379 | IC-A1.2 |
| 1280 | 380 | IC-A1.2 |
| 1281 | 381 | IC-A1.2 |
| 1282 | 382 | IC-A1.2 |
| 1283 | 383 | IC-A1.2 |
| 1284 | 384 | IC-A1.2 |
| 1285 | 385 | IC-A1.2 |
| 1286 | 386 | IC-A1.2 |
| 1287 | 387 | IC-A1.2 |
| 1288 | 388 | IC-A1.2 |
| 1289 | 389 | IC-A1.2 |
| 1290 | 390 | IC-A1.2 |
| 1291 | 391 | IC-A1.2 |
| 1292 | 392 | IC-A1.2 |
| 1293 | 393 | IC-A1.2 |
| 1294 | 394 | IC-A1.2 |
| 1295 | 395 | IC-A1.2 |
| 1296 | 396 | IC-A1.2 |
| 1297 | 397 | IC-A1.2 |
| 1298 | 398 | IC-A1.2 |
| 1299 | 399 | IC-A1.2 |
| 1300 | 400 | IC-A1.2 |
| 1301 | 401 | IC-A1.2 |
| 1302 | 402 | IC-A1.2 |
| 1303 | 403 | IC-A1.2 |
| 1304 | 404 | IC-A1.2 |
| 1305 | 405 | IC-A1.2 |
| 1306 | 406 | IC-A1.2 |
| 1307 | 407 | IC-A1.2 |
| 1308 | 408 | IC-A1.2 |
| 1309 | 409 | IC-A1.2 |
| 1310 | 410 | IC-A1.2 |
| 1311 | 411 | IC-A1.2 |
| 1312 | 412 | IC-A1.2 |
| 1313 | 413 | IC-A1.2 |
| 1314 | 414 | IC-A1.2 |
| 1315 | 415 | IC-A1.2 |
| 1316 | 416 | IC-A1.2 |
| 1317 | 417 | IC-A1.2 |
| 1318 | 418 | IC-A1.2 |
| 1319 | 419 | IC-A1.2 |
| 1320 | 420 | IC-A1.2 |
| 1321 | 421 | IC-A1.2 |
| 1322 | 422 | IC-A1.2 |
| 1323 | 423 | IC-A1.2 |
| 1324 | 424 | IC-A1.2 |
| 1325 | 425 | IC-A1.2 |
| 1326 | 426 | IC-A1.2 |
| 1327 | 427 | IC-A1.2 |
| 1328 | 428 | IC-A1.2 |
| 1329 | 429 | IC-A1.2 |
| 1330 | 430 | IC-A1.2 |
| 1331 | 431 | IC-A1.2 |
| 1332 | 432 | IC-A1.2 |
| 1333 | 433 | IC-A1.2 |
| 1334 | 434 | IC-A1.2 |
| 1335 | 435 | IC-A1.2 |
| 1336 | 436 | IC-A1.2 |
| 1337 | 437 | IC-A1.2 |
| 1338 | 438 | IC-A1.2 |
| 1339 | 439 | IC-A1.2 |
| 1340 | 440 | IC-A1.2 |
| 1341 | 441 | IC-A1.2 |
| 1342 | 442 | IC-A1.2 |
| 1343 | 443 | IC-A1.2 |

TABLE D-continued

| # | Table | Formula |
|---|---|---|
| 1344 | 444 | IC-A1.2 |
| 1345 | 445 | IC-A1.2 |
| 1346 | 446 | IC-A1.2 |
| 1347 | 447 | IC-A1.2 |
| 1348 | 448 | IC-A1.2 |
| 1349 | 449 | IC-A1.2 |
| 1350 | 450 | IC-A1.2 |
| 1351 | 451 | IC-A1.2 |
| 1352 | 452 | IC-A1.2 |
| 1353 | 453 | IC-A1.2 |
| 1354 | 454 | IC-A1.2 |
| 1355 | 455 | IC-A1.2 |
| 1356 | 456 | IC-A1.2 |
| 1357 | 457 | IC-A1.2 |
| 1358 | 458 | IC-A1.2 |
| 1359 | 459 | IC-A1.2 |
| 1360 | 460 | IC-A1.2 |
| 1361 | 461 | IC-A1.2 |
| 1362 | 462 | IC-A1.2 |
| 1363 | 463 | IC-A1.2 |
| 1364 | 464 | IC-A1.2 |
| 1365 | 465 | IC-A1.2 |
| 1366 | 466 | IC-A1.2 |
| 1367 | 467 | IC-A1.2 |
| 1368 | 468 | IC-A1.2 |
| 1369 | 469 | IC-A1.2 |
| 1370 | 470 | IC-A1.2 |
| 1371 | 471 | IC-A1.2 |
| 1372 | 472 | IC-A1.2 |
| 1373 | 473 | IC-A1.2 |
| 1374 | 474 | IC-A1.2 |
| 1375 | 475 | IC-A1.2 |
| 1376 | 476 | IC-A1.2 |
| 1377 | 477 | IC-A1.2 |
| 1378 | 478 | IC-A1.2 |
| 1379 | 479 | IC-A1.2 |
| 1380 | 480 | IC-A1.2 |
| 1381 | 481 | IC-A1.2 |
| 1382 | 482 | IC-A1.2 |
| 1383 | 483 | IC-A1.2 |
| 1384 | 484 | IC-A1.2 |
| 1385 | 485 | IC-A1.2 |
| 1386 | 486 | IC-A1.2 |
| 1387 | 487 | IC-A1.2 |
| 1388 | 488 | IC-A1.2 |
| 1389 | 489 | IC-A1.2 |
| 1390 | 490 | IC-A1.2 |
| 1391 | 491 | IC-A1.2 |
| 1392 | 492 | IC-A1.2 |
| 1393 | 493 | IC-A1.2 |
| 1394 | 494 | IC-A1.2 |
| 1395 | 495 | IC-A1.2 |
| 1396 | 496 | IC-A1.2 |
| 1397 | 497 | IC-A1.2 |
| 1398 | 498 | IC-A1.2 |
| 1399 | 499 | IC-A1.2 |
| 1400 | 500 | IC-A1.2 |
| 1401 | 501 | IC-A1.2 |
| 1402 | 502 | IC-A1.2 |
| 1403 | 503 | IC-A1.2 |
| 1404 | 504 | IC-A1.2 |
| 1405 | 505 | IC-A1.2 |
| 1406 | 506 | IC-A1.2 |
| 1407 | 507 | IC-A1.2 |
| 1408 | 508 | IC-A1.2 |
| 1409 | 509 | IC-A1.2 |
| 1410 | 510 | IC-A1.2 |
| 1411 | 511 | IC-A1.2 |
| 1412 | 512 | IC-A1.2 |
| 1413 | 513 | IC-A1.2 |
| 1414 | 514 | IC-A1.2 |
| 1415 | 515 | IC-A1.2 |
| 1416 | 516 | IC-A1.2 |
| 1417 | 517 | IC-A1.2 |
| 1418 | 518 | IC-A1.2 |
| 1419 | 519 | IC-A1.2 |
| 1420 | 520 | IC-A1.2 |
| 1421 | 521 | IC-A1.2 |
| 1422 | 522 | IC-A1.2 |
| 1423 | 523 | IC-A1.2 |
| 1424 | 524 | IC-A1.2 |
| 1425 | 525 | IC-A1.2 |
| 1426 | 526 | IC-A1.2 |
| 1427 | 527 | IC-A1.2 |
| 1428 | 528 | IC-A1.2 |
| 1429 | 529 | IC-A1.2 |
| 1430 | 530 | IC-A1.2 |
| 1431 | 531 | IC-A1.2 |
| 1432 | 532 | IC-A1.2 |
| 1433 | 533 | IC-A1.2 |
| 1434 | 534 | IC-A1.2 |
| 1435 | 535 | IC-A1.2 |
| 1436 | 536 | IC-A1.2 |
| 1437 | 537 | IC-A1.2 |
| 1438 | 538 | IC-A1.2 |
| 1439 | 539 | IC-A1.2 |
| 1440 | 540 | IC-A1.2 |
| 1441 | 361 | IC.A1.3 |
| 1442 | 362 | IC.A1.3 |
| 1443 | 363 | IC.A1.3 |
| 1444 | 364 | IC.A1.3 |
| 1445 | 365 | IC.A1.3 |
| 1446 | 366 | IC.A1.3 |
| 1447 | 367 | IC.A1.3 |
| 1448 | 368 | IC.A1.3 |
| 1449 | 369 | IC.A1.3 |
| 1450 | 370 | IC.A1.3 |
| 1451 | 371 | IC.A1.3 |
| 1452 | 372 | IC.A1.3 |
| 1453 | 373 | IC.A1.3 |
| 1454 | 374 | IC.A1.3 |
| 1455 | 375 | IC.A1.3 |
| 1456 | 376 | IC.A1.3 |
| 1457 | 377 | IC.A1.3 |
| 1458 | 378 | IC.A1.3 |
| 1459 | 379 | IC.A1.3 |
| 1460 | 380 | IC.A1.3 |
| 1461 | 381 | IC.A1.3 |
| 1462 | 382 | IC.A1.3 |
| 1463 | 383 | IC.A1.3 |
| 1464 | 384 | IC.A1.3 |
| 1465 | 385 | IC.A1.3 |
| 1466 | 386 | IC.A1.3 |
| 1467 | 387 | IC.A1.3 |
| 1468 | 388 | IC.A1.3 |
| 1469 | 389 | IC.A1.3 |
| 1470 | 390 | IC.A1.3 |
| 1471 | 391 | IC.A1.3 |
| 1472 | 392 | IC.A1.3 |
| 1473 | 393 | IC.A1.3 |
| 1474 | 394 | IC.A1.3 |
| 1475 | 395 | IC.A1.3 |
| 1476 | 396 | IC.A1.3 |
| 1477 | 397 | IC.A1.3 |
| 1478 | 398 | IC.A1.3 |
| 1479 | 399 | IC.A1.3 |
| 1480 | 400 | IC.A1.3 |
| 1481 | 401 | IC.A1.3 |
| 1482 | 402 | IC.A1.3 |
| 1483 | 403 | IC.A1.3 |
| 1484 | 404 | IC.A1.3 |
| 1485 | 405 | IC.A1.3 |
| 1486 | 406 | IC.A1.3 |
| 1487 | 407 | IC.A1.3 |
| 1488 | 408 | IC.A1.3 |
| 1489 | 409 | IC.A1.3 |
| 1490 | 410 | IC.A1.3 |
| 1491 | 411 | IC.A1.3 |
| 1492 | 412 | IC.A1.3 |
| 1493 | 413 | IC.A1.3 |
| 1494 | 414 | IC.A1.3 |
| 1495 | 415 | IC.A1.3 |
| 1496 | 416 | IC.A1.3 |
| 1497 | 417 | IC.A1.3 |
| 1498 | 418 | IC.A1.3 |
| 1499 | 419 | IC.A1.3 |

TABLE D-continued

| # | Table | Formula |
|---|---|---|
| 1500 | 420 | IC.A1.3 |
| 1501 | 421 | IC.A1.3 |
| 1502 | 422 | IC.A1.3 |
| 1503 | 423 | IC.A1.3 |
| 1504 | 424 | IC.A1.3 |
| 1505 | 425 | IC.A1.3 |
| 1506 | 426 | IC.A1.3 |
| 1507 | 427 | IC.A1.3 |
| 1508 | 428 | IC.A1.3 |
| 1509 | 429 | IC.A1.3 |
| 1510 | 430 | IC.A1.3 |
| 1511 | 431 | IC.A1.3 |
| 1512 | 432 | IC.A1.3 |
| 1513 | 433 | IC.A1.3 |
| 1514 | 434 | IC.A1.3 |
| 1515 | 435 | IC.A1.3 |
| 1516 | 436 | IC.A1.3 |
| 1517 | 437 | IC.A1.3 |
| 1518 | 438 | IC.A1.3 |
| 1519 | 439 | IC.A1.3 |
| 1520 | 440 | IC.A1.3 |
| 1521 | 441 | IC.A1.3 |
| 1522 | 442 | IC.A1.3 |
| 1523 | 443 | IC.A1.3 |
| 1524 | 444 | IC.A1.3 |
| 1525 | 445 | IC.A1.3 |
| 1526 | 446 | IC.A1.3 |
| 1527 | 447 | IC.A1.3 |
| 1528 | 448 | IC.A1.3 |
| 1529 | 449 | IC.A1.3 |
| 1530 | 450 | IC.A1.3 |
| 1531 | 451 | IC.A1.3 |
| 1532 | 452 | IC.A1.3 |
| 1533 | 453 | IC.A1.3 |
| 1534 | 454 | IC.A1.3 |
| 1535 | 455 | IC.A1.3 |
| 1536 | 456 | IC.A1.3 |
| 1537 | 457 | IC.A1.3 |
| 1538 | 458 | IC.A1.3 |
| 1539 | 459 | IC.A1.3 |
| 1540 | 460 | IC.A1.3 |
| 1541 | 461 | IC.A1.3 |
| 1542 | 462 | IC.A1.3 |
| 1543 | 463 | IC.A1.3 |
| 1544 | 464 | IC.A1.3 |
| 1545 | 465 | IC.A1.3 |
| 1546 | 466 | IC.A1.3 |
| 1547 | 467 | IC.A1.3 |
| 1548 | 468 | IC.A1.3 |
| 1549 | 469 | IC.A1.3 |
| 1550 | 470 | IC.A1.3 |
| 1551 | 471 | IC.A1.3 |
| 1552 | 472 | IC.A1.3 |
| 1553 | 473 | IC.A1.3 |
| 1554 | 474 | IC.A1.3 |
| 1555 | 475 | IC.A1.3 |
| 1556 | 476 | IC.A1.3 |
| 1557 | 477 | IC.A1.3 |
| 1558 | 478 | IC.A1.3 |
| 1559 | 479 | IC.A1.3 |
| 1560 | 480 | IC.A1.3 |
| 1561 | 481 | IC.A1.3 |
| 1562 | 482 | IC.A1.3 |
| 1563 | 483 | IC.A1.3 |
| 1564 | 484 | IC.A1.3 |
| 1565 | 485 | IC.A1.3 |
| 1566 | 486 | IC.A1.3 |
| 1567 | 487 | IC.A1.3 |
| 1568 | 488 | IC.A1.3 |
| 1569 | 489 | IC.A1.3 |
| 1570 | 490 | IC.A1.3 |
| 1571 | 491 | IC.A1.3 |
| 1572 | 492 | IC.A1.3 |
| 1573 | 493 | IC.A1.3 |
| 1574 | 494 | IC.A1.3 |
| 1575 | 495 | IC.A1.3 |
| 1576 | 496 | IC.A1.3 |
| 1577 | 497 | IC.A1.3 |
| 1578 | 498 | IC.A1.3 |
| 1579 | 499 | IC.A1.3 |
| 1580 | 500 | IC.A1.3 |
| 1581 | 501 | IC.A1.3 |
| 1582 | 502 | IC.A1.3 |
| 1583 | 503 | IC.A1.3 |
| 1584 | 504 | IC.A1.3 |
| 1585 | 505 | IC.A1.3 |
| 1586 | 506 | IC.A1.3 |
| 1587 | 507 | IC.A1.3 |
| 1588 | 508 | IC.A1.3 |
| 1589 | 509 | IC.A1.3 |
| 1590 | 510 | IC.A1.3 |
| 1591 | 511 | IC.A1.3 |
| 1592 | 512 | IC.A1.3 |
| 1593 | 513 | IC.A1.3 |
| 1594 | 514 | IC.A1.3 |
| 1595 | 515 | IC.A1.3 |
| 1596 | 516 | IC.A1.3 |
| 1597 | 517 | IC.A1.3 |
| 1598 | 518 | IC.A1.3 |
| 1599 | 519 | IC.A1.3 |
| 1600 | 520 | IC.A1.3 |
| 1601 | 521 | IC.A1.3 |
| 1602 | 522 | IC.A1.3 |
| 1603 | 523 | IC.A1.3 |
| 1604 | 524 | IC.A1.3 |
| 1605 | 525 | IC.A1.3 |
| 1606 | 526 | IC.A1.3 |
| 1607 | 527 | IC.A1.3 |
| 1608 | 528 | IC.A1.3 |
| 1609 | 529 | IC.A1.3 |
| 1610 | 530 | IC.A1.3 |
| 1611 | 531 | IC.A1.3 |
| 1612 | 532 | IC.A1.3 |
| 1613 | 533 | IC.A1.3 |
| 1614 | 534 | IC.A1.3 |
| 1615 | 535 | IC.A1.3 |
| 1616 | 536 | IC.A1.3 |
| 1617 | 537 | IC.A1.3 |
| 1618 | 538 | IC.A1.3 |
| 1619 | 539 | IC.A1.3 |
| 1620 | 540 | IC.A1.3 |
| 1621 | 181 | ID.A1.1 |
| 1622 | 182 | ID.A1.1 |
| 1623 | 183 | ID.A1.1 |
| 1624 | 184 | ID.A1.1 |
| 1625 | 185 | ID.A1.1 |
| 1626 | 186 | ID.A1.1 |
| 1627 | 187 | ID.A1.1 |
| 1628 | 188 | ID.A1.1 |
| 1629 | 189 | ID.A1.1 |
| 1630 | 190 | ID.A1.1 |
| 1631 | 191 | ID.A1.1 |
| 1632 | 192 | ID.A1.1 |
| 1633 | 193 | ID.A1.1 |
| 1634 | 194 | ID.A1.1 |
| 1635 | 195 | ID.A1.1 |
| 1636 | 196 | ID.A1.1 |
| 1637 | 197 | ID.A1.1 |
| 1638 | 198 | ID.A1.1 |
| 1639 | 199 | ID.A1.1 |
| 1640 | 200 | ID.A1.1 |
| 1641 | 201 | ID.A1.1 |
| 1642 | 202 | ID.A1.1 |
| 1643 | 203 | ID.A1.1 |
| 1644 | 204 | ID.A1.1 |
| 1645 | 205 | ID.A1.1 |
| 1646 | 206 | ID.A1.1 |
| 1647 | 207 | ID.A1.1 |
| 1648 | 208 | ID.A1.1 |
| 1649 | 209 | ID.A1.1 |
| 1650 | 210 | ID.A1.1 |
| 1651 | 211 | ID.A1.1 |
| 1652 | 212 | ID.A1.1 |
| 1653 | 213 | ID.A1.1 |
| 1654 | 214 | ID.A1.1 |
| 1655 | 215 | ID.A1.1 |

TABLE D-continued

| # | Table | Formula |
|---|---|---|
| 1656 | 216 | ID.A1.1 |
| 1657 | 217 | ID.A1.1 |
| 1658 | 218 | ID.A1.1 |
| 1659 | 219 | ID.A1.1 |
| 1660 | 220 | ID.A1.1 |
| 1661 | 221 | ID.A1.1 |
| 1662 | 222 | ID.A1.1 |
| 1663 | 223 | ID.A1.1 |
| 1664 | 224 | ID.A1.1 |
| 1665 | 225 | ID.A1.1 |
| 1666 | 226 | ID.A1.1 |
| 1667 | 227 | ID.A1.1 |
| 1668 | 228 | ID.A1.1 |
| 1669 | 229 | ID.A1.1 |
| 1670 | 230 | ID.A1.1 |
| 1671 | 231 | ID.A1.1 |
| 1672 | 232 | ID.A1.1 |
| 1673 | 233 | ID.A1.1 |
| 1674 | 234 | ID.A1.1 |
| 1675 | 235 | ID.A1.1 |
| 1676 | 236 | ID.A1.1 |
| 1677 | 237 | ID.A1.1 |
| 1678 | 238 | ID.A1.1 |
| 1679 | 239 | ID.A1.1 |
| 1680 | 240 | ID.A1.1 |
| 1681 | 241 | ID.A1.1 |
| 1682 | 242 | ID.A1.1 |
| 1683 | 243 | ID.A1.1 |
| 1684 | 244 | ID.A1.1 |
| 1685 | 245 | ID.A1.1 |
| 1686 | 246 | ID.A1.1 |
| 1687 | 247 | ID.A1.1 |
| 1688 | 248 | ID.A1.1 |
| 1689 | 249 | ID.A1.1 |
| 1690 | 250 | ID.A1.1 |
| 1691 | 251 | ID.A1.1 |
| 1692 | 252 | ID.A1.1 |
| 1693 | 253 | ID.A1.1 |
| 1694 | 254 | ID.A1.1 |
| 1695 | 255 | ID.A1.1 |
| 1696 | 256 | ID.A1.1 |
| 1697 | 257 | ID.A1.1 |
| 1698 | 258 | ID.A1.1 |
| 1699 | 259 | ID.A1.1 |
| 1700 | 260 | ID.A1.1 |
| 1701 | 261 | ID.A1.1 |
| 1702 | 262 | ID.A1.1 |
| 1703 | 263 | ID.A1.1 |
| 1704 | 264 | ID.A1.1 |
| 1705 | 265 | ID.A1.1 |
| 1706 | 266 | ID.A1.1 |
| 1707 | 267 | ID.A1.1 |
| 1708 | 268 | ID.A1.1 |
| 1709 | 269 | ID.A1.1 |
| 1710 | 270 | ID.A1.1 |
| 1711 | 271 | ID.A1.1 |
| 1712 | 272 | ID.A1.1 |
| 1713 | 273 | ID.A1.1 |
| 1714 | 274 | ID.A1.1 |
| 1715 | 275 | ID.A1.1 |
| 1716 | 276 | ID.A1.1 |
| 1717 | 277 | ID.A1.1 |
| 1718 | 278 | ID.A1.1 |
| 1719 | 279 | ID.A1.1 |
| 1720 | 280 | ID.A1.1 |
| 1721 | 281 | ID.A1.1 |
| 1722 | 282 | ID.A1.1 |
| 1723 | 283 | ID.A1.1 |
| 1724 | 284 | ID.A1.1 |
| 1725 | 285 | ID.A1.1 |
| 1726 | 286 | ID.A1.1 |
| 1727 | 287 | ID.A1.1 |
| 1728 | 288 | ID.A1.1 |
| 1729 | 289 | ID.A1.1 |
| 1730 | 290 | ID.A1.1 |
| 1731 | 291 | ID.A1.1 |
| 1732 | 292 | ID.A1.1 |
| 1733 | 293 | ID.A1.1 |
| 1734 | 294 | ID.A1.1 |
| 1735 | 295 | ID.A1.1 |
| 1736 | 296 | ID.A1.1 |
| 1737 | 297 | ID.A1.1 |
| 1738 | 298 | ID.A1.1 |
| 1739 | 299 | ID.A1.1 |
| 1740 | 300 | ID.A1.1 |
| 1741 | 301 | ID.A1.1 |
| 1742 | 302 | ID.A1.1 |
| 1743 | 303 | ID.A1.1 |
| 1744 | 304 | ID.A1.1 |
| 1745 | 305 | ID.A1.1 |
| 1746 | 306 | ID.A1.1 |
| 1747 | 307 | ID.A1.1 |
| 1748 | 308 | ID.A1.1 |
| 1749 | 309 | ID.A1.1 |
| 1750 | 310 | ID.A1.1 |
| 1751 | 311 | ID.A1.1 |
| 1752 | 312 | ID.A1.1 |
| 1753 | 313 | ID.A1.1 |
| 1754 | 314 | ID.A1.1 |
| 1755 | 315 | ID.A1.1 |
| 1756 | 316 | ID.A1.1 |
| 1757 | 317 | ID.A1.1 |
| 1758 | 318 | ID.A1.1 |
| 1759 | 319 | ID.A1.1 |
| 1760 | 320 | ID.A1.1 |
| 1761 | 321 | ID.A1.1 |
| 1762 | 322 | ID.A1.1 |
| 1763 | 323 | ID.A1.1 |
| 1764 | 324 | ID.A1.1 |
| 1765 | 325 | ID.A1.1 |
| 1766 | 326 | ID.A1.1 |
| 1767 | 327 | ID.A1.1 |
| 1768 | 328 | ID.A1.1 |
| 1769 | 329 | ID.A1.1 |
| 1770 | 330 | ID.A1.1 |
| 1771 | 331 | ID.A1.1 |
| 1772 | 332 | ID.A1.1 |
| 1773 | 333 | ID.A1.1 |
| 1774 | 334 | ID.A1.1 |
| 1775 | 335 | ID.A1.1 |
| 1776 | 336 | ID.A1.1 |
| 1777 | 337 | ID.A1.1 |
| 1778 | 338 | ID.A1.1 |
| 1779 | 339 | ID.A1.1 |
| 1780 | 340 | ID.A1.1 |
| 1781 | 341 | ID.A1.1 |
| 1782 | 342 | ID.A1.1 |
| 1783 | 343 | ID.A1.1 |
| 1784 | 344 | ID.A1.1 |
| 1785 | 345 | ID.A1.1 |
| 1786 | 346 | ID.A1.1 |
| 1787 | 347 | ID.A1.1 |
| 1788 | 348 | ID.A1.1 |
| 1789 | 349 | ID.A1.1 |
| 1790 | 350 | ID.A1.1 |
| 1791 | 351 | ID.A1.1 |
| 1792 | 352 | ID.A1.1 |
| 1793 | 353 | ID.A1.1 |
| 1794 | 354 | ID.A1.1 |
| 1795 | 355 | ID.A1.1 |
| 1796 | 356 | ID.A1.1 |
| 1797 | 357 | ID.A1.1 |
| 1798 | 358 | ID.A1.1 |
| 1799 | 359 | ID.A1.1 |
| 1800 | 360 | ID.A1.1 |
| 1801 | 181 | ID.A1.2 |
| 1802 | 182 | ID.A1.2 |
| 1803 | 183 | ID.A1.2 |
| 1804 | 184 | ID.A1.2 |
| 1805 | 185 | ID.A1.2 |
| 1806 | 186 | ID.A1.2 |
| 1807 | 187 | ID.A1.2 |
| 1808 | 188 | ID.A1.2 |
| 1809 | 189 | ID.A1.2 |
| 1810 | 190 | ID.A1.2 |
| 1811 | 191 | ID.A1.2 |

TABLE D-continued

| # | Table | Formula |
|---|---|---|
| 1812 | 192 | ID.A1.2 |
| 1813 | 193 | ID.A1.2 |
| 1814 | 194 | ID.A1.2 |
| 1815 | 195 | ID.A1.2 |
| 1816 | 196 | ID.A1.2 |
| 1817 | 197 | ID.A1.2 |
| 1818 | 198 | ID.A1.2 |
| 1819 | 199 | ID.A1.2 |
| 1820 | 200 | ID.A1.2 |
| 1821 | 201 | ID.A1.2 |
| 1822 | 202 | ID.A1.2 |
| 1823 | 203 | ID.A1.2 |
| 1824 | 204 | ID.A1.2 |
| 1825 | 205 | ID.A1.2 |
| 1826 | 206 | ID.A1.2 |
| 1827 | 207 | ID.A1.2 |
| 1828 | 208 | ID.A1.2 |
| 1829 | 209 | ID.A1.2 |
| 1830 | 210 | ID.A1.2 |
| 1831 | 211 | ID.A1.2 |
| 1832 | 212 | ID.A1.2 |
| 1833 | 213 | ID.A1.2 |
| 1834 | 214 | ID.A1.2 |
| 1835 | 215 | ID.A1.2 |
| 1836 | 216 | ID.A1.2 |
| 1837 | 217 | ID.A1.2 |
| 1838 | 218 | ID.A1.2 |
| 1839 | 219 | ID.A1.2 |
| 1840 | 220 | ID.A1.2 |
| 1841 | 221 | ID.A1.2 |
| 1842 | 222 | ID.A1.2 |
| 1843 | 223 | ID.A1.2 |
| 1844 | 224 | ID.A1.2 |
| 1845 | 225 | ID.A1.2 |
| 1846 | 226 | ID.A1.2 |
| 1847 | 227 | ID.A1.2 |
| 1848 | 228 | ID.A1.2 |
| 1849 | 229 | ID.A1.2 |
| 1850 | 230 | ID.A1.2 |
| 1851 | 231 | ID.A1.2 |
| 1852 | 232 | ID.A1.2 |
| 1853 | 233 | ID.A1.2 |
| 1854 | 234 | ID.A1.2 |
| 1855 | 235 | ID.A1.2 |
| 1856 | 236 | ID.A1.2 |
| 1857 | 237 | ID.A1.2 |
| 1858 | 238 | ID.A1.2 |
| 1859 | 239 | ID.A1.2 |
| 1860 | 240 | ID.A1.2 |
| 1861 | 241 | ID.A1.2 |
| 1862 | 242 | ID.A1.2 |
| 1863 | 243 | ID.A1.2 |
| 1864 | 244 | ID.A1.2 |
| 1865 | 245 | ID.A1.2 |
| 1866 | 246 | ID.A1.2 |
| 1867 | 247 | ID.A1.2 |
| 1868 | 248 | ID.A1.2 |
| 1869 | 249 | ID.A1.2 |
| 1870 | 250 | ID.A1.2 |
| 1871 | 251 | ID.A1.2 |
| 1872 | 252 | ID.A1.2 |
| 1873 | 253 | ID.A1.2 |
| 1874 | 254 | ID.A1.2 |
| 1875 | 255 | ID.A1.2 |
| 1876 | 256 | ID.A1.2 |
| 1877 | 257 | ID.A1.2 |
| 1878 | 258 | ID.A1.2 |
| 1879 | 259 | ID.A1.2 |
| 1880 | 260 | ID.A1.2 |
| 1881 | 261 | ID.A1.2 |
| 1882 | 262 | ID.A1.2 |
| 1883 | 263 | ID.A1.2 |
| 1884 | 264 | ID.A1.2 |
| 1885 | 265 | ID.A1.2 |
| 1886 | 266 | ID.A1.2 |
| 1887 | 267 | ID.A1.2 |
| 1888 | 268 | ID.A1.2 |
| 1889 | 269 | ID.A1.2 |
| 1890 | 270 | ID.A1.2 |
| 1891 | 271 | ID.A1.2 |
| 1892 | 272 | ID.A1.2 |
| 1893 | 273 | ID.A1.2 |
| 1894 | 274 | ID.A1.2 |
| 1895 | 275 | ID.A1.2 |
| 1896 | 276 | ID.A1.2 |
| 1897 | 277 | ID.A1.2 |
| 1898 | 278 | ID.A1.2 |
| 1899 | 279 | ID.A1.2 |
| 1900 | 280 | ID.A1.2 |
| 1901 | 281 | ID.A1.2 |
| 1902 | 282 | ID.A1.2 |
| 1903 | 283 | ID.A1.2 |
| 1904 | 284 | ID.A1.2 |
| 1905 | 285 | ID.A1.2 |
| 1906 | 286 | ID.A1.2 |
| 1907 | 287 | ID.A1.2 |
| 1908 | 288 | ID.A1.2 |
| 1909 | 289 | ID.A1.2 |
| 1910 | 290 | ID.A1.2 |
| 1911 | 291 | ID.A1.2 |
| 1912 | 292 | ID.A1.2 |
| 1913 | 293 | ID.A1.2 |
| 1914 | 294 | ID.A1.2 |
| 1915 | 295 | ID.A1.2 |
| 1916 | 296 | ID.A1.2 |
| 1917 | 297 | ID.A1.2 |
| 1918 | 298 | ID.A1.2 |
| 1919 | 299 | ID.A1.2 |
| 1920 | 300 | ID.A1.2 |
| 1921 | 301 | ID.A1.2 |
| 1922 | 302 | ID.A1.2 |
| 1923 | 303 | ID.A1.2 |
| 1924 | 304 | ID.A1.2 |
| 1925 | 305 | ID.A1.2 |
| 1926 | 306 | ID.A1.2 |
| 1927 | 307 | ID.A1.2 |
| 1928 | 308 | ID.A1.2 |
| 1929 | 309 | ID.A1.2 |
| 1930 | 310 | ID.A1.2 |
| 1931 | 311 | ID.A1.2 |
| 1932 | 312 | ID.A1.2 |
| 1933 | 313 | ID.A1.2 |
| 1934 | 314 | ID.A1.2 |
| 1935 | 315 | ID.A1.2 |
| 1936 | 316 | ID.A1.2 |
| 1937 | 317 | ID.A1.2 |
| 1938 | 318 | ID.A1.2 |
| 1939 | 319 | ID.A1.2 |
| 1940 | 320 | ID.A1.2 |
| 1941 | 321 | ID.A1.2 |
| 1942 | 322 | ID.A1.2 |
| 1943 | 323 | ID.A1.2 |
| 1944 | 324 | ID.A1.2 |
| 1945 | 325 | ID.A1.2 |
| 1946 | 326 | ID.A1.2 |
| 1947 | 327 | ID.A1.2 |
| 1948 | 328 | ID.A1.2 |
| 1949 | 329 | ID.A1.2 |
| 1950 | 330 | ID.A1.2 |
| 1951 | 331 | ID.A1.2 |
| 1952 | 332 | ID.A1.2 |
| 1953 | 333 | ID.A1.2 |
| 1954 | 334 | ID.A1.2 |
| 1955 | 335 | ID.A1.2 |
| 1956 | 336 | ID.A1.2 |
| 1957 | 337 | ID.A1.2 |
| 1958 | 338 | ID.A1.2 |
| 1959 | 339 | ID.A1.2 |
| 1960 | 340 | ID.A1.2 |
| 1961 | 341 | ID.A1.2 |
| 1962 | 342 | ID.A1.2 |
| 1963 | 343 | ID.A1.2 |
| 1964 | 344 | ID.A1.2 |
| 1965 | 345 | ID.A1.2 |
| 1966 | 346 | ID.A1.2 |
| 1967 | 347 | ID.A1.2 |

TABLE D-continued

| # | Table | Formula |
|---|---|---|
| 1968 | 348 | ID.A1.2 |
| 1969 | 349 | ID.A1.2 |
| 1970 | 350 | ID.A1.2 |
| 1971 | 351 | ID.A1.2 |
| 1972 | 352 | ID.A1.2 |
| 1973 | 353 | ID.A1.2 |
| 1974 | 354 | ID.A1.2 |
| 1975 | 355 | ID.A1.2 |
| 1976 | 356 | ID.A1.2 |
| 1977 | 357 | ID.A1.2 |
| 1978 | 358 | ID.A1.2 |
| 1979 | 359 | ID.A1.2 |
| 1980 | 360 | ID.A1.2 |
| 1981 | 181 | ID.A1.3 |
| 1982 | 182 | ID.A1.3 |
| 1983 | 183 | ID.A1.3 |
| 1984 | 184 | ID.A1.3 |
| 1985 | 185 | ID.A1.3 |
| 1986 | 186 | ID.A1.3 |
| 1987 | 187 | ID.A1.3 |
| 1988 | 188 | ID.A1.3 |
| 1989 | 189 | ID.A1.3 |
| 1990 | 190 | ID.A1.3 |
| 1991 | 191 | ID.A1.3 |
| 1992 | 192 | ID.A1.3 |
| 1993 | 193 | ID.A1.3 |
| 1994 | 194 | ID.A1.3 |
| 1995 | 195 | ID.A1.3 |
| 1996 | 196 | ID.A1.3 |
| 1997 | 197 | ID.A1.3 |
| 1998 | 198 | ID.A1.3 |
| 1999 | 199 | ID.A1.3 |
| 2000 | 200 | ID.A1.3 |
| 2001 | 201 | ID.A1.3 |
| 2002 | 202 | ID.A1.3 |
| 2003 | 203 | ID.A1.3 |
| 2004 | 204 | ID.A1.3 |
| 2005 | 205 | ID.A1.3 |
| 2006 | 206 | ID.A1.3 |
| 2007 | 207 | ID.A1.3 |
| 2008 | 208 | ID.A1.3 |
| 2009 | 209 | ID.A1.3 |
| 2010 | 210 | ID.A1.3 |
| 2011 | 211 | ID.A1.3 |
| 2012 | 212 | ID.A1.3 |
| 2013 | 213 | ID.A1.3 |
| 2014 | 214 | ID.A1.3 |
| 2015 | 215 | ID.A1.3 |
| 2016 | 216 | ID.A1.3 |
| 2017 | 217 | ID.A1.3 |
| 2018 | 218 | ID.A1.3 |
| 2019 | 219 | ID.A1.3 |
| 2020 | 220 | ID.A1.3 |
| 2021 | 221 | ID.A1.3 |
| 2022 | 222 | ID.A1.3 |
| 2023 | 223 | ID.A1.3 |
| 2024 | 224 | ID.A1.3 |
| 2025 | 225 | ID.A1.3 |
| 2026 | 226 | ID.A1.3 |
| 2027 | 227 | ID.A1.3 |
| 2028 | 228 | ID.A1.3 |
| 2029 | 229 | ID.A1.3 |
| 2030 | 230 | ID.A1.3 |
| 2031 | 231 | ID.A1.3 |
| 2032 | 232 | ID.A1.3 |
| 2033 | 233 | ID.A1.3 |
| 2034 | 234 | ID.A1.3 |
| 2035 | 235 | ID.A1.3 |
| 2036 | 236 | ID.A1.3 |
| 2037 | 237 | ID.A1.3 |
| 2038 | 238 | ID.A1.3 |
| 2039 | 239 | ID.A1.3 |
| 2040 | 240 | ID.A1.3 |
| 2041 | 241 | ID.A1.3 |
| 2042 | 242 | ID.A1.3 |
| 2043 | 243 | ID.A1.3 |
| 2044 | 244 | ID.A1.3 |
| 2045 | 245 | ID.A1.3 |
| 2046 | 246 | ID.A1.3 |
| 2047 | 247 | ID.A1.3 |
| 2048 | 248 | ID.A1.3 |
| 2049 | 249 | ID.A1.3 |
| 2050 | 250 | ID.A1.3 |
| 2051 | 251 | ID.A1.3 |
| 2052 | 252 | ID.A1.3 |
| 2053 | 253 | ID.A1.3 |
| 2054 | 254 | ID.A1.3 |
| 2055 | 255 | ID.A1.3 |
| 2056 | 256 | ID.A1.3 |
| 2057 | 257 | ID.A1.3 |
| 2058 | 258 | ID.A1.3 |
| 2059 | 259 | ID.A1.3 |
| 2060 | 260 | ID.A1.3 |
| 2061 | 261 | ID.A1.3 |
| 2062 | 262 | ID.A1.3 |
| 2063 | 263 | ID.A1.3 |
| 2064 | 264 | ID.A1.3 |
| 2065 | 265 | ID.A1.3 |
| 2066 | 266 | ID.A1.3 |
| 2067 | 267 | ID.A1.3 |
| 2068 | 268 | ID.A1.3 |
| 2069 | 269 | ID.A1.3 |
| 2070 | 270 | ID.A1.3 |
| 2071 | 271 | ID.A1.3 |
| 2072 | 272 | ID.A1.3 |
| 2073 | 273 | ID.A1.3 |
| 2074 | 274 | ID.A1.3 |
| 2075 | 275 | ID.A1.3 |
| 2076 | 276 | ID.A1.3 |
| 2077 | 277 | ID.A1.3 |
| 2078 | 278 | ID.A1.3 |
| 2079 | 279 | ID.A1.3 |
| 2080 | 280 | ID.A1.3 |
| 2081 | 281 | ID.A1.3 |
| 2082 | 282 | ID.A1.3 |
| 2083 | 283 | ID.A1.3 |
| 2084 | 284 | ID.A1.3 |
| 2085 | 285 | ID.A1.3 |
| 2086 | 286 | ID.A1.3 |
| 2087 | 287 | ID.A1.3 |
| 2088 | 288 | ID.A1.3 |
| 2089 | 289 | ID.A1.3 |
| 2090 | 290 | ID.A1.3 |
| 2091 | 291 | ID.A1.3 |
| 2092 | 292 | ID.A1.3 |
| 2093 | 293 | ID.A1.3 |
| 2094 | 294 | ID.A1.3 |
| 2095 | 295 | ID.A1.3 |
| 2096 | 296 | ID.A1.3 |
| 2097 | 297 | ID.A1.3 |
| 2098 | 298 | ID.A1.3 |
| 2099 | 299 | ID.A1.3 |
| 2100 | 300 | ID.A1.3 |
| 2101 | 301 | ID.A1.3 |
| 2102 | 302 | ID.A1.3 |
| 2103 | 303 | ID.A1.3 |
| 2104 | 304 | ID.A1.3 |
| 2105 | 305 | ID.A1.3 |
| 2106 | 306 | ID.A1.3 |
| 2107 | 307 | ID.A1.3 |
| 2108 | 308 | ID.A1.3 |
| 2109 | 309 | ID.A1.3 |
| 2110 | 310 | ID.A1.3 |
| 2111 | 311 | ID.A1.3 |
| 2112 | 312 | ID.A1.3 |
| 2113 | 313 | ID.A1.3 |
| 2114 | 314 | ID.A1.3 |
| 2115 | 315 | ID.A1.3 |
| 2116 | 316 | ID.A1.3 |
| 2117 | 317 | ID.A1.3 |
| 2118 | 318 | ID.A1.3 |
| 2119 | 319 | ID.A1.3 |
| 2120 | 320 | ID.A1.3 |
| 2121 | 321 | ID.A1.3 |
| 2122 | 322 | ID.A1.3 |
| 2123 | 323 | ID.A1.3 |

TABLE D-continued

| # | Table | Formula |
|---|---|---|
| 2124 | 324 | ID.A1.3 |
| 2125 | 325 | ID.A1.3 |
| 2126 | 326 | ID.A1.3 |
| 2127 | 327 | ID.A1.3 |
| 2128 | 328 | ID.A1.3 |
| 2129 | 329 | ID.A1.3 |
| 2130 | 330 | ID.A1.3 |
| 2131 | 331 | ID.A1.3 |
| 2132 | 332 | ID.A1.3 |
| 2133 | 333 | ID.A1.3 |
| 2134 | 334 | ID.A1.3 |
| 2135 | 335 | ID.A1.3 |
| 2136 | 336 | ID.A1.3 |
| 2137 | 337 | ID.A1.3 |
| 2138 | 338 | ID.A1.3 |
| 2139 | 339 | ID.A1.3 |
| 2140 | 340 | ID.A1.3 |
| 2141 | 341 | ID.A1.3 |
| 2142 | 342 | ID.A1.3 |
| 2143 | 343 | ID.A1.3 |
| 2144 | 344 | ID.A1.3 |
| 2145 | 345 | ID.A1.3 |
| 2146 | 346 | ID.A1.3 |
| 2147 | 347 | ID.A1.3 |
| 2148 | 348 | ID.A1.3 |
| 2149 | 361 | IT.A1.1 |
| 2150 | 362 | IT.A1.1 |
| 2151 | 363 | IT.A1.1 |
| 2152 | 364 | IT.A1.1 |
| 2153 | 365 | IT.A1.1 |
| 2154 | 366 | IT.A1.1 |
| 2155 | 367 | IT.A1.1 |
| 2156 | 368 | IT.A1.1 |
| 2157 | 369 | IT.A1.1 |
| 2158 | 370 | IT.A1.1 |
| 2159 | 371 | IT.A1.1 |
| 2160 | 372 | IT.A1.1 |
| 2161 | 373 | IT.A1.1 |
| 2162 | 374 | IT.A1.1 |
| 2163 | 375 | IT.A1.1 |
| 2164 | 376 | IT.A1.1 |
| 2165 | 377 | IT.A1.1 |
| 2166 | 378 | IT.A1.1 |
| 2167 | 379 | IT.A1.1 |
| 2168 | 380 | IT.A1.1 |
| 2169 | 381 | IT.A1.1 |
| 2170 | 382 | IT.A1.1 |
| 2171 | 383 | IT.A1.1 |
| 2172 | 384 | IT.A1.1 |
| 2173 | 385 | IT.A1.1 |
| 2174 | 386 | IT.A1.1 |
| 2175 | 387 | IT.A1.1 |
| 2176 | 388 | IT.A1.1 |
| 2177 | 389 | IT.A1.1 |
| 2178 | 390 | IT.A1.1 |
| 2179 | 391 | IT.A1.1 |
| 2180 | 392 | IT.A1.1 |
| 2181 | 393 | IT.A1.1 |
| 2182 | 394 | IT.A1.1 |
| 2183 | 395 | IT.A1.1 |
| 2184 | 396 | IT.A1.1 |
| 2185 | 397 | IT.A1.1 |
| 2186 | 398 | IT.A1.1 |
| 2187 | 399 | IT.A1.1 |
| 2188 | 400 | IT.A1.1 |
| 2189 | 401 | IT.A1.1 |
| 2190 | 402 | IT.A1.1 |
| 2191 | 403 | IT.A1.1 |
| 2192 | 404 | IT.A1.1 |
| 2193 | 405 | IT.A1.1 |
| 2194 | 406 | IT.A1.1 |
| 2195 | 407 | IT.A1.1 |
| 2196 | 408 | IT.A1.1 |
| 2197 | 409 | IT.A1.1 |
| 2198 | 410 | IT.A1.1 |
| 2199 | 411 | IT.A1.1 |
| 2200 | 412 | IT.A1.1 |
| 2201 | 413 | IT.A1.1 |
| 2202 | 414 | IT.A1.1 |
| 2203 | 415 | IT.A1.1 |
| 2204 | 416 | IT.A1.1 |
| 2205 | 417 | IT.A1.1 |
| 2206 | 418 | IT.A1.1 |
| 2207 | 419 | IT.A1.1 |
| 2208 | 420 | IT.A1.1 |
| 2209 | 421 | IT.A1.1 |
| 2210 | 422 | IT.A1.1 |
| 2211 | 423 | IT.A1.1 |
| 2212 | 424 | IT.A1.1 |
| 2213 | 425 | IT.A1.1 |
| 2214 | 426 | IT.A1.1 |
| 2215 | 427 | IT.A1.1 |
| 2216 | 428 | IT.A1.1 |
| 2217 | 429 | IT.A1.1 |
| 2218 | 430 | IT.A1.1 |
| 2219 | 431 | IT.A1.1 |
| 2220 | 432 | IT.A1.1 |
| 2221 | 433 | IT.A1.1 |
| 2222 | 434 | IT.A1.1 |
| 2223 | 435 | IT.A1.1 |
| 2224 | 436 | IT.A1.1 |
| 2225 | 437 | IT.A1.1 |
| 2226 | 438 | IT.A1.1 |
| 2227 | 439 | IT.A1.1 |
| 2228 | 440 | IT.A1.1 |
| 2229 | 441 | IT.A1.1 |
| 2230 | 442 | IT.A1.1 |
| 2231 | 443 | IT.A1.1 |
| 2232 | 444 | IT.A1.1 |
| 2233 | 445 | IT.A1.1 |
| 2234 | 446 | IT.A1.1 |
| 2235 | 447 | IT.A1.1 |
| 2236 | 448 | IT.A1.1 |
| 2237 | 449 | IT.A1.1 |
| 2238 | 450 | IT.A1.1 |
| 2239 | 451 | IT.A1.1 |
| 2240 | 452 | IT.A1.1 |
| 2241 | 453 | IT.A1.1 |
| 2242 | 454 | IT.A1.1 |
| 2243 | 455 | IT.A1.1 |
| 2244 | 456 | IT.A1.1 |
| 2245 | 457 | IT.A1.1 |
| 2246 | 458 | IT.A1.1 |
| 2247 | 459 | IT.A1.1 |
| 2248 | 460 | IT.A1.1 |
| 2249 | 461 | IT.A1.1 |
| 2250 | 462 | IT.A1.1 |
| 2251 | 463 | IT.A1.1 |
| 2252 | 464 | IT.A1.1 |
| 2253 | 465 | IT.A1.1 |
| 2254 | 466 | IT.A1.1 |
| 2255 | 467 | IT.A1.1 |
| 2256 | 468 | IT.A1.1 |
| 2257 | 469 | IT.A1.1 |
| 2258 | 470 | IT.A1.1 |
| 2259 | 471 | IT.A1.1 |
| 2260 | 472 | IT.A1.1 |
| 2261 | 473 | IT.A1.1 |
| 2262 | 474 | IT.A1.1 |
| 2263 | 475 | IT.A1.1 |
| 2264 | 476 | IT.A1.1 |
| 2265 | 477 | IT.A1.1 |
| 2266 | 478 | IT.A1.1 |
| 2267 | 479 | IT.A1.1 |
| 2268 | 480 | IT.A1.1 |
| 2269 | 481 | IT.A1.1 |
| 2270 | 482 | IT.A1.1 |
| 2271 | 483 | IT.A1.1 |
| 2272 | 484 | IT.A1.1 |
| 2273 | 485 | IT.A1.1 |
| 2274 | 486 | IT.A1.1 |
| 2275 | 487 | IT.A1.1 |
| 2276 | 488 | IT.A1.1 |
| 2277 | 489 | IT.A1.1 |
| 2278 | 490 | IT.A1.1 |
| 2279 | 491 | IT.A1.1 |

TABLE D-continued

| # | Table | Formula |
|---|---|---|
| 2280 | 492 | IT.A1.1 |
| 2281 | 493 | IT.A1.1 |
| 2282 | 494 | IT.A1.1 |
| 2283 | 495 | IT.A1.1 |
| 2284 | 496 | IT.A1.1 |
| 2285 | 497 | IT.A1.1 |
| 2286 | 498 | IT.A1.1 |
| 2287 | 499 | IT.A1.1 |
| 2288 | 500 | IT.A1.1 |
| 2289 | 501 | IT.A1.1 |
| 2290 | 502 | IT.A1.1 |
| 2291 | 503 | IT.A1.1 |
| 2292 | 504 | IT.A1.1 |
| 2293 | 505 | IT.A1.1 |
| 2294 | 506 | IT.A1.1 |
| 2295 | 507 | IT.A1.1 |
| 2296 | 508 | IT.A1.1 |
| 2297 | 509 | IT.A1.1 |
| 2298 | 510 | IT.A1.1 |
| 2299 | 511 | IT.A1.1 |
| 2300 | 512 | IT.A1.1 |
| 2301 | 513 | IT.A1.1 |
| 2302 | 514 | IT.A1.1 |
| 2303 | 515 | IT.A1.1 |
| 2304 | 516 | IT.A1.1 |
| 2305 | 517 | IT.A1.1 |
| 2306 | 518 | IT.A1.1 |
| 2307 | 519 | IT.A1.1 |
| 2308 | 520 | IT.A1.1 |
| 2309 | 521 | IT.A1.1 |
| 2310 | 522 | IT.A1.1 |
| 2311 | 523 | IT.A1.1 |
| 2312 | 524 | IT.A1.1 |
| 2313 | 525 | IT.A1.1 |
| 2314 | 526 | IT.A1.1 |
| 2315 | 527 | IT.A1.1 |
| 2316 | 528 | IT.A1.1 |
| 2317 | 529 | IT.A1.1 |
| 2318 | 530 | IT.A1.1 |
| 2319 | 531 | IT.A1.1 |
| 2320 | 532 | IT.A1.1 |
| 2321 | 533 | IT.A1.1 |
| 2322 | 534 | IT.A1.1 |
| 2323 | 535 | IT.A1.1 |
| 2324 | 536 | IT.A1.1 |
| 2325 | 537 | IT.A1.1 |
| 2326 | 538 | IT.A1.1 |
| 2327 | 539 | IT.A1.1 |
| 2328 | 540 | IT.A1.1 |
| 2329 | 361 | IT.A1.2 |
| 2330 | 362 | IT.A1.2 |
| 2331 | 363 | IT.A1.2 |
| 2332 | 364 | IT.A1.2 |
| 2333 | 365 | IT.A1.2 |
| 2334 | 366 | IT.A1.2 |
| 2335 | 367 | IT.A1.2 |
| 2336 | 368 | IT.A1.2 |
| 2337 | 369 | IT.A1.2 |
| 2338 | 370 | IT.A1.2 |
| 2339 | 371 | IT.A1.2 |
| 2340 | 372 | IT.A1.2 |
| 2341 | 373 | IT.A1.2 |
| 2342 | 374 | IT.A1.2 |
| 2343 | 375 | IT.A1.2 |
| 2344 | 376 | IT.A1.2 |
| 2345 | 377 | IT.A1.2 |
| 2346 | 378 | IT.A1.2 |
| 2347 | 379 | IT.A1.2 |
| 2348 | 380 | IT.A1.2 |
| 2349 | 381 | IT.A1.2 |
| 2350 | 382 | IT.A1.2 |
| 2351 | 383 | IT.A1.2 |
| 2352 | 384 | IT.A1.2 |
| 2353 | 385 | IT.A1.2 |
| 2354 | 386 | IT.A1.2 |
| 2355 | 387 | IT.A1.2 |
| 2356 | 388 | IT.A1.2 |
| 2357 | 389 | IT.A1.2 |
| 2358 | 390 | IT.A1.2 |
| 2359 | 391 | IT.A1.2 |
| 2360 | 392 | IT.A1.2 |
| 2361 | 393 | IT.A1.2 |
| 2362 | 394 | IT.A1.2 |
| 2363 | 395 | IT.A1.2 |
| 2364 | 396 | IT.A1.2 |
| 2365 | 397 | IT.A1.2 |
| 2366 | 398 | IT.A1.2 |
| 2367 | 399 | IT.A1.2 |
| 2368 | 400 | IT.A1.2 |
| 2369 | 401 | IT.A1.2 |
| 2370 | 402 | IT.A1.2 |
| 2371 | 403 | IT.A1.2 |
| 2372 | 404 | IT.A1.2 |
| 2373 | 405 | IT.A1.2 |
| 2374 | 406 | IT.A1.2 |
| 2375 | 407 | IT.A1.2 |
| 2376 | 408 | IT.A1.2 |
| 2377 | 409 | IT.A1.2 |
| 2378 | 410 | IT.A1.2 |
| 2379 | 411 | IT.A1.2 |
| 2380 | 412 | IT.A1.2 |
| 2381 | 413 | IT.A1.2 |
| 2382 | 414 | IT.A1.2 |
| 2383 | 415 | IT.A1.2 |
| 2384 | 416 | IT.A1.2 |
| 2385 | 417 | IT.A1.2 |
| 2386 | 418 | IT.A1.2 |
| 2387 | 419 | IT.A1.2 |
| 2388 | 420 | IT.A1.2 |
| 2389 | 421 | IT.A1.2 |
| 2390 | 422 | IT.A1.2 |
| 2391 | 423 | IT.A1.2 |
| 2392 | 424 | IT.A1.2 |
| 2393 | 425 | IT.A1.2 |
| 2394 | 426 | IT.A1.2 |
| 2395 | 427 | IT.A1.2 |
| 2396 | 428 | IT.A1.2 |
| 2397 | 429 | IT.A1.2 |
| 2398 | 430 | IT.A1.2 |
| 2399 | 431 | IT.A1.2 |
| 2400 | 432 | IT.A1.2 |
| 2401 | 433 | IT.A1.2 |
| 2402 | 434 | IT.A1.2 |
| 2403 | 435 | IT.A1.2 |
| 2404 | 436 | IT.A1.2 |
| 2405 | 437 | IT.A1.2 |
| 2406 | 438 | IT.A1.2 |
| 2407 | 439 | IT.A1.2 |
| 2408 | 440 | IT.A1.2 |
| 2409 | 441 | IT.A1.2 |
| 2410 | 442 | IT.A1.2 |
| 2411 | 443 | IT.A1.2 |
| 2412 | 444 | IT.A1.2 |
| 2413 | 445 | IT.A1.2 |
| 2414 | 446 | IT.A1.2 |
| 2415 | 447 | IT.A1.2 |
| 2416 | 448 | IT.A1.2 |
| 2417 | 449 | IT.A1.2 |
| 2418 | 450 | IT.A1.2 |
| 2419 | 451 | IT.A1.2 |
| 2420 | 452 | IT.A1.2 |
| 2421 | 453 | IT.A1.2 |
| 2422 | 454 | IT.A1.2 |
| 2423 | 455 | IT.A1.2 |
| 2424 | 456 | IT.A1.2 |
| 2425 | 457 | IT.A1.2 |
| 2426 | 458 | IT.A1.2 |
| 2427 | 459 | IT.A1.2 |
| 2428 | 460 | IT.A1.2 |
| 2429 | 461 | IT.A1.2 |
| 2430 | 462 | IT.A1.2 |
| 2431 | 463 | IT.A1.2 |
| 2432 | 464 | IT.A1.2 |
| 2433 | 465 | IT.A1.2 |
| 2434 | 466 | IT.A1.2 |
| 2435 | 467 | IT.A1.2 |

TABLE D-continued

| # | Table | Formula |
|---|---|---|
| 2436 | 468 | IT.A1.2 |
| 2437 | 469 | IT.A1.2 |
| 2438 | 470 | IT.A1.2 |
| 2439 | 471 | IT.A1.2 |
| 2440 | 472 | IT.A1.2 |
| 2441 | 473 | IT.A1.2 |
| 2442 | 474 | IT.A1.2 |
| 2443 | 475 | IT.A1.2 |
| 2444 | 476 | IT.A1.2 |
| 2445 | 477 | IT.A1.2 |
| 2446 | 478 | IT.A1.2 |
| 2447 | 479 | IT.A1.2 |
| 2448 | 480 | IT.A1.2 |
| 2449 | 481 | IT.A1.2 |
| 2450 | 482 | IT.A1.2 |
| 2451 | 483 | IT.A1.2 |
| 2452 | 484 | IT.A1.2 |
| 2453 | 485 | IT.A1.2 |
| 2454 | 486 | IT.A1.2 |
| 2455 | 487 | IT.A1.2 |
| 2456 | 488 | IT.A1.2 |
| 2457 | 489 | IT.A1.2 |
| 2458 | 490 | IT.A1.2 |
| 2459 | 491 | IT.A1.2 |
| 2460 | 492 | IT.A1.2 |
| 2461 | 493 | IT.A1.2 |
| 2462 | 494 | IT.A1.2 |
| 2463 | 495 | IT.A1.2 |
| 2464 | 496 | IT.A1.2 |
| 2465 | 497 | IT.A1.2 |
| 2466 | 498 | IT.A1.2 |
| 2467 | 499 | IT.A1.2 |
| 2468 | 500 | IT.A1.2 |
| 2469 | 501 | IT.A1.2 |
| 2470 | 502 | IT.A1.2 |
| 2471 | 503 | IT.A1.2 |
| 2472 | 504 | IT.A1.2 |
| 2473 | 505 | IT.A1.2 |
| 2474 | 506 | IT.A1.2 |
| 2475 | 507 | IT.A1.2 |
| 2476 | 508 | IT.A1.2 |
| 2477 | 509 | IT.A1.2 |
| 2478 | 510 | IT.A1.2 |
| 2479 | 511 | IT.A1.2 |
| 2480 | 512 | IT.A1.2 |
| 2481 | 513 | IT.A1.2 |
| 2482 | 514 | IT.A1.2 |
| 2483 | 515 | IT.A1.2 |
| 2484 | 516 | IT.A1.2 |
| 2485 | 517 | IT.A1.2 |
| 2486 | 518 | IT.A1.2 |
| 2487 | 519 | IT.A1.2 |
| 2488 | 520 | IT.A1.2 |
| 2489 | 361 | IT.A1.3 |
| 2490 | 362 | IT.A1.3 |
| 2491 | 363 | IT.A1.3 |
| 2492 | 364 | IT.A1.3 |
| 2493 | 365 | IT.A1.3 |
| 2494 | 366 | IT.A1.3 |
| 2495 | 367 | IT.A1.3 |
| 2496 | 368 | IT.A1.3 |
| 2497 | 369 | IT.A1.3 |
| 2498 | 370 | IT.A1.3 |
| 2499 | 371 | IT.A1.3 |
| 2500 | 372 | IT.A1.3 |
| 2501 | 373 | IT.A1.3 |
| 2502 | 374 | IT.A1.3 |
| 2503 | 375 | IT.A1.3 |
| 2504 | 376 | IT.A1.3 |
| 2505 | 377 | IT.A1.3 |
| 2506 | 378 | IT.A1.3 |
| 2507 | 379 | IT.A1.3 |
| 2508 | 380 | IT.A1.3 |
| 2509 | 381 | IT.A1.3 |
| 2510 | 382 | IT.A1.3 |
| 2511 | 383 | IT.A1.3 |
| 2512 | 384 | IT.A1.3 |
| 2513 | 385 | IT.A1.3 |
| 2514 | 386 | IT.A1.3 |
| 2515 | 387 | IT.A1.3 |
| 2516 | 388 | IT.A1.3 |
| 2517 | 389 | IT.A1.3 |
| 2518 | 390 | IT.A1.3 |
| 2519 | 391 | IT.A1.3 |
| 2520 | 392 | IT.A1.3 |
| 2521 | 393 | IT.A1.3 |
| 2522 | 394 | IT.A1.3 |
| 2523 | 395 | IT.A1.3 |
| 2524 | 396 | IT.A1.3 |
| 2525 | 397 | IT.A1.3 |
| 2526 | 398 | IT.A1.3 |
| 2527 | 399 | IT.A1.3 |
| 2528 | 400 | IT.A1.3 |
| 2529 | 401 | IT.A1.3 |
| 2530 | 402 | IT.A1.3 |
| 2531 | 403 | IT.A1.3 |
| 2532 | 404 | IT.A1.3 |
| 2533 | 405 | IT.A1.3 |
| 2534 | 406 | IT.A1.3 |
| 2535 | 407 | IT.A1.3 |
| 2536 | 408 | IT.A1.3 |
| 2537 | 409 | IT.A1.3 |
| 2538 | 410 | IT.A1.3 |
| 2539 | 411 | IT.A1.3 |
| 2540 | 412 | IT.A1.3 |
| 2541 | 413 | IT.A1.3 |
| 2542 | 414 | IT.A1.3 |
| 2543 | 415 | IT.A1.3 |
| 2544 | 416 | IT.A1.3 |
| 2545 | 417 | IT.A1.3 |
| 2546 | 418 | IT.A1.3 |
| 2547 | 419 | IT.A1.3 |
| 2548 | 420 | IT.A1.3 |
| 2549 | 421 | IT.A1.3 |
| 2550 | 422 | IT.A1.3 |
| 2551 | 423 | IT.A1.3 |
| 2552 | 424 | IT.A1.3 |
| 2553 | 425 | IT.A1.3 |
| 2554 | 426 | IT.A1.3 |
| 2555 | 427 | IT.A1.3 |
| 2556 | 428 | IT.A1.3 |
| 2557 | 429 | IT.A1.3 |
| 2558 | 430 | IT.A1.3 |
| 2559 | 431 | IT.A1.3 |
| 2560 | 432 | IT.A1.3 |
| 2561 | 433 | IT.A1.3 |
| 2562 | 434 | IT.A1.3 |
| 2563 | 435 | IT.A1.3 |
| 2564 | 436 | IT.A1.3 |
| 2565 | 437 | IT.A1.3 |
| 2566 | 438 | IT.A1.3 |
| 2567 | 439 | IT.A1.3 |
| 2568 | 440 | IT.A1.3 |
| 2569 | 441 | IT.A1.3 |
| 2570 | 442 | IT.A1.3 |
| 2571 | 443 | IT.A1.3 |
| 2572 | 444 | IT.A1.3 |
| 2573 | 445 | IT.A1.3 |
| 2574 | 446 | IT.A1.3 |
| 2575 | 447 | IT.A1.3 |
| 2576 | 448 | IT.A1.3 |
| 2577 | 449 | IT.A1.3 |
| 2578 | 450 | IT.A1.3 |
| 2579 | 451 | IT.A1.3 |
| 2580 | 452 | IT.A1.3 |
| 2581 | 453 | IT.A1.3 |
| 2582 | 454 | IT.A1.3 |
| 2583 | 455 | IT.A1.3 |
| 2584 | 456 | IT.A1.3 |
| 2585 | 457 | IT.A1.3 |
| 2586 | 458 | IT.A1.3 |
| 2587 | 459 | IT.A1.3 |
| 2588 | 460 | IT.A1.3 |
| 2589 | 461 | IT.A1.3 |
| 2590 | 462 | IT.A1.3 |
| 2591 | 463 | IT.A1.3 |

TABLE D-continued

| # | Table | Formula |
|---|---|---|
| 2592 | 464 | IT.A1.3 |
| 2593 | 465 | IT.A1.3 |
| 2594 | 466 | IT.A1.3 |
| 2595 | 467 | IT.A1.3 |
| 2596 | 468 | IT.A1.3 |
| 2597 | 469 | IT.A1.3 |
| 2598 | 470 | IT.A1.3 |
| 2599 | 471 | IT.A1.3 |
| 2600 | 472 | IT.A1.3 |
| 2601 | 473 | IT.A1.3 |
| 2602 | 474 | IT.A1.3 |
| 2603 | 475 | IT.A1.3 |
| 2604 | 476 | IT.A1.3 |
| 2605 | 477 | IT.A1.3 |
| 2606 | 478 | IT.A1.3 |
| 2607 | 479 | IT.A1.3 |
| 2608 | 480 | IT.A1.3 |
| 2609 | 481 | IT.A1.3 |
| 2610 | 482 | IT.A1.3 |
| 2611 | 483 | IT.A1.3 |
| 2612 | 484 | IT.A1.3 |
| 2613 | 485 | IT.A1.3 |
| 2614 | 486 | IT.A1.3 |
| 2615 | 487 | IT.A1.3 |
| 2616 | 488 | IT.A1.3 |
| 2617 | 489 | IT.A1.3 |
| 2618 | 490 | IT.A1.3 |
| 2619 | 491 | IT.A1.3 |
| 2620 | 492 | IT.A1.3 |
| 2621 | 493 | IT.A1.3 |
| 2622 | 494 | IT.A1.3 |
| 2623 | 495 | IT.A1.3 |
| 2624 | 496 | IT.A1.3 |
| 2625 | 497 | IT.A1.3 |
| 2626 | 498 | IT.A1.3 |
| 2627 | 499 | IT.A1.3 |
| 2628 | 500 | IT.A1.3 |
| 2629 | 501 | IT.A1.3 |
| 2630 | 502 | IT.A1.3 |
| 2631 | 503 | IT.A1.3 |
| 2632 | 504 | IT.A1.3 |
| 2633 | 505 | IT.A1.3 |
| 2634 | 506 | IT.A1.3 |
| 2635 | 507 | IT.A1.3 |
| 2636 | 508 | IT.A1.3 |
| 2637 | 509 | IT.A1.3 |
| 2638 | 510 | IT.A1.3 |
| 2639 | 511 | IT.A1.3 |
| 2640 | 512 | IT.A1.3 |
| 2641 | 513 | IT.A1.3 |
| 2642 | 514 | IT.A1.3 |
| 2643 | 515 | IT.A1.3 |
| 2644 | 516 | IT.A1.3 |
| 2645 | 517 | IT.A1.3 |
| 2646 | 518 | IT.A1.3 |
| 2647 | 519 | IT.A1.3 |
| 2648 | 520 | IT.A1.3 |
| 2649 | 521 | IT.A1.3 |
| 2650 | 522 | IT.A1.3 |
| 2651 | 523 | IT.A1.3 |
| 2652 | 524 | IT.A1.3 |
| 2653 | 525 | IT.A1.3 |
| 2654 | 526 | IT.A1.3 |
| 2655 | 527 | IT.A1.3 |
| 2656 | 528 | IT.A1.3 |
| 2657 | 529 | IT.A1.3 |
| 2658 | 530 | IT.A1.3 |
| 2659 | 531 | IT.A1.3 |
| 2660 | 532 | IT.A1.3 |
| 2661 | 533 | IT.A1.3 |
| 2662 | 534 | IT.A1.3 |
| 2663 | 535 | IT.A1.3 |
| 2664 | 536 | IT.A1.3 |
| 2665 | 537 | IT.A1.3 |
| 2666 | 538 | IT.A1.3 |
| 2667 | 539 | IT.A1.3 |
| 2668 | 540 | IT.A1.3 |
| 2669 | 361 | IY.A1.1 |
| 2670 | 362 | IY.A1.1 |
| 2671 | 363 | IY.A1.1 |
| 2672 | 364 | IY.A1.1 |
| 2673 | 365 | IY.A1.1 |
| 2674 | 366 | IY.A1.1 |
| 2675 | 367 | IY.A1.1 |
| 2676 | 368 | IY.A1.1 |
| 2677 | 369 | IY.A1.1 |
| 2678 | 370 | IY.A1.1 |
| 2679 | 371 | IY.A1.1 |
| 2680 | 372 | IY.A1.1 |
| 2681 | 373 | IY.A1.1 |
| 2682 | 374 | IY.A1.1 |
| 2683 | 375 | IY.A1.1 |
| 2684 | 376 | IY.A1.1 |
| 2685 | 377 | IY.A1.1 |
| 2686 | 378 | IY.A1.1 |
| 2687 | 379 | IY.A1.1 |
| 2688 | 380 | IY.A1.1 |
| 2689 | 381 | IY.A1.1 |
| 2690 | 382 | IY.A1.1 |
| 2691 | 383 | IY.A1.1 |
| 2692 | 384 | IY.A1.1 |
| 2693 | 385 | IY.A1.1 |
| 2694 | 386 | IY.A1.1 |
| 2695 | 387 | IY.A1.1 |
| 2696 | 388 | IY.A1.1 |
| 2697 | 389 | IY.A1.1 |
| 2698 | 390 | IY.A1.1 |
| 2699 | 391 | IY.A1.1 |
| 2700 | 392 | IY.A1.1 |
| 2701 | 393 | IY.A1.1 |
| 2702 | 394 | IY.A1.1 |
| 2703 | 395 | IY.A1.1 |
| 2704 | 396 | IY.A1.1 |
| 2705 | 397 | IY.A1.1 |
| 2706 | 398 | IY.A1.1 |
| 2707 | 399 | IY.A1.1 |
| 2708 | 400 | IY.A1.1 |
| 2709 | 401 | IY.A1.1 |
| 2710 | 402 | IY.A1.1 |
| 2711 | 403 | IY.A1.1 |
| 2712 | 404 | IY.A1.1 |
| 2713 | 405 | IY.A1.1 |
| 2714 | 406 | IY.A1.1 |
| 2715 | 407 | IY.A1.1 |
| 2716 | 408 | IY.A1.1 |
| 2717 | 409 | IY.A1.1 |
| 2718 | 410 | IY.A1.1 |
| 2719 | 411 | IY.A1.1 |
| 2720 | 412 | IY.A1.1 |
| 2721 | 413 | IY.A1.1 |
| 2722 | 414 | IY.A1.1 |
| 2723 | 415 | IY.A1.1 |
| 2724 | 416 | IY.A1.1 |
| 2725 | 417 | IY.A1.1 |
| 2726 | 418 | IY.A1.1 |
| 2727 | 419 | IY.A1.1 |
| 2728 | 420 | IY.A1.1 |
| 2729 | 421 | IY.A1.1 |
| 2730 | 422 | IY.A1.1 |
| 2731 | 423 | IY.A1.1 |
| 2732 | 424 | IY.A1.1 |
| 2733 | 425 | IY.A1.1 |
| 2734 | 426 | IY.A1.1 |
| 2735 | 427 | IY.A1.1 |
| 2736 | 428 | IY.A1.1 |
| 2737 | 429 | IY.A1.1 |
| 2738 | 430 | IY.A1.1 |
| 2739 | 431 | IY.A1.1 |
| 2740 | 432 | IY.A1.1 |
| 2741 | 433 | IY.A1.1 |
| 2742 | 434 | IY.A1.1 |
| 2743 | 435 | IY.A1.1 |
| 2744 | 436 | IY.A1.1 |
| 2745 | 437 | IY.A1.1 |
| 2746 | 438 | IY.A1.1 |
| 2747 | 439 | IY.A1.1 |

TABLE D-continued

| # | Table | Formula |
|---|---|---|
| 2748 | 440 | IY.A1.1 |
| 2749 | 441 | IY.A1.1 |
| 2750 | 442 | IY.A1.1 |
| 2751 | 443 | IY.A1.1 |
| 2752 | 444 | IY.A1.1 |
| 2753 | 445 | IY.A1.1 |
| 2754 | 446 | IY.A1.1 |
| 2755 | 447 | IY.A1.1 |
| 2756 | 448 | IY.A1.1 |
| 2757 | 449 | IY.A1.1 |
| 2758 | 450 | IY.A1.1 |
| 2759 | 451 | IY.A1.1 |
| 2760 | 452 | IY.A1.1 |
| 2761 | 453 | IY.A1.1 |
| 2762 | 454 | IY.A1.1 |
| 2763 | 455 | IY.A1.1 |
| 2764 | 456 | IY.A1.1 |
| 2765 | 457 | IY.A1.1 |
| 2766 | 458 | IY.A1.1 |
| 2767 | 459 | IY.A1.1 |
| 2768 | 460 | IY.A1.1 |
| 2769 | 461 | IY.A1.1 |
| 2770 | 462 | IY.A1.1 |
| 2771 | 463 | IY.A1.1 |
| 2772 | 464 | IY.A1.1 |
| 2773 | 465 | IY.A1.1 |
| 2774 | 466 | IY.A1.1 |
| 2775 | 467 | IY.A1.1 |
| 2776 | 468 | IY.A1.1 |
| 2777 | 469 | IY.A1.1 |
| 2778 | 470 | IY.A1.1 |
| 2779 | 471 | IY.A1.1 |
| 2780 | 472 | IY.A1.1 |
| 2781 | 473 | IY.A1.1 |
| 2782 | 474 | IY.A1.1 |
| 2783 | 475 | IY.A1.1 |
| 2784 | 476 | IY.A1.1 |
| 2785 | 477 | IY.A1.1 |
| 2786 | 478 | IY.A1.1 |
| 2787 | 479 | IY.A1.1 |
| 2788 | 480 | IY.A1.1 |
| 2789 | 481 | IY.A1.1 |
| 2790 | 482 | IY.A1.1 |
| 2791 | 483 | IY.A1.1 |
| 2792 | 484 | IY.A1.1 |
| 2793 | 485 | IY.A1.1 |
| 2794 | 486 | IY.A1.1 |
| 2795 | 487 | IY.A1.1 |
| 2796 | 488 | IY.A1.1 |
| 2797 | 489 | IY.A1.1 |
| 2798 | 490 | IY.A1.1 |
| 2799 | 491 | IY.A1.1 |
| 2800 | 492 | IY.A1.1 |
| 2801 | 493 | IY.A1.1 |
| 2802 | 494 | IY.A1.1 |
| 2803 | 495 | IY.A1.1 |
| 2804 | 496 | IY.A1.1 |
| 2805 | 497 | IY.A1.1 |
| 2806 | 498 | IY.A1.1 |
| 2807 | 499 | IY.A1.1 |
| 2808 | 500 | IY.A1.1 |
| 2809 | 501 | IY.A1.1 |
| 2810 | 502 | IY.A1.1 |
| 2811 | 503 | IY.A1.1 |
| 2812 | 504 | IY.A1.1 |
| 2813 | 505 | IY.A1.1 |
| 2814 | 506 | IY.A1.1 |
| 2815 | 507 | IY.A1.1 |
| 2816 | 508 | IY.A1.1 |
| 2817 | 509 | IY.A1.1 |
| 2818 | 510 | IY.A1.1 |
| 2819 | 511 | IY.A1.1 |
| 2820 | 512 | IY.A1.1 |
| 2821 | 513 | IY.A1.1 |
| 2822 | 514 | IY.A1.1 |
| 2823 | 515 | IY.A1.1 |
| 2824 | 516 | IY.A1.1 |
| 2825 | 517 | IY.A1.1 |
| 2826 | 518 | IY.A1.1 |
| 2827 | 519 | IY.A1.1 |
| 2828 | 520 | IY.A1.1 |
| 2829 | 521 | IY.A1.1 |
| 2830 | 522 | IY.A1.1 |
| 2831 | 523 | IY.A1.1 |
| 2832 | 524 | IY.A1.1 |
| 2833 | 525 | IY.A1.1 |
| 2834 | 526 | IY.A1.1 |
| 2835 | 527 | IY.A1.1 |
| 2836 | 528 | IY.A1.1 |
| 2837 | 529 | IY.A1.1 |
| 2838 | 530 | IY.A1.1 |
| 2839 | 531 | IY.A1.1 |
| 2840 | 532 | IY.A1.1 |
| 2841 | 533 | IY.A1.1 |
| 2842 | 534 | IY.A1.1 |
| 2843 | 535 | IY.A1.1 |
| 2844 | 536 | IY.A1.1 |
| 2845 | 537 | IY.A1.1 |
| 2846 | 538 | IY.A1.1 |
| 2847 | 539 | IY.A1.1 |
| 2848 | 540 | IY.A1.1 |
| 2849 | 361 | IY.A1.2 |
| 2850 | 362 | IY.A1.2 |
| 2851 | 363 | IY.A1.2 |
| 2852 | 364 | IY.A1.2 |
| 2853 | 365 | IY.A1.2 |
| 2854 | 366 | IY.A1.2 |
| 2855 | 367 | IY.A1.2 |
| 2856 | 368 | IY.A1.2 |
| 2857 | 369 | IY.A1.2 |
| 2858 | 370 | IY.A1.2 |
| 2859 | 371 | IY.A1.2 |
| 2860 | 372 | IY.A1.2 |
| 2861 | 373 | IY.A1.2 |
| 2862 | 374 | IY.A1.2 |
| 2863 | 375 | IY.A1.2 |
| 2864 | 376 | IY.A1.2 |
| 2865 | 377 | IY.A1.2 |
| 2866 | 378 | IY.A1.2 |
| 2867 | 379 | IY.A1.2 |
| 2868 | 380 | IY.A1.2 |
| 2869 | 381 | IY.A1.2 |
| 2870 | 382 | IY.A1.2 |
| 2871 | 383 | IY.A1.2 |
| 2872 | 384 | IY.A1.2 |
| 2873 | 385 | IY.A1.2 |
| 2874 | 386 | IY.A1.2 |
| 2875 | 387 | IY.A1.2 |
| 2876 | 388 | IY.A1.2 |
| 2877 | 389 | IY.A1.2 |
| 2878 | 390 | IY.A1.2 |
| 2879 | 391 | IY.A1.2 |
| 2880 | 392 | IY.A1.2 |
| 2881 | 393 | IY.A1.2 |
| 2882 | 394 | IY.A1.2 |
| 2883 | 395 | IY.A1.2 |
| 2884 | 396 | IY.A1.2 |
| 2885 | 397 | IY.A1.2 |
| 2886 | 398 | IY.A1.2 |
| 2887 | 399 | IY.A1.2 |
| 2888 | 400 | IY.A1.2 |
| 2889 | 401 | IY.A1.2 |
| 2890 | 402 | IY.A1.2 |
| 2891 | 403 | IY.A1.2 |
| 2892 | 404 | IY.A1.2 |
| 2893 | 405 | IY.A1.2 |
| 2894 | 406 | IY.A1.2 |
| 2895 | 407 | IY.A1.2 |
| 2896 | 408 | IY.A1.2 |
| 2897 | 409 | IY.A1.2 |
| 2898 | 410 | IY.A1.2 |
| 2899 | 411 | IY.A1.2 |
| 2900 | 412 | IY.A1.2 |
| 2901 | 413 | IY.A1.2 |
| 2902 | 414 | IY.A1.2 |
| 2903 | 415 | IY.A1.2 |

TABLE D-continued

| # | Table | Formula |
|---|---|---|
| 2904 | 416 | IY.A1.2 |
| 2905 | 417 | IY.A1.2 |
| 2906 | 418 | IY.A1.2 |
| 2907 | 419 | IY.A1.2 |
| 2908 | 420 | IY.A1.2 |
| 2909 | 421 | IY.A1.2 |
| 2910 | 422 | IY.A1.2 |
| 2911 | 423 | IY.A1.2 |
| 2912 | 424 | IY.A1.2 |
| 2913 | 425 | IY.A1.2 |
| 2914 | 426 | IY.A1.2 |
| 2915 | 427 | IY.A1.2 |
| 2916 | 428 | IY.A1.2 |
| 2917 | 429 | IY.A1.2 |
| 2918 | 430 | IY.A1.2 |
| 2919 | 431 | IY.A1.2 |
| 2920 | 432 | IY.A1.2 |
| 2921 | 433 | IY.A1.2 |
| 2922 | 434 | IY.A1.2 |
| 2923 | 435 | IY.A1.2 |
| 2924 | 436 | IY.A1.2 |
| 2925 | 437 | IY.A1.2 |
| 2926 | 438 | IY.A1.2 |
| 2927 | 439 | IY.A1.2 |
| 2928 | 440 | IY.A1.2 |
| 2929 | 441 | IY.A1.2 |
| 2930 | 442 | IY.A1.2 |
| 2931 | 443 | IY.A1.2 |
| 2932 | 444 | IY.A1.2 |
| 2933 | 445 | IY.A1.2 |
| 2934 | 446 | IY.A1.2 |
| 2935 | 447 | IY.A1.2 |
| 2936 | 448 | IY.A1.2 |
| 2937 | 449 | IY.A1.2 |
| 2938 | 450 | IY.A1.2 |
| 2939 | 451 | IY.A1.2 |
| 2940 | 452 | IY.A1.2 |
| 2941 | 453 | IY.A1.2 |
| 2942 | 454 | IY.A1.2 |
| 2943 | 455 | IY.A1.2 |
| 2944 | 456 | IY.A1.2 |
| 2945 | 457 | IY.A1.2 |
| 2946 | 458 | IY.A1.2 |
| 2947 | 459 | IY.A1.2 |
| 2948 | 460 | IY.A1.2 |
| 2949 | 461 | IY.A1.2 |
| 2950 | 462 | IY.A1.2 |
| 2951 | 463 | IY.A1.2 |
| 2952 | 464 | IY.A1.2 |
| 2953 | 465 | IY.A1.2 |
| 2954 | 466 | IY.A1.2 |
| 2955 | 467 | IY.A1.2 |
| 2956 | 468 | IY.A1.2 |
| 2957 | 469 | IY.A1.2 |
| 2958 | 470 | IY.A1.2 |
| 2959 | 471 | IY.A1.2 |
| 2960 | 472 | IY.A1.2 |
| 2961 | 473 | IY.A1.2 |
| 2962 | 474 | IY.A1.2 |
| 2963 | 475 | IY.A1.2 |
| 2964 | 476 | IY.A1.2 |
| 2965 | 477 | IY.A1.2 |
| 2966 | 478 | IY.A1.2 |
| 2967 | 479 | IY.A1.2 |
| 2968 | 480 | IY.A1.2 |
| 2969 | 481 | IY.A1.2 |
| 2970 | 482 | IY.A1.2 |
| 2971 | 483 | IY.A1.2 |
| 2972 | 484 | IY.A1.2 |
| 2973 | 485 | IY.A1.2 |
| 2974 | 486 | IY.A1.2 |
| 2975 | 487 | IY.A1.2 |
| 2976 | 488 | IY.A1.2 |
| 2977 | 489 | IY.A1.2 |
| 2978 | 490 | IY.A1.2 |
| 2979 | 491 | IY.A1.2 |
| 2980 | 492 | IY.A1.2 |
| 2981 | 493 | IY.A1.2 |
| 2982 | 494 | IY.A1.2 |
| 2983 | 495 | IY.A1.2 |
| 2984 | 496 | IY.A1.2 |
| 2985 | 497 | IY.A1.2 |
| 2986 | 498 | IY.A1.2 |
| 2987 | 499 | IY.A1.2 |
| 2988 | 500 | IY.A1.2 |
| 2989 | 501 | IY.A1.2 |
| 2990 | 502 | IY.A1.2 |
| 2991 | 503 | IY.A1.2 |
| 2992 | 504 | IY.A1.2 |
| 2993 | 505 | IY.A1.2 |
| 2994 | 506 | IY.A1.2 |
| 2995 | 507 | IY.A1.2 |
| 2996 | 508 | IY.A1.2 |
| 2997 | 509 | IY.A1.2 |
| 2998 | 510 | IY.A1.2 |
| 2999 | 511 | IY.A1.2 |
| 3000 | 512 | IY.A1.2 |
| 3001 | 513 | IY.A1.2 |
| 3002 | 514 | IY.A1.2 |
| 3003 | 515 | IY.A1.2 |
| 3004 | 516 | IY.A1.2 |
| 3005 | 517 | IY.A1.2 |
| 3006 | 518 | IY.A1.2 |
| 3007 | 519 | IY.A1.2 |
| 3008 | 520 | IY.A1.2 |
| 3009 | 521 | IY.A1.2 |
| 3010 | 522 | IY.A1.2 |
| 3011 | 523 | IY.A1.2 |
| 3012 | 524 | IY.A1.2 |
| 3013 | 525 | IY.A1.2 |
| 3014 | 526 | IY.A1.2 |
| 3015 | 527 | IY.A1.2 |
| 3016 | 528 | IY.A1.2 |
| 3017 | 529 | IY.A1.2 |
| 3018 | 530 | IY.A1.2 |
| 3019 | 531 | IY.A1.2 |
| 3020 | 532 | IY.A1.2 |
| 3021 | 533 | IY.A1.2 |
| 3022 | 534 | IY.A1.2 |
| 3023 | 535 | IY.A1.2 |
| 3024 | 536 | IY.A1.2 |
| 3025 | 537 | IY.A1.2 |
| 3026 | 538 | IY.A1.2 |
| 3027 | 539 | IY.A1.2 |
| 3028 | 540 | IY.A1.2 |
| 3029 | 361 | IY.A1.3 |
| 3030 | 362 | IY.A1.3 |
| 3031 | 363 | IY.A1.3 |
| 3032 | 364 | IY.A1.3 |
| 3033 | 365 | IY.A1.3 |
| 3034 | 366 | IY.A1.3 |
| 3035 | 367 | IY.A1.3 |
| 3036 | 368 | IY.A1.3 |
| 3037 | 369 | IY.A1.3 |
| 3038 | 370 | IY.A1.3 |
| 3039 | 371 | IY.A1.3 |
| 3040 | 372 | IY.A1.3 |
| 3041 | 373 | IY.A1.3 |
| 3042 | 374 | IY.A1.3 |
| 3043 | 375 | IY.A1.3 |
| 3044 | 376 | IY.A1.3 |
| 3045 | 377 | IY.A1.3 |
| 3046 | 378 | IY.A1.3 |
| 3047 | 379 | IY.A1.3 |
| 3048 | 380 | IY.A1.3 |
| 3049 | 381 | IY.A1.3 |
| 3050 | 382 | IY.A1.3 |
| 3051 | 383 | IY.A1.3 |
| 3052 | 384 | IY.A1.3 |
| 3053 | 385 | IY.A1.3 |
| 3054 | 386 | IY.A1.3 |
| 3055 | 387 | IY.A1.3 |
| 3056 | 388 | IY.A1.3 |
| 3057 | 389 | IY.A1.3 |
| 3058 | 390 | IY.A1.3 |
| 3059 | 391 | IY.A1.3 |

TABLE D-continued

| # | Table | Formula |
|---|---|---|
| 3060 | 392 | IY.A1.3 |
| 3061 | 393 | IY.A1.3 |
| 3062 | 394 | IY.A1.3 |
| 3063 | 395 | IY.A1.3 |
| 3064 | 396 | IY.A1.3 |
| 3065 | 397 | IY.A1.3 |
| 3066 | 398 | IY.A1.3 |
| 3067 | 399 | IY.A1.3 |
| 3068 | 400 | IY.A1.3 |
| 3069 | 401 | IY.A1.3 |
| 3070 | 402 | IY.A1.3 |
| 3071 | 403 | IY.A1.3 |
| 3072 | 404 | IY.A1.3 |
| 3073 | 405 | IY.A1.3 |
| 3074 | 406 | IY.A1.3 |
| 3075 | 407 | IY.A1.3 |
| 3076 | 408 | IY.A1.3 |
| 3077 | 409 | IY.A1.3 |
| 3078 | 410 | IY.A1.3 |
| 3079 | 411 | IY.A1.3 |
| 3080 | 412 | IY.A1.3 |
| 3081 | 413 | IY.A1.3 |
| 3082 | 414 | IY.A1.3 |
| 3083 | 415 | IY.A1.3 |
| 3084 | 416 | IY.A1.3 |
| 3085 | 417 | IY.A1.3 |
| 3086 | 418 | IY.A1.3 |
| 3087 | 419 | IY.A1.3 |
| 3088 | 420 | IY.A1.3 |
| 3089 | 421 | IY.A1.3 |
| 3090 | 422 | IY.A1.3 |
| 3091 | 423 | IY.A1.3 |
| 3092 | 424 | IY.A1.3 |
| 3093 | 425 | IY.A1.3 |
| 3094 | 426 | IY.A1.3 |
| 3095 | 427 | IY.A1.3 |
| 3096 | 428 | IY.A1.3 |
| 3097 | 429 | IY.A1.3 |
| 3098 | 430 | IY.A1.3 |
| 3099 | 431 | IY.A1.3 |
| 3100 | 432 | IY.A1.3 |
| 3101 | 433 | IY.A1.3 |
| 3102 | 434 | IY.A1.3 |
| 3103 | 435 | IY.A1.3 |
| 3104 | 436 | IY.A1.3 |
| 3105 | 437 | IY.A1.3 |
| 3106 | 438 | IY.A1.3 |
| 3107 | 439 | IY.A1.3 |
| 3108 | 440 | IY.A1.3 |
| 3109 | 441 | IY.A1.3 |
| 3110 | 442 | IY.A1.3 |
| 3111 | 443 | IY.A1.3 |
| 3112 | 444 | IY.A1.3 |
| 3113 | 445 | IY.A1.3 |
| 3114 | 446 | IY.A1.3 |
| 3115 | 447 | IY.A1.3 |
| 3116 | 448 | IY.A1.3 |
| 3117 | 449 | IY.A1.3 |
| 3118 | 450 | IY.A1.3 |
| 3119 | 451 | IY.A1.3 |
| 3120 | 452 | IY.A1.3 |
| 3121 | 453 | IY.A1.3 |
| 3122 | 454 | IY.A1.3 |
| 3123 | 455 | IY.A1.3 |
| 3124 | 456 | IY.A1.3 |
| 3125 | 457 | IY.A1.3 |
| 3126 | 458 | IY.A1.3 |
| 3127 | 459 | IY.A1.3 |
| 3128 | 460 | IY.A1.3 |
| 3129 | 461 | IY.A1.3 |
| 3130 | 462 | IY.A1.3 |
| 3131 | 463 | IY.A1.3 |
| 3132 | 464 | IY.A1.3 |
| 3133 | 465 | IY.A1.3 |
| 3134 | 466 | IY.A1.3 |
| 3135 | 467 | IY.A1.3 |
| 3136 | 468 | IY.A1.3 |
| 3137 | 469 | IY.A1.3 |
| 3138 | 470 | IY.A1.3 |
| 3139 | 471 | IY.A1.3 |
| 3140 | 472 | IY.A1.3 |
| 3141 | 473 | IY.A1.3 |
| 3142 | 474 | IY.A1.3 |
| 3143 | 475 | IY.A1.3 |
| 3144 | 476 | IY.A1.3 |
| 3145 | 477 | IY.A1.3 |
| 3146 | 478 | IY.A1.3 |
| 3147 | 479 | IY.A1.3 |
| 3148 | 480 | IY.A1.3 |
| 3149 | 481 | IY.A1.3 |
| 3150 | 482 | IY.A1.3 |
| 3151 | 483 | IY.A1.3 |
| 3152 | 484 | IY.A1.3 |
| 3153 | 485 | IY.A1.3 |
| 3154 | 486 | IY.A1.3 |
| 3155 | 487 | IY.A1.3 |
| 3156 | 488 | IY.A1.3 |
| 3157 | 489 | IY.A1.3 |
| 3158 | 490 | IY.A1.3 |
| 3159 | 491 | IY.A1.3 |
| 3160 | 492 | IY.A1.3 |
| 3161 | 493 | IY.A1.3 |
| 3162 | 494 | IY.A1.3 |
| 3163 | 495 | IY.A1.3 |
| 3164 | 496 | IY.A1.3 |
| 3165 | 497 | IY.A1.3 |
| 3166 | 498 | IY.A1.3 |
| 3167 | 499 | IY.A1.3 |
| 3168 | 500 | IY.A1.3 |
| 3169 | 501 | IY.A1.3 |
| 3170 | 502 | IY.A1.3 |
| 3171 | 503 | IY.A1.3 |
| 3172 | 504 | IY.A1.3 |
| 3173 | 505 | IY.A1.3 |
| 3174 | 506 | IY.A1.3 |
| 3175 | 507 | IY.A1.3 |
| 3176 | 508 | IY.A1.3 |
| 3177 | 509 | IY.A1.3 |
| 3178 | 510 | IY.A1.3 |
| 3179 | 511 | IY.A1.3 |
| 3180 | 512 | IY.A1.3 |
| 3181 | 513 | IY.A1.3 |
| 3182 | 514 | IY.A1.3 |
| 3183 | 515 | IY.A1.3 |
| 3184 | 516 | IY.A1.3 |
| 3185 | 517 | IY.A1.3 |
| 3186 | 518 | IY.A1.3 |
| 3187 | 519 | IY.A1.3 |
| 3188 | 520 | IY.A1.3 |
| 3189 | 521 | IY.A1.3 |
| 3190 | 522 | IY.A1.3 |
| 3191 | 523 | IY.A1.3 |
| 3192 | 524 | IY.A1.3 |
| 3193 | 525 | IY.A1.3 |
| 3194 | 526 | IY.A1.3 |
| 3195 | 527 | IY.A1.3 |
| 3196 | 528 | IY.A1.3 |
| 3197 | 529 | IY.A1.3 |
| 3198 | 530 | IY.A1.3 |
| 3199 | 531 | IY.A1.3 |
| 3200 | 532 | IY.A1.3 |
| 3201 | 533 | IY.A1.3 |
| 3202 | 534 | IY.A1.3 |
| 3203 | 535 | IY.A1.3 |
| 3204 | 536 | IY.A1.3 |
| 3205 | 537 | IY.A1.3 |
| 3206 | 538 | IY.A1.3 |
| 3207 | 539 | IY.A1.3 |
| 3208 | 540 | IY.A1.3 |
| 3209 | 361 | IA.A5.1 |
| 3210 | 362 | IA.A5.1 |
| 3211 | 363 | IA.A5.1 |
| 3212 | 364 | IA.A5.1 |
| 3213 | 365 | IA.A5.1 |
| 3214 | 366 | IA.A5.1 |
| 3215 | 367 | IA.A5.1 |

TABLE D-continued

| # | Table | Formula |
|---|---|---|
| 3216 | 368 | IA.A5.1 |
| 3217 | 369 | IA.A5.1 |
| 3218 | 370 | IA.A5.1 |
| 3219 | 371 | IA.A5.1 |
| 3220 | 372 | IA.A5.1 |
| 3221 | 373 | IA.A5.1 |
| 3222 | 374 | IA.A5.1 |
| 3223 | 375 | IA.A5.1 |
| 3224 | 376 | IA.A5.1 |
| 3225 | 377 | IA.A5.1 |
| 3226 | 378 | IA.A5.1 |
| 3227 | 379 | IA.A5.1 |
| 3228 | 380 | IA.A5.1 |
| 3229 | 381 | IA.A5.1 |
| 3230 | 382 | IA.A5.1 |
| 3231 | 383 | IA.A5.1 |
| 3232 | 384 | IA.A5.1 |
| 3233 | 385 | IA.A5.1 |
| 3234 | 386 | IA.A5.1 |
| 3235 | 387 | IA.A5.1 |
| 3236 | 388 | IA.A5.1 |
| 3237 | 389 | IA.A5.1 |
| 3238 | 390 | IA.A5.1 |
| 3239 | 391 | IA.A5.1 |
| 3240 | 392 | IA.A5.1 |
| 3241 | 393 | IA.A5.1 |
| 3242 | 394 | IA.A5.1 |
| 3243 | 395 | IA.A5.1 |
| 3244 | 396 | IA.A5.1 |
| 3245 | 397 | IA.A5.1 |
| 3246 | 398 | IA.A5.1 |
| 3247 | 399 | IA.A5.1 |
| 3248 | 400 | IA.A5.1 |
| 3249 | 401 | IA.A5.1 |
| 3250 | 402 | IA.A5.1 |
| 3251 | 403 | IA.A5.1 |
| 3252 | 404 | IA.A5.1 |
| 3253 | 405 | IA.A5.1 |
| 3254 | 406 | IA.A5.1 |
| 3255 | 407 | IA.A5.1 |
| 3256 | 408 | IA.A5.1 |
| 3257 | 409 | IA.A5.1 |
| 3258 | 410 | IA.A5.1 |
| 3259 | 411 | IA.A5.1 |
| 3260 | 412 | IA.A5.1 |
| 3261 | 413 | IA.A5.1 |
| 3262 | 414 | IA.A5.1 |
| 3263 | 415 | IA.A5.1 |
| 3264 | 416 | IA.A5.1 |
| 3265 | 417 | IA.A5.1 |
| 3266 | 418 | IA.A5.1 |
| 3267 | 419 | IA.A5.1 |
| 3268 | 420 | IA.A5.1 |
| 3269 | 421 | IA.A5.1 |
| 3270 | 422 | IA.A5.1 |
| 3271 | 423 | IA.A5.1 |
| 3272 | 424 | IA.A5.1 |
| 3273 | 425 | IA.A5.1 |
| 3274 | 426 | IA.A5.1 |
| 3275 | 427 | IA.A5.1 |
| 3276 | 428 | IA.A5.1 |
| 3277 | 429 | IA.A5.1 |
| 3278 | 430 | IA.A5.1 |
| 3279 | 431 | IA.A5.1 |
| 3280 | 432 | IA.A5.1 |
| 3281 | 433 | IA.A5.1 |
| 3282 | 434 | IA.A5.1 |
| 3283 | 435 | IA.A5.1 |
| 3284 | 436 | IA.A5.1 |
| 3285 | 437 | IA.A5.1 |
| 3286 | 438 | IA.A5.1 |
| 3287 | 439 | IA.A5.1 |
| 3288 | 440 | IA.A5.1 |
| 3289 | 441 | IA.A5.1 |
| 3290 | 442 | IA.A5.1 |
| 3291 | 443 | IA.A5.1 |
| 3292 | 444 | IA.A5.1 |
| 3293 | 445 | IA.A5.1 |
| 3294 | 446 | IA.A5.1 |
| 3295 | 447 | IA.A5.1 |
| 3296 | 448 | IA.A5.1 |
| 3297 | 449 | IA.A5.1 |
| 3298 | 450 | IA.A5.1 |
| 3299 | 451 | IA.A5.1 |
| 3300 | 452 | IA.A5.1 |
| 3301 | 453 | IA.A5.1 |
| 3302 | 454 | IA.A5.1 |
| 3303 | 455 | IA.A5.1 |
| 3304 | 456 | IA.A5.1 |
| 3305 | 457 | IA.A5.1 |
| 3306 | 458 | IA.A5.1 |
| 3307 | 459 | IA.A5.1 |
| 3308 | 460 | IA.A5.1 |
| 3309 | 461 | IA.A5.1 |
| 3310 | 462 | IA.A5.1 |
| 3311 | 463 | IA.A5.1 |
| 3312 | 464 | IA.A5.1 |
| 3313 | 465 | IA.A5.1 |
| 3314 | 466 | IA.A5.1 |
| 3315 | 467 | IA.A5.1 |
| 3316 | 468 | IA.A5.1 |
| 3317 | 469 | IA.A5.1 |
| 3318 | 470 | IA.A5.1 |
| 3319 | 471 | IA.A5.1 |
| 3320 | 472 | IA.A5.1 |
| 3321 | 473 | IA.A5.1 |
| 3322 | 474 | IA.A5.1 |
| 3323 | 475 | IA.A5.1 |
| 3324 | 476 | IA.A5.1 |
| 3325 | 477 | IA.A5.1 |
| 3326 | 478 | IA.A5.1 |
| 3327 | 479 | IA.A5.1 |
| 3328 | 480 | IA.A5.1 |
| 3329 | 481 | IA.A5.1 |
| 3330 | 482 | IA.A5.1 |
| 3331 | 483 | IA.A5.1 |
| 3332 | 484 | IA.A5.1 |
| 3333 | 485 | IA.A5.1 |
| 3334 | 486 | IA.A5.1 |
| 3335 | 487 | IA.A5.1 |
| 3336 | 488 | IA.A5.1 |
| 3337 | 489 | IA.A5.1 |
| 3338 | 490 | IA.A5.1 |
| 3339 | 491 | IA.A5.1 |
| 3340 | 492 | IA.A5.1 |
| 3341 | 493 | IA.A5.1 |
| 3342 | 494 | IA.A5.1 |
| 3343 | 495 | IA.A5.1 |
| 3344 | 496 | IA.A5.1 |
| 3345 | 497 | IA.A5.1 |
| 3346 | 498 | IA.A5.1 |
| 3347 | 499 | IA.A5.1 |
| 3348 | 500 | IA.A5.1 |
| 3349 | 501 | IA.A5.1 |
| 3350 | 502 | IA.A5.1 |
| 3351 | 503 | IA.A5.1 |
| 3352 | 504 | IA.A5.1 |
| 3353 | 505 | IA.A5.1 |
| 3354 | 506 | IA.A5.1 |
| 3355 | 507 | IA.A5.1 |
| 3356 | 508 | IA.A5.1 |
| 3357 | 509 | IA.A5.1 |
| 3358 | 510 | IA.A5.1 |
| 3359 | 511 | IA.A5.1 |
| 3360 | 512 | IA.A5.1 |
| 3361 | 513 | IA.A5.1 |
| 3362 | 514 | IA.A5.1 |
| 3363 | 515 | IA.A5.1 |
| 3364 | 516 | IA.A5.1 |
| 3365 | 517 | IA.A5.1 |
| 3366 | 518 | IA.A5.1 |
| 3367 | 519 | IA.A5.1 |
| 3368 | 520 | IA.A5.1 |
| 3369 | 521 | IA.A5.1 |
| 3370 | 522 | IA.A5.1 |
| 3371 | 523 | IA.A5.1 |

TABLE D-continued

| # | Table | Formula |
|---|---|---|
| 3372 | 524 | IA.A5.1 |
| 3373 | 525 | IA.A5.1 |
| 3374 | 526 | IA.A5.1 |
| 3375 | 527 | IA.A5.1 |
| 3376 | 528 | IA.A5.1 |
| 3377 | 529 | IA.A5.1 |
| 3378 | 530 | IA.A5.1 |
| 3379 | 531 | IA.A5.1 |
| 3380 | 532 | IA.A5.1 |
| 3381 | 533 | IA.A5.1 |
| 3382 | 534 | IA.A5.1 |
| 3383 | 535 | IA.A5.1 |
| 3384 | 536 | IA.A5.1 |
| 3385 | 537 | IA.A5.1 |
| 3386 | 538 | IA.A5.1 |
| 3387 | 539 | IA.A5.1 |
| 3388 | 540 | IA.A5.1 |
| 3389 | 361 | IA.A5.2 |
| 3390 | 362 | IA.A5.2 |
| 3391 | 363 | IA.A5.2 |
| 3392 | 364 | IA.A5.2 |
| 3393 | 365 | IA.A5.2 |
| 3394 | 366 | IA.A5.2 |
| 3395 | 367 | IA.A5.2 |
| 3396 | 368 | IA.A5.2 |
| 3397 | 369 | IA.A5.2 |
| 3398 | 370 | IA.A5.2 |
| 3399 | 371 | IA.A5.2 |
| 3400 | 372 | IA.A5.2 |
| 3401 | 373 | IA.A5.2 |
| 3402 | 374 | IA.A5.2 |
| 3403 | 375 | IA.A5.2 |
| 3404 | 376 | IA.A5.2 |
| 3405 | 377 | IA.A5.2 |
| 3406 | 378 | IA.A5.2 |
| 3407 | 379 | IA.A5.2 |
| 3408 | 380 | IA.A5.2 |
| 3409 | 381 | IA.A5.2 |
| 3410 | 382 | IA.A5.2 |
| 3411 | 383 | IA.A5.2 |
| 3412 | 384 | IA.A5.2 |
| 3413 | 385 | IA.A5.2 |
| 3414 | 386 | IA.A5.2 |
| 3415 | 387 | IA.A5.2 |
| 3416 | 388 | IA.A5.2 |
| 3417 | 389 | IA.A5.2 |
| 3418 | 390 | IA.A5.2 |
| 3419 | 391 | IA.A5.2 |
| 3420 | 392 | IA.A5.2 |
| 3421 | 393 | IA.A5.2 |
| 3422 | 394 | IA.A5.2 |
| 3423 | 395 | IA.A5.2 |
| 3424 | 396 | IA.A5.2 |
| 3425 | 397 | IA.A5.2 |
| 3426 | 398 | IA.A5.2 |
| 3427 | 399 | IA.A5.2 |
| 3428 | 400 | IA.A5.2 |
| 3429 | 401 | IA.A5.2 |
| 3430 | 402 | IA.A5.2 |
| 3431 | 403 | IA.A5.2 |
| 3432 | 404 | IA.A5.2 |
| 3433 | 405 | IA.A5.2 |
| 3434 | 406 | IA.A5.2 |
| 3435 | 407 | IA.A5.2 |
| 3436 | 408 | IA.A5.2 |
| 3437 | 409 | IA.A5.2 |
| 3438 | 410 | IA.A5.2 |
| 3439 | 411 | IA.A5.2 |
| 3440 | 412 | IA.A5.2 |
| 3441 | 413 | IA.A5.2 |
| 3442 | 414 | IA.A5.2 |
| 3443 | 415 | IA.A5.2 |
| 3444 | 416 | IA.A5.2 |
| 3445 | 417 | IA.A5.2 |
| 3446 | 418 | IA.A5.2 |
| 3447 | 419 | IA.A5.2 |
| 3448 | 420 | IA.A5.2 |
| 3449 | 421 | IA.A5.2 |
| 3450 | 422 | IA.A5.2 |
| 3451 | 423 | IA.A5.2 |
| 3452 | 424 | IA.A5.2 |
| 3453 | 425 | IA.A5.2 |
| 3454 | 426 | IA.A5.2 |
| 3455 | 427 | IA.A5.2 |
| 3456 | 428 | IA.A5.2 |
| 3457 | 429 | IA.A5.2 |
| 3458 | 430 | IA.A5.2 |
| 3459 | 431 | IA.A5.2 |
| 3460 | 432 | IA.A5.2 |
| 3461 | 433 | IA.A5.2 |
| 3462 | 434 | IA.A5.2 |
| 3463 | 435 | IA.A5.2 |
| 3464 | 436 | IA.A5.2 |
| 3465 | 437 | IA.A5.2 |
| 3466 | 438 | IA.A5.2 |
| 3467 | 439 | IA.A5.2 |
| 3468 | 440 | IA.A5.2 |
| 3469 | 441 | IA.A5.2 |
| 3470 | 442 | IA.A5.2 |
| 3471 | 443 | IA.A5.2 |
| 3472 | 444 | IA.A5.2 |
| 3473 | 445 | IA.A5.2 |
| 3474 | 446 | IA.A5.2 |
| 3475 | 447 | IA.A5.2 |
| 3476 | 448 | IA.A5.2 |
| 3477 | 449 | IA.A5.2 |
| 3478 | 450 | IA.A5.2 |
| 3479 | 451 | IA.A5.2 |
| 3480 | 452 | IA.A5.2 |
| 3481 | 453 | IA.A5.2 |
| 3482 | 454 | IA.A5.2 |
| 3483 | 455 | IA.A5.2 |
| 3484 | 456 | IA.A5.2 |
| 3485 | 457 | IA.A5.2 |
| 3486 | 458 | IA.A5.2 |
| 3487 | 459 | IA.A5.2 |
| 3488 | 460 | IA.A5.2 |
| 3489 | 461 | IA.A5.2 |
| 3490 | 462 | IA.A5.2 |
| 3491 | 463 | IA.A5.2 |
| 3492 | 464 | IA.A5.2 |
| 3493 | 465 | IA.A5.2 |
| 3494 | 466 | IA.A5.2 |
| 3495 | 467 | IA.A5.2 |
| 3496 | 468 | IA.A5.2 |
| 3497 | 469 | IA.A5.2 |
| 3498 | 470 | IA.A5.2 |
| 3499 | 471 | IA.A5.2 |
| 3500 | 472 | IA.A5.2 |
| 3501 | 473 | IA.A5.2 |
| 3502 | 474 | IA.A5.2 |
| 3503 | 475 | IA.A5.2 |
| 3504 | 476 | IA.A5.2 |
| 3505 | 477 | IA.A5.2 |
| 3506 | 478 | IA.A5.2 |
| 3507 | 479 | IA.A5.2 |
| 3508 | 480 | IA.A5.2 |
| 3509 | 481 | IA.A5.2 |
| 3510 | 482 | IA.A5.2 |
| 3511 | 483 | IA.A5.2 |
| 3512 | 484 | IA.A5.2 |
| 3513 | 485 | IA.A5.2 |
| 3514 | 486 | IA.A5.2 |
| 3515 | 487 | IA.A5.2 |
| 3516 | 488 | IA.A5.2 |
| 3517 | 489 | IA.A5.2 |
| 3518 | 490 | IA.A5.2 |
| 3519 | 491 | IA.A5.2 |
| 3520 | 492 | IA.A5.2 |
| 3521 | 493 | IA.A5.2 |
| 3522 | 494 | IA.A5.2 |
| 3523 | 495 | IA.A5.2 |
| 3524 | 496 | IA.A5.2 |
| 3525 | 497 | IA.A5.2 |
| 3526 | 498 | IA.A5.2 |
| 3527 | 499 | IA.A5.2 |

TABLE D-continued

| # | Table | Formula |
|---|---|---|
| 3528 | 500 | IA.A5.2 |
| 3529 | 501 | IA.A5.2 |
| 3530 | 502 | IA.A5.2 |
| 3531 | 503 | IA.A5.2 |
| 3532 | 504 | IA.A5.2 |
| 3533 | 505 | IA.A5.2 |
| 3534 | 506 | IA.A5.2 |
| 3535 | 507 | IA.A5.2 |
| 3536 | 508 | IA.A5.2 |
| 3537 | 509 | IA.A5.2 |
| 3538 | 510 | IA.A5.2 |
| 3539 | 511 | IA.A5.2 |
| 3540 | 512 | IA.A5.2 |
| 3541 | 513 | IA.A5.2 |
| 3542 | 514 | IA.A5.2 |
| 3543 | 515 | IA.A5.2 |
| 3544 | 516 | IA.A5.2 |
| 3545 | 517 | IA.A5.2 |
| 3546 | 518 | IA.A5.2 |
| 3547 | 519 | IA.A5.2 |
| 3548 | 520 | IA.A5.2 |
| 3549 | 521 | IA.A5.2 |
| 3550 | 522 | IA.A5.2 |
| 3551 | 523 | IA.A5.2 |
| 3552 | 524 | IA.A5.2 |
| 3553 | 525 | IA.A5.2 |
| 3554 | 526 | IA.A5.2 |
| 3555 | 527 | IA.A5.2 |
| 3556 | 528 | IA.A5.2 |
| 3557 | 529 | IA.A5.2 |
| 3558 | 530 | IA.A5.2 |
| 3559 | 531 | IA.A5.2 |
| 3560 | 532 | IA.A5.2 |
| 3561 | 533 | IA.A5.2 |
| 3562 | 534 | IA.A5.2 |
| 3563 | 535 | IA.A5.2 |
| 3564 | 536 | IA.A5.2 |
| 3565 | 537 | IA.A5.2 |
| 3566 | 538 | IA.A5.2 |
| 3567 | 539 | IA.A5.2 |
| 3568 | 540 | IA.A5.2 |

Embodiments 1 to 2017 (#), wherein Tables 1 to 504 are assigned to formulae ## IA.A1.1, IA.A1.2, IA.A1.3, IB.A1.1, IB.A1.2, IB.A1.3, IC.A1.1, IC.A1.2, IC.A1.3, ID.A1.1, ID.A1.2, ID.A1. IT.A1.1, IT.A1.2, IT.A1.3, IY.A1.1, IY.A1.2, IY.A1.3, IA.A5.1, and IA.A5.2

Mixtures

The present invention also relates to a mixture of at least one compound of formula (I) with at least one mixing partner as defined herein. Preferred are binary mixtures of one compound of the invention as compound of formula (I) with one mixing partner as defined herein as component II. Mixing partners can be selected from pesticides, in particular insecticides, nematicides, and acaricides, fungicides, herbicides, plant growth regulators, fertilizers. Preferred mixing partners are insecticides, nematicides and fungicides.

Formulations

The invention also relates to agrochemical compositions comprising an auxiliary and at least one compound of the present invention or a mixture thereof.

An agrochemical composition comprises a pesticidally effective amount of a compound of the present invention or a mixture thereof. The term "pesticidally effective amount" is defined below.

The compounds of the present invention or the mixtures thereof can be converted into customary types of agrochemical compositions, e. g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Mono-graph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Examples for suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, antifreezing agents, antifoaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, al-kylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethox-ylated alcohols, or of fatty acid esters. Examples of phosphates are phosphate esters. Exam-ples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof.

Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Exam-ples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are homo- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compounds of the present invention on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:
i) Water-Soluble Concentrates (SL, LS)

10-60 wt % of a compound of formula (I) and 5-15 wt % wetting agent (e.g. alcohol alkoxylates) are dissolved in water and/or in a water-soluble solvent (e.g. alcohols) up to 100 wt %.

The active substance dissolves upon dilution with water.
ii) Dispersible Concentrates (DC)

5-25 wt % of a compound of formula (I) and 1-10 wt % dispersant (e. g. polyvinylpyrrolidone) are dissolved in up to 100 wt % organic solvent (e.g. cyclohexanone). Dilution with water gives a dispersion.
iii) Emulsifiable Concentrates (EC)

15-70 wt % of a compound of formula (I) and 5-10 wt % emulsifiers (e.g. calcium dodecylbenzenesulfonate and castor oil ethoxylate) are dissolved in up to 100 wt % water-insoluble organic solvent (e.g. aromatic hydrocarbon). Dilution with water gives an emulsion.
iv) Emulsions (EW, EO, ES)

5-40 wt % of a compound of formula (I) and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into up to 100 wt % water by means of an emulsifying machine and made into a homogeneous emulsion. Dilution with water gives an emulsion.
v) Suspensions (SC, OD, FS)

In an agitated ball mill, 20-60 wt % of a compound of formula (I) are comminuted with addition of 2-10 wt % dispersants and wetting agents (e.g. sodium lignosulfonate and alcohol ethoxylate), 0.1-2 wt % thickener (e.g. xanthan gum) and up to 100 wt % water to give a fine active substance suspension. Dilution with water gives a stable suspension of the active sub-stance. For FS type composition up to 40 wt % binder (e.g. polyvinylalcohol) is added.
vi) Water-Dispersible Granules and Water-Soluble Granules (WG, SG)

50-80 wt % of a compound of formula (I) are ground finely with addition of up to 100 wt % dispersants and wetting agents (e.g. sodium lignosulfonate and alcohol ethoxylate) and prepared as water-dispersible or water-soluble granules by means of technical appliances (e. g. extrusion, spray tower, fluidized bed). Dilution with water gives a stable dispersion or solution of the active substance.
vii) Water-Dispersible Powders and Water-Soluble Powders (WP, SP, WS)

50-80 wt % of a compound of formula (I) are ground in a rotor-stator mill with ad-dition of 1-5 wt % dispersants (e.g. sodium lignosulfonate), 1-3 wt % wetting agents (e.g. alcohol ethoxylate) and up to 100 wt % solid carrier, e.g. silica gel. Dilution with water gives a stable dis-persion or solution of the active substance.
viii) Gel (GW, GF)

In an agitated ball mill, 5-25 wt % of a compound of formula (I) are comminuted with addition of 3-10 wt % dispersants (e.g. sodium lignosulfonate), 1-5 wt % thickener (e.g. carboxymethylcellulose) and up to 100 wt % water to give a fine suspension of the active substance. Dilution with water gives a stable suspension of the active substance.
ix) Microemulsion (ME)

5-20 wt % of a compound of formula (I) are added to 5-30 wt % organic solvent blend (e.g. fatty acid dimethylamide and cyclohexanone), 10-25 wt % surfactant blend (e.g. alcohol ethoxylate and arylphenol ethoxylate), and water up to 100%. This mixture is stirred for 1 h to produce spontaneously a thermodynamically stable microemulsion.
x) Microcapsules (CS)

An oil phase comprising 5-50 wt % of a compound of formula (I), 0-40 wt % water insoluble organic solvent (e.g. aromatic hydrocarbon), 2-15 wt % acrylic monomers (e.g. methylmethacrylate, methacrylic acid and a dl. or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound of formula (I), 0-40 wt % water insolu-ble organic solvent (e.g. aromatic hydrocarbon), and an isocyanate monomer (e.g. diphe-nylme-thene-4,4'-diisocyanate) are dispersed into an aqueous solution of a protective colloid (e.g. polyvinyl alcohol). The addition of a polyamine (e.g. hexamethylenediamine)

results in the for-mation of a polyurea microcapsule. The monomers amount to 1-10 wt %. The wt % relate to the total CS composition.

xi) Dustable Powders (DP, DS)

1-10 wt % of a compound of formula (I) are ground finely and mixed intimately with up to 100 wt % solid carrier, e.g. finely divided kaolin.

xii) Granules (GR, FG)

0.5-30 wt % of a compound of formula (I) is ground finely and associated with up to 100 wt % solid carrier (e.g. silicate). Granulation is achieved by extrusion, spray-drying or the fluidized bed.

xiii) Ultra-Low Volume Liquids (UL)

1-50 wt % of a compound of formula (I) are dissolved in up to 100 wt % organic solvent, e.g. aromatic hydrocarbon.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % col-orants.

The agrochemical compositions generally comprise between 0.01 and 95%, preferably between 0.1 and 90%, and most preferably between 0.5 and 75%, by weight of active substance.

The active substances are employed in a purity of from 90% to 100%, preferably from 95% to 100% (according to NMR spectrum).

Various types of oils, wetters, adjuvants, fertilizer, or micronutrients, and other pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially premixed components, e. g. components comprising compounds of the present invention and/or mixing partners as defined above, may be mixed by the user in a spray tank and further auxiliaries and additives may be added, if appropriate.

In a further embodiment, either individual components of the composition according to the invention or partially premixed components, e. g. components comprising compounds of the present invention and/or mixing partners as defined above, can be applied jointly (e.g. after tank mix) or consecutively.

Application Methods

The compounds of the present invention are suitable for use in protecting crops, plants, plant propagation materials, such as seeds, or soil or water, in which the plants are growing, from attack or infestation by animal pests. Therefore, the present invention also relates to a plant protection method, which comprises contacting crops, plants, plant propagation materials, such as seeds, or soil or water, in which the plants are growing, to be protected from attack or infestation by animal pests, with a pesticidally effective amount of a compound of the present invention.

The compounds of the present invention are also suitable for use in combating or controlling animal pests. Therefore, the present invention also relates to a method of combating or controlling animal pests, which comprises contacting the animal pests, their habitat, breeding ground, or food supply, or the crops, plants, plant propagation materials, such as seeds, or soil, or the area, material or environment in which the animal pests are growing or may grow, with a pesticidally effective amount of a compound of the present invention.

The compounds of the present invention are effective through both contact and ingestion. Furthermore, the compounds of the present invention can be applied to any and all developmental stages, such as egg, larva, pupa, and adult.

The compounds of the present invention can be applied as such or in form of compositions comprising them as defined above. Furthermore, the compounds of the present invention can be applied together with a mixing partner as defined above or in form of compositions comprising said mixtures as defined above. The components of said mixture can be applied simultaneously, jointly or separately, or in succession, that is immediately one after another and thereby creating the mixture "in situ" on the desired location, e.g. the plant, the sequence, in the case of separate application, generally not having any effect on the result of the control measures.

The application can be carried out both before and after the infestation of the crops, plants, plant propagation materials, such as seeds, soil, or the area, material or environment by the pests.

Suitable application methods include inter alia soil treatment, seed treatment, in furrow application, and foliar application. Soil treatment methods include drenching the soil, drip irrigation (drip application onto the soil), dipping roots, tubers or bulbs, or soil injection. Seed treatment techniques include seed dressing, seed coating, seed dusting, seed soaking, and seed pelleting. In furrow applications typically include the steps of making a furrow in cultivated land, seeding the furrow with seeds, applying the pesticidally active compound to the furrow, and closing the furrow. Foliar application refers to the application of the pesticidally active compound to plant foliage, e.g. through spray equipment. For foliar applications, it can be advantageous to modify the behavior of the pests by use of pheromones in combination with the compounds of the present invention. Suitable pheromones for specific crops and pests are known to a skilled person and publicly available from databases of pheromones and semiochemicals, such as http://www.pherobase.com.

As used herein, the term "contacting" includes both direct contact (applying the compounds/compositions directly on the animal pest or plant—typically to the foliage, stem or roots of the plant) and indirect contact (applying the compounds/compositions to the locus, i.e. habitat, breeding ground, plant, seed, soil, area, material or environment in which a pest is growing or may grow, of the animal pest or plant).

The term "animal pest" includes arthropods, gastropods, and nematodes. Preferred animal pests according to the invention are arthropods, preferably insects and arachnids, in particular insects. Insects, which are of particular relevance for crops, are typically referred to as crop insect pests.

The term "crop" refers to both, growing and harvested crops.

The term "plant" includes cereals, e.g. durum and other wheat, rye, barley, triticale, oats, rice, or maize (fodder maize and sugar maize/sweet and field corn); beet, e.g. sugar beet or fodder beet; fruits, such as pomes, stone fruits or soft fruits, e.g. apples, pears, plums, peaches, nectarines, almonds, cherries, papayas, strawberries, raspberries, blackberries or gooseberries; leguminous plants, such as beans, lentils, peas, alfalfa or soybeans; oil plants, such as rapeseed (oilseed rape), turnip rape, mustard, olives, sunflowers, coconut, cocoa beans, castor oil plants, oil palms, ground nuts or soybeans; cucurbits, such as squashes, pumpkins, cucumber or melons; fiber plants, such as cotton, flax, hemp or jute; citrus fruit, such as oranges, lemons, grapefruits or mandarins; vegetables, such as eggplant, spinach, lettuce (e.g. iceberg lettuce), chicory, cabbage, asparagus, cabbages, carrots, onions, garlic, leeks, tomatoes, potatoes, cucurbits or sweet peppers; lauraceous plants, such as avocados, cinnamon or camphor; energy and raw material plants, such as corn, soybean, rapeseed, sugar cane or oil palm; tobacco; nuts, e.g. walnuts; pistachios; coffee; tea; bananas; vines (table grapes and grape juice grape vines); hop; sweet leaf (also called Stevia); natural rubber plants or ornamental and forestry plants, such as flowers (e.g. carnation, petunias, geranium/pelargoniums, pansies and impatiens), shrubs, broad-leaved trees (e.g. poplar) or evergreens, e.g. conifers; eucalyptus; turf; lawn; grass such as grass for animal feed or ornamental uses. Preferred plants include potatoes sugar beets, tobacco, wheat, rye, barley, oats, rice, corn, cotton, soybeans, rapeseed, legumes, sunflowers, coffee or sugar cane; fruits; vines; ornamentals; or vegetables, such as cucumbers, tomatoes, beans or squashes.

The term "cultivated plants" is to be understood as including plants which have been modified by mutagenesis or genetic engineering in order to provide a new trait to a plant or to modify an already present trait.

Mutagenesis includes techniques of random mutagenesis using X-rays or mutagenic chemicals, but also techniques of targeted mutagenesis, in order to create mutations at a specific locus of a plant genome. Targeted mutagenesis techniques frequently use oligonucleotides or proteins like CRISPR/Cas, zinc-finger nucleases, TALENs or meganucleases to achieve the targeting effect.

Genetic engineering usually uses recombinant DNA techniques to create modifications in a plant genome which under natural circumstances cannot readily be obtained by cross breeding, mutagenesis or natural recombination. Typically, one or more genes are integrated into the genome of a plant in order to add a trait or improve a trait. These integrated genes are also referred to as transgenes in the art, while plant comprising such transgenes are referred to as transgenic plants. The process of plant transformation usually produces several transformation events, which differ in the genomic locus in which a transgene has been integrated. Plants comprising a specific transgene on a specific genomic locus are usually described as comprising a specific "event", which is referred to by a specific event name. Traits which have been introduced in plants or has been modified include in particular herbicide tolerance, insect resistance, increased yield and tolerance to abiotic conditions, like drought.

Herbicide tolerance has been created by using mutagenesis as well as using genetic engineering. Plants which have been rendered tolerant to acetolactate synthase (ALS) inhibitor herbicides by conventional methods of mutagenesis and breeding comprise plant varieties commercially available under the name Clearfield®. However, most of the herbicide tolerance traits have been created via the use of transgenes.

Herbicide tolerance has been created to glyphosate, glufosinate, 2,4-D, dicamba, oxynil herbicides, like bromoxynil and ioxynil, sulfonylurea herbicides, ALS inhibitor herbicides and 4-hydroxyphenylpyruvate dioxygenase (HPPD) inhibitors, like isoxaflutole and mesotrione.

Transgenes which have been used to provide herbicide tolerance traits comprise: for tolerance to glyphosate: cp4 epsps, epsps grg23ace5, mepsps, 2mepsps, gat4601, gat4621 and goxv247, for tolerance to glufosinate: pat and bar, for tolerance to 2,4-D: aad-1 and aad-12, for tolerance to dicamba: dmo, for tolerance to oxynil herbicides: bxn, for tolerance to sulfonylurea herbicides: zm-hra, csr1-2, gm-hra, S4-HrA, for tolerance to ALS inhibitor herbicides: csr1-2, for tolerance to HPPD inhibitor herbicides: hppdPF, W336 and avhppd-03.

Transgenic corn events comprising herbicide tolerance genes are for example, but not excluding others, DAS40278, MON801, MON802, MON809, MON810, MON832, MON87411, MON87419, MON87427, MON88017, MON89034, NK603, GA21, MZHG0JG, HCEM485, VCO-Ø1981-5, 676, 678, 680, 33121, 4114, 59122, 98140, Bt10, Bt176, CBH-351, DBT418, DLL25, MS3, MS6, MZIR098, T25, TC1507 and TC6275.

Transgenic soybean events comprising herbicide tolerance genes are for example, but not excluding others, GTS 40-3-2, MON87705, MON87708, MON87712, MON87769, MON89788, A2704-12, A2704-21, A5547-127, A5547-35, DP356043, DAS44406-6, DAS68416-4, DAS81419-2, GU262, SYHTØH2, W62, W98, FG72 and CV127.

Transgenic cotton events comprising herbicide tolerance genes are for example, but not excluding others, 19-51a, 31707, 42317, 81910, 281-24-236, 3006-210-23, BXN10211, BXN10215, BXN10222, BXN10224, MON1445, MON1698, MON88701, MON88913, GHB119, GHB614, LLCotton25, T303-3 and T304-40.

Transgenic canola events comprising herbicide tolerance genes are for example, but not excluding others, MON88302, HCR-1, HCN10, HCN28, HCN92, MS1, MS8, PHY14, PHY23, PHY35, PHY36, RF1, $RF_2$ and RF3.

Insect resistance has mainly been created by transferring bacterial genes for insecticidal proteins to plants. Transgenes which have most frequently been used are toxin genes of *Bacillus* spec. and synthetic variants thereof, like cry1A, cry1Ab, cry1Ab-Ac, cry1Ac, cry1A.105, cry1F, cry1Fa2, cry2Ab2, cry2Ae, mcry3A, ecry3.1Ab, cry3Bb1, cry34Ab1, cry35Ab1, cry9C, vip3A(a), vip3Aa20. However, also genes of plant origin have been transferred to other plants. In particular genes coding for protease inhibitors, like CpTI and pinII. A further approach uses transgenes in order to produce double stranded RNA in plants to target and downregulate insect genes. An example for such a transgene is dvsnf7.

Transgenic corn events comprising genes for insecticidal proteins or double stranded RNA are for example, but not excluding others, Bt10, Bt11, Bt176, MON801, MON802, MON809, MON810, MON863, MON87411, MON88017, MON89034, 33121, 4114, 5307, 59122, TC1507, TC6275, CBH-351, MIR162, DBT418 and MZIR098.

Transgenic soybean events comprising genes for insecticidal proteins are for example, but not excluding others, MON87701, MON87751 and DAS-81419.

Transgenic cotton events comprising genes for insecticidal proteins are for example, but not excluding others, SGK321, MON531, MON757, MON1076, MON15985, 31707, 31803, 31807, 31808, 42317, BNLA-601, Event1, COT67B, COT102, T303-3, T304-40, GFM Cry1A, GK12, MLS 9124, 281-24-236, 3006-210-23, GHB119 and SGK321.

Increased yield has been created by increasing ear biomass using the transgene athb17, being present in corn event MON87403, or by enhancing photosynthesis using the transgene bbx32, being present in the soybean event MON87712.

Cultivated plants comprising a modified oil content have been created by using the transgenes: gm-fad2-1, Pj.D6D, Nc.Fad3, fad2-1A and fatb1-A. Soybean events comprising at least one of these genes are: 260-05, MON87705 and MON87769.

Tolerance to abiotic conditions, in particular to tolerance to drought, has been created by using the transgene cspB, comprised by the corn event MON87460 and by using the transgene Hahb-4, comprised by soybean event IND-00410-5.

Traits are frequently combined by combining genes in a transformation event or by combining different events during the breeding process. Preferred combination of traits are herbicide tolerance to different groups of herbicides, insect tolerance to different kind of insects, in particular tolerance to lepidopteran and coleopteran insects, herbicide tolerance with one or several types of insect resistance, herbicide tolerance with increased yield as well as a combination of herbicide tolerance and tolerance to abiotic conditions.

Plants comprising singular or stacked traits as well as the genes and events providing these traits are well known in the art. For example, detailed information as to the mutagenized or integrated genes and the respective events are available from websites of the organizations "International Service for the Acquisition of Agrl.biotech Applications (ISAAA)" (http://www.isaaa.org/gmapprovaldatabase) and the "Center for Environmental Risk Assessment (CERA)" (http://cera-gmc.org/GMCropDatabase), Further information on specific events and methods to detect them can be found for canola events MS1, MS8, RF3, GT73, MON88302, KK179 in WO01/031042, WO01/041558, WO01/041558, WO02/036831, WO11/153186, WO13/003558, for cotton events MON1445, MON15985, MON531(MON15985), LLCotton25, MON88913, COT102, 281-24-236, 3006-210-23, COT67B, GHB614, T304-40, GHB119, MON88701, 81910 in WO02/034946, WO02/100163, WO02/100163, WO03/013224, WO04/072235, WO04/039986, WO05/103266, WO05/103266, WO06/128573, WO07/017186, WO08/122406, WO08/151780, WO12/134808, WO13/112527, for corn events GA21, MON810, DLL25, TC1507, MON863, MIR604, LY038, MON88017, 3272, 59122, NK603, MIR162, MON89034, 98140, 32138, MON87460, 5307, 4114, MON87427, DAS40278, MON87411, 33121, MON87403, MON87419 in WO98/044140, U.S. Ser. No. 02/102,582, U.S. Ser. No. 03/126,634, WO04/099447, WO04/011601, WO05/103301, WO05/061720, WO05/059103, WO06/098952, WO06/039376, US2007/292854, WO07/142840, WO07/140256, WO08/112019, WO09/103049, WO09/111263, WO10/077816, WO11/084621, WO11/062904, WO11/022469, WO13/169923, WO14/116854, WO15/053998, WO15/142571, for potato events E12, F10, J3, J55, V11, X17, Y9 in WO14/178910, WO14/178913, WO14/178941, WO14/179276, WO16/183445, WO17/062831, WO17/062825, for rice events LLRICE06, LLRICE601, LLRICE62 in WO00/026345, WO00/026356, WO00/026345 for soybean events H7-1, MON89788, A2704-12, A5547-127, DP305423, DP356043, MON87701, MON87769, CV127, MON87705, DAS68416-4, MON87708, MON87712, SYHT0H2, DAS81419, DAS81419×DAS44406-6, MON87751 in WO04/074492, WO06/130436, WO06/108674, WO06/108675, WO08/054747, WO08/002872, WO09/064652, WO09/102873, WO10/080829, WO10/037016, WO11/066384, WO11/034704, WO12/051199, WO12/082548, WO13/016527, WO13/016516, WO14/201235.

The use of compositions according to the invention on cultivated plants may result in effects which are specific to a cultivated plant comprising a certain gene or event. These effects might involve changes in growth behavior or changed resistance to biotic or abiotic stress factors. Such effects may in particular comprise enhanced yield, enhanced resistance or tolerance to insects, nematodes, fungal, bacterial, mycoplasma, viral or viroid pathogens as well as early vigour, early or delayed ripening, cold or heat tolerance as well as changed amino acid or fatty acid spectrum or content.

It has surprisingly been found that the pesticidal activity of the compounds of the present invention may be enhanced by the insecticidal trait of a modified plant. Furthermore, it has been found that the compounds of the present invention are suitable for preventing insects to become resistant to the insecticidal trait or for combating pests, which already have become resistant to the insecticidal trait of a modified plant. Moreover, the compounds of the present invention are suitable for combating pests, against which the insecticidal trait is not effective, so that a complementary insecticidal activity can advantageously be used.

The term "plant propagation material" refers to all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "seed" embraces seeds and plant propagules of all kinds including but not limited to true seeds, seed pieces, suckers, corms, bulbs, fruit, tubers, grains, cuttings, cut shoots and the like, and means in a preferred embodiment true seeds.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment, in furrow application or of application to the pests dwelling place or nest, the quantity of active ingredient ranges from 0.0001 to 500 g per 100 m$^2$, preferably from 0.001 to 20 g per 100 m$^2$.

For use in treating crop plants, e.g. by foliar application, the rate of application of the active ingredients of this invention may be in the range of 0.0001 g to 4000 g per hectare, e.g. from 1 g to 2 kg per hectare or from 1 g to 750 g per hectare, desirably from 1 g to 100 g per hectare, more desirably from 10 g to 50 g per hectare, e.g., 10 to 20 g per hectare, 20 to 30 g per hectare, 30 to 40 g per hectare, or 40 to 50 g per hectare.

The compounds of the invention are particularly suitable for use in the treatment of seeds in order to protect the seeds from insect pests, in particular from soil-living insect pests, and the resulting seedling's roots and shoots against soil pests and foliar insects. The invention therefore also relates to a method for the protection of seeds from insects, in particular from soil insects, and of the seedling's roots and shoots from insects, in particular from soil and foliar insects, said method comprising treating the seeds before sowing and/or after pregermination with a compound of the invention. The protection of the seedling's roots and shoots is preferred. More preferred is the protection of seedling's shoots from piercing and sucking insects, chewing insects and nematodes.

The term "seed treatment" comprises all suitable seed treatment techniques known in the art, such as seed dressing, seed coating, seed dusting, seed soaking, seed pelleting, and in-furrow application methods. Preferably, the seed treatment application of the active compound is carried out by spraying or by dusting the seeds before sowing of the plants and before emergence of the plants.

The invention also comprises seeds coated with or containing the active compound. The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is for example seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the active compound may also be used for the treatment of seeds from plants, which have been modified by mutagenesis or genetic engineering, and which e.g. tolerate the action of herbicides or fungicides or insecticides. Such modified plants have been described in detail above.

Conventional seed treatment formulations include for example flowable concentrates FS, solutions LS, suspoemulsions (SE), powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter. Preferably, the formulations are applied such that germination is not included.

The active substance concentrations in ready-to-use formulations, which may be obtained after two-to-tenfold dilution, are preferably from 0.01 to 60% by weight, more preferably from 0.1 to 40% by weight.

In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of the compounds of the invention for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an antifreeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

In the treatment of seed, the application rates of the compounds of the invention are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed, e.g. from 1 g to 100 g or from 5 g to 100 g per 100 kg of seed.

The invention therefore also relates to seed comprising a compound of the invention, or an agriculturally useful salt thereof, as defined herein. The amount of the compound of the invention or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

The compounds of the invention may also be used for improving the health of a plant. Therefore, the invention also relates to a method for improving plant health by treating a plant, plant propagation material and/or the locus where the plant is growing or is to grow with an effective and non-phytotoxic amount of a compound of the invention.

As used herein "an effective and non-phytotoxic amount" means that the compound is used in a quantity which allows to obtain the desired effect but which does not give rise to any phytotoxic symptom on the treated plant or on the plant grown from the treated propagule or treated soil.

The terms "plant" and "plant propagation material" are defined above.

"Plant health" is defined as a condition of the plant and/or its products which is determined by several aspects alone or in combination with each other such as yield (for example increased biomass and/or increased content of valuable ingredients), quality (for example improved content or composition of certain ingredients or shelf life), plant vigour (for example improved plant growth and/or greener leaves ("greening effect"), tolerance to abiotic (for example drought) and/or biotic stress (for example disease) and production efficiency (for example, harvesting efficiency, processability).

The above identified indicators for the health condition of a plant may be interdependent and may result from each other. Each indicator is defined in the art and can be determined by methods known to a skilled person.

The compounds of the invention are also suitable for use against non-crop insect pests. For use against said non-crop pests, compounds of the invention can be used as bait composition, gel, general insect spray, aerosol, as ultra-low volume application and bed net (impregnated or surface applied). Furthermore, drenching and rodding methods can be used.

As used herein, the term "non-crop insect pest" refers to pests, which are particularly relevant for non-crop targets, such as ants, termites, wasps, flies, ticks, mosquitos, crickets, or cockroaches.

The bait can be a liquid, a solid or a semisolid preparation (e.g. a gel). The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature (e.g. http://www.pherobase.com), and are known to those skilled in the art.

For use in bait compositions, the typical content of active ingredient is from 0.001 weight % to 15 weight %, desirably from 0.001 weight % to 5% weight % of active compound.

Formulations of the compounds of the invention as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents, furthermore auxiliaries such as emulsifiers, perfume oils, if appropriate stabilizers, and, if required, propellants.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of the invention and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of the invention and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder.

The compounds of the invention and its compositions can be used for protecting wooden materials such as trees, board fences, sleepers, frames, artistic artifacts, etc. and buildings, but also construction materials, furniture, leathers, fibers, vinyl articles, electric wires and cables etc. from ants and/or termites, and for controlling ants and termites from doing harm to crops or human being (e.g. when the pests invade into houses and public facilities).

Customary application rates in the protection of materials are, for example, from 0.001 g to 2000 g or from 0.01 g to 1000 g of active compound per $m^2$ treated material, desirably from 0.1 g to 50 g per $m^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

Pests

The compounds of the invention are especially suitable for efficiently combating animal pests such as arthropods, gastropods and nematodes including but not limited to:

insects from the order of Lepidoptera, for example *Achroia grisella, Acleris* spp. such as *A. fimbriana, A. gloverana, A. variana; Acrolepiopsis assectella, Acronicta major, Adoxophyes* spp. such as *A. cyrtosema, A. orana; Aedia leucomelas, Agrotis* spp. such as *A. exclamationis, A. fucosa, A. ipsilon, A. orthogoma, A. segetum, A. subterranea; Alabama argillacea, Aleurodicus dispersus, Alsophila pometaria, Ampelophaga rubiginosa, Amyelois transitella, Anacampsis sarcitella, Anagasta kuehniella, Anarsia lineatella, Anisota senatoria, Antheraea pernyi, Anticarsia* (=Thermesia) spp. such as *A. gemmatalis; Apamea* spp., *Aproaerema modicella, Archips* spp. such as *A. argyrospila, A. fuscocupreanus, A. rosana, A. xyloseanus; Argyresthia conjugella, Argyroploce* spp., *Argyrotaenia* spp. such as *A. velutinana; Athetis mindara, Austroasca viridigrisea, Autographa gamma, Autographa nigrisigna, Barathra brassicae, Bedellia* spp., *Bonagota salubricola, Borbo cinnara, Bucculatrix thurberiella, Bupalus piniarius, Busseola* spp., *Cacoecia* spp. such as *C. murinana, C. podana; Cactoblastis cactorum, Cadra cautella, Calingo braziliensis, Caloptilis theivora, Capua reticulana, Carposina* spp. such as *C. niponensis, C. sasakii; Cephus* spp., *Chaetocnema aridula, Cheimatobia brumata, Chilo* spp. such as *C. indicus, C. suppressalis, C. partellus; Choreutis pariana, Choristoneura* spp. such as *C. conflictana, C. fumiferana, C. longicellana, C. murinana, C. occidentalis, C. rosaceana; Chrysodeixis* (=Pseudoplusia) spp. such as *C. eriosoma, C. includens; Cirphis unipuncta, Clysia ambiguella, Cnaphalocerus* spp., *Cnaphalocrocis medinalis, Cnephasia* spp., *Cochylis hospes, Coleophora* spp., *Colias eurytheme, Conopomorpha* spp., *Conotrachelus* spp., *Copitarsia* spp., *Corcyra cephalonica, Crambus caliginosellus, Crambus teterrellus, Crocidosema* (=Epinotia) *aporema, Cydalima* (=Diaphania) *perspectalis, Cydia* (=Carpocapsa) spp. such as *C. pomonella, C. latiferreana; Dalaca noctuides, Datana integerrima, Dasychira pinicola, Dendrolimus* spp. such as *D. pini, D. spectabilis, D. sibiricus; Desmia funeralis, Diaphania* spp. such as *D. nitidalis, D. hyalinata; Diatraea grandiosella, Diatraea saccharalis, Diphthera festiva, Earias* spp. such as *E. insulana, E. vittella; Ecdytolopha aurantianu, Egira* (=Xylomyges) *curialis, Elasmopalpus lignosellus, Eldana saccharina, Endopiza viteana, Ennomos subsignaria, Eoreuma loftini, Ephestia* spp. such as *E. cautella, E. elutella, E. kuehniella; Epinotia aporema, Epiphyas postvittana, Erannis tiliaria, Erionota thrax, Etiella* spp., *Eulia* spp., *Eupoecilia ambiguella, Euproctis chrysorrhoea, Euxoa* spp., *Evetria bouliana, Faronta albilinea, Feltia* spp. such as *F. subterranean; Galleria mellonella, Gracillaria* spp., *Grapholita* spp. such as *G. funebrana, G. molesta, G. inopinata; Halysidota* spp., *Harrisina americana, Hedylepta* spp., *Helicoverpa* spp. such as *H. armigera* (=Heliothis armigera), H. zea (=Heliothis zea); Heliothis spp. such as H. assulta, H. subflexa, H. virescens; Hellula spp. such as H. undalis, H. rogatalis; Helocoverpa gelotopoeon, Hemileuca oliviae, Herpetogramma licarsisalis, Hibernia defoliaria, Hofmannophila pseudospretella, Homoeosoma electellum, Homona magnanima, Hypena scabra, Hyphantria cunea, Hyponomeuta padella, Hyponomeuta malinellus, Kakivoria flavofasciata, Keiferia lycopersicella, Lambdina fiscellaria fiscellaria, Lambdina fiscellaria lugubrosa, Lamprosema indicata, Laspeyresia molesta, Leguminivora glycinivorella, Lerodea eufala, Leucinodes orbonalis, Leucoma salicis, Leucoptera spp. such as L. coffeella, L. scitella; Leuminivora lycinivorella, Lithocolletis blancardella, Lithophane antennata, Llattia octo (=Amyna axis), Lobesia botrana, Lophocampa spp., Loxagrotis albicosta, Loxostege spp. such as L. sticticalis, L. cereralis; Lymantria spp. such as L. dispar, L. monacha; Lyonetia clerkella, Lyonetia prunifoliella, Malacosoma spp. such as M. americanum, M. californicum, M. constrictum, M. neustria; Mamestra spp. such as M. brassicae, M. configurata; Mamstra brassicae, Manduca spp. such as M. quinquemaculata, M. sexta; Marasmia spp, Marmara spp., Maruca testulalis, Megalopyge lanata, Melanchra picta, Melanitis leda, Mocis spp. such as M. lapites, M. repanda; Mocis latipes, Monochroa fragariae, Mythimna separata, Nemapogon cloacella, Neoleucinodes elegantalis, Nepytia spp., Nymphula spp., Oiketicus spp., Omiodes indicata, Omphisa anastomosalis, Operophtera brumata, Orgyia pseudotsugata, Oria spp., Orthaga thyrisalis, Ostrinia spp. such as O. nubilalis, Oulema oryzae, Paleacrita vernata, Panolis flammea, Parnara spp., Papaipema nebris, Papilio cresphontes, Paramyelois transitella, Paranthrene regalis, Paysandisia archon, Pectinophora spp. such as P. gossypiella; Peridroma saucia, Perileucoptera spp., such as P. coffeella; Phalera bucephala, Phryganidia californica, Phthorimaea spp. such as P. operculella; Phyllocnistis citrella, Phyllonorycter spp. such as P. blancardella, P. crataegella, P. issikii, P. ringoniella; Pieris spp. such as P. brassicae, P. rapae, P. napi; Pilocrocis tripunctata, Plathypena scabra, Platynota spp. such as P. flavedana, P. idaeusalis, P. stultana; Platyptilia carduidactyla, Plebejus argus, Plodia interpunctella, Plusia spp, Plutella maculipennis, Plutella xylostella, Pontia protodica, Prays spp., Prodenia spp., Proxenus lepigone, Pseudaletia spp. such as P. sequax, P. unipuncta; Pyrausta nubilalis, Rachiplusia nu, Richia albicosta, Rhizobius ventralis, Rhyacionia frustrana, Sabulodes aegrotata, Schizura concinna, Schoenobius spp., Schreckensteinia festaliella, Scirpophaga spp. such as S. incertulas, S. innotata; Scotia segetum, Sesamia spp. such as S. inferens, Seudyra subflava, Sitotroga cerealella, Sparganothis pilleriana, Spilonota lechriaspis, S. ocellana, Spodoptera (=Lamphygma) spp. such as S. cosmoides, S. eridania, S. exigua, S. frugiperda, S. latisfascia, S. littoralis, S. litura, S. omithogalli; Stigmella spp., Stomopteryx subsecivella, Strymon bazochii, Sylepta derogata, Synanthedon spp. such as S. exitiosa, Tecia solanivora, Telehin licus, Thaumatopoea pityocampa, Thaumatotibia (=Cryptophlebia) leucotreta, Thaumetopoea pityocampa, Thecla spp., Theresimima ampelophaga, Thyrinteina spp, Tildenia inconspicuella, Tinea spp. such as T. cloacella, T. pellionella; Tineola bisselliella, Tortrix spp. such as T. viridana; Trichophaga tapetzella, Trichoplusia spp. such as T. ni; Tuta (=Scrobipalpula) absoluta, Udea spp. such as U. rubigalis, U. rubigalis; Virachola spp., Yponomeuta padella, and Zeiraphera canadensis;

insects from the order of Coleoptera, for example Acalymma vittatum, Acanthoscehdes obtectus, Adoretus spp., Agelastica alni, Agrilus spp. such as A. anxius, A. planipennis, A. sinuatus; Agriotes spp. such as A. fuscicollis, A. lineatus, A. obscurus; Alphitobius diaperinus, Amphimallus solstitialis, Anisandrus dispar, Anisoplia austriaca, Anobium punctatum, Anomala corpulenta, Anomala rufocuprea, Anoplophora spp. such as A. glabripennis; Anthonomus spp. such as A. eugenii, A. grandis, A. pomorum; Anthrenus spp., Aphthona euphoridae, Apion spp., Apogonia spp., Athous haemorrhoidalis, Atomaria spp. such as A. linearis; Attagenus spp., Aulacophora femoralis, Blastophagus piniperda, Blitophaga undata, Bruchidius obtectus, Bruchus spp. such as B. lentis, B. pisorum, B. rufimanus; Byctiscus betulae, Callidiellum rufipenne, Callopistria floridensis, Callosobruchus chinensis, Cameraria ohridella, Cassida nebulosa, Cerotoma trifurcata, Cetonia aurata, Ceuthorhynchus spp. such as C. assimilis, C. napi; Chaetocnema tibialis, Cleonus mendicus, Conoderus spp. such as C. vespertinus; Conotrachelus nenuphar, Cosmopolites spp., Costelytra zealandica, Crioceris asparagi, Cryptolestes ferrugineus, Cryptorhynchus lapathi, Ctenicera spp. such as C. destructor; Curculio spp., Cylindrocopturus spp., Cyclocephala spp., Dactylispa balyi, Dectes texanus, Dermestes spp., Diabrotica spp. such as D. undecimpunctata, D. speciosa, D. longicornis, D. semipunctata, D. virgifera; Diaprepes abbreviates, Dichocrocis spp., Dicladispa armigera, Diloboderus abderus, Diocalandra frumenti (Diocalandra stigmaticollis), Enaphalodes rufulus, Epilachna spp. such as E. varivestis, E. vigintioctomaculata; Epitrix spp. such as E. hirtipennis, E. similaris; Eutheola humilis, Eutinobothrus brasiliensis, Faustinus cubae, Gibbium psylloides, Gnathocerus cornutus, Hellula undalis, Heteronychus arator, Hylamorpha elegans, Hylobius abietis, Hylotrupes bajulus, Hypera spp. such as H. brunneipennis, H. postica; Hypomeces squamosus, Hypothenemus spp., Ips typographus, Lachnosterna consanguinea, Lasioderma serricorne, Latheticus oryzae, Lathridius spp., Lema spp. such as L. bilineata, L. melanopus; Leptinotarsa spp. such as L. decemlineata; Leptispa pygmaea, Limonius californicus, Lissorhoptrus oryzophilus, Lixus spp., Luperodes spp., Lyctus spp. such as L. bruneus; Liogenys fuscus, Macrodactylus spp. such as M. subspinosus; Maladera matrida, Megaplatypus mutates, Megascelis spp., Melanotus communis, Meligethes spp. such as M. aeneus; Melolontha spp. such as M. hippocastani, M. melolontha; Metamasius hemipterus, Microtheca spp., Migdolus spp. such as M. fryanus, Monochamus spp. such as M. alternatus; Naupactus xanthographus, Niptus hololeucus, Oberia brevis, Oemona hirta, Oryctes rhinoceros, Oryzaephilus surinamensis, Oryzaphagus oryzae, Otiorrhynchus sulcatus, Otiorrhynchus ovatus, Otiorrhynchus sulcatus, Oulema melanopus, Oulema oryzae, Oxycetonia jucunda, Phaedon spp. such as P. brassicae, P. cochleariae; Phoracantha recurva, Phyllobius pyri, Phyllopertha horticola, Phyllophaga spp. such as P. helleri; Phyllotreta spp. such as P. chrysocephala, P. nemorum, P. striolata, P. vittula; Phyllopertha horticola, Popillia japonica, Premnotrypes spp., Psacothea hilaris, Psylliodes chrysocephala, Pros-

*tephanus truncates*, *Psylliodes* spp., *Ptinus* spp., *Pulga saltona*, *Rhizopertha dominica*, *Rhynchophorus* spp. such as *R. billineatus*, *R. ferrugineus*, *R. palmarum*, *R. phoenicis*, *R. vulneratus*; *Saperda candida*, *Scolytus schevyrewi*, *Scyphophorus acupunctatus*, *Sitona lineatus*, *Sitophilus* spp. such as *S. granaria*, *S. oryzae*, *S. zeamais*; *Sphenophorus* spp. such as *S. levis*; *Stegobium paniceum*, *Sternechus* spp. such as *S. subsignatus*; *Strophomorphus ctenotus*, *Symphyletes* spp., *Tanymecus* spp., *Tenebrio molitor*, *Tenebrioides mauretanicus*, *Tribolium* spp. such as *T. castaneum*; *Trogoderma* spp., *Tychius* spp., *Xylotrechus* spp. such as *X. pyrrhoderus*; and, *Zabrus* spp. such as *Z. tenebrioides*;

insects from the order of Diptera e.g. *Aedes* spp. such as *A. aegypti*, *A. albopictus*, *A. vexans*; *Anastrepha ludens*, *Anopheles* spp. such as *A. albimanus*, *A. crucians*, *A. freeborni*, *A. gambiae*, *A. leucosphyrus*, *A. maculipennis*, *A. minimus*, *A. quadrimaculatus*, *A. sinensis*; *Bactrocera invadens*, *Bibio hortulanus*, *Calliphora erythrocephala*, *Calliphora vicina*, *Ceratitis capitata*, *Chrysomyia* spp. such as *C. bezziana*, *C. hominivorax*, *C. macellaria*; *Chrysops atlanticus*, *Chrysops discalis*, *Chrysops silacea*, *Cochliomyia* spp. such as *C. hominivorax*; *Contarinia* spp. such as *C. sorghicola*; *Cordylobia anthropophaga*, *Culex* spp. such as *C. nigripalpus*, *C. pipiens*, *C. quinquefasciatus*, *C. tarsalis*, *C. tritaeniorhynchus*; *Culicoides furens*, *Culiseta inornata*, *Culiseta melanura*, *Cuterebra* spp., *Dacus cucurbitae*, *Dacus oleae*, *Dasineura brassicae*, *Dasineura oxycoccana*, *Delia* spp. such as *D. antique*, *D. coarctata*, *D. platura*, *D. radicum*; *Dermatobia hominis*, *Drosophila* spp. such as *D. suzukii*, *Fannia* spp. such as *F. canicularis*; *Gastraphilus* spp. such as *G. intestinalis*; *Geomyza tipunctata*, *Glossina* spp. such as *G. fuscipes*, *G. morsitans*, *G. palpalis*, *G. tachinoides*; *Haematobia irritans*, *Haplodiplosis equestris*, *Hippelates* spp., *Hylemyia* spp. such as *H. platura*; *Hypoderma* spp. such as *H. lineata*; *Hyppobosca* spp., *Hydrellia philippina*, *Leptoconops torrens*, *Liriomyza* spp. such as *L. sativae*, *L. trifolii*; *Lucilia* spp. such as *L. caprina*, *L. cuprina*, *L. sericata*; *Lycoria pectoralis*, *Mansonia titillanus*, *Mayetiola* spp. such as *M. destructor*; *Musca* spp. such as *M. autumnalis*, *M. domestica*; *Muscina stabulans*, *Oestrus* spp. such as *O. ovis*; *Opomyza* forum, *Oscinella* spp. such as *O. frit*; *Orseolia oryzae*, *Pegomya hysocyami*, *Phlebotomus argentipes*, *Phorbia* spp. such as *P. antiqua*, *P. brassicae*, *P. coarctata*; *Phytomyza gymnostoma*, *Prosimulium mixtum*, *Psila rosae*, *Psorophora columbiae*, *Psorophora discolor*, *Rhagoletis* spp. such as *R. cerasi*, *R. cingulate*, *R. indifferens*, *R. mendax*, *R. pomonella*; *Rivellia quadrifasciata*, *Sarcophaga* spp. such as *S. haemorrhoidalis*; *Simulium vittatum*, *Sitodiplosis mosellana*, *Stomoxys* spp. such as *S. calcitrans*; *Tabanus* spp. such as *T. atratus*, *T. bovinus*, *T. lineola*, *T. similis*; *Tannia* spp., *Thecodiplosis japonensis*, *Tipula oleracea*, *Tipula paludosa*, and *Wohlfahrtia* spp;

insects from the order of Thysanoptera for example, *Baliothrips biformis*, *Dichromothrips corbetti*, *Dichromothrips* ssp., *Echinothrips americanus*, *Enneothrips flavens*, *Frankliniella* spp. such as *F. fusca*, *F. occidentalis*, *F. tritici*; *Heliothrips* spp., *Hercinothrips femoralis*, *Kakothrips* spp., *Microcephalothrips abdominalis*, *Neohydatothrips samayunkur*, *Pezothrips kellyanus*, *Rhipiphorothrips cruentatus*, *Scirtothrips* spp. such as *S. citri*, *S. dorsalis*, *S. perseae*; *Stenchaetothrips* spp, *Taeniothrips cardamoni*, *Taeniothrips inconsequens*, *Thrips* spp. such as *T. imagines*, *T. hawaiiensis*, *T. oryzae*, *T. palmi*, *T. parvispinus*, *T. tabaci*;

insects from the order of Hemiptera for example, *Acizzia jamatonica*, *Acrosternum* spp. such as *A. hilare*; *Acyrthosipon* spp. such as *A. onobrychis*, *A. pisum*; *Adelges laricis*, *Adelges tsugae*, *Adelphocoris* spp., such as *A. rapidus*, *A. superbus*; *Aeneolamia* spp., *Agonoscena* spp., *Aulacorthum solani*, *Aleurocanthus woglumi*, *Aleurodes* spp., *Aleurodicus disperses*, *Aleurolobus barodensis*, *Aleurothrixus* spp., *Amrasca* spp., *Anasa tristis*, *Antestiopsis* spp., *Anuraphis cardui*, *Aonidiella* spp., *Aphanostigma piri*, *Aphidula nasturtii*, *Aphis* spp. such as *A. craccivora*, *A. fabae*, *A. forbesi*, *A. gossypii*, *A. grossulariae*, *A. maidiradicis*, *A. pomi*, *A. sambuci*, *A. schneideri*, *A. spiraecola*; *Arboridia apicalis*, *Arilus critatus*, *Aspidiella* spp., *Aspidiotus* spp., *Atanus* spp., *Aulacaspis yasumatsui*, *Aulacorthum solani*, *Bactericera cockerelli* (*Paratrioza cockerelli*), *Bemisia* spp. such as *B. argentifolii*, *B. tabaci* (*Aleurodes tabaci*); *Blissus* spp. such as *B. leucopterus*; *Brachycaudus* spp. such as *B. cardui*, *B. helichrysi*, *B. persicae*, *B. prunicola*; *Brachycolus* spp., *Brachycorynella asparagi*, *Brevicoryne brassicae*, *Cacopsylla* spp. such as *C. fulguralis*, *C. pyricola* (*Psylla piri*); *Calligypona marginata*, *Calocoris* spp., *Campylomma livida*, *Capitophorus horni*, *Carneocephala fulgida*, *Cavelerius* spp., *Ceraplastes* spp., *Ceratovacuna lanigera*, *Ceroplastes ceriferus*, *Cerosipha gossypii*, *Chaetosiphon fragaefolii*, *Chionaspis tegalensis*, *Chlorita onukii*, *Chromaphis juglandicola*, *Chrysomphalus ficus*, *Cicadulina mbila*, *Cimex* spp. such as *C. hemipterus*, *C. lectularius*; *Coccomytilus halli*, *Coccus* spp. such as *C. hesperidum*, *C. pseudomagnoliarum*; *Corythucha arcuata*, *Creontiades dilutus*, *Cryptomyzus ribis*, *Chrysomphalus aonidum*, *Cryptomyzus ribis*, *Ctenarytaina spatulata*, *Cyrtopeltis notatus*, *Dalbulus* spp., *Dasynus piperis*, *Dialeurodes* spp. such as *D. citrifolii*; *Dalbulus maidis*, *Diaphorina* spp. such as *D. citri*; *Diaspis* spp. such as *D. bromeliae*; *Dichelops furcatus*, *Diconocoris hewetti*, *Doralis* spp., *Dreyfusia nordmannianae*, *Dreyfusia piceae*, *Drosicha* spp., *Dysaphis* spp. such as *D. plantaginea*, *D. pyri*, *D. radicola*; *Dysaulacorthum pseudosolani*, *Dysdercus* spp. such as *D. cingulatus*, *D. intermedius*; *Dysmicoccus* spp., *Edessa* spp., *Geocoris* spp., *Empoasca* spp. such as *E. fabae*, *E. solana*; *Epidiaspis leperii*, *Eriosoma* spp. such as *E. lanigerum*, *E. pyricola*; *Erythroneura* spp., *Eurygaster* spp. such as *E. integriceps*; *Euscelis bilobatus*, *Euschistus* spp. such as *E. heros*, *E. impictiventris*, *E. servus*; *Fiorinia theae*, *Geococcus coffeae*, *Glycaspis brimblecombei*, *Halyomorpha* spp. such as *H. halys*; *Heliopeltis* spp., *Homalodisca vitripennis* (=*H. coagulata*), *Horcias nobilellus*, *Hyalopterus pruni*, *Hyperomyzus lactucae*, *Icerya* spp. such as *I. purchase*; *Idiocerus* spp., *Idioscopus* spp., *Laodelphax striatellus*, *Lecanium* spp., *Lecanoideus floccissimus*, *Lepidosaphes* spp. such as *L. ulmi*; *Leptocorisa* spp., *Leptoglossus phyllopus*, *Lipaphis erysimi*, *Lygus* spp. such as *L. hesperus*, *L. lineolaris*, *L. pratensis*; *Maconellicoccus hirsutus*, *Marchalina hellenica*, *Macropes excavatus*, *Macrosiphum* spp. such as *M. rosae*, *M. avenae*, *M. euphorbiae*; *Macrosteles quadrilineatus*, *Mahanarva fimbriolata*, *Megacopta cribraria*, *Megoura viciae*, *Melanaphis pyrarius*, *Melanaphis sacchari*, *Melanocallis* (=*Tinocallis*) *caryaefoliae*, *Metcafiella* spp., *Metopolophium dirhodum*, *Monellia costalis*, *Monelliopsis pecanis*, *Myzocallis coryli*, *Mur-* gantia spp., *Myzus* spp. such as *M. ascalonicus, M. cerasi, M. nicotianae, M. persicae, M. varians; Nasonovia ribis-nigri, Neotoxoptera formosana, Neomegalotomus* spp, *Nephotettix* spp. such as *N. malayanus, N. nigropictus, N. parvus, N. virescens; Nezara* spp. such as *N. viridula; Nilaparvata lugens, Nysius huttoni, Oebalus* spp. such as *O. pugnax; Oncometopia* spp., *Orthezia prae longa, Oxycaraenus hyalinipennis, Parabemisia myricae, Parlatoria* spp., *Parthenolecanium* spp. such as *P. corni, P. persicae; Pemphigus* spp. such as *P. bursarius, P. populivenae; Peregrinus maidis, Perkinsiella saccharicida, Phenacoccus* spp. such as *P. aceris, P. gossypii; Phloeomyzus passerinii, Phorodon humuli, Phylloxera* spp. such as *P. devastatrix, Piesma quadrata, Piezodorus* spp. such as *P. guildinii; Pinnaspis aspidistrae, Planococcus* spp. such as *P. citri, P. ficus; Prosapia bicincta, Protopulvinaria pyriformis, Psallus seriatus, Pseudacysta persea, Pseudaulacaspis pentagona, Pseudococcus* spp. such as *P. comstocki; Psylla* spp. such as *P. mali; Pteromalus* spp., *Pulvinaria amygdali, Pyrilla* spp., *Quadraspidiotus* spp., such as *Q. perniciosus; Quesada gigas, Rastrococcus* spp., *Reduvius senilis, Rhizoecus americanus, Rhodnius* spp., *Rhopalomyzus ascalonicus, Rhopalosiphum* spp. such as *R. pseudobrassicas, R. insertum, R. maidis, R. padi; Sagatodes* spp., *Sahlbergella singularis, Saissetia* spp., *Sappaphis mala, Sappaphis mali, Scaptocoris* spp., *Scaphoides titanus, Schizaphis graminum, Schizoneura lanuginosa, Scotinophora* spp., *Selenaspidus articulatus, Sitobion avenae, Sogata* spp., *Sogatella furcifera, Solubea insularis, Spissistilus festinus* (=*Stictocephala festina*), *Stephanitis nashi, Stephanitis pyrioides, Stephanitis takeyai, Tenalaphara malayensis, Tetraleurodes perseae, Therioaphis maculate, Thyanta* spp. such as *T. accerra, T. perditor; Tibraca* spp., *Tomaspis* spp., *Toxoptera* spp. such as *T. aurantii; Trialeurodes* spp. such as *T. abutilonea, T. ricini, T. vaporariorum; Triatoma* spp., *Trioza* spp., *Typhlocyba* spp., *Unaspis* spp. such as *U. citri, U. yanonensis;* and *Viteus vitifolii,* Insects from the order Hymenoptera for example *Acanthomyops interjectus, Athalia rosae, Atta* spp. such as *A. capiguara, A. cephalotes, A. cephalotes, A. laevigata, A. robusta, A. sexdens, A. texana, Bombus* spp., *Brachymyrmex* spp., *Camponotus* spp. such as *C. floridanus, C. pennsylvanicus, C. modoc; Cardiocondyla nuda, Chalibion* sp, *Crematogaster* spp., *Dasymutilla occidentalis, Diprion* spp., *Dolichovespula maculata, Dorymyrmex* spp., *Dryocosmus kuriphilus, Formica* spp., *Hoplocampa* spp. such as *H. minuta, H. testudinea; Iridomyrmex humilis, Lasius* spp. such as *L. niger, Linepithema humile, Liometopum* spp., *Leptocybe invasa, Monomorium* spp. such as *M. pharaonis, Monomorium, Nylandria fulva, Pachycondyla chinensis, Paratrechina longicornis, Paravespula* spp., such as *P. germanica, P. pennsylvanica, P. vulgaris; Pheidole* spp. such as *P. megacephala; Pogonomyrmex* spp. such as *P. barbatus, P. californicus, Polistes rubiginosa, Prenolepis impairs, Pseudomyrmex gracilis, Schelipron* spp., *Sirex cyaneus, Solenopsis* spp. such as *S. geminata, S.invicta, S. molesta, S. richteri, S. xyloni, Sphecius speciosus, Sphex* spp., *Tapinoma* spp. such as *T. melanocephalum, T. sessile; Tetramorium* spp. such as *T. caespitum, T. bicarinatum, Vespa* spp. such as *V. crabro; Vespula* spp. such as *V. squamosal; Wasmannia auropunctata, Xylocopa* sp;

Insects from the order Orthoptera for example *Acheta domesticus, Calliptamus italicus, Chortoicetes terminifera, Ceuthophilus* spp., *Diastrammena asynamora, Dociostaurus maroc canus, Gryllotalpa* spp. such as *G. africana, G. gryllotalpa; Gryllus* spp., *Hieroglyphus daganensis, Kraussaria angulifera, Locusta* spp. such as *L. migratoria, L. pardalina; Melanoplus* spp. such as *M. bivittatus, M. femurrubrum, M. mexicanus, M. sanguinipes, M. spretus; Nomadacris septemfasciata, Oedaleus senegalensis, Scapteriscus* spp., *Schistocerca* spp. such as *S. americana, S. gregaria, Stemopelmatus* spp., *Tachycines asynamorus,* and *Zonozerus variegatus;*

Pests from the Class Arachnida for example *Acari,* e.g. of the families Argasidae, Ixodidae and Sarcoptidae, such as *Amblyomma* spp. (e.g. *A. americanum, A. variegatum, A. maculatum*), *Argas* spp. such as *A. persicu*), *Boophilus* spp. such as *B. annulatus, B. decoloratus, B. microplus, Dermacentor* spp. such as *D. silvarum, D. andersoni, D. variabilis, Hyalomma* spp. such as *H. truncatum, Ixodes* spp. such as *I. ricinus, I. rubicundus, I. scapularis, I. holocyclus, I. pacificus, Rhipicephalus sanguineus, Ornithodorus* spp. such as *O. moubata, O. hermsi, O. turicata, Ornithonyssus bacoti, Otobius megnini, Dermanyssus gallinae, Psoroptes* spp. such as *P. ovis, Rhipicephalus* spp. such as *R. sanguineus, R. appendiculatus, Rhipicephalus evertsi, Rhizoglyphus* spp., *Sarcoptes* spp. such as *S. scabiei;* and Family Eriophyidae including *Aceria* spp. such as *A. sheldoni, A. anthocoptes, Acallitus* spp., *Aculops* spp. such as *A. lycopersici, A. pelekassi; Aculus* spp. such as *A. schlechtendali; Colomerus vitis, Epitrimerus pyri, Phyllocoptruta oleivora; Eriophytes ribis* and *Eriophyes* spp. such as *Eriophyes sheldoni;* Family Tarsonemidae including *Hemitarsonemus* spp., *Phytonemus pallidus* and *Polyphagotarsonemus latus, Stenotarsonemus* spp. *Steneotarsonemus spinki;* Family Tenuipalpidae including *Brevipalpus* spp. such as *B. phoenicis;* Family Tetranychidae including *Eotetranychus* spp., *Eutetranychus* spp., *Oligonychus* spp., *Petrobia latens, Tetranychus* spp. such as *T. cinnabarinus, T. evansi, T. kanzawai, T, pacificus, T. phaseulus, T. telarius* and *T. urticae; Bryobia praetiosa; Panonychus* spp. such as *P. ulmi, P. citri; Metatetranychus* spp. and *Oligonychus* spp. such as *O. pratensis, O. perseae, Vasates lycopersici; Raoiella indica,* Family Carpoglyphidae including *Carpoglyphus* spp.; Penthaleidae spp. such as *Halotydeus destructor;* Family Demodicidae with species such as *Demodex* spp.; Family Trombicidea including *Trombicula* spp.; Family Macronyssidae including *Ornothonyssus* spp.; Family Pyemotidae including *Pyemotes tritici; Tyrophagus putrescentiae;* Family Acaridae including *Acarus siro;* Family Araneida including *Latrodectus mactans, Tegenaria agrestis, Chiracanthium* sp, *Lycosa* sp *Achaearanea tepidariorum* and *Loxosceles reclusa;*

Pests from the Phylum Nematoda, for example, plant parasitic nematodes such as root-knot nematodes, *Meloidogyne* spp. such as *M. hapla, M. incognita, M. javanica;* cyst-forming nematodes, *Globodera* spp. such as *G. rostochiensis; Heterodera* spp. such as *H. avenae, H. glycines, H. schachtii, H. trifolii;* Seed gall nematodes, *Anguina* spp.; Stem and foliar nematodes, *Aphelenchoides* spp. such as *A. besseyi;* Sting nematodes, *Belonolaimus* spp. such as *B. longicaudatus;* Pine nematodes, *Bursaphelenchus* spp. such as *B. lignicolus, B. xylophilus;* Ring nematodes, *Criconema* spp., *Criconemella* spp. such as *C. xenoplax* and *C. ornata*; and, *Criconemoides* spp. such as *Criconemoides informis; Mesocriconema* spp.; Stem and bulb nematodes, *Ditylenchus* spp. such as *D. destructor, D. dipsaci*; Awl nematodes, *Dolichodorus* spp.; Spiral nematodes, *Heliocotylenchus multicinctus*; Sheath and sheathoid nematodes, *Hemicycliophora* spp. and *Hemicriconemoides* spp.; *Hirshmanniella* spp.; Lance nematodes, *Hoploaimus* spp.; False root-knot nematodes, *Nacobbus* spp.; Needle nematodes, *Longidorus* spp. such as *L. elongatus*; Lesion nematodes, *Pratylenchus* spp. such as *P. brachyurus, P. neglectus, P. penetrans, P. curvitatus, P. goodeyi*; Burrowing nematodes, *Radopholus* spp. such as *R. similis; Rhadopholus* spp.; *Rhodopholus* spp.; Reniform nematodes, *Rotylenchus* spp. such as *R. robustus, R. reniformis; Scutellonema* spp.; Stubby-root nematode, *Trichodorus* spp. such as *T. obtusus, T. primitivus; Paratrichodorus* spp. such as *P. minor*; Stunt nematodes, *Tylenchorhynchus* spp. such as *T. claytoni, T. dubius*; Citrus nematodes, *Tylenchulus* spp. such as *T. semipenetrans*; Dagger nematodes, *Xiphinema* spp.; and other plant parasitic nematode species;

Insects from the order Isoptera for example *Calotermes flavicollis, Coptotermes* spp. such as *C. formosanus, C. gestroi, C. acinaciformis; Cornitermes cumulans, Cryptotermes* spp. such as *C. brevis, C. cavifrons; Globitermes sulfureus, Heterotermes* spp. such as *H. aureus, H. longiceps, H. tenuis; Leucotermes flavipes, Odontotermes* spp., *Incisitermes* spp. such as *I. minor*, I. Snyder; *Marginitermes hubbardi, Mastotermes* spp. such as *M. darwiniensis Neocapritermes* spp. such as *N. opacus, N. parvus; Neotermes* spp., *Procornitermes* spp., *Zootermopsis* spp. such as *Z. angusticollis, Z. nevadensis, Reticulitermes* spp. such as *R. hesperus, R. tibialis, R. speratus, R. flavipes, R. grassei, R. lucifugus, R. santonensis, R. virginicus; Termes natalensis*, Insects from the order *Blattaria* for example *Blatta* spp. such as *B. orientalis, B. lateralis; Blattella* spp. such as *B. asahinae, B. germanica; Leucophaea maderae, Panchlora nivea, Periplaneta* spp. such as *P. americana, P. australasiae, P. brunnea, P. fuligginosa, P. japonica; Supella longipalpa, Parcoblatta pennsylvanica, Eurycotis floridana, Pycnoscelus surinamensis*, Insects from the order Siphonoptera for example *Cediopsylla simples, Ceratophyllus* spp., *Ctenocephalides* spp. such as *C. felis, C. canis, Xenopsylla cheopis, Pulex irritans, Trichodectes canis, Tunga penetrans*, and *Nosopsyllus fasciatus*, Insects from the order Thysanura for example *Lepisma saccharina, Ctenolepisma urbana*, and *Thermobia domestica*, Pests from the class Chilopoda for example *Geophilus* spp., *Scutigera* spp. such as *Scutigera coleoptrata*;

Pests from the class Diplopoda for example *Blaniulus guttulatus, Julus* spp., *Narceus* spp., Pests from the class Symphyla for example *Scutigerella immaculata*, Insects from the order Dermaptera, for example *Forficula auricularia*, Insects from the order Collembola, for example *Onychiurus* spp., such as *Onychiurus armatus*, Pests from the order Isopoda for example, *Armadillidium vulgare, Oniscus asellus, Porcellio scaber*, Insects from the order Phthiraptera, for example *Damalinia* spp., *Pediculus* spp. such as *Pediculus humanus capitis, Pediculus humanus corporis, Pediculus humanus humanus; Pthirus pubis, Haematopinus* spp. such as *Haematopinus eurysternus, Haematopinus suis; Linognathus* spp. such as *Linognathus vituli; Bovicola bovis, Menopon gallinae, Menacanthus stramineus* and *Solenopotes capillatus, Trichodectes* spp., Examples of further pest species which may be controlled by compounds of formula (I) include: from the Phylum Mollusca, class Bivalvia, for example, *Dreissena* spp.; class Gastropoda, for example, *Anon* spp., *Biomphalaria* spp., *Bulinus* spp., *Deroceras* spp., *Galba* spp., *Lymnaea* spp., *Oncomelania* spp., *Pomacea canaliclata, Succinea* spp.; from the class of the helminths, for example, *Ancylostoma duodenale, Ancylostoma ceylanicum, Acylostoma braziliensis, Ancylostoma* spp., *Ascaris lumbricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus flaria, Diphyllobothrium latum, Dracunculus medinensis, Echinococcus granulosus, Echinococcus multilocularis, Enterobius vermicularis, Faciola* spp., *Haemonchus* spp. such as *Haemonchus contortus; Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti*.

Animal Health

The compounds of the invention are suitable for use in treating or protecting animals against infestation or infection by parasites. Therefore, the invention also relates to the use of a compound of the invention for the manufacture of a medicament for the treatment or protection of animals against infestation or infection by parasites. Furthermore, the invention relates to a method of treating or protecting animals against infestation and infection by parasites, which comprises orally, topically or parenterally administering or applying to the animals a parasiticidally effective amount of a compound of the invention.

The present invention also relates to the non-therapeutic use of compounds of the invention for treating or protecting animals against infestation and infection by parasites. Moreover, the invention relates to a non-therapeutic method of treating or protecting animals against infestation and infection by parasites, which comprises applying to a locus a parasiticidally effective amount of a compound of the invention.

The compounds of the invention are further suitable for use in combating or controlling parasites in and on animals. Furthermore, the invention relates to a method of combating or controlling parasites in and on animals, which comprises contacting the parasites with a parasitically effective amount of a compound of the invention.

The invention also relates to the non-therapeutic use of compounds of the invention for controlling or combating parasites. Moreover, the invention relates to a non-therapeutic method of combating or controlling parasites, which comprises applying to a locus a parasiticidally effective amount of a compound of the invention.

The compounds of the invention can be effective through both contact (via soil, glass, wall, bed net, carpet, blankets or animal parts) and ingestion (e.g. baits). Furthermore, the compounds of the invention can be applied to any and all developmental stages.

The compounds of the invention can be applied as such or in form of compositions comprising the compounds of the invention.

The compounds of the invention can also be applied together with a mixing partner, which acts against pathogenic parasites, e.g. with synthetic coccidiosis compounds, polyetherantibiotics such as Amprolium, Robenidin, Toltrazuril, Monensin, Salinomycin, Maduramicin, Lasalocid, Narasin or Semduramicin, or with other mixing partners as defined above, or in form of compositions comprising said mixtures.

The compounds of the invention and compositions comprising them can be applied orally, parenterally or topically, e.g. dermally. The compounds of the invention can be systemically or non-systemically effective.

The application can be carried out prophylactically, therapeutically or non-therapeutically. Furthermore, the application can be carried out preventively to places at which occurrence of the parasites is expected.

As used herein, the term "contacting" includes both direct contact (applying the compounds/compositions directly on the parasite, including the application directly on the animal or excluding the application directly on the animal, e.g. at it's locus for the latter) and indirect contact (applying the compounds/compositions to the locus of the parasite). The contact of the parasite through application to its locus is an example of a non-therapeutic use of the compounds of the invention.

The term "locus" means the habitat, food supply, breeding ground, area, material or environment in which a parasite is growing or may grow outside of the animal.

As used herein, the term "parasites" includes endo- and ectoparasites. In some embodiments of the invention, endoparasites can be preferred. In other embodiments, ectoparasites can be preferred. Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of the invention are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans*, and *Nosopsyllus fasciatus*; cockroaches (*Blattaria*-Blattodea), e.g. *Blattella germanica, Blattella asahinae, Periplaneta americana, Periplaneta japonica, Periplaneta brunnea, Periplaneta fuliginosa, Periplaneta australasiae*, and *Blatta orientalis*; flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia* hominis, *Fannia canicularis, Gasterophilus intestinalis, Glossina morsitans, Glossina palpalis, Glossina fuscipes, Glossina tachinoides, Haematobia irritans, Haplodiplosis equestris*, Hippelates spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium* mixtum, *Sarcophaga haemorrhoidalis, Sarcophaga* sp., *Simulium vittatum, Stomoxys calcitrans, Tabanus bovinus, Tabanus atratus, Tabanus lineola*, and *Tabanus similis*; lice (Phthiraptera), e.g. *Pediculus humanus* capitis, *Pediculus humanus* corporis, *Pthirus pubis, Haematopinus eurysternus, Haematopinus suis, Linognathus vituli, Bovicola bovis, Menopon gallinae, Menacanthus stramineus* and *Solenopotes capillatus*; ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae*; Actinedida (Prostigmata) und Acaridida (Astigmata), e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp; Bugs (Heteropterida): *Cimex lectularius, Cimex hemipterus, Reduvius senilis, Triatoma* spp., *Rhodnius* ssp., *Panstrongylus* ssp., and *Arilus critatus*; Anoplurida, e.g. *Haematopinus* spp., *Linognathus* spp., *Pediculus* spp., *Phtirus* spp., and *Solenopotes* spp.; Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp.; Roundworms Nematoda: Wipeworms and Trichinosis (Trichosyringida), e.g. Trichinellidae (*Trichinella* spp.), (Trichuridae) *Trichuris* spp., *Capillaria* spp.; Rhabditida, e.g. *Rhabditis* spp., *Strongyloides* spp., *Helicephalobus* spp.; Strongylida, e.g. *Strongylus* spp., *Ancylostoma* spp., *Necator americanus, Bunostomum* spp. (*Hookworm*), *Trichostrongylus* spp., *Haemonchus contortus, Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp., *Aleurostrongylus abstrusus*, and *Dioctophyma renale*; Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi*; Camallanida, e.g. *Dracunculus medinensis* (guinea worm); Spirurida, e.g. *Thelazia* spp., *Wuchereria* spp., *Brugia* spp., *Onchocerca* spp., *Dirofilari* spp.a, *Dipetalonema* spp., *Setaria* spp., *Elaeophora* spp., *Spirocerca lupi*, and *Habronema* spp.; Thorny headed worms (Acanthocephala), e.g. *Acanthocephalus* spp., *Macracanthorhynchus hirudinaceus* and *Oncicola* spp.; Planarians (Plathelminthes): Flukes (Trematoda), e.g. *Faciola* spp., *Fascioloides magna, Paragonimus* spp., *Dicrocoelium* spp., *Fasciolopsis*

*buski, Clonorchis sinensis, Schistosoma* spp., *Trichobilharzia* spp., *Alaria alata, Paragonimus* spp., and *Nanocyetes* spp.; Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

As used herein, the term "animal" includes warm-blooded animals (including humans) and fish. Preferred are mammals, such as cattle, sheep, swine, camels, deer, horses, pigs, poultry, rabbits, goats, dogs and cats, water buffalo, donkeys, fallow deer and reindeer, and also in furbearing animals such as mink, chinchilla and raccoon, birds such as hens, geese, turkeys and ducks and fish such as fresh- and salt-water fish such as trout, carp and eels. Particularly preferred are domestic animals, such as dogs or cats.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

Generally, it is favorable to apply the compounds of the invention in total amounts of 0.5 mg/kg to 100 mg/kg per day, preferably 1 mg/kg to 50 mg/kg per day.

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the formula I compound.

The formula I compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds may be formulated as ear tags for animals, particularly quadrupeds such as cattle and sheep.

Suitable preparations are:
Solutions such as oral solutions, concentrates for oral administration after dilution, solutions for use on the skin or in body cavities, pouring-on formulations, gels;
Emulsions and suspensions for oral or dermal administration; semisolid preparations;
Formulations in which the active compound is processed in an ointment base or in an oil-in-water or water-in-oil emulsion base;
Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further auxiliaries such as acids, bases, buffer salts, preservatives, and solubilizers. Suitable auxiliaries for injection solutions are known in the art. The solutions are filtered and filled sterile.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on. Solutions for use on the skin are prepared according to the state of the art and according to what is described above for injection solutions, sterile procedures not being necessary.

Gels are applied to or spread on the skin or introduced into body cavities. Gels are prepared by treating solutions which have been prepared as described in the case of the injection solutions with sufficient thickener that a clear material having an ointment-like consistency results. Suitable thickeners are known in the art.

Pour-on formulations are poured or sprayed onto limited areas of the skin, the active compound penetrating the skin and acting systemically. Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added. Suitable such auxiliaries are known in the art.

Emulsions can be administered orally, dermally or as injections. Emulsions are either of the water-in-oil type or of the oil-in-water type. They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances. Suitable hydrophobic phases (oils), suitable hydrophilic phases, suitable emulsifiers, and suitable further auxiliaries for emulsions are known in the art.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers. Suitable suspending agents, and suitable other auxiliaries for suspensions including wetting agents are known in the art.

Semisolid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form. Suitable auxiliaries for this purpose are known in the art.

The compositions which can be used in the invention can comprise generally from about 0.001 to 95% of the compound of the invention.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of formula I against endoparasites in concentrations of 10 ppm to 2 percent by weight, preferably of 0.05 to 0.9 percent by weight, very particularly preferably of 0.005 to 0.25 percent by weight.

Topical application may be conducted with compound-containing shaped articles such as collars, medallions, ear tags, bands for fixing at body parts, and adhesive strips and foils.

Generally, it is favorable to apply solid formulations which release compounds of the invention in total amounts of 10 mg/kg to 300 mg/kg, preferably 20 mg/kg to 200 mg/kg, most preferably 25 mg/kg to 160 mg/kg body weight of the treated animal in the course of three weeks.

The following examples illustrate the invention.

A. PREPARATION OF COMPOUNDS

Materials: Unless otherwise noted, reagents and solvents were purchased at highest commercial quality and used without further purification. Dry tetrahydrofuran (THF), ethylacetate (EtOAc), dimethylsulfoxide (DMSO), acetone, ethanol (EtOH), benzene, dimethylformamide (DMF), diisopropylethylamine (DIPEA), hexafluorophosphate azabenzotriazole tetramethyl uronium (HATU), pyridine, and $CH_2Cl_2$ were purchased from commercial providers.

All reactions were monitored by thin-layer chromatography (TLC) using Merck silica gel 60 $F_2$54 pre-coated plates (0.25 mm). Flash chromatography was carried out with Kanto Chemical silica gel (Kanto Chemical, silica gel 60N, spherical neutral, 0.040-0.050 mm, Cat.-No. 37563-84). $^1$H NMR spectra were recorded on JEOL JNM-ECA-500 (500 MHz). Chemical shifts are expressed in ppm downfield from the internal solvent peaks for acetone-$d_6$ ($^1$H; δ=2.05 ppm) and $CD_3OD$ ($^1$H; δ=3.30 ppm), and J values are given in Hertz. The following abbreviations were used to explain the multiplicities: s=singlet, d=doublet, t=triplet, q=quartet, dd=double doublet, dt=double triplet, m=multiplet, br=broad. High-resolution mass spectra were measured on a JEOL JMS-T100LP.

Characterization: The compounds were characterized by coupled High Performance Liquid Chromatography with mass spectrometry (HPLC/MS). Method A: UHPLC-MS on Shimadzu Nexera UHPLC & Shimadzu LCMS 20-20 ESI. Analytical UHPLC column: Phenomenex Kinetex 1.7 μm XB-C18 100A; 50×2.1 mm; mobile phase: A: water+0.1% TFA; B: acetonitrile; gradient: 5-100% B in 1.50 minutes; 100% B 0.20 min; flow: 0.8-1.0 mL/min in 1.50 minutes at 60° C. MS-method: ESI positive; mass range (m/z) 100-700.

Synthesis Example A: 2-[3-ethylsulfonyl-5-(trifluoromethyl)-2-pyridyl]-1-methyl-6-(trifluoromethoxy)imidazo[4,5-c]quinoline (Compound I.1)

Step 1) Manufacture of N-methyl-3-nitro-8-(trifluoromethoxy)quinolin-4-amine (Compound I.1a)

To a solution of 4-chloro-3-nitro-8-(trifluoromethoxy)quinoline (4 g) in THF (40 mL), at 20 to 25° C., was added methylamine (40 mL, 2M solution in THF). The resulting reaction mixture was then warmed to 50° C. and stirred for 1 h. The reaction mixture was then concentrated in vacuo, to afford a residue containing compound I.1a (3.9 g, 100% yield), which was used in Step 2 without further purification. Characterization of compound I.1a by HPLC-MS (Method A): mass found for $C_{11}H_8N_3O_3F_3$ [M+H]$^+$ 287.8; $t_R$=0.791 min.

Step 2: Manufacture of N4-methyl-8-(trifluoromethoxy)quinoline-3,4-diamine (Compound I.1b)

To a suspension of Zn-powder (3.6 g) in $CH_3COOH$ (60 mL) was slowly added a solution of compound I.1a (3.9 g) in 10 mL EtOAc at a temperature of up to 30° C. The reaction mixture was stirred for an additional 2 h at 20 to 25° C. The reaction mixture was diluted with EtOAc and filtrated. The filtrate was washed with $H_2O$. The combined $H_2O$-phases were adjusted to an alkaline pH with aqueous NaOH and extracted with EtOAc. The combined organic extracts were dried and concentrated in vacuo to afford a residue containing compound I.1b (2.35 g, 67% yield), which was used in Step 3 without further purification. Characterization of compound I.1b by HPLC-MS (Method A): mass found 257.8; $t_R$=0.665 min.

Step 3: Manufacture of 3-ethylsulfanyl-N-[4-(methylamino)-8-(trifluoromethoxy)-3-quinolyl]-5-(trifluoromethyl)pyridine-2-carboxamide (Compound I.1c)

To a solution of compound I.1b (300 mg) and 3-ethylsulfanyl-5-(trifluoromethyl)pyridine-2-carboxylic acid prepared from commercial ethyl 3-chloro-5-(trifluoromethyl)pyridine-2-carboxylate according to WO 2017/50685 p. 53-54 (235 mg) in DMF (6 mL) was added HATU (580 mg) and DIPEA (240 mg). The reaction mixture was then stirred at 20 to 25° C. overnight. The reaction mixture was subsequently worked-up by extraction and the combined organic phases were dried and concentrated in vacuo to afford a residue. The residue was purified by reversed-phase HPLC to afford compound I.1c (293 mg, 64%). Characterization of compound I.1c by H PLC-MS (Method A): mass found 491; $t_R$=0.952 min.

Step 4: Manufacture of 2-[3-ethylsulfanyl-5-(trifluoromethyl)-2-pyridyl]-1-methyl-6-(trifluoromethoxy)imidazo[4,5-c]quinoline (Compound I.1d)

A solution of compound I.1c (202 mg) in $CH_3COOH$ (5 mL) was heated at reflux overnight. The reaction mixture was then cooled to 20 to 25° C., followed by and concentration in vacuo to obtain a residue. The residue was worked-up by extraction and the combined organic phases were dried, and concentrated in vacuo to afford crude compound I.1d, which was used in Step 5 without further purification. Characterization of compound I.1d by HPLC-MS (Method A): mass found 473; $t_R$=1.152 min.

Step 5: Manufacture of Compound I.1

To a solution of compound I.1d (200 mg) in $CH_3COOH$ (5 mL) was added $Na_2WO_4$ (4 mg) and $H_2O_2$ (30% solution in $H_2O$, 120 mg). The reaction mixture was stirred at 20 to 25° C. for 5 h and then concentrated in vacuo to obtain a residue. The residue was worked-up by extraction and the combined organic phases were dried and concentrated to afford compound I.1 (170 mg, 80% yield). Characterization of compound I.1 by HPLC-MS (Method A): mass found 505; $t_R$=1.150 min.

By analogous procedures to the procedure described above for compound I.1, the following examples of formula IA.A1.1,

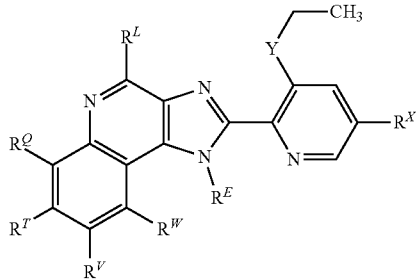

wherein $R^E$ is $CH_3$, $R^L$, $R^V$, and R are H, and the variables $R^Q$, $R^T$, $R^X$ and Y have a meaning as defined in Table E, were prepared and characterized, wherein the measured data was included in Table E.

By analogous procedures to the procedure described above for compound I.1, the following examples of formula IB.A1.1

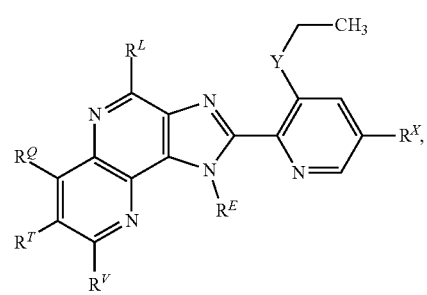

wherein $R^V$ and $R^Q$ are $CF_3$, $R^L$, $R^M$ and $R^T$ are H, and the variables $R^E$, $R^X$ and Y have a meaning as defined in Table F, were prepared and characterized, wherein the measured data was included in Table F.

TABLE E

Compounds of formula (I) that were synthesized in analogy to the Synthesis Example A.

| Compound | $R^Q$ | $R^T$ | $R^X$ | Y | Phys. Chem. Data*: HPLC Method; Retention time; m/z |
|---|---|---|---|---|---|
| I.1 | $OCF_3$ | H | $CF_3$ | $SO_2$ | A; 1.15; 505 |
| I.2 | $OCF_3$ | H | H | $SO_2$ | A; 0.933; 437 |
| I.3 | $CF_3$ | H | H | $SO_2$ | A; 1.019; 421 |
| I.4 | H | $CF_3$ | H | $SO_2$ | A; 0.843; 421 |
| I.5 | $OCF_3$ | H | $CF_3$ | S | A; 1.125; 473 |
| I.6 | $OCF_3$ | H | H | S | A; 1.002; 405 |
| I.7 | $CF_3$ | H | H | S | A; 1.093; 389 |
| I.8 | $CF_3$ | H | $CF_3$ | S | A; 1.287; 457 |
| I.9 | $CF_3$ | H | $CF_3$ | $SO_2$ | A; 1.19; 489 |
| I.10 | H | $CF_3$ | H | S | A; 0.945; 389 |
| I.11 | H | $CF_3$ | $CF_3$ | S | A; 1.164; 475 |
| I.12 | H | $CF_3$ | $CF_3$ | $SO_2$ | A; 1.032; 489 |
| I.13 | $OCF_3$ | H | $SO_2CH_2CH_3$ | $SO_2$ | A; 1.009; 529 |
| I.14 | $OCF_3$ | H | Br | S | A; 1.141; 484 |
| I.15 | $CF_3$ | H | Br | S | A; 1.235; 468 |
| I.16 | $CF_3$ | H | Br | $SO_2$ | A; 1.181; 500 |
| I.17 | $CF_3$ | H | 4-fluorophenyl | $SO_2$ | A; 1.228; 515 |
| I.18 | $CF_3$ | H | 3-fluorophenyl | $SO_2$ | A; 1.26; 515 |
| I.19 | $OCF_3$ | H | Br | $SO_2$ | A; 1.044; 516 |
| I.20 | $OCF_3$ | H | 4-fluorophenyl | $SO_2$ | A; 1.076; 531 |
| I.21 | $OCF_3$ | H | 3-fluorophenyl | $SO_2$ | A; 1.082; 531 |
| I.22 | H | $CF_3$ | Br | $SO_2$ | A; 0.972; 500 |
| I.23 | H | $CF_3$ | Br | S | A; 1.06; 468 |
| I.24 | H | $CF_3$ | 4-fluorophenyl | $SO_2$ | A; 1.143; 515 |
| I.25 | H | $CF_3$ | 3-fluorophenyl | $SO_2$ | A; 1.154; 515 |
| I.26 | $OCH_2CH_3$ | H | H | $SO_2$ | A; 0.778; 451 |
| I.27 | $OCH_2CH_3$ | H | H | $SO_2$ | A; 0.93; 520 |
| I.28 | $OCHF_2$ | H | H | $SO_2$ | A; 0.756; 419 |
| I.29 | $OCHF_2$ | H | $CF_3$ | $SO_2$ | A; 0.949; 487 |
| I.30 | $OCH_2CF_3$ | H | 4-fluorophenyl | $SO_2$ | A; 1.002; 545 |
| I.31 | $OCHF_2$ | H | 4-fluorophenyl | $SO_2$ | A; 0.997; 513 |
| I.32 | H | $OCF_3$ | H | $SO_2$ | A; 0.842; 437 |
| I.33 | H | $OCF_3$ | $CF_3$ | $SO_2$ | A; 1.078; 505 |
| I.34 | H | $OCF_3$ | 4-fluorophenyl | $SO_2$ | A; 1.097; 531 |
| I.35 | $CF_3$ | H | $C(CN)(CH_3)_2$ | $SO_2$ | A; 1.131; 488 |
| I.36 | H | $CF_3$ | $C(CN)(CH_3)_2$ | $SO_2$ | A; 1012; 488 |
| I.37 | H | $OCF_3$ | $C(CN)(CH_3)_2$ | $SO_2$ | A; 0.98; 504 |
| I.38 | H | $OCF_3$ | 1-cyanocyclopropyl | $SO_2$ | A; 0.945; 502 |
| I.39 | $OCF_3$ | H | $C(CN)(CH_3)_2$ | $SO_2$ | A; 1.02; 504 |

*HPLC Method: retention time in minutes, mass charge ratio m/z.

TABLE F

Compounds of formula (I) that were synthesized in analogy to the Synthesis Example A of compound I.1.

| Compound | $R^E$ | $R^X$ | Y | Phys. Chem. Data*: HPLC Method; Retention time; m/z |
|---|---|---|---|---|
| I.40 | $CH_3$ | H | S | A; 1.375; 457 |
| I.41 | $CH_3$ | H | $SO_2$ | A; 1.286; 489 |
| I.42 | $CH_3$ | 4-fluorophenyl | $SO_2$ | A; 1.458; 583 |
| I.43 | H | $CF_3$ | $SO_2$ | A; 1.373; 543 |
| I.44 | H | 4-fluoromethyl | $SO_2$ | A; 1.428; 549 |
| I.45 | $CH_3$ | $CF_3$ | $SO_2$ | A; 1.46; 557 |

*HPLC Method: retention time in minutes, mass charge ratio m/z.

By analogous procedures to the procedure described above for compound I.1, the following examples of formula IA.A5.1

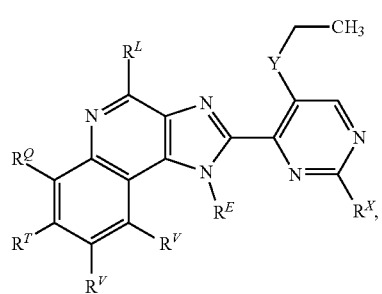

(I-A-5-1)

wherein $R^E$ is $CH_3$, $R^L$, $R^V$, $R^W$ and $R^X$ are H, and the variables $R^Q$, $R^T$ and Y have a meaning as defined in Table G, were prepared and characterized, wherein the measured data was included in Table G.

TABLE G

Compounds of formula (I) that were synthesized in analogy to the Synthesis Example A.

| Compound | $R^Q$ | $R^T$ | Y | Phys. Chem. Data*: HPLC Method; Retention time; m/z |
|---|---|---|---|---|
| I.46 | H | $CF_3$ | $SO_2$ | A; 0.975; 422 |
| I.47 | $OCF_3$ | H | $SO_2$ | A; 0.969; 438 |
| I.48 | $CF_3$ | H | $SO_2$ | A; 1.038; 422 |

*HPLC Method: retention time in minutes, mass charge ratio m/z.

Synthesis Example B: 8-(3-ethylsulfonyl-2-pyridyl)-2,4-bis(trifluoromethyl)imidazo[1,2-a][1,8]naphthyridine (Compound I.54)

Step 1: Manufacture of 8-(3-fluoro-2-pyridyl)-2,4-bis(trifluoromethyl)imidazo[1,2-a][1,8]naphthyridine (Compound I.54a)

A suspension of 7-amino-2,4-bis(trifluormethyl)1-8,naphthyridin (628 mg) and 2-bromo-1-(3-fluoro-2-pyridyl)ethanone (584 mg) in tert.-butanol (15 mL) was stirred under reflux overnight. After 24 h all of the 2-bromo-1-(3-fluoro-2-pyridyl)ethanone was consumed and additional 243 mg of 2-bromo-1-(3-fluoro-2-pyridyl)ethanone were added. The resulting reaction mixture was refluxed again overnight. The reaction mixture was then evaporated to dryness and the resulting crude residue taken up in EtOAc and $H_2O$. The aqueous phase was extracted with EtOAc. The combined organic layers were washed, dried, and concentrated in vacuo to afford a residue, which was subsequently purified by column chromatography under reversed phase conditions to afford compound I.54a (247 mg, 28% yield). Characterization of compound I.54a by HPLC-MS (Method A): mass found for $C_{17}H_7N_4F_7[M+H]^+$ 400.8; $t_R$: =1,127 min.

Step 2: Manufacture of 8-(3-ethylsulfanyl-2-pyridyl)-2,4-bis(trifluoromethyl)imidazo[1,2-a][1,8]naphthyridine (Compound I.54b)

To a solution of compound I.54a (247 mg) as obtained in Step 1 in DMF (10 mL) was added ethyl thiolate (115 mg) at 0° C. The resulting reaction mixture was warmed to 20 to 25° C. and stirred overnight. Additional ethyl thiolate (52 mg) was then added to the reaction mixture, which was stirred for 2 more hours. The reaction mixture was concentrated in vacuo and the crude residue taken up in EtOAc. The organic layer was washed, dried and concentrated in vacuo to afford a residue, which was purified by column chromatography under reversed phase conditions to afford compound I.56b (50 mg, yield 18%). Characterization of compound I.54b by HPLC-MS (Method A): mass found for $C_{19}H_{12}N_4F_6S$ $[M+H]^+$ 402.8; $t_R$: =1,164 min.

Step 3: Manufacture of 8-(3-ethylsulfonyl-2-pyridyl)-2,4-bis(trifluoromethyl)imidazo[1,2-a][1,8]naphthyridine (Compound I.54)

To a mixture of compound I.54c (50 mg) as obtained in Step 2 with $CH_3COOH$ (5 mL) was added $Na_2WO_4$ (4 mg) and $H_2O_2$ (30% solution in water, 0.34 mmol). The reaction mixture was stirred at 20 to 25° C. overnight and then concentrated in vacuo to obtain a crude residue. The residue was taken up in EtOAc, washed, dried, and concentrated in vacuo to obtain compound I.54 in sufficient purity (55 mg, yield 97%).

By analogous procedures to the procedure described above for compound I.54, the following examples of formula IC.A1.1,

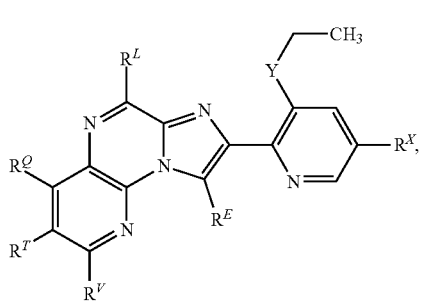

(IA.A1.1)

wherein $R^E$, $R^T$, $R^M$ and $R^L$ are H; Y is $SO_2$; and $R^Q$, $R^V$ and $R^X$ have a meaning as defined in Table H, were prepared and characterized, wherein the measured data was included in Table H.

TABLE H

Compounds of formula (I) that were synthesized
in analogy to the Synthesis Example B.

| Compound | $R^Q$ | $R^V$ | $R^X$ | Phys. Chem. Data*: HPLC Method; Retention time; m/z |
|---|---|---|---|---|
| I.49 | $CF_3$ | $CF_3$ | Br | A; 1.374; 554.7 |
| I.50 | $CF_3$ | $CF_3$ | $CF_3$ | A; 1.38; 542.8 |
| I.51 | $CF_3$ | Cl | $CF_3$ | A; 1.363; 509 |
| I.52 | $CF_3$ | H | $CF_3$ | A; 1.264; 474.8 |
| I.53 | $CF_3$ | $CF_3$ | 4-fluorophenyl | A; 1.399; 568.8 |
| I.54 | $CF_3$ | $CF_3$ | H | A; 1.219; 474.8 |
| I.55 | $CF_3$ | H | H | A; 0.997; 407 |
| I.56 | $CF_3$ | H | 4-fluorophenyl | A; 1.256; 501.1 |

*HPLC Method: retention time in minutes, mass charge ratio m/z.

By analogous procedures to the procedure described above for compound I.54, the following examples of formula IT.A1.1,

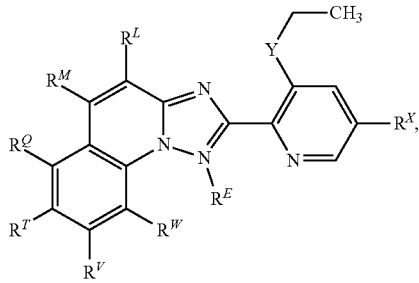

(IT.A1.1)

wherein $R^E$, $R^L$ and $R^W$ are H; Y is $SO_2$; and $R^M$, $R^Q$, $R^T$, $R^V$ and $R^X$ have a meaning as defined in Table K, were prepared and characterized, wherein the measured data was included in Table K.

TABLE K

Compounds of formula (I) that were synthesized in analogy to the Synthesis Example B.

| Compound | $R^M$ | $R^Q$ | $R^T$ | $R^V$ | $R^X$ | Phys. Chem. Data*: HPLC Method; Retention time; m/z |
|---|---|---|---|---|---|---|
| 1.57 | $CF_3$ | H | H | H | $CF_3$ | A; 1.33; 473.8 |
| 1.58 | $CF_3$ | H | H | H | 4-fluorophenyl | A; 1.356; 500 |
| 1.59 | $CF_3$ | H | H | H | H | A; 1.149; 405.9 |
| 1.60 | H | H | $OCF_3$ | H | $CF_3$ | A; 1.271; 489.8 |
| 1.61 | H | $CF_3$ | H | CF3 | $CF_3$ | A; 1.419; 542 |
| 1.62 | H | H | $OCF_3$ | H | 4-fluorophenyl | A; 1.203; 515.9 |
| 1.63 | H | $CF_3$ | H | CF3 | H | A; 1.263; 473.9 |
| 1.64 | H | H | $OCF_3$ | H | H | A; 1.038; 422 |

*HPLC Method: retention time in minutes, mass charge ratio m/z.

Synthesis Example C: 2-(3-ethylsulfonyl-2-pyridyl)-5-(trifluoromethyl)-[1,2,4]triazolo[1,5-a]quinoline (Compound I.65)

Step 1: Manufacture of [2-imino-4-(trifluoromethyl)-1-quinolyl]ammonium Tosylate (Compound I.65a)

To a solution of 4-(trifluoromethyl)quinolin-2-amine (500 mg) in DCM (5 mL) was added a solution of O-tosylhydroxylamine (670 mg) in 5 ml DCM at 20 to 25° C. The resulting reaction mixture was stirred for 1 hour while a precipitate formed. The solid precipitate (765 mg) was collected by filtration, washed with DCM, and applied in Step 2 without further purification.

Step 2: Manufacture of 2-(3-fluoro-2-pyridyl)-5-(trifluoromethyl)-[1,2,4]triazolo[1,5-a]quinoline (Compound I.65b)

To a solution of compound I.65a (300 mg) as obtained in Step 1 and 3-fluoropyridine-2-carbaldehyde (136 mg) in 8 ml $CH_3OH$ was added a solution of KOH (420 mg) in 2 ml $H_2O$ at 20 to 25° C. The resulting reaction mixture was stirred overnight. Any formed precipitate was removed by filtration and, and the solution was concentrated in vacuo to dryness. The resulting residue was taken up in DCM, washed, dried, and concentrated in vacuo to afford a crude residue, which was purified by column chromatography under reversed phase conditions to afford compound I.65b (190 mg, yield 76%). Characterization of compound I.65b by HPLC-MS (Method A): mass found 332.9; $t_R$: =1,150 min.

Step 3: Manufacture of 2-(3-ethylsulfanyl-2-pyridyl)-5-(trifluoromethyl)-[1,2,4]triazolo[1,5-a]quinoline (Compound I.65c)

To a solution of compound I.65b (180 mg) in DMF (5 mL) was added ethyl thiolate (101 mg) at 0° C. The resulting reaction mixture was warmed to 20 to 25° C. and stirred overnight. The reaction mixture was subsequently concentrated in vacuo and the resulting crude residue taken up in EtOAc. The organic layer was washed, dried, and concentrated in vacuo to afford a residue containing compound I.65c at sufficient purity to be used in the next step without further purification (194 mg, yield 96%). Characterization of compound I.65c by HPLC-MS (Method A): mass found 374.8; $t_R$: =1,172 min.

Step 4: Manufacture of 2-(3-ethylsulfonyl-2-pyridyl)-5-(trifluoromethyl)-[1,2,4]triazolo[1,5-a]quinoline (Compound I.65)

To a solution of compound I.65c (194 mg, 0.52 mmol) as obtained in Step 3 in $CH_3COOH$ (5 mL) was added $Na_2WO_4$ (17 mg) and $H_2O_2$ (30% solution in water, 1.3 mmol). The resulting reaction mixture was stirred at 20 to 25° C. overnight and then concentrated in vacuo to obtain a crude residue. The crude residue was taken up in EtOAc, washed with an aqueous solution of $NaHCO_3$, dried, and concentrated in vacuo to afford a residue containing 2-(3-ethylsulfonyl-2-pyridyl)-5-(trifluoromethyl)-[1,2,4]triazolo[1,5-a]quinoline in sufficient purity (188 mg, yield 89%).

The compound I.65, having a structure as represented by formula (IY.A1.1)

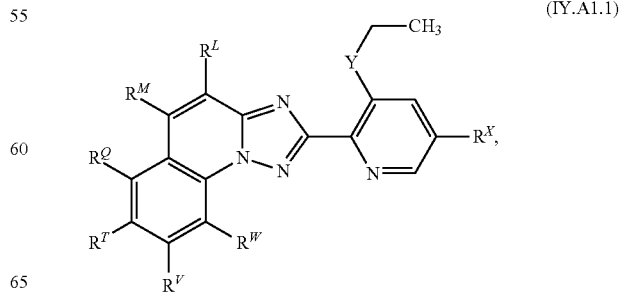

(IY.A1.1)

wherein $R^L$, $R^Q$, $R^T$, $R^V$, and $R^W$, are H; and Y, $R^M$, and $R^X$ have a meaning as defined in Table L, was characterized and the measured data included in Table L:

TABLE L

Compounds of formula (I) that were synthesized according to Synthesis Example C.

| Compound | $R^M$ | $R^X$ | Y | Phys. Chem. Data*: HPLC Method; Retention time; m/z |
|---|---|---|---|---|
| I.65 | $CF_3$ | H | $SO_2$ | A; 406.8; 1.115 |

*HPLC Method: retention time in minutes, mass charge ratio m/z.

B. BIOLOGICAL EXAMPLES

The activity of the compounds of formula (I) of the present invention could be demonstrated and evaluated in biological tests described in the following. If not otherwise specified, the test solutions are prepared as follows: The active compound is dissolved at the desired concentration in a mixture of 1:1 (vol:vol) distilled water:acteone. The test solution is prepared at the day of use. Test solutions are prepared in general at concentrations of 1000 ppm, 500 ppm, 300 ppm, 100 ppm and 30 ppm (wt/vol).

Boll Weevil (*Anthonomus grandis*)

For evaluating control of boll weevil (*Anthonomus grandis*) the test unit consisted of 96-well-microtiter plates containing an insect diet and 5-10 *A. grandis* eggs. The compounds were formulated using a solution containing 75% v/v water and 25% v/v DMSO. Different concentrations of formulated compounds were sprayed onto the insect diet at 5 μl, using a custom built micro atomizer, at two replications. After application, microtiter plates were incubated at about 25±1° C. and about 75±5% relative humidity for 5 days. Egg and larval mortality was then visually assessed. In this test, compounds I.1, I.2, I.3, I.4, I.5, I.6, I.7, I.8, I.9, I.10, I.11, I.12, I.13, I.14, I.15, I.16, I.17, I.18, I.19, I.20, I.21, I.22, I.23, I.24, I.25, I.27, I.28, I.29, I.30, I.31, I.33, I.34, I.40, I.41, I.42, I.44, I.45, I.46, I.47, I.48, I.49, I.50, I.51, I.52, I.53, I.54, I.55, I.56, I.59, I.60, I.61, I.62, I.65 at 2500 ppm showed over 75% mortality in comparison with untreated controls. Compound I.26 at 2500 ppm showed over 50% mortality in comparison with untreated controls.

Tobacco Budworm (*Heliothis virescens*)

For evaluating control of tobacco budworm (*Heliothis virescens*) the test unit consisted of 96-well-microtiter plates containing an insect diet and 15-25 *H. virescens* eggs. The compounds were formulated using a solution containing 75% v/v water and 25% v/v DMSO. Different concentrations of formulated compounds were sprayed onto the insect diet at 10 μl, using a custom built micro atomizer, at two replications. After application, microtiter plates were incubated at about 28±1° C. and about 80±5% relative humidity for 5 days. Egg and larval mortality was then visually assessed. In this test, compounds I.1, I.2, I.3, I.4, I.5, I.7, I.8, I.9, I.11, I.13, I.14, I.15, I.16, I.17, I.18, I.19, I.20, I.21, I.22, I.23, I.24, I.25, I.27, I.28, I.29, I.30, I.31, I.32, I.33, I.34, I.40, I.41, I.42, I.43 I.44, I.45, I.46, I.47, I.48, I.49, I.50, I.52, I.53, I.54, I.55, I.56, I.57, I.58, I.59, I.60, I.61, I.62, I.65 at 2500 ppm showed over 75% mortality in comparison with untreated controls.

Vetch Aphid (*Megoura viciae*)

For evaluating control of vetch aphid (*Megoura viciae*) through contact or systemic means the test unit consisted of 24-well-microtiter plates containing broad bean leaf disks. The compounds were formulated using a solution containing 75% v/v water and 25% v/v DMSO. Different concentrations of formulated compounds were sprayed onto the leaf disks at 2.5 μl, using a custom built micro atomizer, at two replications. After application, the leaf disks were air-dried and 5-8 adult aphids placed on the leaf disks inside the microtiter plate wells. The aphids were then allowed to suck on the treated leaf disks and incubated at about 23±1° C. and about 50±5% relative humidity for 5 days. Aphid mortality and fecundity was then visually assessed. In this test, compounds I.1, I.2, I.3, I.6, I.7, I.9, I.12, I.13, I.14, I.15, I.16, I.17, I.19, I.20, I.21, I.22, I.24, I.25 I.29, I.32, I.34, I.41, I.48, I.52, I.54, I.55, I.56, I.57, I.58, I.59, I.65 at 2500 ppm showed over 75% mortality in comparison with untreated controls. Compounds 1.23, 1.28, 1.42 at 2500 ppm showed over 50% mortality in comparison with untreated controls.

Green Peach Aphid (*Myzus persicae*)

For evaluating control of green peach aphid (*Myzus persicae*) through systemic means the test unit consisted of 96-well-microtiter plates containing liquid artificial diet under an artificial membrane. The compounds were formulated using a solution containing 75% v/v water and 25% v/v DMSO. Different concentrations of formulated compounds were pipetted into the aphid diet, using a custom built pipetter, at two replications. After application, 5-8 adult aphids were placed on the artificial membrane inside the microtiter plate wells. The aphids were then allowed to suck on the treated aphid diet and incubated at about 23±1° C. and about 50±5% relative humidity for 3 days. Aphid mortality and fecundity was then visually assessed. In this test, compounds I.1, I.2, I.3, I.6, I.7, I.9, I.10, I.12, I.13, I.16, I.17, I.19, I.20, I.21, I.22, I.26, I.28, I.29, I.31, I.32, I.33, I.34, I.41, I.42, I.45, I.47, I.48, I.52, I.53, I.55, I.56, I.57, I.58, I.59, I.61, I.62, I.65 at 2500 ppm showed over 75% mortality in comparison with untreated controls. Compound I.27, 1.44 at 2500 ppm showed over 50% mortality in comparison with untreated controls.

Greenhouse Whitefly (*Trialeurodes vaporariorum*)

For evaluating control of Greenhouse Whitefly (*Trialeurodes vaporariorum*) the test unit consisted of 96-well-microtiter plates containing a leaf disk of egg plant leaf disk with white fly eggs. The compounds or mixtures were formulated using a solution containing 75% water and 25% DMSO. Different concentrations of formulated were sprayed onto the insect diet at 2.5 μl, using a custom built micro atomizer, at two replications. After application, microtiter plates were incubated at 23±1° C., 65±5% RH for 6 days. Mortality of hatched crawlers was then visually assessed. In this test, compounds I.3, I.13, I.14, I.17, I.18, I.19, I.20, I.21, I.22, I.24, I.59 at 2500 ppm showed over 75% mortality in comparison with untreated controls. In this test, compound I.23, I.30, I.50, I.57, I.61 at 2500 ppm showed over 50% mortality in comparison with untreated controls.

The invention claimed is:

1. A compound of formula (I), or an agrochemically or veterinarily acceptable salt, stereoisomer, tautomer, or N-oxide thereof

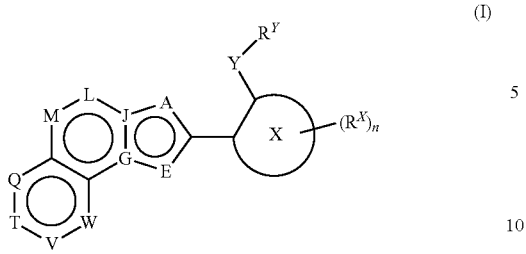
(I)

wherein variables in formula (I) have the following meaning

A is CH, N, or NH;
E is N, O, S, $NR^E$, or $CR^E$;
G, J are independently C or N;
L is N or $CR^L$;
M is N or $CR^M$;
Q is N or $CR^Q$;
T is N or $CR^T$;
V is N or $CR^V$;
W is N or $CR^W$;
X is phenyl, or a 5- or 6-membered hetaryl;
Y is S, S(O), or $S(O)_2$;
$R^E$, $R^L$, $R^M$, $R^Q$, $R^T$, $R^V$, and $R^W$ are independently H, halogen, $N_3$, CN, $NO_2$, SCN, $SF_5$;
$C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, which groups are halogenated or non-halogenated;
$C(=O)OR^1$, $NR^2R^3$, $C_1$-$C_6$-alkylen-$NR^2R^3$, O-$C_1$-$C_6$-alkylen-$NR^2R^3$, $C_1$-$C_6$-alkylen-CN, NH—$C_1$-$C_6$-alkylen-$NR^2R^3$, $C(=O)NR^2R^3$, $C(=O)R^4$, $SO_2NR^2R^3$, $S(=O)_mR^5$, $OR^6$, $SR^6$, or $CH_2R^6$;
phenyl, which is unsubstituted or substituted with one or more, same or different substituents $R^{11}$;
$R^1$ is H;
$C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, or $C_3$-$C_6$-cycloalkoxy-$C_1$-$C_4$-alkyl, which groups are halogenated or non-halogenated; or
$C_1$-$C_6$-alkylen-$NR^2R^3$, $C_1$-$C_6$-alkylen-CN, or $CH_2R^6$; or
phenyl, which is unsubstituted, or substituted with one or more, same or different substituents $R^{11}$;
$R^{11}$ is halogen, $N_3$, OH, CN, $NO_2$, SCN, $SF_5$;
$C_1$-$C_6$-alkyl, $C_1$-$C_6$-alkoxy, $C_2$-$C_6$-alkenyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, which groups are halogenated or non-halogenated;
$R^2$ is H;
$C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which groups are unsubstituted, or substituted with one or more, same or different substituents selected from halogen, CN and OH;
$C(=O)R^{21}$, $C(=O)OR^{21}$, $C(=O)NR^{21}$, $C_1$-$C_6$-alkylen-CN, or $CH_2R^6$; or
phenyl, which is unsubstituted or substituted with one or more, same or different substituents $R^{11}$;
$R^{21}$ is H;
$C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl;
$C_3$-$C_6$-cycloalkyl-$C_1$-$C_4$-alkyl, $C_3$-$C_6$-cycloalkoxy-$C_1$-$C_4$ alkyl, phenyl, or a saturated, partially-, or fully unsaturated 5- or 6-membered heterocycle, wherein the cyclic moieties are unsubstituted or substituted with one or more, same or different substituents $R^{11}$;
$R^3$ is H;
$C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which groups are halogenated or non-halogenated;
$C_1$-$C_6$-alkylen-CN, or $CH_2R^6$;
phenyl, which is unsubstituted or substituted with one or more, same or different substituents $R^{11}$; or
$NR^2R^3$ form an N-bound, saturated 3- to 8-membered heterocycle, which in addition to the nitrogen atom may have 1 or 2 further heteroatoms or heteroatom moieties selected from O, $S(=O)_m$, NH, and N—$C_1$-$C_6$-alkyl, and wherein the N-bound heterocycle is unsubstituted or substituted with one or more, same or different substituents selected from halogen, $C_1$-$C_4$-alkyl, $C_1$-$C_4$-haloalkyl, $C_1$-$C_4$-alkoxy and $C_1$-$C_4$-haloalkoxy;
$R^4$ is H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, or $C_3$-$C_6$-cycloalkoxy-$C_1$-$C_4$-alkyl, which are unsubstituted or substituted with one or more, same of different substituents selected from halogen, CN, and OH;
$CH_2R^6$, or phenyl, which is unsubstituted, or substituted with one or more, same or different substituents $R^{11}$;
$R^5$ is $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, or $C_3$-$C_6$-cycloalkoxy-$C_1$-$C_4$-alkyl, which groups are halogenated or non-halogenated;
$C_1$-$C_6$-alkylen-$NR^2R^3$, $C_1$-$C_6$-alkylen-CN, $CH_2R^6$; or
phenyl, which is unsubstituted, or substituted with one or more, same or different substituents $R^{11}$;
$R^6$ is phenyl, which is unsubstituted or substituted with one or more, same or different substituents $R^{11}$;
$R^X$ is halogen, $N_3$, OH, CN, $NO_2$, SCN, $SF_5$;
$C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, which groups are halogenated or non-halogenated;
$C(=O)OR^1$, $NR^2R^3$, $C_1$-$C_6$-alkylen-$NR^2R^3$, O-$C_1$-$C_6$-alkylen-$NR^2R^3$, $C_1$-$C_6$-alkylen-CN, NH—$C_1$-$C_6$-alkylen-$NR^2R^3$, $C(=O)NR^2R^3$, $C(=O)R^4$, $SO_2NR^2R^3$, $S(=O)_mR^1$, $OR^6$, $SR^6$, $CH_2R^6$; or
$OC(=O)R^4$, $OC(=O)OR^1$, $OC(=O)NR^2R^3$, $OC(=O)SR^1$, $OC(=S)NR^2R^3$, $OC(=S)SR^1$, $ONR^2R^3$, $ON=CR^1R^4$, $N=CR^1R^4$, $NNR^2$, $NC(=O)R^4$, $SC(=O)SR^1$, $SC(=O)NR^2R^3$, $C(=S)R^6$, $C(=S)OR^4$, $C(=NR^2)R^4$, $C(=NOR^2)R^4$, $C(CN)R^7R^8$;

phenyl, which is unsubstituted or substituted with one or more, same or different substituents $R^{11}$;

a 5- or 6-membered saturated, partially unsaturated, or fully unsaturated heterocyclic ring, wherein said heterocyclic ring comprises one or more, same or different heteroatoms O, N, or S, and is unsubstituted, or substituted with one or more, same or different substituents $R^{31}$, and wherein said N- and S-atoms are independently oxidized, or non-oxidized; or $C_3$-$C_6$-cycloalkyl, which substituted with one or more, same or different substituents $R^9$;

$R^7$, $R^8$ are independently H, halogen, CN, $C_1$-$C_6$-alkyl, $C_1$-$C_6$-haloalkyl, $C_3$-$C_6$-cycloalkyl, $C_1$-$C_4$-alkoxy, $C_1$-$C_4$-alkoxy-$C_1$-$C_4$-alkyl, $C_1$-$C_4$-alkylsulfanyl, $C_1$-$C_4$-alkylsulfanyl-$C_1$-$C_4$-alkyl, $C_1$-$C_4$-alkylsulfinyl-$C_1$-$C_4$-alkyl, $C_1$-$C_4$-alkylsulfonyl-$C_1$-$C_4$-alkyl or $C_1$-$C_4$-alkoxycarbonyl;

$R^9$ CN, $NH_2$, C(=O)H, OH, $C_3$-$C_6$-cycloalkyl, C(=O)OH, C(=O)$NH_2$, $C_1$-$C_4$-haloalkoxy, $C_1$-$C_4$-alkoxy, $C_1$-$C_4$-haloalkylsulfanyl, $C_1$-$C_4$-haloalkylsulfinyl, $C_1$-$C_4$-haloalkylsulfonyl, $C_1$-$C_4$-alkoxycarbonyl, $C_1$-$C_4$-haloalkoxycarbonyl, $C_1$-$C_4$-alkylcarbonyl, $C_1$-$C_4$-haloalkylcarbonyl, di-($C_1$-$C_4$)alkylaminocarbonyl, $C_1$-$C_4$-alkylaminocarbonyl, $C_1$-$C_4$-alkylcarbonylamino, di-($C_1$-$C_4$)alkylcarbonylamino, C1-$C_4$-alkoxycarbonylamino, or a group —C($R^{91}$)=NO$R^{92}$;

phenyl, which is unsubstituted or substituted with one or more, same or different substituents selected from halogen, CN, $C_1$-$C_4$-alkyl, $C_1$-$C_4$-haloalkyl, $C_1$-$C_4$-haloalkoxy, $C_1$-$C_4$-alkoxy, $C_1$-$C_4$-haloalkylsulfanyl, $C_1$-$C_4$-haloalkylsulfinyl, $C_1$-$C_4$haloalkylsulfonyl and C(=O)$C_1$-$C_4$-haloalkyl;

$C_1$-$C_4$-alkyl which is unsubstituted or substituted with one or more, same or different substituents $R^{93}$;

$R^{31}$ is halogen, $N_3$, OH, CN, $NO_2$, SCN, $SF_5$;

$C_1$-$C_6$-alkyl, $C_1$-$C_6$-haloalkyl, $C_1$-$C_6$-alkoxy, $C_2$-$C_6$-alkenyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_1$-$C_6$-alkoxycarbonyl, $C_3$-$C_6$-cycloalkyl;

$C_3$-$C_6$-cycloalkoxy, $C_3$-$C_6$-cycloalkyl-$C_1$-$C_4$-alkyl, $C_3$-$C_6$-cycloalkoxy-$C_1$-$C_4$ alkyl, phenyl, or a saturated, partially-, or fully unsaturated 5- or 6-membered heterocycle, wherein the cyclic moieties are unsubstituted or substituted with one or more, same or different substituents $R^{11}$; or two geminal substituents $R^{31}$ form together with the atom to which they are bound a group =O or =S;

$R^{91}$ and $R^{92}$ are independently H, $C_1$-$C_4$-alkyl, or $C_1$-$C_4$-haloalkyl;

$R^{93}$ is halogen, CN, $NH_2$, C(=O)H, OH, $C_3$-$C_6$-cycloalkyl, hydroxycarbonyl, aminocarbonyl, $C_1$-$C_4$-haloalkoxy, C1-$C_4$-alkoxy, $C_1$-$C_4$-haloalkylsulfanyl, $C_1$-$C_4$-haloalkylsulfinyl, $C_1$-$C_4$-haloalkylsulfonyl, $C_1$-$C_4$-alkoxycarbonyl, $C_1$-$C_4$-haloalkoxycarbonyl, $C_1$-$C_4$-alkylcarbonyl, $C_1$-$C_4$-haloalkylcarbonyl, di-($C_1$-$C_4$)alkylaminocarbonyl, $C_1$-$C_4$alkylaminocarbonyl, $C_1$-$C_4$-alkylcarbonylamino, di-($C_1$-$C_4$)alkylcarbonylamino, $C_1$-$C_4$-alkoxycarbonylamino, a group —C($R^{91}$)=NO$R^{92}$;

$R^Y$ is $C_1$-$C_6$-alkyl, $C_3$-$C_6$-cycloalkyl, $C_3$-$C_6$-cycloalkyl-$C_1$-$C_4$-alkyl, which groups are halogenated or non-halogenated;

$CH_2R^6$, or phenyl, which is unsubstituted or substituted with $R^{11}$;

the index n is 0, 1, 2, 3, or 4 if X is phenyl or a 6-membered hetaryl;

or 0, 1, 2, or 3 if X is a 5-membered hetaryl; and the index m is 0, 1, or 2.

2. The compound of formula (I) according to claim 1, wherein A is N.

3. The compound of formula (I) according to claim 1, wherein formula (I) is selected from formulae (IA), (IB), (IC), (IT) and (IY)

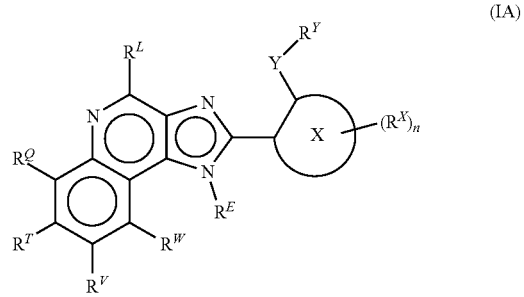

(IA)

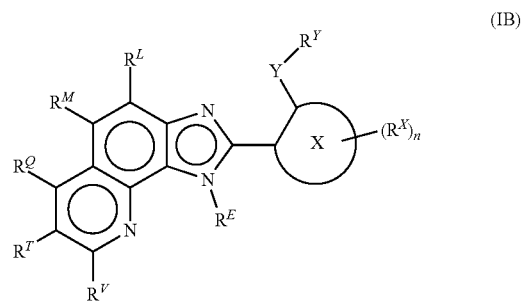

(IB)

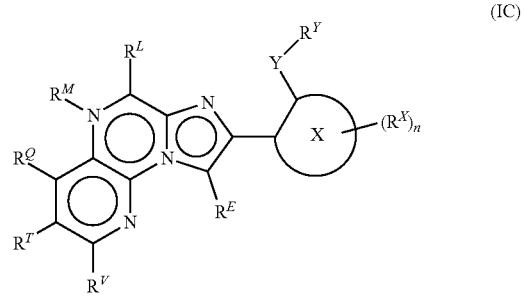

(IC)

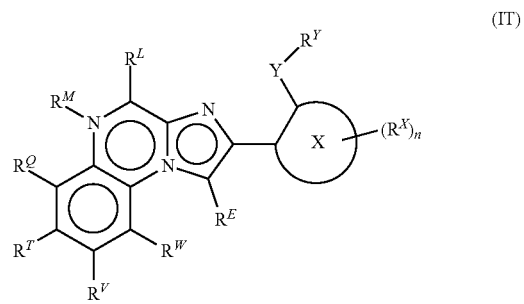

(IT)

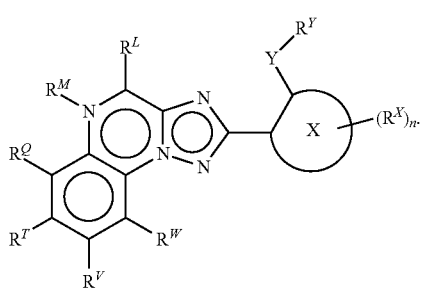

(I-Y)

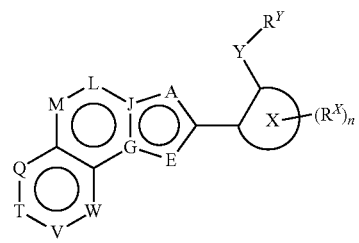

(I)

4. The compound of formula (I) according to claim 1, wherein X is phenyl, 2-pyridyl, or 4-pyrimidinyl.

5. The compound of formula (I) according to claim 1, wherein $R^M$, $R^Q$, $R^T$, and $R^V$ are independently H, halogen; or $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, $C_3$-$C_6$-cycloalkoxy, or $C_1$-$C_6$-alkyl-$S(O)_m$, which groups are halogenated or non-halogenated.

6. The compound of formula (I) according to claim 1, wherein $R^Y$ is $C_1$-$C_4$-alkyl, which is halogenated or non-halogenated.

7. The compound of formula (I) according to claim 1, wherein $R^E$ and $R^L$ are independently H, halogen; or $C_1$-$C_4$-alkyl, $C_1$-$C_4$-alkoxy, $C_2$-$C_4$-alkenyl, or $C_2$-$C_4$-alkynyl, which groups are halogenated or non-halogenated.

8. The compound of formula (I) according to claim 1, wherein $R^X$ is halogen;

$C_1$-$C_3$-alkyl, $C_2$-$C_3$-alkenyl, $C_2$-$C_3$-alkynyl, which groups are halogenated or non-halogenated;

$SO_2NR^2R^3$, $S(=O)_mR^1$;

phenyl, which is unhalogenated or halogenated;

$C(CN)R^7R^8$; or $C_3$-$C_6$-cycloalkyl, which is unsubstituted or substituted with one or more, same or different substituents $R^9$.

9. A compound of formula (I) as defined in claim 1 for use as an agrochemical pesticide.

10. A pesticidal mixture comprising a compound of formula (I) as defined in claim 1, and another agrochemically active ingredient.

11. An agrochemical or veterinary composition comprising a compound of formula (I) as defined in claim 1 and a liquid or solid carrier.

12. A method for controlling invertebrate pests, infestation, or infection by invertebrate pests, comprising contacting the invertebrate pests, their food supply, habitat, breeding grounds or their locus with a compound of formula (I), or an agrochemically or veterinarily acceptable salt, stereoisomer, tautomer, or N-oxide thereof wherein variables in formula (I) have the following meaning A is CH, N, or NH;
E is N, O, S, $NR^E$, or $CR^E$;
G, J are independently C or N;
L is N or $CR^L$;
M is N or $CR^M$;
Q is N or $CR^Q$;
T is N or $CR^T$;
V is N or $CR^V$;
W is N or $CR^W$;
X is phenyl, or a 5- or 6-membered hetaryl;
Y is S, S(O), or $S(O)_2$;
$R^E$, $R^L$, $R^M$, $R^Q$, $R^T$, $R^V$, and $R^W$ are independently H, halogen, $N_3$, CN, $NO_2$, SCN, $SF_5$;

$C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, which groups are halogenated or non-halogenated;

$C(=O)OR^1$, $NR^2R^3$, $C_1$-$C_6$-alkylen-$NR^2R^3$, O-$C_1$-$C_6$-alkylen-$NR^2R^3$, $C_1$-$C_6$-alkylen-CN, NH—$C_1$-$C_6$-alkylen-$NR^2R^3$, $C(=O)NR^2R^3$, $C(=O)R^4$, $SO_2NR^2R^3$, $S(=O)_mR^5$, $OR^6$, $SR^6$, or $CH_2R^6$;

phenyl, which is unsubstituted or substituted with one or more, same or different substituents $R^{11}$;

$R^1$ is H;

$C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, or $C_3$-$C_6$-cycloalkoxy-$C_1$-$C_4$-alkyl, which groups are halogenated or non-halogenated;

$C_1$-$C_6$-alkylen-$NR^2R^3$, $C_1$-$C_6$-alkylen-CN, or $CH_2R^6$; or phenyl, which is unsubstituted, or substituted with one or more, same or different substituents $R^{11}$;

$R^{11}$ is halogen, $N_3$, OH, CN, $NO_2$, SCN, $SF_5$;

$C_1$-$C_6$-alkyl, $C_1$-$C_6$-alkoxy, $C_2$-$C_6$-alkenyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, which groups are halogenated or non-halogenated;

$R^2$ is H;

$C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which groups are unsubstituted, or substituted with one or more, same or different substituents selected from halogen, CN and OH;

$C(=O)R^{21}$, $C(=O)OR^{21}$, $C(=O)NR^{21}$, $C_1$-$C_6$-alkylen-CN, or $CH_2R^6$; or phenyl, which is unsubstituted or substituted with one or more, same or different substituents $R^{11}$;

$R^{21}$ is H;

$C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl;

$C_3$-$C_6$-cycloalkyl-$C_1$-$C_4$-alkyl, $C_3$-$C_6$-cycloalkoxy-$C_1$-$C_4$ alkyl, phenyl, or a saturated, partially-, or fully unsaturated 5- or 6-membered heterocycle, wherein the cyclic moieties are unsubstituted or substituted with one or more, same or different substituents $R^{11}$;

$R^3$ is H;

$C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which groups are halogenated or non-halogenated;

$C_1$-$C_6$-alkylen-CN, or $CH_2R^6$;

phenyl, which is unsubstituted or substituted with one or more, same or different substituents $R^{11}$; or $NR^2R^3$ form an N-bound, saturated 3- to 8-membered heterocycle, which in addition to the nitrogen atom may have 1 or 2 further heteroatoms or heteroatom moieties selected from O, S($=$O)$_m$, NH, and N—$C_1$-$C_6$-alkyl, and wherein the N-bound heterocycle is unsubstituted or substituted with one or more, same or different substituents selected from halogen, $C_1$-$C_4$-alkyl, $C_1$-$C_4$-haloalkyl, $C_1$-$C_4$-alkoxy and $C_1$-$C_4$-haloalkoxy;

$R^4$ is H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, or $C_3$-$C_6$-cycloalkoxy-$C_1$-$C_4$-alkyl, which are unsubstituted or substituted with one or more, same of different substituents selected from halogen, CN, and OH;

$CH_2R^6$, or phenyl, which is unsubstituted, or substituted with one or more, same or different substituents $R^{11}$;

$R^5$ is $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, or $C_3$-$C_6$-cycloalkoxy-$C_1$-$C_4$-alkyl, which groups are halogenated or non-halogenated;

$C_1$-$C_6$-alkylen-$NR^2R^3$, $C_1$-$C_6$-alkylen-CN, $CH_2R^6$; or phenyl, which is unsubstituted, or substituted with one or more, same or different substituents $R^{11}$;

$R^6$ is phenyl, which is unsubstituted or substituted with one or more, same or different substituents $R^{11}$;

$R^X$ is halogen, $N_3$, OH, CN, $NO_2$, SCN, $SF_5$;

$C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, which groups are halogenated or non-halogenated;

C($=$O)$OR^1$, $NR^2R^3$, $C_1$-$C_6$-alkylen-$NR^2R^3$, O-$C_1$-$C_6$-alkylen-$NR^2R^3$, $C_1$-$C_6$-alkylen-CN, NH—$C_1$-$C_6$-alkylen-$NR^2R^3$, C($=$O)$NR^2R^3$, C($=$O)$R^4$, $SO_2NR^2R^3$, S($=$O)$_mR^1$, $OR^6$, $SR^6$, $CH_2R^6$; or OC($=$O)$R^4$, OC($=$O)$OR^1$, OC($=$O)$NR^2R^3$, OC($=$O)$SR^1$, OC($=$S)$NR^2R^3$, OC($=$S)$SR^1$, $ONR^2R^3$, ON$=$$CR^1R^4$, N$=$$CR^1R^4$, $NNR^2$, NC($=$O)$R^4$, SC($=$O)$SR^1$, SC($=$O)$NR^2R^3$, C($=$S)$R^6$, C($=$S)$OR^4$, C($=$NR^2$)$R^4$, C($=$NOR^2$)$R^4$, C(CN)$R^7R^8$;

phenyl, which is unsubstituted or substituted with one or more, same or different substituents $R^{11}$;

a 5- or 6-membered saturated, partially unsaturated, or fully unsaturated heterocyclic ring, wherein said heterocyclic ring comprises one or more, same or different heteroatoms O, N, or S, and is unsubstituted, or substituted with one or more, same or different substituents $R^{31}$, and wherein said N- and S-atoms are independently oxidized, or non-oxidized; or $C_3$-$C_6$-cycloalkyl, which substituted with one or more, same or different substituents $R^9$;

$R^7$, $R^8$ are independently H, halogen, CN, $C_1$-$C_6$-alkyl, $C_1$-$C_6$-haloalkyl, $C_3$-$C_6$-cycloalkyl, $C_1$-$C_4$-alkoxy, $C_1$-$C_4$-alkoxy-$C_1$-$C_4$-alkyl, $C_1$-$C_4$-alkylsulfanyl, $C_1$-$C_4$-alkylsulfanyl-$C_1$-$C_4$-alkyl, $C_1$-$C_4$-alkylsulfinyl-$C_1$-$C_4$-alkyl, $C_1$-$C_4$-alkylsulfonyl-$C_1$-$C_4$-alkyl or $C_1$-$C_4$-alkoxycarbonyl;

$R^9$ CN, $NH_2$, C($=$O)H, OH, $C_3$-$C_6$-cycloalkyl, C($=$O)OH, C($=$O)$NH_2$, $C_1$-$C_4$-haloalkoxy, $C_1$-$C_4$-alkoxy, $C_1$-$C_4$-haloalkylsulfanyl, $C_1$-$C_4$-haloalkylsulfinyl, $C_1$-$C_4$-haloalkylsulfonyl, $C_1$-$C_4$-alkoxycarbonyl, $C_1$-$C_4$-haloalkoxycarbonyl, $C_1$-$C_4$-alkylcarbonyl, $C_1$-$C_4$-haloalkylcarbonyl, di-($C_1$-$C_4$)alkylaminocarbonyl, $C_1$-$C_4$-alkylaminocarbonyl, $C_1$-$C_4$-alkylcarbonylamino, di-($C_1$-$C_4$)alkylcarbonylamino, C1-$C_4$-alkoxycarbonylamino, or a group —C($R^{91}$)$=$$NOR^{92}$;

phenyl, which is unsubstituted or substituted with one or more, same or different substituents selected from halogen, CN, $C_1$-$C_4$-alkyl, $C_1$-$C_4$-haloalkyl, $C_1$-$C_4$-haloalkoxy, $C_1$-$C_4$-alkoxy, $C_1$-$C_4$-haloalkylsulfanyl, $C_1$-$C_4$-haloalkylsulfinyl, $C_1$-$C_4$haloalkylsulfonyl and C($=$O)$C_1$-$C_4$-haloalkyl;

$C_1$-$C_4$-alkyl which is unsubstituted or substituted with one or more, same or different substituents $R^{93}$;

$R^{31}$ is halogen, $N_3$, OH, CN, $NO_2$, SCN, $SF_5$;

$C_1$-$C_6$-alkyl, $C_1$-$C_6$-haloalkyl, $C_1$-$C_6$-alkoxy, $C_2$-$C_6$-alkenyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_1$-$C_6$-alkoxycarbonyl, $C_3$-$C_6$-cycloalkyl;

$C_3$-$C_6$-cycloalkoxy, $C_3$-$C_6$-cycloalkyl-$C_1$-$C_4$-alkyl, $C_3$-$C_6$-cycloalkoxy-$C_1$-$C_4$ alkyl, phenyl, or a saturated, partially-, or fully unsaturated 5- or 6-membered heterocycle, wherein the cyclic moieties are unsubstituted or substituted with one or more, same or different substituents $R^{11}$; or two geminal substituents $R^{31}$ form together with the atom to which they are bound a group $=$O or $=$S;

$R^{91}$ and $R^{92}$ are independently H, $C_1$-$C_4$-alkyl, or $C_1$-$C_4$-haloalkyl;

$R^{93}$ is halogen, CN, $NH_2$, C($=$O)H, OH, $C_3$-$C_6$-cycloalkyl, hydroxycarbonyl, aminocarbonyl, $C_1$-$C_4$-haloalkoxy, C1-$C_4$-alkoxy, $C_1$-$C_4$-haloalkylsulfanyl, $C_1$-$C_4$-haloalkylsulfinyl, $C_1$-$C_4$-haloalkylsulfonyl, $C_1$-$C_4$-alkoxycarbonyl, $C_1$-$C_4$-haloalkoxycarbonyl, $C_1$-$C_4$-alkylcarbonyl, $C_1$-$C_4$-haloalkylcarbonyl, di-($C_1$-$C_4$)alkylaminocarbonyl, $C_1$-$C_4$alkylaminocarbonyl, $C_1$-$C_4$-alkylcarbonylamino, di-($C_1$-$C_4$)alkylcarbonylamino, $C_1$-$C_4$-alkoxycarbonylamino, a group —C($R^{91}$)$=$$NOR^{92}$;

$R^Y$ is $C_1$-$C_6$-alkyl, $C_3$-$C_6$-cycloalkyl, $C_3$-$C_6$-cycloalkyl-$C_1$-$C_4$-alkyl, which groups are halogenated or non-halogenated;

CH$_2$R$^6$, or phenyl, which is unsubstituted or substituted with R$^{11}$;

the index n is 0, 1, 2, 3, or 4 if X is phenyl or a 6-membered hetaryl;

or 0, 1, 2, or 3 if X is a 5-membered hetaryl; and the index m is 0, 1, or 2, in a pesticidally effective amount.

13. A seed, comprising a compound of formula (I) as defined in claim 1 in an amount of from 0.1 g to 10 kg per 100 kg of seeds.

14. A method for treating, or protecting an animal against infestation or infection by parasites, or controlling, or preventing infestations or infections of animals by parasites, by administering or applying orally, topically or parenterally to the animal a compound of general formula (I), or an agrochemically or veterinarily acceptable salt, stereoisomer, tautomer, or N-oxide thereof

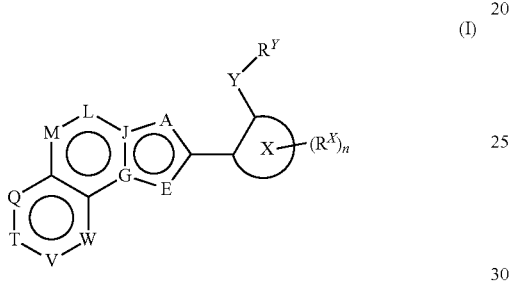

(I)

wherein variables in formula (I) have the following meaning

A is CH, N, or NH;
E is N, O, S, NR$^E$, or CR$^E$;
G, J are independently C or N;
L is N or CR$^L$;
M is N or CR$^M$;
Q is N or CR$^Q$;
T is N or CR$^T$;
V is N or CR$^V$;
W is N or CR$^W$;
X is phenyl, or a 5- or 6-membered hetaryl;
Y is S, S(O), or S(O)$_2$;
R$^E$, R$^L$, R$^M$, R$^Q$, R$^T$, R$^V$, and R$^W$ are independently H, halogen, N$_3$, CN, NO$_2$, SCN, SF$_5$;

C$_1$-C$_6$-alkyl, C$_1$-C$_6$-alkoxy, C$_2$-C$_6$-alkenyl, tri-C$_1$-C$_6$-alkylsilyl, C$_2$-C$_6$-alkynyl, C$_1$-C$_6$-alkoxy-C$_1$-C$_4$-alkyl, C$_1$-C$_6$-alkoxy-C$_1$-C$_4$-alkoxy, C$_3$-C$_6$-cycloalkyl, C$_3$-C$_6$-cycloalkoxy, C$_3$-C$_6$-cycloalkyl-C$_1$-C$_4$-alkyl, C$_3$-C$_6$-cycloalkoxy-C$_1$-C$_4$-alkyl, which groups are halogenated or non-halogenated;

C(=O)OR$^1$, NR$^2$R$^3$, C$_1$-C$_6$-alkylen-NR$^2$R$^3$, O-C$_1$-C$_6$-alkylen-NR$^2$R$^3$, C$_1$-C$_6$-alkylen-CN, NH—C$_1$-C$_6$-alkylen-NR$^2$R$^3$, C(=O)NR$^2$R$^3$, C(=O)R$^4$, SO$_2$NR$^2$R$^3$, S(=O)$_m$R$^5$, OR$^6$, SR$^6$, or CH$_2$R$^6$;

phenyl, which is unsubstituted or substituted with one or more, same or different substituents R$^{11}$;

R$^1$ is H;

C$_1$-C$_6$-alkyl, C$_2$-C$_6$-alkenyl, C$_2$-C$_6$-alkynyl, C$_1$-C$_6$-alkoxy-C$_1$-C$_4$-alkyl, C$_3$-C$_6$-cycloalkyl, C$_3$-C$_6$-cycloalkyl-C$_1$-C$_4$-alkyl, or C$_3$-C$_6$-cycloalkoxy-C$_1$-C$_4$-alkyl, which groups are halogenated or non-halogenated;

C$_1$-C$_6$-alkylen-NR$^2$R$^3$, C$_1$-C$_6$-alkylen-CN, or CH$_2$R$^6$; or phenyl, which is unsubstituted, or substituted with one or more, same or different substituents R$^{11}$;

R$^{11}$ is halogen, N$_3$, OH, CN, NO$_2$, SCN, SF$_5$;

C$_1$-C$_6$-alkyl, C$_1$-C$_6$-alkoxy, C$_2$-C$_6$-alkenyl, C$_2$-C$_6$-alkynyl, C$_1$-C$_6$-alkoxy-C$_1$-C$_4$-alkyl, C$_1$-C$_6$-alkoxy-C$_1$-C$_4$-alkoxy, C$_3$-C$_6$-cycloalkyl, C$_3$-C$_6$-cycloalkoxy, C$_3$-C$_6$-cycloalkyl-C$_1$-C$_4$-alkyl, C$_3$-C$_6$-cycloalkoxy-C$_1$-C$_4$-alkyl, which groups are halogenated or non-halogenated;

R$^2$ is H;

C$_1$-C$_6$-alkyl, C$_2$-C$_6$-alkenyl, C$_2$-C$_6$-alkynyl, C$_1$-C$_6$-alkoxy-C$_1$-C$_4$-alkyl, C$_3$-C$_6$-cycloalkyl, C$_3$-C$_6$-cycloalkyl-C$_1$-C$_4$-alkyl, C$_3$-C$_6$-cycloalkoxy-C$_1$-C$_4$-alkyl, which groups are unsubstituted, or substituted with one or more, same or different substituents selected from halogen, CN and OH;

C(=O)R$^{21}$, C(=O)OR$^{21}$, C(=O)NR$^{21}$, C$_1$-C$_6$-alkylen-CN, or CH$_2$R$^6$; or phenyl, which is unsubstituted or substituted with one or more, same or different substituents R$^{11}$;

R$^{21}$ is H;

C$_1$-C$_6$-alkyl, C$_1$-C$_6$-haloalkyl, C$_2$-C$_6$-alkenyl, C$_2$-C$_6$-alkynyl, C$_1$-C$_6$-alkoxy-C$_1$-C$_4$-alkyl, C$_3$-C$_6$-cycloalkyl;

C$_3$-C$_6$-cycloalkyl-C$_1$-C$_4$-alkyl, C$_3$-C$_6$-cycloalkoxy-C$_1$-C$_4$ alkyl, phenyl, or a saturated, partially-, or fully unsaturated 5- or 6-membered heterocycle, wherein the cyclic moieties are unsubstituted or substituted with one or more, same or different substituents R$^{11}$;

R$^3$ is H;

C$_1$-C$_6$-alkyl, C$_2$-C$_6$-alkenyl, C$_2$-C$_6$-alkynyl, C$_1$-C$_6$-alkoxy-C$_1$-C$_4$-alkyl, C$_3$-C$_6$-cycloalkyl, C$_3$-C$_6$-cycloalkyl-C$_1$-C$_4$-alkyl, C$_3$-C$_6$-cycloalkoxy-C$_1$-C$_4$-alkyl, which groups are halogenated or non-halogenated;

C$_1$-C$_6$-alkylen-CN, or CH$_2$R$^6$;

phenyl, which is unsubstituted or substituted with one or more, same or different substituents R$^{11}$; or NR$^2$R$^3$ form an N-bound, saturated 3- to 8-membered heterocycle, which in addition to the nitrogen atom may have 1 or 2 further heteroatoms or heteroatom moieties selected from O, S(=O)$_m$, NH, and N—C$_1$-C$_6$-alkyl, and wherein the N-bound heterocycle is unsubstituted or substituted with one or more, same or different substituents selected from halogen, C$_1$-C$_4$-alkyl, C$_1$-C$_4$-haloalkyl, C$_1$-C$_4$-alkoxy and C$_1$-C$_4$-haloalkoxy;

R$^4$ is H, C$_1$-C$_6$-alkyl, C$_2$-C$_6$-alkenyl, C$_2$-C$_6$-alkynyl, C$_1$-C$_6$-alkoxy-C$_1$-C$_4$-alkyl, C$_3$-C$_6$-cycloalkyl, C$_3$-C$_6$-cycloalkyl-C$_1$-C$_4$-alkyl, or C$_3$-C$_6$-cycloalkoxy-C$_1$-C$_4$-alkyl, which are unsubstituted or substituted with one or more, same of different substituents selected from halogen, CN, and OH;

CH$_2$R$^6$, or phenyl, which is unsubstituted, or substituted with one or more, same or different substituents R$^{11}$;

R$^5$ is C$_1$-C$_6$-alkyl, C$_2$-C$_6$-alkenyl, C$_2$-C$_6$-alkynyl, C$_1$-C$_6$-alkoxy-C$_1$-C$_4$-alkyl, C$_3$-C$_6$-cycloalkyl, C$_3$-C$_6$-cycloalkyl-C$_1$-C$_4$-alkyl, or C$_3$-C$_6$-cycloalkoxy-C$_1$-C$_4$-alkyl, which groups are halogenated or non-halogenated;

C$_1$-C$_6$-alkylen-NR$^2$R$^3$, C$_1$-C$_6$-alkylen-CN, CH$_2$R$^6$; or phenyl, which is unsubstituted, or substituted with one or more, same or different substituents R$^{11}$;

$R^6$ is phenyl, which is unsubstituted or substituted with one or more, same or different substituents $R^{11}$;

$R^x$ is halogen, $N_3$, OH, CN, $NO_2$, SCN, $SF_5$;

$C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, which groups are halogenated or non-halogenated;

C(=O)OR$^1$, NR$^2$R$^3$, $C_1$-$C_6$-alkylen-NR$^2$R$^3$, O-$C_1$-$C_6$-alkylen-NR$^2$R$^3$, $C_1$-$C_6$-alkylen-CN, NH—$C_1$-$C_6$-alkylen-NR$^2$R$^3$, C(=O)NR$^2$R$^3$, C(=O)R$^4$, SO$_2$NR$^2$R$^3$, S(=O)$_m$R$^1$, OR$^6$, SR$^6$, CH$_2$R$^6$; or OC(=O)R$^4$, OC(=O)OR$^1$, OC(=O)NR$^2$R$^3$, OC(=O)SR$^1$, OC(=S)NR$^2$R$^3$, OC(=S)SR$^1$, ONR$^2$R$^3$, ON=CR$^1$R$^4$, N=CR$^1$R$^4$, NNR$^2$, NC(=O)R$^4$, SC(=O)SR$^1$, SC(=O)NR$^2$R$^3$, C(=S)R$^6$, C(=S)OR$^4$, C(=NR$^2$)R$^4$, C(=NOR$^2$)R$^4$, C(CN)R$^7$R$^8$;

phenyl, which is unsubstituted or substituted with one or more, same or different substituents $R^{11}$;

a 5- or 6-membered saturated, partially unsaturated, or fully unsaturated heterocyclic ring, wherein said heterocyclic ring comprises one or more, same or different heteroatoms O, N, or S, and is unsubstituted, or substituted with one or more, same or different substituents $R^{31}$, and wherein said N- and S-atoms are independently oxidized, or non-oxidized; or $C_3$-$C_6$-cycloalkyl, which substituted with one or more, same or different substituents $R^9$;

$R^7$, $R^8$ are independently H, halogen, CN, $C_1$-$C_6$-alkyl, $C_1$-$C_6$-haloalkyl, $C_3$-$C_6$-cycloalkyl, $C_1$-$C_4$-alkoxy, $C_1$-$C_4$-alkoxy-$C_1$-$C_4$-alkyl, $C_1$-$C_4$-alkylsulfanyl, $C_1$-$C_4$-alkylsulfanyl-$C_1$-$C_4$-alkyl, $C_1$-$C_4$-alkylsulfinyl-$C_1$-$C_4$-alkyl, $C_1$-$C_4$-alkylsulfonyl-$C_1$-$C_4$-alkyl or $C_1$-$C_4$-alkoxycarbonyl;

$R^9$ CN, NH$_2$, C(=O)H, OH, $C_3$-$C_6$-cycloalkyl, C(=O)OH, C(=O)NH$_2$, $C_1$-$C_4$-haloalkoxy, $C_1$-$C_4$-alkoxy, $C_1$-$C_4$-haloalkylsulfanyl, $C_1$-$C_4$-haloalkylsulfinyl, $C_1$-$C_4$-haloalkylsulfonyl, $C_1$-$C_4$-alkoxycarbonyl, $C_1$-$C_4$-haloalkoxycarbonyl, $C_1$-$C_4$-alkylcarbonyl, $C_1$-$C_4$-haloalkylcarbonyl, di-($C_1$-$C_4$)alkylaminocarbonyl, $C_1$-$C_4$-alkylaminocarbonyl, $C_1$-$C_4$-alkylcarbonylamino, di-($C_1$-$C_4$)alkylcarbonylamino, C1-$C_4$-alkoxycarbonylamino, or a group —C(R$^{91}$)=NOR$^{92}$;

phenyl, which is unsubstituted or substituted with one or more, same or different substituents selected from halogen, CN, $C_1$-$C_4$-alkyl, $C_1$-$C_4$-haloalkyl, $C_1$-$C_4$-haloalkoxy, $C_1$-$C_4$-alkoxy, $C_1$-$C_4$-haloalkylsulfanyl, $C_1$-$C_4$-haloalkylsulfinyl, $C_1$-$C_4$haloalkylsulfonyl and C(=O)$C_1$-$C_4$-haloalkyl;

$C_1$-$C_4$-alkyl which is unsubstituted or substituted with one or more, same or different substituents $R^{93}$;

$R^{31}$ is halogen, $N_3$, OH, CN, $NO_2$, SCN, $SF_5$;

$C_1$-$C_6$-alkyl, $C_1$-$C_6$-haloalkyl, $C_1$-$C_6$-alkoxy, $C_2$-$C_6$-alkenyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_1$-$C_6$-alkoxycarbonyl, $C_3$-$C_6$-cycloalkyl:

$C_3$-$C_6$-cycloalkoxy, $C_3$-$C_6$-cycloalkyl-$C_1$-$C_4$-alkyl, $C_3$-$C_6$-cycloalkoxy-$C_1$-$C_4$ alkyl, phenyl, or a saturated, partially-, or fully unsaturated 5- or 6-membered heterocycle, wherein the cyclic moieties are unsubstituted or substituted with one or more, same or different substituents $R^{11}$; or two geminal substituents $R^{31}$ form together with the atom to which they are bound a group =O or =S;

$R^{91}$ and $R^{92}$ are independently H, $C_1$-$C_4$-alkyl, or $C_1$-$C_4$-haloalkyl;

$R^{93}$ is halogen, CN, NH$_2$, C(=O)H, OH, $C_3$-$C_6$-cycloalkyl, hydroxycarbonyl, aminocarbonyl, $C_1$-$C_4$-haloalkoxy, C1-$C_4$-alkoxy, $C_1$-$C_4$-haloalkylsulfanyl, $C_1$-$C_4$-haloalkylsulfinyl, $C_1$-$C_4$-haloalkylsulfonyl, $C_1$-$C_4$-alkoxycarbonyl, $C_1$-$C_4$-haloalkoxycarbonyl, $C_1$-$C_4$-alkylcarbonyl, $C_1$-$C_4$-haloalkylcarbonyl, di-($C_1$-$C_4$)alkylaminocarbonyl, $C_1$-$C_4$alkylaminocarbonyl, $C_1$-$C_4$-alkylcarbonylamino, di-($C_1$-$C_4$)alkylcarbonylamino, $C_1$-$C_4$-alkoxycarbonylamino, a group —C(R$^{91}$)=NOR$^{92}$;

$R^Y$ is $C_1$-$C_6$-alkyl, $C_3$-$C_6$-cycloalkyl, $C_3$-$C_6$-cycloalkyl-$C_1$-$C_4$-alkyl, which groups are halogenated or non-halogenated;

CH$_2$R$^6$, or phenyl, which is unsubstituted or substituted with $R^{11}$;

the index n is 0, 1, 2, 3, or 4 if X is phenyl or a 6-membered hetaryl;

or 0, 1, 2, or 3 if X is a 5-membered hetaryl; and the index m is 0, 1, or 2.

15. The pesticidal mixture of claim 10 wherein the other agrochemically active ingredient is a pesticide.

16. The pesticidal mixture of claim 10 wherein the other agrochemically active ingredient is an insecticide and/or a fungicide.

* * * * *